United States Patent
Harlow et al.

(10) Patent No.: US 12,115,227 B2
(45) Date of Patent: *Oct. 15, 2024

(54) FORMULATION FOR ANTIBODY AND DRUG CONJUGATE THEREOF

(71) Applicant: GENMAB A/S, Valby (DK)

(72) Inventors: Lene Schantz Harlow, Frederiksberg (DK); Timothy Warren Paul, Bloomington, IN (US); Brendan M. Mayhugh, Bloomington, IN (US); Kelly Ann Roby, Bloomington, IN (US); Gregory Allan Sacha, Bargersville, IN (US); Xiaona Jing, Riehen (CH); Andrew Hagarman, Durham, NC (US); Cale Halbleib, Apex, NC (US)

(73) Assignee: GENMAB A/S, Valby (DK)

(*) Notice: Subject to any disclaimer, the term of this patent is extended or adjusted under 35 U.S.C. 154(b) by 0 days.

This patent is subject to a terminal disclaimer.

(21) Appl. No.: 16/069,391

(22) PCT Filed: Jan. 13, 2017

(86) PCT No.: PCT/EP2017/050700
§ 371 (c)(1),
(2) Date: Jul. 11, 2018

(87) PCT Pub. No.: WO2017/121867
PCT Pub. Date: Jul. 20, 2017

(65) Prior Publication Data
US 2019/0030180 A1    Jan. 31, 2019

Related U.S. Application Data

(60) Provisional application No. 62/278,217, filed on Jan. 13, 2016.

(51) Int. Cl.
| | |
|---|---|
| *A61K 39/395* | (2006.01) |
| *A61K 9/00* | (2006.01) |
| *A61K 9/19* | (2006.01) |
| *A61K 38/07* | (2006.01) |
| *A61K 47/18* | (2017.01) |
| *A61K 47/26* | (2006.01) |
| *A61K 47/68* | (2017.01) |
| *A61K 47/69* | (2017.01) |
| *C07K 16/28* | (2006.01) |
| *A61K 39/00* | (2006.01) |

(52) U.S. Cl.
CPC ........ *A61K 47/6849* (2017.08); *A61K 9/0019* (2013.01); *A61K 9/19* (2013.01); *A61K 38/07* (2013.01); *A61K 39/39591* (2013.01); *A61K 47/183* (2013.01); *A61K 47/26* (2013.01); *A61K 47/6803* (2017.08); *A61K 47/6811* (2017.08); *A61K 47/6921* (2017.08); *C07K 16/2863* (2013.01); *A61K 2039/505* (2013.01); *C07K 2317/24* (2013.01); *C07K 2317/31* (2013.01); *C07K 2317/34* (2013.01); *C07K 2317/622* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 10,201,607 B2 | 2/2019 | Breij et al. | |
| 10,500,276 B2 | 12/2019 | Breij et al. | |
| 10,512,688 B2 | 12/2019 | Breij et al. | |
| 10,765,743 B2 | 9/2020 | Breij et al. | |
| 2005/0074821 A1* | 4/2005 | Wild, Jr. | A61P 11/08 530/388.25 |
| 2009/0142361 A1* | 6/2009 | Amphlett | A61K 9/19 424/181.1 |
| 2013/0108644 A1 | 5/2013 | Giaccia et al. | |
| 2014/0302041 A1* | 10/2014 | Robert | C07K 16/40 424/139.1 |
| 2017/0027940 A1 | 2/2017 | Peeper et al. | |
| 2017/0157250 A1 | 6/2017 | Breij et al. | |
| 2018/0214549 A1 | 8/2018 | Breij et al. | |
| 2018/0326084 A1 | 11/2018 | Boshuizen et al. | |
| 2019/0022243 A1 | 1/2019 | Boshuizen et al. | |

(Continued)

FOREIGN PATENT DOCUMENTS

| | | |
|---|---|---|
| EP | 2371388 A2 | 10/2011 |
| WO | 2011/159980 A1 | 12/2011 |

(Continued)

OTHER PUBLICATIONS

Kishore et al., Journal of Pharmaceutical Sciences, vol. 100, pp. 721-731, 2011.*

(Continued)

*Primary Examiner* — Yunsoo Kim
(74) *Attorney, Agent, or Firm* — Nelson Mullins Riley & Scarborough LLP; Jane E. Remillard, Esq.; Christopher L. Frank

(57) ABSTRACT

Disclosed herein are surfactant free antibody and antibody-drug-conjugate (ADC) formulations for anti-AXL antibodies and ADCs, including aqueous formulations, lyophilized formulations, and reconstituted formulations, as well as related processes and uses. The formulations are particularly suitable for an anti-AXL ADC based on an auristatin or DM1 derivative or other similarly hydrophobic drugs. Some formulations comprise histidine and mannitol.

91 Claims, 9 Drawing Sheets
Specification includes a Sequence Listing.

(56) References Cited

U.S. PATENT DOCUMENTS

| | | |
|---|---|---|
| 2019/0160170 A1 | 5/2019 | Breij et al. |
| 2019/0233522 A1 | 8/2019 | Forssmann et al. |
| 2019/0275149 A1 | 9/2019 | Breij et al. |
| 2020/0171152 A1 | 6/2020 | Breij et al. |
| 2020/0397913 A1 | 12/2020 | Boshuizen et al. |
| 2021/0070869 A1 | 3/2021 | Janmaat et al. |
| 2022/0133721 A1 | 5/2022 | Peeper et al. |

FOREIGN PATENT DOCUMENTS

| | | |
|---|---|---|
| WO | 2014/174111 A1 | 10/2014 |
| WO | 2015/075201 A1 | 5/2015 |
| WO | 2016/005593 A1 | 1/2016 |
| WO | 2017/009258 A1 | 1/2017 |
| WO | 2017/121877 A1 | 7/2017 |
| WO | 2018/007592 A1 | 1/2018 |
| WO | 2019/197506 A1 | 10/2019 |

OTHER PUBLICATIONS

Ngo et al., The protein folding problem and tertiary structure prediction, p. 492-495 (Year: 1994).*
U.S. Appl. No. 16/673,383, filed Nov. 4, 2019, Esther Breij.
U.S. Appl. No. 16/270,317, filed Feb. 7, 2019, Esther Breij.
U.S. Appl. No. 16/248,402, filed Jan. 15, 2019, Esther Breij.
U.S. Appl. No. 15/325,364, filed Jan. 10, 2017, Esther Breij.
U.S. Appl. No. 15/938,961, filed Mar. 28, 2018, Esther Breij.
U.S. Appl. No. 15/742,818, filed Jan. 8, 2018, Julia Boshuizen.
U.S. Appl. No. 16/316,000, filed Jan. 7, 2019, Ulf Forssmann.
U.S. Appl. No. 16/069,395, filed Jul. 11, 2018, Julia Boshuizen.
U.S. Appl. No. 15/302,787, filed Oct. 7, 2016, Daniel Simon Peeper.
U.S. Appl. No. 16/270,317, Aug. 1, 2019.
U.S. Appl. No. 16/270,317, Apr. 1, 2019.
U.S. Appl. No. 16/248,402, Nov. 21, 2019.
U.S. Appl. No. 16/248,402, Jul. 29, 2019.
U.S. Appl. No. 15/325,364, Aug. 5, 2019.
U.S. Appl. No. 15/325,364, Aug. 30, 2018.
U.S. Appl. No. 15/325,364, Apr. 19, 2018.
U.S. Appl. No. 15/325,364, Dec. 6, 2017.
U.S. Appl. No. 15/938,961, Sep. 13, 2018.
U.S. Appl. No. 15/938,961, May 2, 2018.
U.S. Appl. No. 15/742,818, Dec. 19, 2019.
U.S. Appl. No. 15/302,787, Dec. 26, 2019.
U.S. Appl. No. 15/302,787, Oct. 5, 2018.
U.S. Appl. No. 15/302,787, Dec. 20, 2017.
U.S. Appl. No. 15/302,787, Jul. 24, 2017.
International Search Report and Written Opinion, PCT/EP2017/050700, dated Jun. 22, 2017, 20 pages.
International Preliminary Report on Patentability, PCT/EP2017/050700, dated Jul. 17, 2018, 13 pages.
U.S. Appl. No. 16/891,796, filed Jun. 3, 2020, Julia Boshuizen, US 2020-0397913.
U.S. Appl. No. 17/346,851, filed Jun. 14, 2021, Daniel Simon Peeper.
U.S. Appl. No. 17/967,552, filed Oct. 17, 2022, Julia Boshuizen.
U.S. Appl. No. 17/957,302, filed Sep. 30, 2022, Julia Boshuizen.

* cited by examiner

SEQUENCE LISTING

```
<160> NUMBER OF SEQ ID NOS: 147

<210> SEQ ID NO 1
<211> LENGTH: 116
<212> TYPE: PRT
<213> ORGANISM: homo sapiens

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Thr Ser Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Trp Ile Ala Phe Asp Ile Trp Gly Gln Gly Thr Met Val
            100                 105                 110

Thr Val Ser Ser
            115

<210> SEQ ID NO 2
<211> LENGTH: 108
```

```
<212> TYPE: PRT
<213> ORGANISM: homo sapiens

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 3
<211> LENGTH: 120
<212> TYPE: PRT
<213> ORGANISM: homo sapiens

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Ser Ile Ser Gly Ala Ser Thr Phe Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Phe Cys
                85                  90                  95

Arg Gly Tyr Ser Gly Tyr Val Tyr Asp Ala Phe Asp Ile Trp Gly Gln
            100                 105                 110

Gly Thr Met Val Thr Val Ser Ser
        115                 120

<210> SEQ ID NO 4
<211> LENGTH: 107
<212> TYPE: PRT
<213> ORGANISM: homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Tyr Asn Ser Tyr Pro Leu
                    85                  90                  95

Thr Phe Gly Gly Gly Thr Lys Val Glu Ile Lys
                    100                 105

<210> SEQ ID NO 5
<211> LENGTH: 120
<212> TYPE: PRT
<213> ORGANISM: homo sapiens

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Thr Trp Val Arg Gln Ala Pro Gly Lys Gly Leu Glu Trp Val
                35                  40                  45

Ser Ala Ile Ser Ile Ser Gly Gly Ser Thr Phe Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Arg Gly Tyr Ser Gly Tyr Val Tyr Asp Ala Phe Asp Phe Trp Gly Gln
                100                 105                 110

Gly Thr Met Val Thr Val Ser Ser
            115                 120

<210> SEQ ID NO 6
<211> LENGTH: 107
<212> TYPE: PRT
<213> ORGANISM: homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Tyr Gln Gln Lys Pro Glu Lys Ala Pro Lys Ser Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
                100                 105

<210> SEQ ID NO 7
<211> LENGTH: 121
<212> TYPE: PRT
<213> ORGANISM: homo sapiens

<400> SEQUENCE: 7

Glu Val Gln Leu Leu Asp Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ile Gly Gly Gly Asn Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Ala Asp Thr Ala Val Tyr Tyr Cys
                85                  90                  95

Ala Lys Pro Gly Phe Ile Met Val Arg Gly Pro Leu Asp Tyr Trp Gly
            100                 105                 110

Gln Gly Ala Leu Val Thr Val Ser Ser
            115                 120

<210> SEQ ID NO 8
<211> LENGTH: 121
<212> TYPE: PRT
<213> ORGANISM: homo sapiens

<400> SEQUENCE: 8

Glu Val Gln Leu Leu Asp Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ile Gly Gly Gly Asn Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Ala Asp Thr Ala Val Tyr Tyr Cys
                85                  90                  95

Ala Lys Pro Gly Phe Ile Leu Val Arg Gly Pro Leu Asp Tyr Trp Gly
            100                 105                 110

Gln Gly Ala Leu Val Thr Val Ser Ser
            115                 120

<210> SEQ ID NO 9
<211> LENGTH: 108
<212> TYPE: PRT
<213> ORGANISM: homo sapiens

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

-continued

Tyr Thr Phe Gly Gln Gly Thr Lys Leu Glu Ile Lys
            100                 105

<210> SEQ ID NO 10
<211> LENGTH: 125
<212> TYPE: PRT
<213> ORGANISM: homo sapiens

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Val Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Tyr Ile Trp Phe Gly Glu Ser Leu Ser Tyr Ala Phe
            100                 105                 110

Asp Ile Trp Gly Gln Gly Thr Met Val Thr Val Ser Ser
        115                 120                 125

<210> SEQ ID NO 11
<211> LENGTH: 107
<212> TYPE: PRT
<213> ORGANISM: homo sapiens

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Phe
                85                  90                  95

Thr Phe Gly Pro Gly Thr Lys Val Asp Ile Lys
            100                 105

<210> SEQ ID NO 12
<211> LENGTH: 125
<212> TYPE: PRT
<213> ORGANISM: homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

```
Ala Met Ser Trp Val Arg Gln Ala Pro Gly Lys Gly Leu Glu Trp Val
            35                  40                  45

Ser Asp Ile Ser Val Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Glu Gly Tyr Ile Trp Phe Gly Glu Ser Leu Ser Tyr Ala Phe
                100                 105                 110

Asp Ile Trp Gly Gln Gly Thr Met Val Thr Val Ser Ser
            115                 120                 125

<210> SEQ ID NO 13
<211> LENGTH: 107
<212> TYPE: PRT
<213> ORGANISM: homo sapiens

<400> SEQUENCE: 13

Glu Ile Val Leu Thr Gln Ser Pro Gly Thr Leu Ser Leu Ser Pro Gly
 1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Arg Ser Phe
                85                  90                  95

Thr Phe Gly Pro Gly Thr Lys Val Asp Ile Lys
                100                 105

<210> SEQ ID NO 14
<211> LENGTH: 125
<212> TYPE: PRT
<213> ORGANISM: homo sapiens

<400> SEQUENCE: 14

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Asp Ile Ser Val Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu His Met Asn Ser Leu Arg Ala Glu Asp Thr Ala Val Tyr Tyr Cys
                    85                  90                  95

Ala Lys Glu Gly Tyr Ile Trp Phe Gly Glu Ser Leu Ser Tyr Ala Phe
                100                 105                 110

Asp Ile Trp Gly Gln Gly Thr Met Val Thr Val Ser Ser
            115                 120                 125
```

<210> SEQ ID NO 15
<211> LENGTH: 107
<212> TYPE: PRT
<213> ORGANISM: homo sapiens

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Phe
                85                  90                  95

Thr Phe Gly Pro Gly Thr Lys Val Asp Ile Lys
            100                 105

<210> SEQ ID NO 16
<211> LENGTH: 117
<212> TYPE: PRT
<213> ORGANISM: homo sapiens

<400> SEQUENCE: 16

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn Gln Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ser Val Tyr Tyr Cys Ala
                85                  90                  95

Ser Gly Asn Trp Asp His Phe Phe Asp Tyr Trp Gly Gln Gly Thr Leu
            100                 105                 110

Val Thr Val Ser Ser
        115

<210> SEQ ID NO 17
<211> LENGTH: 117
<212> TYPE: PRT
<213> ORGANISM: homo sapiens

<400> SEQUENCE: 17

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Gln Gln Ser Gly Ser Thr Asn Tyr Asn Pro Ser Leu Lys

```
                        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ser Val Tyr Tyr Cys Ala
                 85                  90                  95

Ser Gly Asn Trp Asp His Phe Phe Asp Tyr Trp Gly Gln Gly Thr Leu
            100                 105                 110

Val Thr Val Ser Ser
        115

<210> SEQ ID NO 18
<211> LENGTH: 107
<212> TYPE: PRT
<213> ORGANISM: homo sapiens

<400> SEQUENCE: 18

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln His Lys Pro Gly Lys Ala Pro Lys Leu Leu Ile
         35                  40                  45

Tyr Ala Thr Ser Ser Leu Gln Ser Gly Val Thr Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Lys Ser Phe Pro Trp
                 85                  90                  95

Thr Phe Gly Gln Gly Thr Lys Val Glu Ile Lys
            100                 105

<210> SEQ ID NO 19
<211> LENGTH: 123
<212> TYPE: PRT
<213> ORGANISM: homo sapiens

<400> SEQUENCE: 19

Gln Val Pro Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

His Trp Ser Trp Ile Arg Gln Pro Pro Gly Lys Gly Leu Glu Trp Ile
         35                  40                  45

Gly Glu Ile Ser His Ser Gly Arg Thr Asn Tyr Asn Pro Ser Leu Lys
 50                  55                  60

Ser Arg Val Thr Ile Ser Ile Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Ser Phe Ile Thr Met Ile Arg Gly Thr Ile Ile Thr His Phe Asp Tyr
            100                 105                 110

Trp Gly Gln Gly Thr Leu Val Thr Val Ser Ser
            115                 120

<210> SEQ ID NO 20
<211> LENGTH: 107
<212> TYPE: PRT
```

```
<213> ORGANISM: homo sapiens

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Tyr Pro Tyr
                85                  90                  95

Thr Phe Gly Gln Gly Thr Lys Leu Glu Ile Lys
            100                 105

<210> SEQ ID NO 21
<211> LENGTH: 124
<212> TYPE: PRT
<213> ORGANISM: homo sapiens

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Ile Ala Asn Tyr Val Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ala Glu Asp Thr Ala Val Tyr Tyr Cys
                85                  90                  95

Ala Arg Arg Gly Asp Tyr Tyr Gly Ser Gly Ser Pro Asp Val Phe Asp
            100                 105                 110

Ile Trp Gly Gln Gly Thr Met Val Thr Val Ser Ser
        115                 120

<210> SEQ ID NO 22
<211> LENGTH: 107
<212> TYPE: PRT
<213> ORGANISM: homo sapiens

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105

<210> SEQ ID NO 23
<211> LENGTH: 124
<212> TYPE: PRT
<213> ORGANISM: homo sapiens

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Ile Ala Asn Tyr Val Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ala Glu Asp Thr Ala Val Tyr Tyr Cys
                85                  90                  95

Ala Arg Arg Gly Asn Tyr Tyr Gly Ser Gly Ser Pro Asp Val Phe Asp
            100                 105                 110

Ile Trp Gly Gln Gly Thr Met Val Thr Val Ser Ser
        115                 120

<210> SEQ ID NO 24
<211> LENGTH: 107
<212> TYPE: PRT
<213> ORGANISM: homo sapiens

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105

<210> SEQ ID NO 25
<211> LENGTH: 124
<212> TYPE: PRT
<213> ORGANISM: homo sapiens

<400> SEQUENCE: 25

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Thr Phe Ser Ser Tyr
            20                  25                  30

Ala Ile Asn Trp Met Arg Gln Ala Pro Gly Gln Gly Leu Glu Trp Met
        35                  40                  45

Gly Arg Ile Ile Pro Ile Phe Gly Ile Val Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asn Tyr Tyr Gly Ser Gly Ser Pro Asp Val Phe Asp
            100                 105                 110

Ile Trp Gly Gln Gly Thr Met Val Thr Val Ser Ser
            115                 120

<210> SEQ ID NO 26
<211> LENGTH: 107
<212> TYPE: PRT
<213> ORGANISM: homo sapiens

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105

<210> SEQ ID NO 27
<211> LENGTH: 124
<212> TYPE: PRT
<213> ORGANISM: homo sapiens

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Met Arg Gln Ala Pro Gly Gln Gly Leu Glu Trp Met
        35                  40                  45

Gly Arg Ile Ile Pro Ile Phe Gly Ile Val Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asn Tyr Tyr Gly Ser Gly Ser Pro Asp Val Phe Asp
            100                 105                 110
```

Ile Trp Gly Gln Gly Thr Met Val Thr Val Ser Ser
         115                 120

<210> SEQ ID NO 28
<211> LENGTH: 106
<212> TYPE: PRT
<213> ORGANISM: homo sapiens

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Leu Thr
                85                  90                  95

Phe Gly Gly Gly Thr Lys Val Glu Ile Lys
            100                 105

<210> SEQ ID NO 29
<211> LENGTH: 124
<212> TYPE: PRT
<213> ORGANISM: homo sapiens

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Asn Tyr Tyr Gly Ser Gly Ser Pro Asp Val Phe Asp
            100                 105                 110

Ile Trp Gly Gln Gly Thr Met Val Thr Val Ser Ser
         115                 120

<210> SEQ ID NO 30
<211> LENGTH: 107
<212> TYPE: PRT
<213> ORGANISM: homo sapiens

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu

```
                35                  40                  45
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Tyr
                 85                  90                  95

Thr Phe Gly Gln Gly Thr Lys Leu Glu Ile Lys
            100                 105
```

<210> SEQ ID NO 31
<211> LENGTH: 123
<212> TYPE: PRT
<213> ORGANISM: homo sapiens

<400> SEQUENCE: 31

```
Gln Val Gln Leu Gln Gln Trp Gly Ala Gly Leu Leu Lys Pro Ser Glu
 1               5                  10                  15

Thr Leu Ser Leu Thr Cys Ala Ile Asp Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Ser His Ser Gly Arg Thr Asn Tyr Asn Pro Ser Leu Lys
 50                  55                  60

Ser Arg Val Thr Ile Ser Ile Asp Thr Ser Lys Asn Gln Phe Ser Leu
 65                  70                  75                  80

Lys Leu Ser Ser Val Ala Ala Ala Asp Thr Ala Val Tyr Tyr Cys Ala
                 85                  90                  95

Arg Phe Ile Thr Met Ile Arg Gly Ala Ile Ile Thr His Phe Asp Tyr
            100                 105                 110

Trp Gly Gln Gly Ala Leu Val Thr Val Ser Ser
            115                 120
```

<210> SEQ ID NO 32
<211> LENGTH: 123
<212> TYPE: PRT
<213> ORGANISM: homo sapiens

<400> SEQUENCE: 32

```
Gln Val Gln Leu Gln Gln Trp Gly Ala Gly Leu Leu Lys Pro Ser Glu
 1               5                  10                  15

Thr Leu Ser Leu Thr Cys Ala Ile Asp Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Ser His Ser Gly Arg Thr Asn Tyr Asn Pro Ser Leu Lys
 50                  55                  60

Ser Arg Val Thr Ile Ser Ile Asp Thr Ser Lys Asn Gln Phe Ser Leu
 65                  70                  75                  80

Lys Leu Ser Ser Val Ala Ala Ala Asp Thr Ala Val Tyr Tyr Cys Ala
                 85                  90                  95

Arg Phe Ile Thr Leu Ile Arg Gly Ala Ile Ile Thr His Phe Asp Tyr
            100                 105                 110

Trp Gly Gln Gly Ala Leu Val Thr Val Ser Ser
            115                 120
```

```
<210> SEQ ID NO 33
<211> LENGTH: 107
<212> TYPE: PRT
<213> ORGANISM: homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Tyr Pro Tyr
                85                  90                  95

Thr Phe Gly Gln Gly Thr Lys Leu Glu Ile Lys
            100                 105

<210> SEQ ID NO 34
<211> LENGTH: 120
<212> TYPE: PRT
<213> ORGANISM: homo sapiens

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asp Asn Lys Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Lys Leu Gly Ile Asp Ala Phe Asp Ile Trp Gly Gln
            100                 105                 110

Gly Thr Met Val Thr Val Ser Ser
        115                 120

<210> SEQ ID NO 35
<211> LENGTH: 107
<212> TYPE: PRT
<213> ORGANISM: homo sapiens

<400> SEQUENCE: 35

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60
```

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105

<210> SEQ ID NO 36
<211> LENGTH: 8
<212> TYPE: PRT
<213> ORGANISM: homo sapiens

<400> SEQUENCE: 36

Gly Phe Thr Phe Ser Ser Tyr Ala
1               5

<210> SEQ ID NO 37
<211> LENGTH: 8
<212> TYPE: PRT
<213> ORGANISM: homo sapiens

<400> SEQUENCE: 37

Thr Ser Gly Ser Gly Ala Ser Thr
1               5

<210> SEQ ID NO 38
<211> LENGTH: 9
<212> TYPE: PRT
<213> ORGANISM: homo sapiens

<400> SEQUENCE: 38

Ala Lys Ile Trp Ile Ala Phe Asp Ile
1               5

<210> SEQ ID NO 39
<211> LENGTH: 7
<212> TYPE: PRT
<213> ORGANISM: homo sapiens

<400> SEQUENCE: 39

Gln Ser Val Ser Ser Ser Tyr
1               5

<210> SEQ ID NO 40
<211> LENGTH: 9
<212> TYPE: PRT
<213> ORGANISM: homo sapiens

<400> SEQUENCE: 40

Gln Gln Tyr Gly Ser Ser Pro Tyr Thr
1               5

<210> SEQ ID NO 41
<211> LENGTH: 8
<212> TYPE: PRT
<213> ORGANISM: homo sapiens

<400> SEQUENCE: 41

Gly Phe Thr Phe Ser Ser Tyr Ala
1               5

<210> SEQ ID NO 42
<211> LENGTH: 8

```
<212> TYPE: PRT
<213> ORGANISM: homo sapiens

<400> SEQUENCE: 42

Ile Ser Ile Ser Gly Ala Ser Thr
1               5

<210> SEQ ID NO 43
<211> LENGTH: 13
<212> TYPE: PRT
<213> ORGANISM: homo sapiens

<400> SEQUENCE: 43

Arg Gly Tyr Ser Gly Tyr Val Tyr Asp Ala Phe Asp Ile
1               5                   10

<210> SEQ ID NO 44
<211> LENGTH: 6
<212> TYPE: PRT
<213> ORGANISM: homo sapiens

<400> SEQUENCE: 44

Gln Gly Ile Ser Asn Trp
1               5

<210> SEQ ID NO 45
<211> LENGTH: 9
<212> TYPE: PRT
<213> ORGANISM: homo sapiens

<400> SEQUENCE: 45

Gln Gln Tyr Asn Ser Tyr Pro Leu Thr
1               5

<210> SEQ ID NO 46
<211> LENGTH: 8
<212> TYPE: PRT
<213> ORGANISM: homo sapiens

<400> SEQUENCE: 46

Gly Phe Thr Phe Ser Ser Tyr Ala
1               5

<210> SEQ ID NO 47
<211> LENGTH: 8
<212> TYPE: PRT
<213> ORGANISM: homo sapiens

<400> SEQUENCE: 47

Ile Ser Ile Ser Gly Gly Ser Thr
1               5

<210> SEQ ID NO 48
<211> LENGTH: 13
<212> TYPE: PRT
<213> ORGANISM: homo sapiens

<400> SEQUENCE: 48

Arg Gly Tyr Ser Gly Tyr Val Tyr Asp Ala Phe Asp Phe
1               5                   10

<210> SEQ ID NO 49
<211> LENGTH: 6
<212> TYPE: PRT
<213> ORGANISM: homo sapiens
```

```
<400> SEQUENCE: 49

Gln Gly Ile Ser Asn Trp
1               5

<210> SEQ ID NO 50
<211> LENGTH: 9
<212> TYPE: PRT
<213> ORGANISM: homo sapiens

<400> SEQUENCE: 50

Gln Gln Tyr Asn Ser Tyr Pro Leu Thr
1               5

<210> SEQ ID NO 51
<211> LENGTH: 8
<212> TYPE: PRT
<213> ORGANISM: homo sapiens

<400> SEQUENCE: 51

Gly Phe Thr Phe Ser Ser Tyr Ala
1               5

<210> SEQ ID NO 52
<211> LENGTH: 8
<212> TYPE: PRT
<213> ORGANISM: homo sapiens

<400> SEQUENCE: 52

Ile Ser Ile Gly Gly Gly Asn Ala
1               5

<210> SEQ ID NO 53
<211> LENGTH: 14
<212> TYPE: PRT
<213> ORGANISM: homo sapiens

<400> SEQUENCE: 53

Ala Lys Pro Gly Phe Ile Met Val Arg Gly Pro Leu Asp Tyr
1               5                   10

<210> SEQ ID NO 54
<211> LENGTH: 14
<212> TYPE: PRT
<213> ORGANISM: homo sapiens

<400> SEQUENCE: 54

Ala Lys Pro Gly Phe Ile Leu Val Arg Gly Pro Leu Asp Tyr
1               5                   10

<210> SEQ ID NO 55
<211> LENGTH: 7
<212> TYPE: PRT
<213> ORGANISM: homo sapiens

<400> SEQUENCE: 55

Gln Ser Val Ser Asn Ser Tyr
1               5

<210> SEQ ID NO 56
<211> LENGTH: 9
<212> TYPE: PRT
<213> ORGANISM: homo sapiens

<400> SEQUENCE: 56
```

Gln Gln Tyr Gly Ser Ser Pro Tyr Thr
1               5

<210> SEQ ID NO 57
<211> LENGTH: 8
<212> TYPE: PRT
<213> ORGANISM: homo sapiens

<400> SEQUENCE: 57

Gly Phe Thr Phe Ser Ser Tyr Ala
1               5

<210> SEQ ID NO 58
<211> LENGTH: 8
<212> TYPE: PRT
<213> ORGANISM: homo sapiens

<400> SEQUENCE: 58

Ile Ser Val Ser Gly Gly Ser Thr
1               5

<210> SEQ ID NO 59
<211> LENGTH: 18
<212> TYPE: PRT
<213> ORGANISM: homo sapiens

<400> SEQUENCE: 59

Ala Lys Glu Gly Tyr Ile Trp Phe Gly Glu Ser Leu Ser Tyr Ala Phe
1               5                   10                  15

Asp Ile

<210> SEQ ID NO 60
<211> LENGTH: 7
<212> TYPE: PRT
<213> ORGANISM: homo sapiens

<400> SEQUENCE: 60

Gln Ser Val Ser Ser Ser Tyr
1               5

<210> SEQ ID NO 61
<211> LENGTH: 8
<212> TYPE: PRT
<213> ORGANISM: homo sapiens

<400> SEQUENCE: 61

Gln Gln Tyr Gly Arg Ser Phe Thr
1               5

<210> SEQ ID NO 62
<211> LENGTH: 8
<212> TYPE: PRT
<213> ORGANISM: homo sapiens

<400> SEQUENCE: 62

Gly Phe Thr Phe Ser Asn Tyr Ala
1               5

<210> SEQ ID NO 63
<211> LENGTH: 8
<212> TYPE: PRT
<213> ORGANISM: homo sapiens

<400> SEQUENCE: 63

Ile Ser Val Ser Gly Gly Ser Thr
1               5

<210> SEQ ID NO 64
<211> LENGTH: 18
<212> TYPE: PRT
<213> ORGANISM: homo sapiens

<400> SEQUENCE: 64

Ala Lys Glu Gly Tyr Ile Trp Phe Gly Glu Ser Leu Ser Tyr Ala Phe
1               5                   10                  15

Asp Ile

<210> SEQ ID NO 65
<211> LENGTH: 7
<212> TYPE: PRT
<213> ORGANISM: homo sapiens

<400> SEQUENCE: 65

Gln Ser Val Ser Ser Ser Tyr
1               5

<210> SEQ ID NO 66
<211> LENGTH: 8
<212> TYPE: PRT
<213> ORGANISM: homo sapiens

<400> SEQUENCE: 66

Gln Gln Tyr Gly Arg Ser Phe Thr
1               5

<210> SEQ ID NO 67
<211> LENGTH: 8
<212> TYPE: PRT
<213> ORGANISM: homo sapiens

<400> SEQUENCE: 67

Gly Phe Thr Phe Ser Ser Tyr Ala
1               5

<210> SEQ ID NO 68
<211> LENGTH: 8
<212> TYPE: PRT
<213> ORGANISM: homo sapiens

<400> SEQUENCE: 68

Ile Ser Val Ser Gly Gly Ser Thr
1               5

<210> SEQ ID NO 69
<211> LENGTH: 18
<212> TYPE: PRT
<213> ORGANISM: homo sapiens

<400> SEQUENCE: 69

Ala Lys Glu Gly Tyr Ile Trp Phe Gly Glu Ser Leu Ser Tyr Ala Phe
1               5                   10                  15

Asp Ile

<210> SEQ ID NO 70
<211> LENGTH: 7
<212> TYPE: PRT
<213> ORGANISM: homo sapiens

<400> SEQUENCE: 70

Gln Ser Val Ser Ser Tyr
1               5

<210> SEQ ID NO 71
<211> LENGTH: 8
<212> TYPE: PRT
<213> ORGANISM: homo sapiens

<400> SEQUENCE: 71

Gln Gln Tyr Gly Arg Ser Phe Thr
1               5

<210> SEQ ID NO 72
<211> LENGTH: 8
<212> TYPE: PRT
<213> ORGANISM: homo sapiens

<400> SEQUENCE: 72

Gly Gly Ser Phe Ser Gly Tyr Tyr
1               5

<210> SEQ ID NO 73
<211> LENGTH: 5
<212> TYPE: PRT
<213> ORGANISM: homo sapiens

<400> SEQUENCE: 73

Ile Asn Gln Ser Gly
1               5

<210> SEQ ID NO 74
<211> LENGTH: 7
<212> TYPE: PRT
<213> ORGANISM: homo sapiens

<400> SEQUENCE: 74

Ile Gln Gln Ser Gly Ser Thr
1               5

<210> SEQ ID NO 75
<211> LENGTH: 11
<212> TYPE: PRT
<213> ORGANISM: homo sapiens

<400> SEQUENCE: 75

Ala Ser Gly Asn Trp Asp His Phe Phe Asp Tyr
1               5                   10

<210> SEQ ID NO 76
<211> LENGTH: 6
<212> TYPE: PRT
<213> ORGANISM: homo sapiens

<400> SEQUENCE: 76

Gln Gly Ile Ser Ser Trp
1               5

<210> SEQ ID NO 77
<211> LENGTH: 9
<212> TYPE: PRT
<213> ORGANISM: homo sapiens

<400> SEQUENCE: 77

Gln Gln Ala Lys Ser Phe Pro Trp Thr
1               5

<210> SEQ ID NO 78
<211> LENGTH: 8
<212> TYPE: PRT
<213> ORGANISM: homo sapiens

<400> SEQUENCE: 78

Gly Gly Ser Phe Ser Gly Tyr His
1               5

<210> SEQ ID NO 79
<211> LENGTH: 7
<212> TYPE: PRT
<213> ORGANISM: homo sapiens

<400> SEQUENCE: 79

Ile Ser His Ser Gly Arg Thr
1               5

<210> SEQ ID NO 80
<211> LENGTH: 17
<212> TYPE: PRT
<213> ORGANISM: homo sapiens

<400> SEQUENCE: 80

Ala Ser Phe Ile Thr Met Ile Arg Gly Thr Ile Ile Thr His Phe Asp
1               5                   10                  15

Tyr

<210> SEQ ID NO 81
<211> LENGTH: 6
<212> TYPE: PRT
<213> ORGANISM: homo sapiens

<400> SEQUENCE: 81

Gln Gly Ile Ser Ser Trp
1               5

<210> SEQ ID NO 82
<211> LENGTH: 9
<212> TYPE: PRT
<213> ORGANISM: homo sapiens

<400> SEQUENCE: 82

Gln Gln Tyr His Ser Tyr Pro Tyr Thr
1               5

<210> SEQ ID NO 83
<211> LENGTH: 8
<212> TYPE: PRT
<213> ORGANISM: homo sapiens

<400> SEQUENCE: 83

Gly Gly Thr Phe Ser Ser Tyr Ala
1               5

<210> SEQ ID NO 84
<211> LENGTH: 8
<212> TYPE: PRT
<213> ORGANISM: homo sapiens

<400> SEQUENCE: 84

```
Ile Ile Pro Ile Phe Gly Ile Ala
1               5
```

<210> SEQ ID NO 85
<211> LENGTH: 17
<212> TYPE: PRT
<213> ORGANISM: homo sapiens

<400> SEQUENCE: 85

```
Ala Arg Arg Gly Asp Tyr Tyr Gly Ser Gly Ser Pro Asp Val Phe Asp
1               5                   10                  15

Ile
```

<210> SEQ ID NO 86
<211> LENGTH: 7
<212> TYPE: PRT
<213> ORGANISM: homo sapiens

<400> SEQUENCE: 86

```
Gln Ser Val Ser Ser Ser Tyr
1               5
```

<210> SEQ ID NO 87
<211> LENGTH: 8
<212> TYPE: PRT
<213> ORGANISM: homo sapiens

<400> SEQUENCE: 87

```
Gln Gln Tyr Gly Ser Ser Tyr Thr
1               5
```

<210> SEQ ID NO 88
<211> LENGTH: 8
<212> TYPE: PRT
<213> ORGANISM: homo sapiens

<400> SEQUENCE: 88

```
Gly Gly Thr Phe Ser Ser Tyr Ala
1               5
```

<210> SEQ ID NO 89
<211> LENGTH: 8
<212> TYPE: PRT
<213> ORGANISM: homo sapiens

<400> SEQUENCE: 89

```
Ile Ile Pro Ile Phe Gly Ile Ala
1               5
```

<210> SEQ ID NO 90
<211> LENGTH: 17
<212> TYPE: PRT
<213> ORGANISM: homo sapiens

<400> SEQUENCE: 90

```
Ala Arg Arg Gly Asn Tyr Tyr Gly Ser Gly Ser Pro Asp Val Phe Asp
1               5                   10                  15

Ile
```

<210> SEQ ID NO 91
<211> LENGTH: 7
<212> TYPE: PRT
<213> ORGANISM: homo sapiens

```
<400> SEQUENCE: 91

Gln Ser Val Ser Ser Tyr
1               5

<210> SEQ ID NO 92
<211> LENGTH: 8
<212> TYPE: PRT
<213> ORGANISM: homo sapiens

<400> SEQUENCE: 92

Gln Gln Tyr Gly Ser Ser Tyr Thr
1               5

<210> SEQ ID NO 93
<211> LENGTH: 8
<212> TYPE: PRT
<213> ORGANISM: homo sapiens

<400> SEQUENCE: 93

Gly Gly Thr Phe Ser Ser Tyr Ala
1               5

<210> SEQ ID NO 94
<211> LENGTH: 8
<212> TYPE: PRT
<213> ORGANISM: homo sapiens

<400> SEQUENCE: 94

Ile Ile Pro Ile Phe Gly Ile Val
1               5

<210> SEQ ID NO 95
<211> LENGTH: 17
<212> TYPE: PRT
<213> ORGANISM: homo sapiens

<400> SEQUENCE: 95

Ala Arg Arg Gly Asn Tyr Tyr Gly Ser Gly Ser Pro Asp Val Phe Asp
1               5                   10                  15

Ile

<210> SEQ ID NO 96
<211> LENGTH: 7
<212> TYPE: PRT
<213> ORGANISM: homo sapiens

<400> SEQUENCE: 96

Gln Ser Val Ser Ser Tyr
1               5

<210> SEQ ID NO 97
<211> LENGTH: 8
<212> TYPE: PRT
<213> ORGANISM: homo sapiens

<400> SEQUENCE: 97

Gln Gln Tyr Gly Ser Ser Tyr Thr
1               5

<210> SEQ ID NO 98
<211> LENGTH: 8
<212> TYPE: PRT
<213> ORGANISM: homo sapiens
```

```
<400> SEQUENCE: 98

Gly Gly Thr Phe Ser Ser Tyr Ala
1               5

<210> SEQ ID NO 99
<211> LENGTH: 8
<212> TYPE: PRT
<213> ORGANISM: homo sapiens

<400> SEQUENCE: 99

Ile Ile Pro Ile Phe Gly Ile Val
1               5

<210> SEQ ID NO 100
<211> LENGTH: 17
<212> TYPE: PRT
<213> ORGANISM: homo sapiens

<400> SEQUENCE: 100

Ala Arg Arg Gly Asn Tyr Tyr Gly Ser Gly Ser Pro Asp Val Phe Asp
1               5                   10                  15

Ile

<210> SEQ ID NO 101
<211> LENGTH: 6
<212> TYPE: PRT
<213> ORGANISM: homo sapiens

<400> SEQUENCE: 101

Gln Ser Val Ser Ser Tyr
1               5

<210> SEQ ID NO 102
<211> LENGTH: 8
<212> TYPE: PRT
<213> ORGANISM: homo sapiens

<400> SEQUENCE: 102

Gln Gln Arg Ser Asn Trp Leu Thr
1               5

<210> SEQ ID NO 103
<211> LENGTH: 8
<212> TYPE: PRT
<213> ORGANISM: homo sapiens

<400> SEQUENCE: 103

Gly Gly Thr Phe Ser Ser Tyr Ala
1               5

<210> SEQ ID NO 104
<211> LENGTH: 8
<212> TYPE: PRT
<213> ORGANISM: homo sapiens

<400> SEQUENCE: 104

Ile Ile Pro Ile Phe Gly Ile Ala
1               5

<210> SEQ ID NO 105
<211> LENGTH: 18
<212> TYPE: PRT
<213> ORGANISM: homo sapiens
```

```
<400> SEQUENCE: 105

Ala Arg Arg Gly Asn Tyr Tyr Gly Ser Gly Ser Pro Asp Val Phe Asp
1               5                   10                  15

Ile Ser

<210> SEQ ID NO 106
<211> LENGTH: 7
<212> TYPE: PRT
<213> ORGANISM: homo sapiens

<400> SEQUENCE: 106

Gln Ser Val Ser Ser Ser Tyr
1               5

<210> SEQ ID NO 107
<211> LENGTH: 8
<212> TYPE: PRT
<213> ORGANISM: homo sapiens

<400> SEQUENCE: 107

Gln Gln Tyr Gly Ser Ser Tyr Thr
1               5

<210> SEQ ID NO 108
<211> LENGTH: 8
<212> TYPE: PRT
<213> ORGANISM: homo sapiens

<400> SEQUENCE: 108

Gly Gly Ser Phe Ser Gly Tyr Tyr
1               5

<210> SEQ ID NO 109
<211> LENGTH: 7
<212> TYPE: PRT
<213> ORGANISM: homo sapiens

<400> SEQUENCE: 109

Ile Ser His Ser Gly Arg Thr
1               5

<210> SEQ ID NO 110
<211> LENGTH: 17
<212> TYPE: PRT
<213> ORGANISM: homo sapiens

<400> SEQUENCE: 110

Ala Arg Phe Ile Thr Met Ile Arg Gly Ala Ile Ile Thr His Phe Asp
1               5                   10                  15

Tyr

<210> SEQ ID NO 111
<211> LENGTH: 17
<212> TYPE: PRT
<213> ORGANISM: homo sapiens

<400> SEQUENCE: 111

Ala Arg Phe Ile Thr Leu Ile Arg Gly Ala Ile Ile Thr His Phe Asp
1               5                   10                  15

Tyr
```

```
<210> SEQ ID NO 112
<211> LENGTH: 6
<212> TYPE: PRT
<213> ORGANISM: homo sapiens

<400> SEQUENCE: 112

Gln Gly Ile Ser Ser Trp
1               5

<210> SEQ ID NO 113
<211> LENGTH: 9
<212> TYPE: PRT
<213> ORGANISM: homo sapiens

<400> SEQUENCE: 113

Gln Gln Tyr His Ser Tyr Pro Tyr Thr
1               5

<210> SEQ ID NO 114
<211> LENGTH: 8
<212> TYPE: PRT
<213> ORGANISM: homo sapiens

<400> SEQUENCE: 114

Gly Phe Ser Phe Ser Thr Tyr Ala
1               5

<210> SEQ ID NO 115
<211> LENGTH: 8
<212> TYPE: PRT
<213> ORGANISM: homo sapiens

<400> SEQUENCE: 115

Ile Ser Tyr Asp Gly Asp Asn Lys
1               5

<210> SEQ ID NO 116
<211> LENGTH: 13
<212> TYPE: PRT
<213> ORGANISM: homo sapiens

<400> SEQUENCE: 116

Ala Arg Gly Arg Lys Leu Gly Ile Asp Ala Phe Asp Ile
1               5                   10

<210> SEQ ID NO 117
<211> LENGTH: 6
<212> TYPE: PRT
<213> ORGANISM: homo sapiens

<400> SEQUENCE: 117

Gln Gly Ile Ser Ser Ala
1               5

<210> SEQ ID NO 118
<211> LENGTH: 9
<212> TYPE: PRT
<213> ORGANISM: homo sapiens

<400> SEQUENCE: 118

Gln Gln Phe Asn Ser Tyr Pro Phe Thr
1               5

<210> SEQ ID NO 119
<211> LENGTH: 8
```

```
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: Wherein X is A or G

<400> SEQUENCE: 119

Ile Ser Ile Ser Gly Xaa Ser Thr
1               5

<210> SEQ ID NO 120
<211> LENGTH: 13
<212> TYPE: PRT
<213> ORGANISM: homo sapiens
<220> FEATURE:
<221> NAME/KEY: Misc
<222> LOCATION: (13)..(13)
<223> OTHER INFORMATION: Wherein X is I of F

<400> SEQUENCE: 120

Arg Gly Tyr Ser Gly Tyr Val Tyr Asp Ala Phe Asp Xaa
1               5                   10

<210> SEQ ID NO 121
<211> LENGTH: 8
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: Wherein X is I or F

<400> SEQUENCE: 121

Gly Gly Ser Phe Ser Gly Tyr Xaa
1               5

<210> SEQ ID NO 122
<211> LENGTH: 17
<212> TYPE: PRT
<213> ORGANISM: homo sapiens
<220> FEATURE:
<221> NAME/KEY: MISC_FEATURE
<222> LOCATION: (2)..(2)
<223> OTHER INFORMATION: Wherein X is S or R
<220> FEATURE:
<221> NAME/KEY: MISC_FEATURE
<222> LOCATION: (10)..(10)
<223> OTHER INFORMATION: Wherein X is T or A

<400> SEQUENCE: 122

Ala Xaa Phe Ile Thr Met Ile Arg Gly Xaa Ile Ile Thr His Phe Asp
1               5                   10                  15
Tyr

<210> SEQ ID NO 123
<211> LENGTH: 8
<212> TYPE: PRT
<213> ORGANISM: homo sapiens
<220> FEATURE:
<221> NAME/KEY: MISC_FEATURE
<222> LOCATION: (6)..(6)
<223> OTHER INFORMATION: Wherein X is S or N

<400> SEQUENCE: 123

Gly Phe Thr Phe Ser Xaa Tyr Ala
1               5
```

<210> SEQ ID NO 124
<211> LENGTH: 8
<212> TYPE: PRT
<213> ORGANISM: homo sapiens

<400> SEQUENCE: 124

Ile Ser Val Ser Gly Gly Ser Thr
1               5

<210> SEQ ID NO 125
<211> LENGTH: 18
<212> TYPE: PRT
<213> ORGANISM: homo sapiens

<400> SEQUENCE: 125

Ala Lys Glu Gly Tyr Ile Trp Phe Gly Glu Ser Leu Ser Tyr Ala Phe
1               5                   10                  15

Asp Ile

<210> SEQ ID NO 126
<211> LENGTH: 8
<212> TYPE: PRT
<213> ORGANISM: homo sapiens
<220> FEATURE:
<221> NAME/KEY: MISC_FEATURE
<222> LOCATION: (8)..(8)
<223> OTHER INFORMATION: Wherein X is A or V

<400> SEQUENCE: 126

Ile Ile Pro Ile Phe Gly Ile Xaa
1               5

<210> SEQ ID NO 127
<211> LENGTH: 17
<212> TYPE: PRT
<213> ORGANISM: homo sapiens
<220> FEATURE:
<221> NAME/KEY: MISC_FEATURE
<222> LOCATION: (5)..(5)
<223> OTHER INFORMATION: Wherein X is D or N

<400> SEQUENCE: 127

Ala Arg Arg Gly Xaa Tyr Tyr Gly Ser Gly Ser Pro Asp Val Phe Asp
1               5                   10                  15

Ile

<210> SEQ ID NO 128
<211> LENGTH: 7
<212> TYPE: PRT
<213> ORGANISM: homo sapiens
<220> FEATURE:
<221> NAME/KEY: MISC_FEATURE
<222> LOCATION: (4)..(4)
<223> OTHER INFORMATION: Wherein X is S or deleted

<400> SEQUENCE: 128

Gln Ser Val Xaa Ser Ser Tyr
1               5

<210> SEQ ID NO 129
<211> LENGTH: 8
<212> TYPE: PRT
<213> ORGANISM: homo sapiens
<220> FEATURE:
<221> NAME/KEY: MISC_FEATURE
<222> LOCATION: (3)..(3)
<223> OTHER INFORMATION: Wherein X is R or Y

```
<220> FEATURE:
<221> NAME/KEY: MISC_FEATURE
<222> LOCATION: (4)..(4)
<223> OTHER INFORMATION: Wherein X is S or G
<220> FEATURE:
<221> NAME/KEY: MISC_FEATURE
<222> LOCATION: (4)..(4)
<223> OTHER INFORMATION: Wherein X is S or G
<220> FEATURE:
<221> NAME/KEY: MISC_FEATURE
<222> LOCATION: (5)..(5)
<223> OTHER INFORMATION: Wherein X is N or S
<220> FEATURE:
<221> NAME/KEY: MISC_FEATURE
<222> LOCATION: (6)..(6)
<223> OTHER INFORMATION: Wherein X is W or S
<220> FEATURE:
<221> NAME/KEY: MISC_FEATURE
<222> LOCATION: (6)..(6)
<223> OTHER INFORMATION: Wherein X is W or S
<220> FEATURE:
<221> NAME/KEY: MISC_FEATURE
<222> LOCATION: (7)..(7)
<223> OTHER INFORMATION: Wherein X is L or Y

<400> SEQUENCE: 129

Gln Gln Xaa Xaa Xaa Xaa Xaa Thr
1               5

<210> SEQ ID NO 130
<211> LENGTH: 894
<212> TYPE: PRT
<213> ORGANISM: homo sapiens

<400> SEQUENCE: 130

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220
```

```
Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
            245                 250                 255

His Cys Thr Leu Gln Ala Val Leu Ser Asp Asp Gly Met Gly Ile Gln
        260                 265                 270

Ala Gly Glu Pro Asp Pro Pro Glu Glu Pro Leu Thr Ser Gln Ala Ser
    275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
                420                 425                 430

Pro Val His Gln Leu Val Lys Glu Pro Ser Thr Pro Ala Phe Ser Trp
            435                 440                 445

Pro Trp Trp Tyr Val Leu Leu Gly Ala Val Val Ala Ala Ala Cys Val
450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu
530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

Glu Arg Glu Ser Phe Pro Ala Pro Val Val Ile Leu Pro Phe Met Lys
    610                 615                 620

His Gly Asp Leu His Ser Phe Leu Leu Tyr Ser Arg Leu Gly Asp Gln
625                 630                 635                 640
```

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
    850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 131
<211> LENGTH: 904
<212> TYPE: PRT
<213> ORGANISM: Mus Musculus

<400> SEQUENCE: 131

Met Ala Trp Arg Cys Pro Arg Met Gly Arg Val Pro Leu Ala Trp Cys
1               5                   10                  15

Leu Ala Leu Cys Gly Trp Ala Cys Met Tyr Pro Tyr Asp Val Pro Asp
            20                  25                  30

Tyr Ala Ala His Lys Asp Thr Gln Thr Glu Ala Gly Ser Pro Phe Val
        35                  40                  45

Gly Asn Pro Gly Asn Ile Thr Gly Ala Arg Gly Leu Thr Gly Thr Leu
    50                  55                  60

Arg Cys Glu Leu Gln Val Gln Gly Glu Pro Pro Glu Val Val Trp Leu
65                  70                  75                  80

Arg Asp Gly Gln Ile Leu Glu Leu Ala Asp Asn Thr Gln Thr Gln Val
                85                  90                  95

Pro Leu Gly Glu Asp Trp Gln Asp Glu Trp Lys Val Val Ser Gln Leu
            100                 105                 110

Arg Ile Ser Ala Leu Gln Leu Ser Asp Ala Gly Glu Tyr Gln Cys Met
        115                 120                 125

```
Val His Leu Glu Gly Arg Thr Phe Val Ser Gln Pro Gly Phe Val Gly
    130                 135                 140

Leu Glu Gly Leu Pro Tyr Phe Leu Glu Glu Pro Glu Asp Lys Ala Val
145                 150                 155                 160

Pro Ala Asn Thr Pro Phe Asn Leu Ser Cys Gln Ala Gln Gly Pro Pro
                165                 170                 175

Glu Pro Val Thr Leu Leu Trp Leu Gln Asp Ala Val Pro Leu Ala Pro
            180                 185                 190

Val Thr Gly His Ser Ser Gln His Ser Leu Gln Thr Pro Gly Leu Asn
        195                 200                 205

Lys Thr Ser Ser Phe Ser Cys Glu Ala His Asn Ala Lys Gly Val Thr
    210                 215                 220

Thr Ser Arg Thr Ala Thr Ile Thr Val Leu Pro Gln Arg Pro His His
225                 230                 235                 240

Leu His Val Val Ser Arg Gln Pro Thr Glu Leu Glu Val Ala Trp Thr
                245                 250                 255

Pro Gly Leu Ser Gly Ile Tyr Pro Leu Thr His Cys Asn Leu Gln Ala
            260                 265                 270

Val Leu Ser Asp Asp Gly Val Gly Ile Trp Leu Gly Lys Ser Asp Pro
        275                 280                 285

Pro Glu Asp Pro Leu Thr Leu Gln Val Ser Val Pro Pro His Gln Leu
    290                 295                 300

Arg Leu Glu Lys Leu Leu Pro His Thr Pro Tyr His Ile Arg Ile Ser
305                 310                 315                 320

Cys Ser Ser Ser Gln Gly Pro Ser Pro Trp Thr His Trp Leu Pro Val
                325                 330                 335

Glu Thr Thr Glu Gly Val Pro Leu Gly Pro Pro Glu Asn Val Ser Ala
            340                 345                 350

Met Arg Asn Gly Ser Gln Val Leu Val Arg Trp Gln Glu Pro Arg Val
        355                 360                 365

Pro Leu Gln Gly Thr Leu Leu Gly Tyr Arg Leu Ala Tyr Arg Gly Gln
    370                 375                 380

Asp Thr Pro Glu Val Leu Met Asp Ile Gly Leu Thr Arg Glu Val Thr
385                 390                 395                 400

Leu Glu Leu Arg Gly Asp Arg Pro Val Ala Asn Leu Thr Val Ser Val
                405                 410                 415

Thr Ala Tyr Thr Ser Ala Gly Asp Gly Pro Trp Ser Leu Pro Val Pro
            420                 425                 430

Leu Glu Pro Trp Arg Pro Gly Gln Gly Gln Pro Leu His Leu Val
        435                 440                 445

Ser Glu Pro Pro Arg Ala Phe Ser Trp Pro Trp Trp Tyr Val Leu
    450                 455                 460

Leu Gly Ala Val Val Ala Ala Cys Val Leu Ile Leu Ala Leu Phe
465                 470                 475                 480

Leu Val His Arg Arg Lys Lys Glu Thr Arg Tyr Gly Glu Val Phe Glu
                485                 490                 495

Pro Thr Val Glu Arg Gly Glu Leu Val Val Arg Tyr Arg Val Arg Lys
            500                 505                 510

Ser Tyr Ser Arg Arg Thr Thr Glu Ala Thr Leu Asn Ser Leu Gly Ile
        515                 520                 525

Ser Glu Glu Leu Lys Glu Lys Leu Arg Asp Val Met Val Asp Arg His
    530                 535                 540
```

```
Lys Val Ala Leu Gly Lys Thr Leu Gly Glu Gly Glu Phe Gly Ala Val
545                 550                 555                 560

Met Glu Gly Gln Leu Asn Gln Asp Asp Ser Ile Leu Lys Val Ala Val
            565                 570                 575

Lys Thr Met Lys Ile Ala Ile Cys Thr Arg Ser Glu Leu Glu Asp Phe
            580                 585                 590

Leu Ser Glu Ala Val Cys Met Lys Glu Phe Asp His Pro Asn Val Met
    595                 600                 605

Arg Leu Ile Gly Val Cys Phe Gln Gly Ser Glu Arg Glu Ser Phe Pro
    610                 615                 620

Ala Pro Val Val Ile Leu Pro Phe Met Lys His Gly Asp Leu His Ser
625                 630                 635                 640

Phe Leu Leu Tyr Ser Arg Leu Gly Asp Gln Pro Val Tyr Leu Pro Thr
                645                 650                 655

Gln Met Leu Val Lys Phe Met Ala Asp Ile Ala Ser Gly Met Glu Tyr
            660                 665                 670

Leu Ser Thr Lys Arg Phe Ile His Arg Asp Leu Ala Ala Arg Asn Cys
    675                 680                 685

Met Leu Asn Glu Asn Met Ser Val Cys Val Ala Asp Phe Gly Leu Ser
690                 695                 700

Lys Lys Ile Tyr Asn Gly Asp Tyr Tyr Arg Gln Gly Arg Ile Ala Lys
705                 710                 715                 720

Met Pro Val Lys Trp Ile Ala Ile Glu Ser Leu Ala Asp Arg Val Tyr
                725                 730                 735

Thr Ser Lys Ser Asp Val Trp Ser Phe Gly Val Thr Met Trp Glu Ile
            740                 745                 750

Ala Thr Arg Gly Gln Thr Pro Tyr Pro Gly Val Glu Asn Ser Glu Ile
    755                 760                 765

Tyr Asp Tyr Leu Arg Gln Gly Asn Arg Leu Lys Gln Pro Ala Asp Cys
770                 775                 780

Leu Asp Gly Leu Tyr Ala Leu Met Ser Arg Cys Trp Glu Leu Asn Pro
785                 790                 795                 800

Gln Asp Arg Pro Ser Phe Thr Glu Leu Arg Glu Asp Leu Glu Asn Thr
                805                 810                 815

Leu Lys Ala Leu Pro Pro Ala Gln Glu Pro Asp Glu Ile Leu Tyr Val
            820                 825                 830

Asn Met Asp Glu Gly Gly Gly Tyr Pro Glu Pro Gly Ala Ala Gly
    835                 840                 845

Gly Ala Asp Pro Pro Thr Gln Pro Asp Pro Lys Asp Ser Cys Ser Cys
850                 855                 860

Leu Thr Ala Ala Glu Val His Pro Ala Gly Arg Tyr Val Leu Cys Pro
865                 870                 875                 880

Ser Thr Thr Pro Ser Pro Ala Gln Pro Ala Asp Arg Gly Ser Pro Ala
                885                 890                 895

Ala Pro Gly Gln Glu Asp Gly Ala
            900

<210> SEQ ID NO 132
<211> LENGTH: 894
<212> TYPE: PRT
<213> ORGANISM: homo sapiens

<400> SEQUENCE: 132

Met Ala Trp Arg Cys Pro Arg Met Gly Arg Val Pro Leu Ala Trp Cys
1               5                   10                  15
```

-continued

Leu Ala Leu Cys Gly Trp Ala Cys Met Ala Pro Arg Gly Thr Gln Ala
              20                  25                  30

Glu Glu Ser Pro Phe Val Gly Asn Pro Gly Asn Ile Thr Gly Ala Arg
          35                  40                  45

Gly Leu Thr Gly Thr Leu Arg Cys Gln Leu Gln Val Gln Gly Glu Pro
      50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Gln Asp Asp Asp Trp
                  85                  90                  95

Ile Val Val Ser Gln Leu Arg Ile Thr Ser Leu Gln Leu Ser Asp Thr
              100                 105                 110

Gly Gln Tyr Gln Cys Leu Val Phe Leu Gly His Gln Thr Phe Val Ser
          115                 120                 125

Gln Pro Gly Tyr Val Gly Leu Glu Gly Leu Pro Tyr Phe Leu Glu Glu
      130                 135                 140

Pro Glu Asp Lys Ala Val Pro Ala Asn Thr Pro Phe Asn Leu Ser Cys
145                 150                 155                 160

Gln Ala Gln Gly Pro Pro Glu Pro Val Thr Leu Leu Trp Leu Gln Asp
                  165                 170                 175

Ala Val Pro Leu Ala Pro Val Thr Gly His Ser Ser Gln His Ser Leu
              180                 185                 190

Gln Thr Pro Gly Leu Asn Lys Thr Ser Ser Phe Ser Cys Glu Ala His
          195                 200                 205

Asn Ala Lys Gly Val Thr Thr Ser Arg Thr Ala Thr Ile Thr Val Leu
      210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                  245                 250                 255

His Cys Thr Leu Gln Ala Val Leu Ser Asp Asp Gly Met Gly Ile Gln
              260                 265                 270

Ala Gly Glu Pro Asp Pro Pro Glu Glu Pro Leu Thr Ser Gln Ala Ser
          275                 280                 285

Val Pro Pro His Gln Leu Arg Leu Gly Ser Leu His Pro His Thr Pro
      290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                  325                 330                 335

Pro Glu Asn Ile Ser Ala Thr Arg Asn Gly Ser Gln Ala Phe Val His
              340                 345                 350

Trp Gln Glu Pro Arg Ala Pro Leu Gln Gly Thr Leu Leu Gly Tyr Arg
          355                 360                 365

Leu Ala Tyr Gln Gly Gln Asp Thr Pro Glu Val Leu Met Asp Ile Gly
      370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                  405                 410                 415

Trp Ser Leu Pro Val Pro Leu Glu Ala Trp Arg Pro Gly Gln Ala Gln
              420                 425                 430

```
Pro Val His Gln Leu Val Lys Glu Pro Ser Thr Pro Ala Phe Ser Trp
        435                 440                 445

Pro Trp Trp Tyr Val Leu Leu Gly Ala Val Ala Ala Ala Cys Val
450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
                500                 505                 510

Leu Asn Ser Leu Gly Ile Ser Glu Glu Leu Lys Glu Lys Leu Arg Asp
                515                 520                 525

Val Met Val Asp Arg His Lys Val Ala Leu Gly Lys Thr Leu Gly Glu
530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
                580                 585                 590

Asp His Pro Asn Val Met Arg Leu Ile Gly Val Cys Phe Gln Gly Ser
                595                 600                 605

Glu Arg Glu Ser Phe Pro Ala Pro Val Val Ile Leu Pro Phe Met Lys
                610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
                660                 665                 670

Leu Ala Ala Arg Asn Cys Met Leu Asn Glu Asn Met Ser Val Cys Val
                675                 680                 685

Ala Asp Phe Gly Leu Ser Lys Lys Ile Tyr Asn Gly Asp Tyr Tyr Arg
690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
                740                 745                 750

Val Glu Asn Ser Glu Ile Tyr Asp Tyr Leu Arg Gln Gly Asn Arg Leu
                755                 760                 765

Lys Gln Pro Ala Asp Cys Leu Asp Gly Leu Tyr Ala Leu Met Ser Arg
                770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Tyr Pro Glu
                820                 825                 830

Pro Pro Gly Ala Ala Gly Gly Ala Asp Pro Thr Gln Pro Asp Pro
835                 840                 845

Lys Asp Ser Cys Ser Cys Leu Thr Ala Ala Glu Val His Pro Ala Gly
```

```
            850                 855                 860
Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                    885                 890

<210> SEQ ID NO 133
<211> LENGTH: 894
<212> TYPE: PRT
<213> ORGANISM: homo sapiens

<400> SEQUENCE: 133

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65              70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Lys Ala Val Pro Ala Asn Thr Pro Phe Asn Leu Ser Cys
145                 150                 155                 160

Gln Ala Gln Gly Pro Pro Glu Pro Val Thr Leu Leu Trp Leu Gln Asp
                165                 170                 175

Ala Val Pro Leu Ala Pro Val Thr Gly His Ser Ser Gln His Ser Leu
            180                 185                 190

Gln Thr Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335
```

Pro Glu Asn Ile Ser Ala Thr Arg Asn Gly Ser Gln Ala Phe Val His
          340                 345                 350

Trp Gln Glu Pro Arg Ala Pro Leu Gln Gly Thr Leu Leu Gly Tyr Arg
          355                 360                 365

Leu Ala Tyr Gln Gly Gln Asp Thr Pro Glu Val Leu Met Asp Ile Gly
      370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
          420                 425                 430

Pro Val His Gln Leu Val Lys Glu Pro Ser Thr Pro Ala Phe Ser Trp
          435                 440                 445

Pro Trp Trp Tyr Val Leu Leu Gly Ala Val Val Ala Ala Ala Cys Val
      450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
          500                 505                 510

Leu Asn Ser Leu Gly Ile Ser Glu Glu Leu Lys Glu Lys Leu Arg Asp
          515                 520                 525

Val Met Val Asp Arg His Lys Val Ala Leu Gly Lys Thr Leu Gly Glu
      530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
          580                 585                 590

Asp His Pro Asn Val Met Arg Leu Ile Gly Val Cys Phe Gln Gly Ser
          595                 600                 605

Glu Arg Glu Ser Phe Pro Ala Pro Val Val Ile Leu Pro Phe Met Lys
      610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
          660                 665                 670

Leu Ala Ala Arg Asn Cys Met Leu Asn Glu Asn Met Ser Val Cys Val
          675                 680                 685

Ala Asp Phe Gly Leu Ser Lys Lys Ile Tyr Asn Gly Asp Tyr Tyr Arg
      690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
          740                 745                 750

Val Glu Asn Ser Glu Ile Tyr Asp Tyr Leu Arg Gln Gly Asn Arg Leu

```
                755                 760                 765
Lys Gln Pro Ala Asp Cys Leu Asp Gly Leu Tyr Ala Leu Met Ser Arg
770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
                820                 825                 830

Pro Pro Gly Ala Ala Gly Gly Ala Asp Pro Pro Thr Gln Pro Asp Pro
                835                 840                 845

Lys Asp Ser Cys Ser Cys Leu Thr Ala Ala Glu Val His Pro Ala Gly
850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890
```

<210> SEQ ID NO 134
<211> LENGTH: 894
<212> TYPE: PRT
<213> ORGANISM: homo sapiens

<400> SEQUENCE: 134

```
Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
                100                 105                 110

Gly Gln Tyr Gln Cys Leu Val Phe Leu Gly His Gln Thr Phe Val Ser
            115                 120                 125

Gln Pro Gly Tyr Val Gly Leu Glu Gly Leu Pro Tyr Phe Leu Glu Glu
        130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
                180                 185                 190

His Val Pro Gly Leu Asn Lys Thr Ser Ser Phe Ser Cys Glu Ala His
            195                 200                 205

Asn Ala Lys Gly Val Thr Thr Ser Arg Thr Ala Thr Ile Thr Val Leu
        210                 215                 220

Pro Gln Arg Pro His His Leu His Val Val Ser Arg Gln Pro Thr Glu
225                 230                 235                 240
```

-continued

```
Leu Glu Val Ala Trp Thr Pro Gly Leu Ser Gly Ile Tyr Pro Leu Thr
                245                 250                 255

His Cys Asn Leu Gln Ala Val Leu Ser Asp Asp Gly Val Gly Ile Trp
            260                 265                 270

Leu Gly Lys Ser Asp Pro Pro Glu Asp Pro Leu Thr Leu Gln Val Ser
        275                 280                 285

Val Pro Pro His Gln Leu Arg Leu Glu Lys Leu Leu Pro His Thr Pro
    290                 295                 300

Tyr His Ile Arg Ile Ser Cys Ser Ser Ser Gln Gly Pro Ser Pro Trp
305                 310                 315                 320

Thr His Trp Leu Pro Val Glu Thr Thr Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro Trp Trp Tyr Val Leu Leu Gly Ala Val Val Ala Ala Ala Cys Val
    450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu
    530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

Glu Arg Glu Ser Phe Pro Ala Pro Val Val Ile Leu Pro Phe Met Lys
    610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
```

```
                 660                 665                 670
Leu Ala Ala Arg Asn Cys Met Leu Asn Glu Asn Met Ser Val Cys Val
            675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
    850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 135
<211> LENGTH: 894
<212> TYPE: PRT
<213> ORGANISM: homo sapiens

<400> SEQUENCE: 135

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140
```

```
Pro Glu Asp Arg Thr Val Ala Ala Asn Thr Pro Phe Asn Leu Ser Cys
145                 150                 155                 160

Gln Ala Gln Gly Pro Glu Pro Val Asp Leu Leu Trp Leu Gln Asp
            165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
            195                 200                 205

Asn Ala Lys Gly Val Thr Thr Ser Arg Thr Ala Thr Ile Thr Val Leu
210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
            245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
            275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
            325                 330                 335

Pro Glu Asn Val Ser Ala Met Arg Asn Gly Ser Gln Val Leu Val Arg
            340                 345                 350

Trp Gln Glu Pro Arg Val Pro Leu Gln Gly Thr Leu Leu Gly Tyr Arg
            355                 360                 365

Leu Ala Tyr Arg Gly Gln Asp Thr Pro Glu Val Leu Met Asp Ile Gly
            370                 375                 380

Leu Thr Arg Glu Val Thr Leu Glu Leu Arg Gly Asp Arg Pro Val Ala
385                 390                 395                 400

Asn Leu Thr Val Ser Val Thr Ala Tyr Thr Ser Ala Gly Asp Gly Pro
            405                 410                 415

Trp Ser Leu Pro Val Pro Leu Glu Pro Trp Arg Pro Gly Gln Gly Gln
            420                 425                 430

Pro Leu His His Leu Val Ser Glu Pro Pro Arg Ala Phe Ser Trp
            435                 440                 445

Pro Trp Trp Tyr Val Leu Leu Gly Ala Val Val Ala Ala Ala Cys Val
            450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
            485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
            515                 520                 525

Val Met Val Asp Arg His Lys Val Ala Leu Gly Lys Thr Leu Gly Glu
            530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
```

```
                565                 570                 575

Ser Glu Leu Glu Asp Phe Leu Ser Glu Ala Val Cys Met Lys Glu Phe
                580                 585                 590

Asp His Pro Asn Val Met Arg Leu Ile Gly Val Cys Phe Gln Gly Ser
                595                 600                 605

Glu Arg Glu Ser Phe Pro Ala Pro Val Val Ile Leu Pro Phe Met Lys
            610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
                660                 665                 670

Leu Ala Ala Arg Asn Cys Met Leu Asn Glu Asn Met Ser Val Cys Val
                675                 680                 685

Ala Asp Phe Gly Leu Ser Lys Lys Ile Tyr Asn Gly Asp Tyr Tyr Arg
            690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
                740                 745                 750

Val Glu Asn Ser Glu Ile Tyr Asp Tyr Leu Arg Gln Gly Asn Arg Leu
                755                 760                 765

Lys Gln Pro Ala Asp Cys Leu Asp Gly Leu Tyr Ala Leu Met Ser Arg
            770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
                820                 825                 830

Pro Pro Gly Ala Ala Gly Gly Ala Asp Pro Pro Thr Gln Pro Asp Pro
            835                 840                 845

Lys Asp Ser Cys Ser Cys Leu Thr Ala Ala Glu Val His Pro Ala Gly
            850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 136
<211> LENGTH: 124
<212> TYPE: PRT
<213> ORGANISM: homo sapiens

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45
```

```
Ser Gly Ile Ser Gly Ser Gly Gly His Thr Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Asp Ile Leu Thr Gly Tyr Tyr Asn Leu Leu Asp
                100                 105                 110

Tyr Trp Gly Gln Gly Thr Leu Val Thr Val Ser Ser
            115                 120
```

<210> SEQ ID NO 137
<211> LENGTH: 8
<212> TYPE: PRT
<213> ORGANISM: homo sapiens

<400> SEQUENCE: 137

```
Gly Phe Thr Phe Ser Ser Tyr Ala
1               5
```

<210> SEQ ID NO 138
<211> LENGTH: 8
<212> TYPE: PRT
<213> ORGANISM: homo sapiens

<400> SEQUENCE: 138

```
Ile Ser Gly Ser Gly Gly His Thr
1               5
```

<210> SEQ ID NO 139
<211> LENGTH: 17
<212> TYPE: PRT
<213> ORGANISM: homo sapiens

<400> SEQUENCE: 139

```
Ala Lys Asp Arg Tyr Asp Ile Leu Thr Gly Tyr Tyr Asn Leu Leu Asp
1               5                   10                  15
Tyr
```

<210> SEQ ID NO 140
<211> LENGTH: 107
<212> TYPE: PRT
<213> ORGANISM: homo sapiens

<400> SEQUENCE: 140

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Glu Ala Pro Lys Ser Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Ala Lys Val Glu Ile Lys
                100                 105
```

```
<210> SEQ ID NO 141
<211> LENGTH: 6
<212> TYPE: PRT
<213> ORGANISM: homo sapiens

<400> SEQUENCE: 141

Gln Gly Ile Ser Ser Trp
1               5

<210> SEQ ID NO 142
<211> LENGTH: 9
<212> TYPE: PRT
<213> ORGANISM: homo sapiens

<400> SEQUENCE: 142

Gln Gln Tyr Asn Ser Tyr Pro Leu Thr
1               5

<210> SEQ ID NO 143
<211> LENGTH: 123
<212> TYPE: PRT
<213> ORGANISM: homo sapiens

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Gly Tyr
                20                  25                  30

Gly Ile Ser Trp Val Arg Gln Ala Pro Gly Gln Gly Leu Glu Trp Ile
            35                  40                  45

Gly Trp Ile Ser Ala Tyr Asn Gly Asn Thr Asn Tyr Val Gln Asn Leu
    50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp His Ile Ser Met Leu Arg Gly Ile Ile Ile Arg Asn Tyr
            100                 105                 110

Trp Gly Gln Gly Thr Leu Val Thr Val Ser Ser
        115                 120

<210> SEQ ID NO 144
<211> LENGTH: 108
<212> TYPE: PRT
<213> ORGANISM: homo sapiens

<400> SEQUENCE: 144

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Trp Pro Arg
                85                  90                  95
```

Leu Thr Phe Gly Gly Gly Thr Lys Val Glu Ile Lys
            100                 105

<210> SEQ ID NO 145
<211> LENGTH: 124
<212> TYPE: PRT
<213> ORGANISM: homo sapiens

<400> SEQUENCE: 145

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Ser Trp Val Arg Gln Ala Pro Gly Gln Gly Leu Glu Trp Met
        35                  40                  45

Gly Arg Ile Ile Pro Ile Val Gly Ile Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Gly Tyr Ser Ser Ser Trp Tyr Ala Glu Tyr Phe Gln
            100                 105                 110

His Trp Gly Gln Gly Thr Leu Val Thr Val Ser Ser
        115                 120

<210> SEQ ID NO 146
<211> LENGTH: 108
<212> TYPE: PRT
<213> ORGANISM: homo sapiens

<400> SEQUENCE: 146

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Phe Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 147
<211> LENGTH: 893
<212> TYPE: PRT
<213> ORGANISM: Macaca fascicularis

<400> SEQUENCE: 147

Ala Trp Arg Cys Pro Arg Met Gly Arg Val Pro Leu Ala Trp Cys Leu
1               5                   10                  15

Ala Leu Cys Gly Trp Val Cys Met Ala Pro Arg Gly Thr Gln Ala Glu
            20                  25                  30

```
Glu Ser Pro Phe Val Gly Asn Pro Gly Asn Ile Thr Gly Ala Arg Gly
         35                  40                  45

Leu Thr Gly Thr Leu Arg Cys Gln Leu Gln Val Gln Gly Glu Pro Pro
     50                  55                  60

Glu Val His Trp Leu Arg Asp Gly Gln Ile Leu Glu Leu Ala Asp Ser
 65                  70                  75                  80

Thr Gln Thr Gln Val Pro Leu Gly Glu Asp Glu Gln Asp Asp Trp Ile
                 85                  90                  95

Val Val Ser Gln Leu Arg Ile Ala Ser Leu Gln Leu Ser Asp Ala Gly
             100                 105                 110

Gln Tyr Gln Cys Leu Val Phe Leu Gly His Gln Asn Phe Val Ser Gln
         115                 120                 125

Pro Gly Tyr Val Gly Leu Glu Gly Leu Pro Tyr Phe Leu Glu Glu Pro
     130                 135                 140

Glu Asp Arg Thr Val Ala Ala Asn Thr Pro Phe Asn Leu Ser Cys Gln
145                 150                 155                 160

Ala Gln Gly Pro Pro Glu Pro Val Asp Leu Leu Trp Leu Gln Asp Ala
                165                 170                 175

Val Pro Leu Ala Thr Ala Pro Gly His Gly Pro Gln Arg Asn Leu His
             180                 185                 190

Val Pro Gly Leu Asn Lys Thr Ser Ser Phe Ser Cys Glu Ala His Asn
         195                 200                 205

Ala Lys Gly Val Thr Thr Ser Arg Thr Ala Thr Ile Thr Val Leu Pro
     210                 215                 220

Gln Gln Pro Arg Asn Leu His Leu Val Ser Arg Gln Pro Thr Glu Leu
225                 230                 235                 240

Glu Val Ala Trp Thr Pro Gly Leu Ser Gly Ile Tyr Pro Leu Thr His
                245                 250                 255

Cys Thr Leu Gln Ala Val Leu Ser Asp Asp Gly Met Gly Ile Gln Ala
             260                 265                 270

Gly Glu Pro Asp Pro Pro Glu Glu Pro Leu Thr Leu Gln Ala Ser Val
         275                 280                 285

Pro Pro His Gln Leu Arg Leu Gly Ser Leu His Pro His Thr Pro Tyr
     290                 295                 300

His Ile Arg Val Ala Cys Thr Ser Ser Gln Gly Pro Ser Ser Trp Thr
305                 310                 315                 320

His Trp Leu Pro Val Glu Thr Pro Glu Gly Val Pro Leu Gly Pro Pro
                325                 330                 335

Glu Asn Ile Ser Ala Thr Arg Asn Gly Ser Gln Ala Phe Val His Trp
             340                 345                 350

Gln Glu Pro Arg Ala Pro Leu Gln Gly Thr Leu Leu Gly Tyr Arg Leu
         355                 360                 365

Ala Tyr Gln Gly Gln Asp Thr Pro Glu Val Leu Met Asp Ile Gly Leu
     370                 375                 380

Arg Gln Glu Val Thr Leu Glu Leu Gln Gly Asp Gly Ser Val Ser Asn
385                 390                 395                 400

Leu Thr Val Cys Val Ala Ala Tyr Thr Ala Ala Gly Asp Gly Pro Trp
                405                 410                 415

Ser Leu Pro Val Pro Leu Glu Ala Trp Arg Pro Gly Gln Ala Gln Pro
             420                 425                 430

Val His Gln Leu Val Lys Glu Thr Ser Ala Pro Ala Phe Ser Trp Pro
         435                 440                 445

Trp Trp Tyr Ile Leu Leu Gly Ala Val Val Ala Ala Ala Cys Val Leu
```

```
                450             455             460
    Ile Leu Ala Leu Phe Leu Val His Arg Arg Lys Lys Glu Thr Arg Tyr
    465                 470                 475                 480

Gly Glu Val Phe Glu Pro Thr Val Glu Arg Gly Glu Leu Val Val Arg
                        485                 490                 495

Tyr Arg Val Arg Lys Ser Tyr Ser Arg Arg Thr Thr Glu Ala Thr Leu
                    500                 505                 510

Asn Ser Leu Gly Ile Ser Glu Glu Leu Lys Glu Lys Leu Arg Asp Val
                515                 520                 525

Met Val Asp Arg His Lys Val Ala Leu Gly Lys Thr Leu Gly Glu Gly
    530                 535                 540

Glu Phe Gly Ala Val Met Glu Gly Gln Leu Asn Gln Asp Asp Ser Ile
    545                 550                 555                 560

Leu Lys Val Ala Val Lys Thr Met Lys Ile Ala Ile Cys Thr Arg Ser
                        565                 570                 575

Glu Leu Glu Asp Phe Leu Ser Glu Ala Val Cys Met Lys Glu Phe Asp
                    580                 585                 590

His Pro Asn Val Met Arg Leu Ile Gly Val Cys Phe Gln Gly Ser Glu
                595                 600                 605

Arg Glu Ser Phe Pro Ala Pro Val Val Ile Leu Pro Phe Met Lys His
    610                 615                 620

Gly Asp Leu His Ser Phe Leu Leu Tyr Ser Arg Leu Gly Asp Gln Pro
    625                 630                 635                 640

Val Tyr Leu Pro Thr Gln Met Leu Val Lys Phe Met Ala Asp Ile Ala
                        645                 650                 655

Ser Gly Met Glu Tyr Leu Ser Thr Lys Arg Phe Ile His Arg Asp Leu
                    660                 665                 670

Ala Ala Arg Asn Cys Met Leu Asn Glu Asn Met Ser Val Cys Val Ala
                675                 680                 685

Asp Phe Gly Leu Ser Lys Lys Ile Tyr Asn Gly Asp Tyr Tyr Arg Gln
    690                 695                 700

Gly Arg Ile Ala Lys Met Pro Val Lys Trp Ile Ala Ile Glu Ser Leu
    705                 710                 715                 720

Ala Asp Arg Val Tyr Thr Ser Lys Ser Asp Val Trp Ser Phe Gly Val
                        725                 730                 735

Thr Met Trp Glu Ile Ala Thr Arg Gly Gln Thr Pro Tyr Pro Gly Val
                    740                 745                 750

Glu Asn Ser Glu Ile Tyr Asp Tyr Leu Arg Gln Gly Asn Arg Leu Lys
                755                 760                 765

Gln Pro Ala Asp Cys Leu Asp Gly Leu Tyr Ala Leu Met Ser Arg Cys
    770                 775                 780

Trp Glu Leu Asn Pro Gln Asp Arg Pro Ser Phe Thr Glu Leu Arg Glu
    785                 790                 795                 800

Asp Leu Glu Asn Thr Leu Lys Ala Leu Pro Pro Ala Gln Glu Pro Asp
                        805                 810                 815

Glu Ile Leu Tyr Val Asn Met Asp Glu Gly Gly Gly Tyr Pro Glu Pro
                    820                 825                 830
```

```
Pro Gly Ala Ala Gly Gly Ala Asp Pro Pro Thr Gln Leu Asp Pro Lys
        835                 840                 845

Asp Ser Cys Ser Cys Leu Thr Ser Ala Glu Val His Pro Ala Gly Arg
    850                 855                 860

Tyr Val Leu Cys Pro Ser Thr Ala Pro Ser Pro Ala Gln Pro Ala Asp
865                 870                 875                 880

Arg Gly Ser Pro Ala Ala Pro Gly Gln Glu Asp Gly Ala
                885                 890
```

FORMULATION FOR ANTIBODY AND DRUG CONJUGATE THEREOF

CROSS-REFERENCE TO RELATED APPLICATIONS

This application is a 35 U.S.C. 371 national stage filing of International Application No. PCT/EP2017/050700, filed Jan. 13, 2017, which claims priority to U.S. Provisional Application No. 62/278,217, filed Jan. 13, 2016. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Jul. 11, 2018, is named Sequence_Listing_GMI155US.txt and is 113923 bytes in size.

FIELD OF THE INVENTION

The present invention relates to lyophilized and aqueous formulations, suitable in particular for antibodies and antibody drug conjugates (ADCs) binding to AXL, and to methods of preparing and using such formulations in e.g. cancer therapy.

BACKGROUND OF THE INVENTION

The TAM subfamily of mammalian Receptor Tyrosine Kinases (RTKs) consists of AXL, Tyro3 and Mer, with AXL being a 104-140 kDa transmembrane protein which has transforming abilities [1]. Targeted inhibition of RTKs may be effective as anti-tumor and/or metastatic therapy. Anti-AXL monoclonal antibodies for these and other purposes have been described in the literature, including antibodies which block the binding of the ligand Gas6 to AXL. ADCs are highly potent and specific agents for the treatment of cancer and other conditions, where the antibody portion specifically binds to its antigen on a target cell, so that the drug can exert its cytotoxic or other therapeutic effect on the target cell, optionally after internalization. Like other protein pharmaceuticals, however, antibodies are prone to degradation such as oxidation, deamidation and fragmentation as well as particle and aggregate formation. To provide for an antibody or ADC pharmaceutical that is stable during transport and storage, the carriers, excipients, and/or stabilizers in the pharmaceutical formulation must therefore be carefully selected. Lyophilized or freeze dried formulations for antibodies or ADC preparations have been described in patent literature, see, e.g. [14]-[28].

For ADCs, there is an additional challenge in that the drug conjugation in itself can reduce the stability and alter the physicochemical properties of the antibody. For example, it has been reported that the conjugation of the drug moiety DM1 to the anti-HER2 antibody trastuzumab resulted in destabilization of the CH2 domain of the antibody [29]. Further, cytotoxic drugs often being hydrophobic, the ADC conjugate as a whole can be less soluble than the unconjugated antibody, thus becoming more prone to aggregation, particle formation and surface adsorption. Both antibody and ADC formulations therefore typically include a surfactant, frequently polysorbate 20 or 80, to reduce aggregation and adsorption (see, e.g., [14]-[27], [30]). However, many surfactants are more or less toxic because of the amphiphilic nature and ability to react with biological membranes. Further, autooxidation or the exposure to light of polysorbates can result in the formation of hydrogen peroxide which in turn can oxidize the antibody molecule leading to an unstable product [31][32]. This not only reduces the efficacy of the ADC, but can lead to the formation of potentially harmful degradation products of the same.

Thus, there still remains a need for surfactant-free pharmaceutical formulations for antibodies and ADCs.

The present invention relates to liquid and lyophilized formulations for anti-AXL antibodies and AXL-ADCs that are stable during storage and transport and substantially free of particles, aggregates and degradation products.

SUMMARY OF THE INVENTION

The present inventors have discovered lyophilized formulations of anti-AXL antibody-drug conjugates (also referred to as "AXL-ADCs", "AXL-specific ADCs" and "anti-AXL ADCs") in which the AXL-ADCs remain stable. The inventors have also discovered aqueous formulations of anti-AXL antibodies in which the antibodies remain stable during freezing and thawing. Surprisingly, both the lyophilized and aqueous formulations could be prepared without including surfactants such as polysorbate 20 or 80, and/or without inorganic salts. Moreover, it was discovered that mannitol, which functions efficiently as a bulking agent for AXL-ADCs, functions efficiently as a stabilizer for the corresponding anti-AXL antibody.

So, in one aspect, the invention provides for stable, surfactant-free lyophilized formulations of AXL-ADCs with one or more suitable excipients. Optionally, the lyophilized formulation can also be essentially free of any salt.

In one aspect, the invention relates to a lyophilized, optionally surfactant-free, formulation of an AXL-ADC, the lyophilized formulation obtainable or obtained by lyophilizing an aqueous formulation comprising the AXL-ADC; a buffer, at least one bulking agent, and at least one non-reducing sugar which forms an amorphous phase with the ADC in solid state.

Exemplary ingredients for such lyophilized formulations include, but are not limited to (a) buffer components such as, e.g., histidine, citrate, 2-(N-morpholino) ethanesulfonic acid (MES), succinate, glycolate, carbonic acid, phosphate, and combinations thereof, typically providing for a pH between about 5 and about 7 in the aqueous formulation before lyophilization and/or after reconstitution;

(b) one or more non-reducing sugars such as sucrose and/or trehalose;

(c) one or more bulking agents such as mannitol and/or glycine.

In one aspect, the invention provides for a stable, surfactant free aqueous formulation of anti-AXL antibodies with pharmaceutically acceptable excipients, optionally wherein the formulation is essentially free of any salt.

In one aspect, the invention relates to an aqueous, optionally surfactant-free, formulation of an anti-AXL antibody comprising a buffer and at least one stabilizer, wherein the pH of the aqueous formulation is between about 5 and about 7.

Exemplary ingredients for such aqueous formulations include, but are not limited to (a) buffer components such as, e.g., histidine, citrate, MES, succinate, glycolate, carbonic acid, phosphate, and combinations thereof, typically providing for a pH between about 5 and about 7;
(b) optionally, one or more non-reducing sugars such as sucrose and/or trehalose;
(c) one or more stabilizers such as mannitol.

These and other aspects and embodiments are described in more detail in the following sections.

LEGENDS TO THE FIGURES

Figure 6:
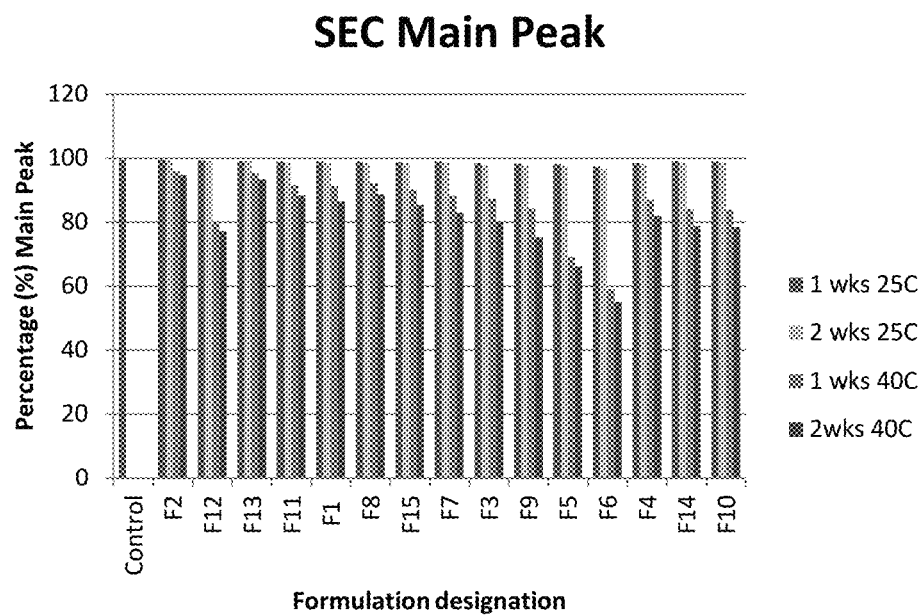

FIG. 6 shows the SEC (% Main Peak) result for HuMax-AXL-ADC buffer DoE study. Samples were analyzed following 1 and 2 weeks after storage at 25° C. and 40° C.

Figure 7A:
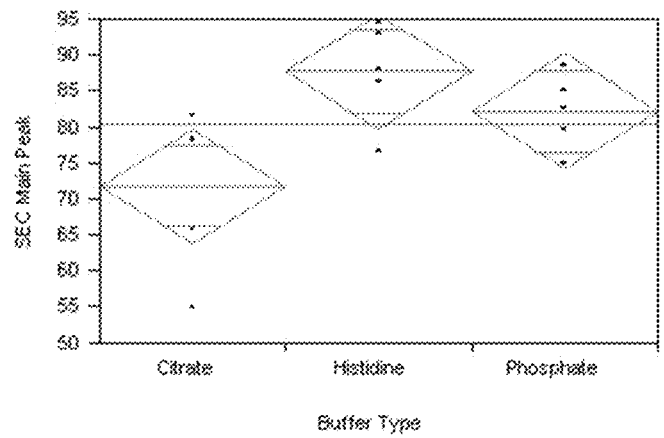
Figure 7B:
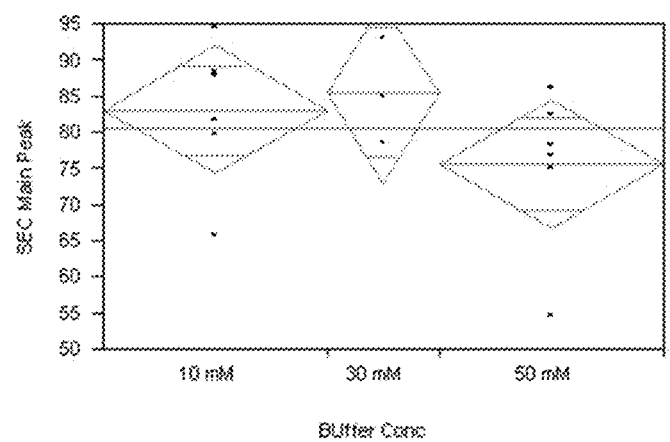
Figure 7C:
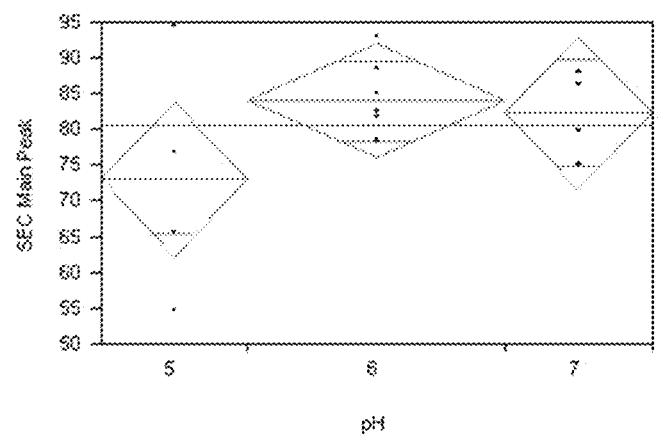

FIGS. 7A-7C show the one way analysis of variance data (ANOVA) comparing SEC % Main Peak by buffer type (FIG. 7A), buffer concentration (FIG. 7B) and pH (FIG. 7C) for samples stored at either 25° C. or 40° C. in the HuMax-AXL-ADC buffer DoE study.

Figure 8A:
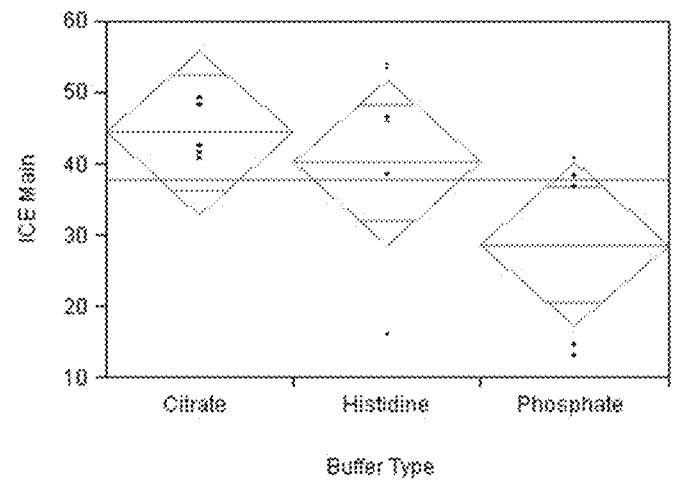
Figure 8B:
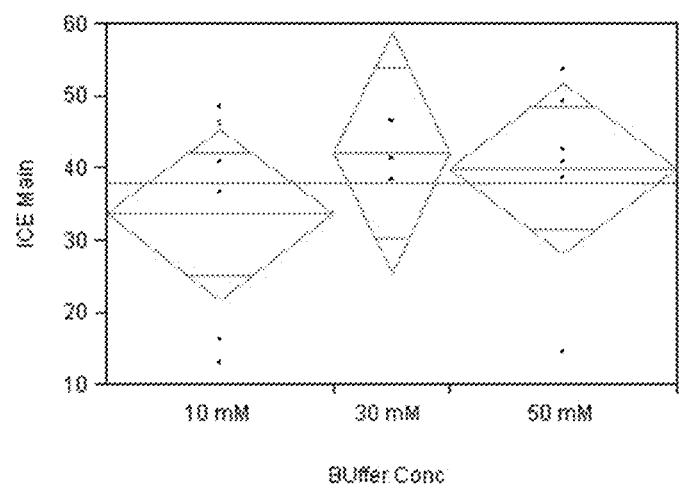
Figure 8C:
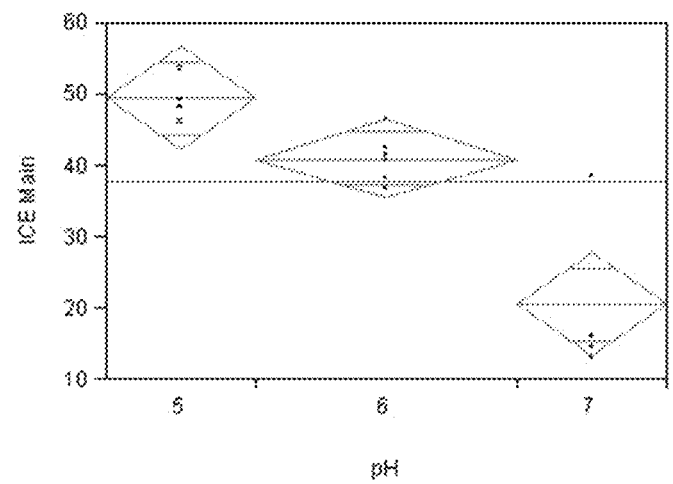

FIGS. 8A-8C show the one way analysis of variance data (ANOVA) comparing cIEF % Main Peak by buffer type (FIG. 8A), buffer concentration (FIG. 8B) and pH (FIG. 8C) for samples stored at either 25° C. or 40° C. in the HuMax-AXL-ADC buffer DoE study.

Figure 9A:
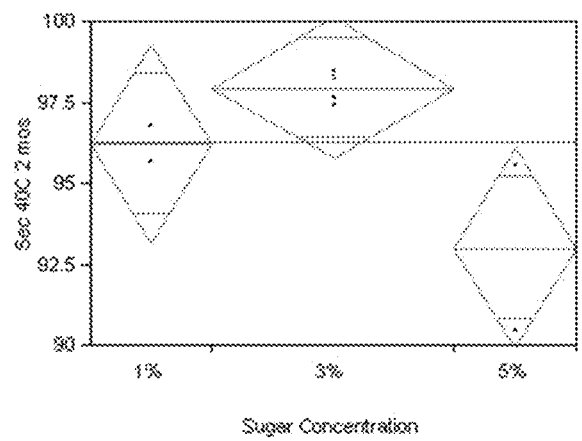
Figure 9B:
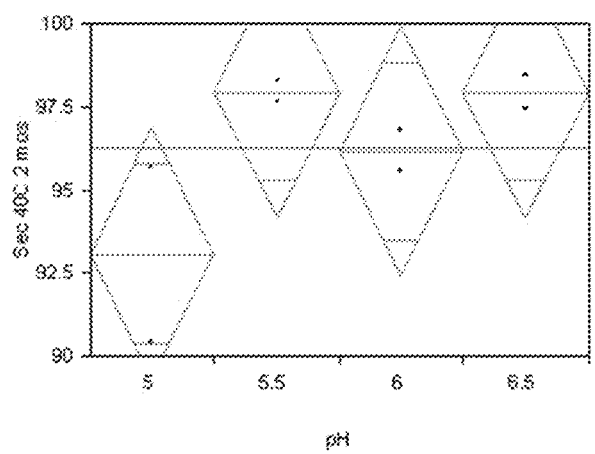
Figure 9C:
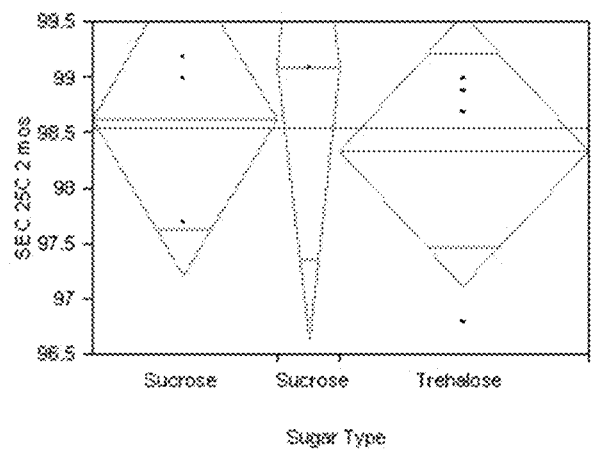

FIGS. 9A-9C show the one way analysis of variance data (ANOVA) comparing SEC % Main Peak by sugar type (FIG. 9A), sugar concentration (FIG. 9B) and pH (FIG. 9C) for samples stored at either 25° C. or 40° C. in the HuMax-AXL-ADC lyophilization excipient DoE study.

Figure 10:
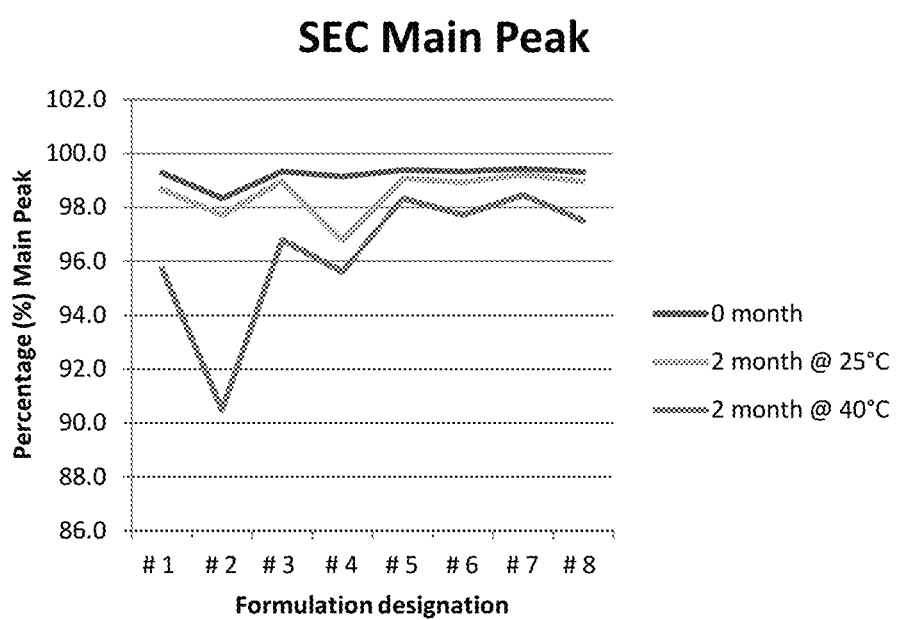

FIG. 10 shows the SEC data (% Main Peak) for samples stored at 25° C. and 40° C. in the HuMax-AXL-ADC lyophilization excipient DoE study.

Figure 11A:
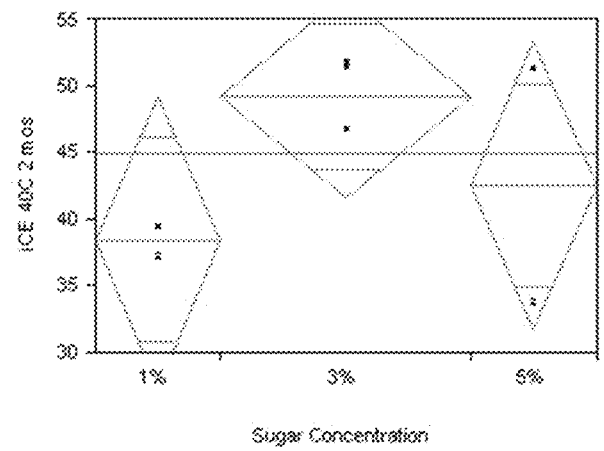
Figure 11B:
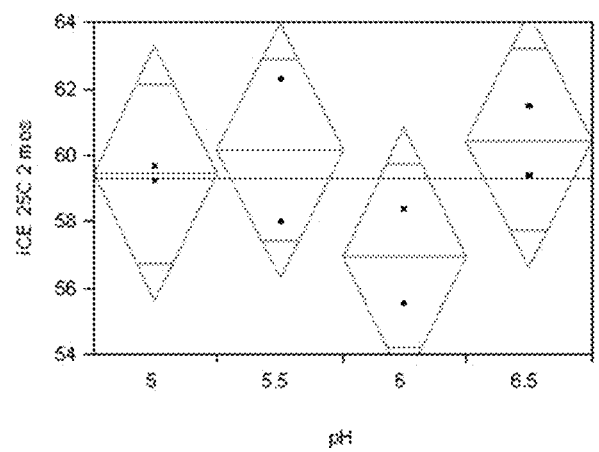
Figure 11C:
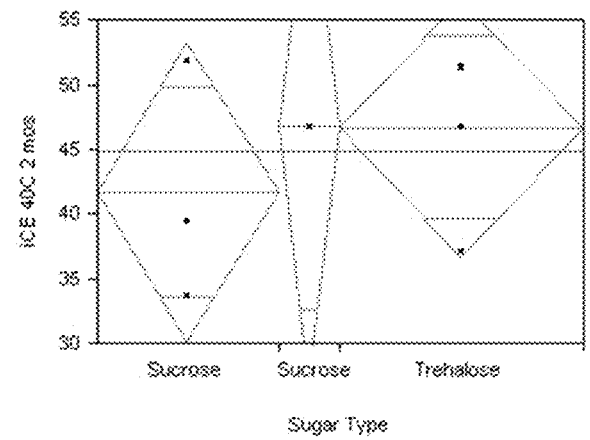

FIGS. 11A-11C show the one way analysis of variance data (ANOVA) comparing cIEF % Main Peak by sugar type (FIG. 11A), sugar concentration (FIG. 11B) and pH (FIG. 11C) for samples stored at either 25° C. or 40° C. in the HuMax-AXL-ADC lyophilization excipient DoE study.

Figure 12:
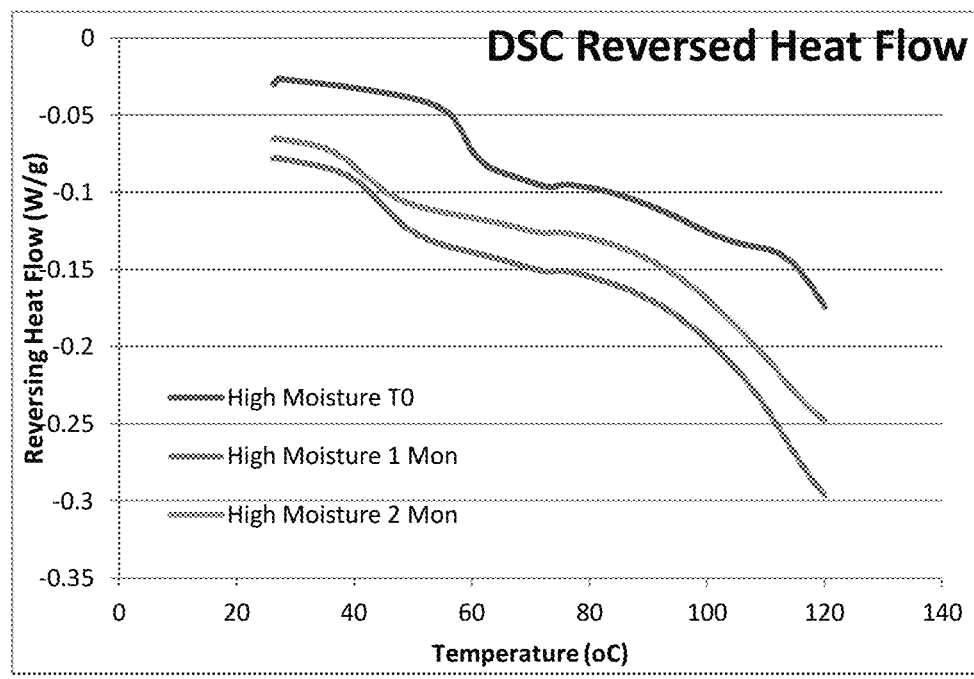

FIG. 12 shows the DSC reversing heat flow data for High, Medium, and Low Moisture of HuMax-AXL-ADC lyophilized samples after 2 months at 40° C. The midpoint values for the Tg range from approximately 60° C. to 45° C.

Figure 13:
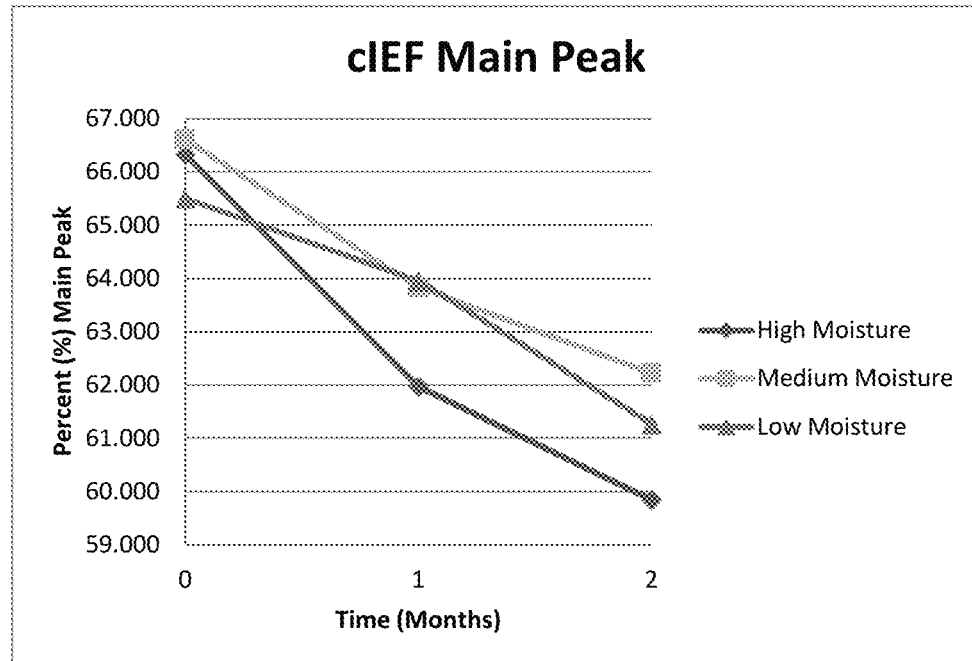

FIG. 13 shows the cIEF data (% Main Peak) for High, Medium, and Low Moisture samples after 2 months at 40° C.

DETAILED DISCLOSURE OF THE INVENTION

Definitions

The terms "lyophilized" and "freeze-dried" are used interchangeably herein and refer to a material that is dehydrated by first freezing and then reducing the surrounding pressure to allow the frozen water in the material to sublimate.

The term "buffer" as used herein denotes a pharmaceutically acceptable buffer. The term "buffer" encompasses those agents which maintain the pH value of a solution, e.g., in an acceptable range and includes, but is not limited to, histidine, citrate, MES, phosphate, TRIS® (tris (hydroxymethyl) aminomethane), carbonic acid, succinate, glycolate and the like, as described herein. Generally, the "buffer" as used herein has a pka and buffering capacity suitable for the pH range of about 5 to about 7, preferably of about 5.5 to 6.5, preferably about 5.8 to 6.2, such as about pH 6 or about pH 6.0.

The term "bulking agent" includes agents that can provide additional structure to a freeze-dried product (e.g., to provide a pharmaceutically acceptable cake). Commonly used bulking agents include mannitol, glycine, and the like. In addition to providing a pharmaceutically acceptable cake, bulking agents also typically impart useful qualities to the lyophilized composition such as modifying the collapse temperature, providing freeze-thaw protection, further enhancing the protein stability over long-term storage, and the like. These agents can also serve as tonicity modifiers.

The term "stabilizer" as used herein includes agents that provide stability to a protein, e.g., serving as a cryoprotectant during freezing and/or a lyoprotectant during a (freeze-) drying or 'dehydration' process. Suitable stabilizers include non-reducing sugars or saccharides and sugar alcohols such as sucrose, trehalose, mannitol, xylitol and the like, as well as amino acids such as glycine, alanine and lysine. Stabilizers can also serve as bulking agents, tonicity-modifying and/or viscosity-increasing agents.

A "surfactant" as used herein is a compound that is typically used in pharmaceutical formulations to prevent drug adsorption to surfaces and or aggregation. Furthermore, surfactants lower the surface tension (or interfacial tension) between two liquids or between a liquid and a solid. For example, an exemplary surfactant can significantly lower the surface tension when present at very low concentrations (e.g., 5% w/w or less, such as 3% w/w or less, such as 1% w/w or less). Surfactants are amphiphilic, which means they are usually composed of both hydrophilic and hydrophobic or lipophilic groups, thus being capable of forming micelles or similar self-assembled structures in aqueous solutions. Known surfactants for pharmaceutical use include glycerol monooleat, benzethonium chloride, sodium docusate, phospholipids, polyethylene alkyl ethers, sodium lauryl sulfate and tricaprylin (anionic surfactants); benzalkonium chloride, citrimide, cetylpyridinium chloride and phospholipids (cationic surfactants); and alpha tocopherol, glycerol monooleate, myristyl alcohol, phospholipids, poloxamers, polyoxyethylene alkyl ethers, polyoxyethylene castor oil derivatives, polyoxyethylene sorbintan fatty acid esters, polyoxyethylene sterarates, polyoxyl 15 hydroxystearate, polyoxylglycerides, polysorbates, propylene glycol dilaurate, propylene glycol monolaurate, sorbitan esters sucrose palmitate, sucrose stearate, tricaprylin and TPGS (Nonionic and zwitterionic surfactants).

A "diluent" of interest herein is one which is pharmaceutically acceptable (safe and non-toxic for administration to a human) and is useful for the preparation of a reconstituted formulation. Exemplary diluents are liquids, preferably aqueous, and include sterile water, bacteriostatic water for injection (BWFI), a pH buffered solution (e.g. phosphate-buffered saline), sterile saline solution, Ringer's solution or dextrose solution.

The term "antibody" as used herein is intended to refer to an immunoglobulin molecule, a fragment of an immunoglobulin molecule, or a derivative of either thereof, which has the ability to specifically bind to an antigen under typical physiological and/or tumor-specific conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to be internalized). The binding region (or binding domain which may be used herein, both having the same meaning) which interacts with an antigen, comprises variable regions of both the heavy and light chains of the immunoglobulin molecule. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody as used herein, unless otherwise stated or clearly contradicted by context, includes fragments of an antibody that retain the ability to specifically interact, such as bind, to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the VL, VH, CL and CH1 domains, or a monovalent antibody as described in [35]; (ii) F(ab')$_2$ fragments, bivalent fragments comprising two Fab fragments linked by a disulfide bridge at the hinge region; (iii) an Fd fragment consisting essentially of the VH and CH1 domains; (iv) an Fv fragment consisting essentially of the VL and VH domains of a single arm of an antibody, (v) a dAb fragment [36], which consists essentially of a VH domain and is also called domain antibody [37]; (vi) camelid or nanobodies and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance and [40]). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), antibody-like polypeptides, such as chimeric antibodies and humanized antibodies, as well as 'antibody fragments' or 'fragments thereof' retaining the ability to specifically bind to the antigen (antigen-binding fragments) provided by any known technique, such as enzymatic cleavage, peptide synthesis, and recombinant techniques, and retaining the ability to be conjugated to a toxin. An antibody as generated can possess any isotype.

The term "antigen-binding region" or "binding region" as used herein, refers to a region of an antibody which is capable of binding to the antigen. The terms "antigen" and "target" may, unless contradicted by the context, be used interchangeably in the context of the present invention.

The term "binding" as used herein refers to the binding of an antibody to a predetermined antigen or target, typically a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and wherein the antibody binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its $K_D$ of binding to a non-specific antigen (e.g., BSA, casein) other than the predetermined antigen or a closely-related antigen. The amount with which the $K_D$ of binding is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold. Affinity, as used herein, and $K_D$ are inversely related, that is higher affinity is intended to refer to lower $K_D$, and lower affinity is intended to refer to higher $K_D$.

As used herein:

The term "$K_D$" (M) refers to the dissociation equilibrium constant of a particular antibody-antigen interaction, and is obtained by dividing $k_d$ by $k_a$.

The term "$k_d$" (sec$^{-1}$) refers to the dissociation rate constant of a particular antibody-antigen interaction. Said value is also referred to as the $K_{off}$ value or off-rate.

The term "$k_a$" (M$^{-1}$×sec$^{-1}$) refers to the association rate constant of a particular antibody-antigen interaction. Said value is also referred to as the $k_{on}$ value or on-rate.

The term "$K_A$" (M$^{-1}$) refers to the association equilibrium constant of a particular antibody-antigen interaction and is obtained by dividing $k_a$ by $k_d$.

The term "antibody binding AXL" as used herein, refers to any antibody binding an epitope on the extracellular portion of AXL.

The term "epitope" means a protein determinant capable of specific binding to an antibody. Epitopes usually consist of surface groupings of molecules such as amino acids, sugar side chains or a combination thereof and usually have specific three dimensional structural characteristics, as well as specific charge characteristics. Conformational and non-conformational epitopes are distinguished in that the binding to the former but not the latter is lost in the presence of denaturing solvents. The epitope may comprise amino acid residues which are directly involved in the binding, and other amino acid residues, which are not directly involved in the binding, such as amino acid residues which are effectively blocked or covered by the specific antigen binding peptide (in other words, the amino acid residue is within the footprint of the specific antigen binding peptide).

The term "AXL" as used herein, refers to the protein entitled AXL, which is also referred to as UFO or JTK11, a 894 amino acid protein with a molecular weight of 104-140 kDa that is part of the subfamily of mammalian TAM Receptor Tyrosine Kinases (RTKs). The molecular weight is variable due to potential differences in glycosylation of the protein. The AXL protein consists of two extracellular immunoglobulin-like (Ig-like) domains on the N-terminal end of the protein, two membrane-proximal extracellular fibronectin type III (FNIII) domains, a transmembrane domain and an intracellular kinase domain. AXL is activated upon binding of its ligand Gas6, by ligand-independent homophilic interactions between AXL extracellular domains, by autophosphorylation in presence of reactive oxygen species or by transactivation through EGFR, and is aberrantly expressed in several tumor types. In humans, the AXL protein is encoded by a nucleic acid sequence encoding the amino acid sequence shown in SEQ ID NO: 130 (human AXL protein: Swissprot P30530; cynomolgus AXL protein: Genbank accession HB387229.1)).

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be produced by a hybridoma which includes a B cell obtained from a transgenic or transchromosomal non-human animal, such as a transgenic mouse, having a genome comprising a human heavy chain transgene and a light chain transgene, fused to an immortalized cell.

In the context of the present invention the term "ADC" refers to an antibody drug conjugate, which in the context of the present invention refers to an anti-AXL antibody which is coupled to a therapeutic moiety, e.g., a cytotoxic moiety as described in the present application. It may e.g. be coupled with a linker to e.g. cysteine or with other conjugation methods to other amino acids. The moiety may e.g. be a drug or a toxin or the like.

As used herein, a "therapeutic moiety" means a compound which exerts a therapeutic or preventive effect when administered to a subject, particularly when delivered as an ADC as described herein. A "cytotoxic" or "cytostatic" moiety is a compound that is detrimental to (e.g., kills) cells. Some cytotoxic or cytostatic moieties for use in ADCs are hydrophobic, meaning that they have no or only a limited solubility in water, e.g., 1 g/L or less (very slightly soluble), such as 0.8 g/L or less, such as 0.6 g/L or less, such as 0.4 g/L or less, such as 0.3 g/L or less, such as 0.2 g/L or less, such as 0.1 g/L or less (practically insoluble). Exemplary hydrophobic cytotoxic or cytostatic moieties include, but are not limited to, certain microtubulin inhibitors such as auristatin and its derivatives, e.g., MMAF and MMAE, as well as maytansine and its derivatives, e.g., DM1.

When used herein in the context of an antibody and a ligand or in the context of two or more antibodies, the term "competes with" or "cross-competes with" indicates that the antibody competes with the ligand or another antibody, e.g., a "reference" antibody in binding to an antigen, respectively. Example 13 describes an example of how to test competition of an anti-AXL antibody with the AXL-ligand Gas6. Preferred reference antibodies for cross-competition between two antibodies are those comprising a binding region comprising the VH region and VL region of an antibody herein designated 107, 148, 733, 154, 171, 183, 613, 726, 140, 154-M103L, 172, 181, 183-N52Q, 187, 608-01, 610-01, 613-08, 620-06 or 726-M101L, as set forth in Table 1. A particularly preferred reference antibody is the antibody designated 107.

The present invention also provides, in one embodiment, formulations of antibodies comprising functional variants of the VL region, VH region, or one or more CDRs of the antibodies described herein. A functional variant of a VL, VH, or CDR used in the context of an anti-AXL antibody still allows the antibody to retain at least a substantial proportion (at least about 50%, 60%, 70%, 80%, 90%, 95%, 99% or more) of the affinity/avidity and/or the specificity/selectivity of the parent antibody and in some cases such an anti-AXL antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, as described below.

For purposes of the present invention, the sequence identity between two amino acid sequences is determined using the Needleman-Wunsch algorithm (Needleman and Wunsch, 1970, J. Mol. Biol. 48:443-453) as implemented in the Needle program of the EMBOSS package (EMBOSS: The European Molecular Biology Open Software Suite, Rice et al., 2000, Trends Genet. 16:276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows: (Identical Residues×100)/(Length of Alignment−Total Number of Gaps in Alignment).

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 99%) similarity to the parent sequence.

The sequence of CDR, VH or VL variants may differ from the sequence of the CDR, VH or VL of the parent antibody through mostly conservative substitutions; for instance at least about 35%, about 50% or more, about 60% or more, about 70% or more, about 75% or more, about 80% or more, about 85% or more, about 90% or more, about 95% or more such as about 96%, 97% or 98% or 99% of the substitutions in the variant are conservative amino acid residue replacements. For example, the sequences of CDR, VH or VL variants may differ from the sequence of the CDRs, VH or VL of the parent antibody through mostly conservative substitutions; for instance at least 10, such as at least 9, 8, 7, 6, 5, 4, 3, 2 or 1 of the substitutions in the variant are conservative amino acid residue replacements.

In the context of the present invention, conservative substitutions may be defined by substitutions within the classes of amino acids reflected in one or more of the following tables:

Amino acid residue of conservative class:

| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

Alternative Physical and Functional Classifications of Amino Acid Residues:

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

The term "isotype" as used herein refers to the immunoglobulin class (for instance IgG1, IgG2, IgG3, IgG4, IgD, IgA, IgE, or IgM) or any allotypes thereof, such as IgG1m (za) and IgG1m (f)) that is encoded by heavy chain constant region genes. Further, each heavy chain isotype can be combined with either a kappa (x) or lambda (2) light chain. In one embodiment, the isotype is IgG1, optionally allotype IgG1m (f). In one embodiment, the antibody is a full-length monoclonal antibody, optionally a full-length monoclonal IgG1,κ antibody.

The term "full-length antibody" when used herein, refers to an antibody (e.g., a parent or variant antibody) which contains all heavy and light chain constant and variable domains corresponding to those that are normally found in a wild-type antibody of that isotype. A full-length antibody according to the present invention may be produced by a method comprising the steps of (i) cloning the CDR sequences into a suitable vector comprising complete heavy chain sequences and complete light chain sequence, and (ii) expressing the complete heavy and light chain sequences in suitable expression systems. It is within the knowledge of the skilled person to produce a full-length antibody when starting out from either CDR sequences or full variable region sequences. Thus, the skilled person would know how to generate a full-length antibody according to the present invention.

In one preferred aspect, any one of the formulations described herein comprises an exact quantity or exact quantities of one or more components as comprised therein and/or an exact pH value. In other words, one or more of the terms "about" are deleted in this other preferred aspect of the invention.

In each aspect or embodiment relating to a formulation "comprising" certain features or components, such a formulation which "consists essentially of" such features or components is also a separate aspect or embodiment of the invention.

Specific Embodiments of the Invention

The present invention is based, at least in part, on the discovery of certain aqueous compositions, particularly formulations, of AXL-ADCs which, when lyophilized, provide for stable lyophilized formulations suitable for pharmaceutical purposes and for therapeutic applications of the AXL-ADCs. Such lyophilized formulations may, for example, be reconstituted into pharmaceutically acceptable liquid formulations by adding a diluent, typically an aqueous diluent.

The present invention is also based, in part, on the discovery of certain aqueous compositions, particularly, formulations of anti-AXL antibodies wherein the antibody is stable during freezing and thawing. The formulations disclosed herein also provide for the option of excluding surfactants such as, e.g., polysorbate 20 and 80; inorganic salts such as, e.g., NaCl; or both.

In order to ensure efficacy and safety during long term storage (shelf life) of the pharmaceutical product, the product is stored under selected conditions, typically including storage both at the intended storage temperature and at elevated temperature(s), and is analysed for stability at regular time intervals. The stability tests may, for example, include analyses of the identity, purity and/or potency of the product. Purity can be analysed using, e.g., sodium dodecyl sulfate polyacrylamide gel electrophoresis (SDS-PAGE), capillary electrophoresis sodium dodecyl sulfate (CE-SDS), capillary isoelectrofocusing (cIEF), immunoelectrophoresis, reverse-phase chromatography (RP-HPLC), size-exclusion chromatograhy (SEC), ion exchange and affinity chromatography. Stability analyses may also include, for example, visual appearance such as colour and transparency, particulates, pH, moisture and reconstitution time.

The resulting degradation profile, particularly as regards purity and potency, during long term storage (shelf life) is affected by the composition and/or the formulation of the pharmaceutical product. In particular, proper choice of formulation may significantly improve the degradation profile. Typical degradation profiles of monoclonal antibodies and conjugated drug products derived from monoclonal antibodies includes the formation of covalent and non-covalent high molecular weight aggregates, fragments, deamidation and oxidation products. Particularly, deamidation and oxidation products, as well as acidic species, usually develop during long-term storage (shelf life). In some cases these degradation products limits the acceptable shelf life of the pharmaceutical composition. The degradation products can be identified by a variety of analytical tests such as cIEF, SEC, SDS-PAGE, CE-SDS, dynamic light scattering (DLS), analytical ultracentrifugation (AUC) and field flow fractionation (FFF).

Specifically, cIEF separates antibody isomers by differences in their isoelectric point (pI) which results from the overall charge on the molecule being a function of the pH of its surroundings. The cIEF electropherograms of non-stressed HuMax-AXL samples typically showed one major peak accounting for more than 60% of the total peak area, as well as both acidic and basic isoforms. For the comparison of cIEF data between various formulations, the percentage main, acidic and basic isoforms was used.

SEC is a chromatographic method in which molecules in solution are separated by their size and/or molecular weight. The SEC chromatograms of non-stressed HuMax-AXL samples typically showed one major peak that corresponded to the monomeric antibody, and accounted for more than 90% of the total peak area. This one major SEC peak reflected the antibody's size homogeneity in each formulation. For the comparison of SEC data between various formulations, the peak area values for species that eluted before the main peak were combined and reported as percent HMW (High molecular weight) species and usually represent an aggregated form. Similarly, the peak area values for species that eluted after the main peak were combined and reported as percent LMW (low molecular weight) species and usually represent degraded forms.

"A280" is a spectrophotometric method measuring the ultraviolet absorbance at 280 nm. Determination of the protein concentration by ultraviolet absorption (280 nm) depends on the presence of aromatic amino acids in the protein. The concentration of the solution can be calculated using Beer-Lambert Law: $(c=A/\varepsilon^{-}l)$; where c is the molar concentration, l is the path-length of the cuvette (units cm), $\varepsilon$ is the molar extinction coefficient (units $M^{-1}$ $cm^{-1}$) and A is the absorbance at 280 nm.

For example, a lyophilized AXL-ADC formulation of the invention of pharmaceutically acceptable stability can be one wherein, when stored at a temperature of about 5±3° C. or 25±2° C. for a period of least about 3 months, preferably about 6 months, and more preferably about 12 months or longer, such as 18 months or longer, such as for at least 24 or even 36 months, the amount of aggregates is less than about 10%, preferably less than about 5%, more preferably less than about 2%, when determined using SEC analysis e.g.

according to Example 9. Additionally or alternatively, a stable lyophilized AXL-ADC formulation of the invention can be one wherein, when stored at a temperature of about 5±3° C. or 25±2° C. for a period of least about 3 months, preferably about 6 months, and more preferably about 12 months or longer, the changes of main isoform are less than 15%, preferably less than 10%, more preferably less than 8%, most preferably less than 5%, when determined using cIEF analysis, e.g., according to Example 9.

In one embodiment, a lyophilized AXL-ADC formulation of pharmaceutically acceptable stability can be one wherein, when stored at 2-8° C., such as at about 5° C. for at least 6 months, such as for at least 9 months, such as for at least 15 months or preferably for at least 18 months, or even more preferred for at least 24 months, or most preferred for at least 36 months, the amount of aggregates is less than 10%, such as less than 5.0%, such as less than 3.0%, such as less than 2.0%.

In one embodiment, an aqueous anti-AXL antibody formulation of pharmaceutically acceptable stability can be one wherein, when stored at −70° C.±10° C., such as at about- 70° C. for at least 6 months, such as for at least 9 months, such as for at least 15 months, such as for at least 18 months, such as for at least 24 months, or such as for at least 36 months, the amount of aggregates is less than 15%, such as less than 10%, such as less than 8.0%, such as less than 5.0%.

AXL-ADCS:
1) Lyophilized Formulations:

The invention thus provides for the following exemplary and non-limiting lyophilized formulations of AXL-ADCs, each representing a specific embodiment:

In one embodiment, the invention provides a lyophilized formulation of an anti-AXL antibody-drug conjugate (AXL-ADC), the lyophilized formulation obtainable or obtained by lyophilizing an aqueous formulation comprising said AXL-ADC and one or more excipients, wherein the formulation is free, or at least essentially free, of surfactant. Suitable excipients include a buffer which provides for a pH of between about 5 and about 7 in the aqueous formulation, at least one non-reducing sugar which forms an amorphous phase with the AXL-ADC in solid state; and at least one bulking agent.

In another embodiment, the invention provides a lyophilized formulation of an AXL-ADC, the lyophilized formulation obtainable or obtained by lyophilizing an aqueous formulation comprising
  (a) an AXL-ADC;
  (b) a buffer providing for a pH of between about 5 and about 7 in the aqueous formulation;
  (c) at least one bulking agent; and
  (d) at least one non-reducing sugar which forms an amorphous phase with the ADC in solid state.

In one embodiment, the invention relates to a lyophilized formulation obtained or obtainable by lyophilizing an aqueous formulation having a pH in the range of about 5 to about 7, such as about 5.5 to about 6.5, and comprising about 5 mg/ml to about 30 mg/ml AXL-ADC; about 10 mM to about 100 mM histidine buffer; about 15 mM to about 200 mM sucrose or trehalose; and about 50 mM to about 300 mM mannitol or glycine.

In one embodiment, the invention relates to a lyophilized formulation obtained or obtainable by lyophilizing an aqueous formulation having a pH in the range of about 5 to about 7, such as of about 5.5 to about 6.5, and comprising about 5 mg/mL to about 30 mg/ml AXL-ADC and about 5 mM to about 100 mM histidine buffer; about 15 mM to about 200 mM sucrose or trehalose; and about 100 mM to about 225 mM mannitol or glycine.

In one embodiment, the invention relates to a lyophilized formulation obtained or obtainable by lyophilizing an aqueous formulation having a pH in the range of about 5 to about 7, optionally of about 5.5 to about 6.5; comprising about 5 mg/ml to about 30 mg/mL AXL-ADC; about 5 mM to about 100 mM histidine buffer; about 30 mM to about 150 mM sucrose or trehalose; and about 100 mM to about 225 mM mannitol or glycine.

In one embodiment, the invention relates to a lyophilized formulation obtained or obtainable by lyophilizing an aqueous formulation having a pH in the range of about 5 to about 7, optionally of about 5.5 to about 6.5; comprising about 5 mg/ml to about 30 mg/ml AXL-ADC; about 10 mM to about 50 mM histidine buffer; about 30 mM to 150 mM sucrose or trehalose; and about 100 mM to about 225 mM mannitol or glycine.

In one embodiment, the invention relates to a lyophilized formulation obtained or obtainable by lyophilizing an aqueous formulation having a pH in the range of about 5 to about 7, optionally of about 5.5 to about 6.5; comprising about 5 mg/ml to about 30 mg/ml AXL-ADC; about 10 mM to about 50 mM histidine buffer; about 30 mM to about 150 mM sucrose or trehalose; and about 150 mM to about 180 mM, such as about 160 mM to about 170 mM mannitol or glycine.

In one embodiment, the invention relates to a lyophilized formulation obtained or obtainable by lyophilizing an aqueous formulation having a pH in the range of about 5 to about 7, optionally of about 5.5 to about 6.5; comprising about 5 mg/ml to about 30 mg/mL AXL-ADC; about 10 mM to about 50 mM histidine buffer; about 30 mM to about 150 mM sucrose or trehalose, such as about 80 mM to 100 mM; and about 100 mM to about 225 mM mannitol or glycine.

In one embodiment, the invention relates to a lyophilized formulation obtained or obtainable by lyophilizing an aqueous formulation having a pH in the range of about 5 to about 7, optionally of about 5.5 to about 6.5; comprising about 5 mg/ml to about 30 mg/ml AXL-ADC; about 10 mM to about 50 mM histidine buffer; about 30 mM to about 150 mM sucrose; and about 100 mM to about 225 mM mannitol.

In one embodiment, the invention relates to a lyophilized formulation obtained or obtainable by lyophilizing an aqueous formulation having a pH in the range of about 5 to about 7, optionally between about 5.5 and about 6.5, and comprising about 5 mg/ml to about 30 mg/mL AXL-ADC; about 10 mM to about 50 mM histidine buffer; about 30 mM to about 150 mM sucrose or trehalose; and about 150 mM to about 180 mM mannitol or glycine.

In one embodiment, the invention relates to a lyophilized formulation obtained or obtainable by lyophilizing an aqueous formulation having a pH in the range of about 5 to about 7, optionally of about 5.5 to about 6.5; comprising about 5 mg/ml to about 30 mg/mL AXL-ADC; about 10 mM to about 50 mM histidine buffer; about 15 mM to 120 mM sucrose or trehalose; and about 100 mM to about 225 mM mannitol or glycine.

In one embodiment, the invention relates to a lyophilized formulation obtained or obtainable by lyophilizing an aqueous formulation having a pH in the range of about 5 to about 7, optionally of about 5.5 to about 6.5; comprising about 5 mg/mL to about 30 mg/ml AXL-ADC; about 10 mM to about 50 mM histidine buffer; about 15 mM to about 120 mM sucrose or trehalose; and about 150 mM to about 180 mM, such as about 160 mM to about 170 mM mannitol or glycine.

In one embodiment, the invention relates to a lyophilized formulation obtained or obtainable by lyophilizing an aqueous formulation having a pH in the range of about 5 to about 7, optionally of about 5.5 to about 6.5; comprising about 5 mg/ml to about 30 mg/ml AXL-ADC; about 10 mM to about 50 mM histidine buffer; about 15 mM to about 120 mM sucrose or trehalose, such as about 80 mM to 100 mM; and about 100 mM to about 225 mM mannitol or glycine.

In one embodiment, the invention relates to a lyophilized formulation obtained or obtainable by lyophilizing an aqueous formulation having a pH in the range of about 5 to about 7, optionally of about 5.5 to about 6.5; comprising about 5 mg/ml to about 30 mg/mL AXL-ADC; about 10 mM to about 50 mM histidine buffer; about 15 mM to about 120 mM sucrose; and about 100 mM to about 225 mM mannitol.

In one embodiment, the invention relates to a lyophilized formulation obtained or obtainable by lyophilizing an aqueous formulation having a pH of about 5 to about 7, optionally between about 5.5 and about 6.5, and comprising about 5 mg/mL to about 30 mg/mL AXL-ADC; about 10 mM to about 50 mM histidine buffer; about 15 mM to about 120 mM sucrose or trehalose; and about 150 mM to about 180 mM mannitol or glycine.

In one embodiment, the invention relates to a lyophilized formulation obtained or obtainable by lyophilizing an aqueous formulation having a pH in the range of about 5 to about 7, such as of about 5.5 to about 6.5, and comprising about 5 mg/mL to about 30 mg/ml AXL-ADC and about 5 mM to about 100 mM histidine buffer; about 20 mM to about 100 mM, such as about 30 mM to about 90 mM, such as about 70 to about 90 mM sucrose or trehalose; and about 100 mM to about 225 mM mannitol or glycine.

In one embodiment, the invention relates to a lyophilized formulation obtained or obtainable by lyophilizing an aqueous formulation having a pH in the range of about 5 to about 7, such as of about 5.5 to about 6.5, and comprising about 5 mg/mL to about 30 mg/mL AXL-ADC and about 10 mM to to about 50 mM histidine buffer; about 20 mM to about 100 mM, such as about 30 mM to about 90 mM, such as about 70 to about 90 mM sucrose or trehalose; and about 150 mM to about 180 mM mannitol or glycine.

In one embodiment, the invention relates to a lyophilized formulation obtained or obtainable by lyophilizing an aqueous formulation having a pH of about 5 to about 7, optionally between about 5.5 and about 6.5; comprising about 5 mg/ml to about 30 mg/ml AXL-ADC; about 10 mM to about 50 mM histidine buffer; about 80 mM to about 100 mM sucrose or trehalose; and about 150 mM to about 180 mM mannitol or glycine.

In one embodiment, the invention relates to a lyophilized formulation obtained or obtainable by lyophilizing an aqueous formulation having a pH of about 5 to about 7, optionally between about 5.5 and about 6.5; comprising about 5 mg/ml to about 30 mg/ml AXL-ADC; about 10 mM to about 50 mM histidine buffer; about 80 mM to about 100 mM sucrose; and about 150 mM to about 180 mM mannitol.

In one embodiment, the invention relates to a lyophilized formulation obtained or obtainable by lyophilizing an aqueous formulation having a pH between about 5.5 and about 6.5 and comprising about 5 mg/mL to about 30 mg/mL AXL-ADC; about 20 mM to about 40 mM histidine buffer; about 80 mM to about 100 mM sucrose; and about 150 mM to about 180 mM mannitol.

In one embodiment, the invention relates to a lyophilized formulation obtained or obtainable by lyophilizing an aqueous formulation having a pH between about 5.5 and about 6.5 and comprising about 7 mg/mL to about 20 mg/mL AXL-ADC; about 20 mM to about 40 mM histidine buffer; about 80 mM to about 100 mM sucrose; and about 150 mM to about 180 mM mannitol.

In one embodiment, the invention relates to a lyophilized formulation obtained or obtainable by lyophilizing an aqueous formulation having a pH between about 5.5 and about 6.5 and comprising about 7 mg/mL to about 20 mg/ml AXL-ADC; about 20 mM to about 40 mM histidine buffer; about 80 mM to about 100 mM sucrose; and about 158 mM to about 172 mM mannitol.

In one embodiment, the invention relates to a lyophilized formulation obtained or obtainable by lyophilizing an aqueous formulation having a pH between about 5.5 and about 6.5 and comprising about 7 mg/mL to about 20 mg/mL AXL-ADC; about 20 mM to about 40 mM histidine buffer; about 84 mM to about 92 mM sucrose; and about 158 mM to about 172 mM mannitol.

In one embodiment, the invention relates to a lyophilized formulation obtained or obtainable by lyophilizing an aqueous formulation having a pH between about 5.5 and about 6.5 and comprising about 9 mg/mL to about 11 mg/ml AXL-ADC; about 20 mM to about 40 mM histidine buffer; about 84 mM to about 92 mM sucrose; and about 158 mM to about 172 mM mannitol.

In one embodiment, the invention relates to a lyophilized formulation obtained or obtainable by lyophilizing an aqueous formulation having a pH of about 6 and comprising about 10 mg/mL AXL-ADC; about 30 mM histidine buffer; about 88 mM sucrose; and about 165 mM mannitol.

In one embodiment, the invention relates to a lyophilized formulation obtained or obtainable by lyophilizing an aqueous formulation comprising about 9 mg/ml to about 11 mg/mL AXL-ADC, such as about 10 mg/mL AXL-ADC wherein the AXL-ADC is HuMax-AXL-ADC (IgG1, vcMMAE), which is an ADC composed of a human monoclonal IgG1,κ antibody herein referred to as "107", conjugated via a protease cleavable valine citrulline linker, mc-vc-PAB, to the drug monomethyl auristatin E (vcMMAE), and pharmaceutically acceptable excipients comprising about 30 mM histidine buffer providing for a pH of about 6; about 88 mM sucrose; and about 165 mM mannitol or glycine.

In one preferred embodiment, the antibody moiety of the AXL-ADC, comprises at least one antigen-binding region which comprises a VH region comprising the CDR1, CDR2, and CDR3 sequences of SEQ ID Nos.: 36, 37, and 38, respectively; and a VL region comprising the CDR1, CDR2, and CDR3 sequences of SEQ ID Nos.: 39, GAS, and 40, respectively, [107].

In separate and specific embodiments, the formulations are essentially free of surfactant.

In other separate and specific embodiments, the formulations are free of surfactant.

In one embodiment, the invention relates to a lyophilized formulation of an AXL-ADC, the lyophilized formulation obtained or obtainable by lyophilizing an aqueous formulation comprising: a buffer which provides for a pH of the aqueous formulation and the reconstituted formulation in the range of about 5 to about 7, at least one non-reducing sugar which forms an amorphous phase with the AXL-ADC in solid state and at least one bulking agent, wherein the AXL-ADC comprises a linker which is selected from mc-vc-PAB and SSP, a cytotoxic agent selected from MMAE, MMAF and DM1 and an anti-AXL antibody which competes for binding to AXL with a reference antibody comprising the VH and VL regions from an anti-AXL antibody selected from the group consisting of 107, 148, 733, 154, 171, 183, 613, 726, 140, M103L, 172, 181, 183-N52Q, 187, 608-01, 610-01, 613-08, 620-06 and M101L; optionally wherein the lyophilized formulation is essentially free of any surfactant.

In other separate and specific embodiments, the invention provides for a lyophilized formulation of any one of the preceding embodiments, which is essentially free of any polysorbate, optionally of any surfactant.

In one specific embodiment of any one of the preceding embodiments, the lyophilized formulation of any one of the preceding embodiments comprises mannitol and sucrose, wherein the weight ratio of mannitol to sucrose is at least about 1, such as between about 1 and about 20, such as between about 1 and about 10, such as between about 1 and about 5, such as between about 1 and about 2, such as about 1.

In one specific embodiment of any one of the preceding embodiments, the lyophilized formulation of any one of the preceding embodiments comprises mannitol and trehalose, wherein the weight ratio of mannitol to trehalose is at least about 1, such as between about 1 and about 20, such as between about 1 and about 10, such as between about 1 and about 5, such as between about 1 and about 2, such as about 1.

In one specific embodiment of any one of the preceding embodiments, the lyophilized formulation of any one of the preceding embodiments comprises mannitol and sucrose, wherein the weight ratio of mannitol to sucrose is between about 1 and about 10 and the weight ratio of mannitol to ADC is at least about 3, such as between about 3 and about 20, such as between about 3 and about 10.

The invention also provides for a lyophilized formulation obtained or obtainable by lyophilizing an aqueous formulation having a pH in the range of about 5.5 to about 6.5 and comprising, optionally consisting of, from about 9 mg/ml to about 11 mg/ml AXL-ADC; about 30 mM histidine; about 88 mM sucrose; and about 165 mM mannitol.

In one embodiment, the invention relates to a lyophilized formulation obtained or obtainable by lyophilizing an aqueous formulation having a pH between about 5.5 and about 6.5 and comprising about 7 mg/mL to about 20 mg/mL AXL-ADC; about 20 mM to about 40 mM histidine buffer; about 84 mM to about 92 mM sucrose; and about 2.5% to about 3.5% (w/v), such as about 3% (w/v) mannitol, glycine or a combination thereof.

In one embodiment, the invention relates to a lyophilized formulation obtained or obtainable by lyophilizing an aqueous formulation having a pH between about 5.5 and about 6.5 and comprising about 7 mg/mL to about 20 mg/mL AXL-ADC; about 20 mM to about 40 mM histidine buffer; about 2.5% (w/v) to about 3.5% (w/v) sucrose, trehalose or a combination thereof; and about 2.5% to about 3.5% (w/v) of mannitol, glycine or a combination thereof.

A lyophilized formulation of an AXL-ADC can be prepared by lyophilizing an aqueous formulation comprising, or consisting essentially of, about 9 mg/mL to about 11 mg/mL AXL-ADC and pharmaceutically acceptable excipients comprising: about 30 mM histidine buffer providing for a pH of about 5.5 to about 6.5 in the aqueous formulation; about 88 mM sucrose; and about 165 mM mannitol; wherein the antibody comprises at least one binding region comprising a VH region and a VL region comprising the VH and VL CDRs, or the VH and VL sequences of, an antibody selected from the group consisting of 107, 148, 733, 154, 171, 183, 613, 726, 140, M103L, 172, 181, 183-N52Q, 187, 608-01, 610-01, 613-08, 620-06 and M101L; wherein the drug is MMAE or DM1, e.g., a linker-drug which is mc-vc-PAB-MMAE or SSP-DM1. In one embodiment, the AXL-ADC comprises at least one binding region comprising the VH and VL CDRs, or the VH and VL sequences of, antibody 107, and the linker-drug is mc-vc-PAB-MMAE. Additionally, the antibody moiety of the AXL-ADC may preferably be a full-length antibody, such as a full-length monoclonal IgG1,κ antibody.

In one embodiment, the lyophilized AXL-ADC formulation of the invention contains less than 3.0% moisture (wt/wt). In one embodiment, the lyophilized formulation of the invention contains less than 2.0% moisture. In one embodiment, the lyophilized formulation of the invention contains less than 1.0% moisture. In one embodiment, the lyophilized formulation of the invention contains less than 0.5% moisture.

In one embodiment, in the lyophilized formulation, the AXL-ADC is stable at 2-8° C., such as at 5° C. for pharmaceutical use for at least 6 months, such as for at least 9 months, such as for at least 15 months or preferably for at least 18 months, or even more preferred for at least 24 months, or most preferred for at least 36 months.

In one embodiment, the lyophilized formulation is stable when it has less than 10% aggregates, such as less than 5.0% aggregates, such as less than 3.0% aggregates, such as less than 2.0% aggregates when stored at 5° C. for at least 6 months, such as for at least 9 months, such as for at least 15 months or preferably for at least 18 months, or even more preferred for at least 24 months, or most preferred for at least 36 months.

In one embodiment, the stability is determined by size-exclusion analysis, cIEF, or both.

In one embodiment, the lyophilized formulation is free of any inorganic salts.

The following are additional embodiments contemplated:
1. A lyophilized formulation of an AXL-ADC, the lyophilized formulation obtainable or obtained by lyophilizing an aqueous formulation comprising the AXL-ADC and one or more excipients, wherein the aqueous formulation is free of any surfactant.
2. A lyophilized formulation of an AXL-ADC, the lyophilized formulation obtainable or obtained by lyophilizing an aqueous formulation comprising the AXL-ADC and
    (a) a buffer providing for a pH of between about 5 and about 7 in the aqueous formulation;
    (b) at least one bulking agent; and
    (c) at least one non-reducing sugar which forms an amorphous phase with the ADC in solid state.
3. The lyophilized formulation of embodiment 2, wherein the aqueous formulation is free of any surfactant.
4. The lyophilized formulation of any one of the preceding embodiments, wherein the aqueous formulation comprises a buffer selected from the group consisting of histidine, citrate, 2-(N-morpholino) ethanesulfonic acid (MES), succinate, glycolate, carbonic acid and phosphate, or a combination of any thereof, wherein the pH of the aqueous formulation is in a range from about 5 to about 7.
5. The lyophilized formulation of any one of the preceding embodiments, wherein the aqueous formulation comprises a histidine buffer.
6. The lyophilized formulation of any one of the preceding embodiments, wherein the aqueous formulation comprises a buffer at a concentration of about 5 mM to about 100 mM, such as from about 10 mM to about 50 mM buffer, such as from about 20 mM to about 40 mM, such as from about 28 mM to about 32 mM, such as about 30 mM buffer.
7. The lyophilized formulation of any one of the preceding embodiments, comprising a bulking agent selected from mannitol, glycine, and a combination thereof.
8. The lyophilized formulation of any one of the preceding embodiments, comprising mannitol.
9. The lyophilized formulation of any one of the preceding embodiments, wherein the aqueous formulation comprises a bulking agent at a concentration of about 1% (w/v) to about 5% (w/v), such as about 2% (w/v) to about 4% (w/v), such as from about 2.5% (w/v) to about 3.5% (w/v), such as about 3% (w/v).
10. The lyophilized formulation of any one of the preceding embodiments, wherein the aqueous formulation comprises a bulking agent at a concentration of about 50 mM to about 300 mM, such as from about 100 mM to about 225 mM, such as from about 150 mM to about 180 mM, such as about 165 mM.
11. The lyophilized formulation of any one of the preceding embodiments, comprising a non-reducing sugar selected from sucrose, trehalose, and a combination thereof.
12. The lyophilized formulation of any one of the preceding embodiments, comprising sucrose.
13. The lyophilized formulation of any one of the preceding embodiments, wherein the aqueous formulation comprises a non-reducing sugar at a concentration of about 0.5% (w/v) to about 7% (w/v), such as from about 0.5% (w/v) to about 4% (w/v), such as from about 1% (w/v) to about 3% (w/v) or from about 2.5% to about 3.5%, such as about 3% (w/v).
14. The lyophilized formulation of any one of the preceding embodiments, wherein the aqueous formulation comprises a non-reducing sugar at a concentration of about 15 mM to about 200 mM, such as from about 15 mM to about 120 mM, such as from about 30 mM to about 90 mM, such as 80 mM to about 100 mM, such as from about 84 mM to about 92 mM sucrose, such as about 88 mM.
15. The lyophilized formulation of any one of the preceding embodiments, wherein the AXL-ADC concentration in the aqueous formulation is from about 5 mg/mL to about 30 mg/mL, such as from about 7 mg/mL to about 20 mg/mL, such as from about 8 mg/ml to about 15 mg/mL, such as from about 9 mg/ml to about 11 mg/mL, such as about 10 mg/mL.
16. The lyophilized formulation of any one of the preceding embodiments, wherein the pH of the aqueous formulation is in a range from about 5.5 to 6.5, such as from about 5.8 to about 6.2, such as about 6.
17. A lyophilized formulation obtainable or obtained by lyophilizing an aqueous formulation having a pH of about 5 to about 7 and comprising
    (a) from about 5 mg/mL to about 30 mg/ml of an AXL-ADC and
    (b) from about 10 mM to about 50 mM histidine;
    (c) from about 15 mM to about 120 mM sucrose or trehalose; and
    (d) from about 150 mM to about 180 mM mannitol or glycine.
18. The lyophilized formulation of embodiment 17, wherein the aqueous formulation has a pH in the range of about 5.5 to about 6.5 and comprises
    (a) from about 9 mg/mL to about 11 mg/mL AXL-ADC, such as about 10 mg/ml of the AXL-ADC;
    (b) from about 20 mM to about 40 mM histidine, such as about 30 mM histidine;
    (c) from about 80 mM to about 100 mM sucrose, such as about 88 mM sucrose; and
    (d) from about 150 mM to about 180 mM mannitol, such as about 165 mM;
    wherein the aqueous formulation is free of any surfactant.

In a preferred embodiment, in the AXL-ADC of the lyophilized formulation,
  the antibody moiety comprises the VH and VL CDRs, optionally the VH (SEQ ID NO:1) and VL (SEQ ID NO: 2) sequences, of human anti-ADC antibody 107, and
  the linker is mc-vc-PAB and the cytotoxic agent is MMAE.

In another preferred embodiment, in the AXL-ADC of the lyophilized formulation,
  the antibody moiety comprises the VH and VL CDRs, optionally the VH (SEQ ID NO:1) and VL (SEQ ID NO:2) sequences, of human anti-ADC antibody 107, and
  the linker is SSP and the cytotoxic agent is DM1.

Additionally, the antibody moiety of the AXL-ADC may preferably be a full-length antibody, such as a full-length monoclonal IgG1,κ antibody.

2) Liquid Formulation:

The invention also provides for a pharmaceutically acceptable liquid formulation obtained or obtainable by reconstituting the lyophilized formulation of any one of the preceding aspects or embodiments in a sterile aqueous diluent.

For example, such a liquid formulation may have a pH of between about 5 and about 7 and comprise or consist essentially of about 5 mg/ml to about 30 mg/ml AXL-ADC, about 10 mM to about 50 mM histidine; about 30 mM to about 150 mM sucrose or trehalose; and about 50 mM to about 300 mM mannitol or glycine.

In one embodiment, the liquid formulation has a pH of about 5 to about 7 and comprises or consist essentially of about 5 mg/mL to about 30 mg/mL AXL-ADC, about 10 mM to about 50 mM histidine; about 15 mM to about 120 mM sucrose or trehalose; and about 100 mM to about 225 mM mannitol or glycine.

In one embodiment, the liquid formulation has a pH of between about 5.5 and about 6.5 and comprises or consists essentially of from about 9 mg/mL to about 11 mg/mL AXL-ADC; from about 20 mM to about 40 mM histidine; from about 80 mm to about 100 mM sucrose; and from about 150 mM to about 180 mM mannitol; wherein the liquid formulation is essentially free of any surfactant.

In one embodiment, the liquid formulation has a pH of about 6 and comprises or consists essentially of about 10 mg/ml of the AXL-ADC; about 30 mM histidine; about 88 mM sucrose; and about 165 mM mannitol; wherein the liquid formulation is free of any surfactant.

In one embodiment, the liquid formulation has a pH of between about 5.5 and about 6.5 and comprises or consists essentially of from about 9 mg/ml to about 11 mg/ml AXL-ADC, about 28 mM to about 34 mM histidine, about 84 mM to about 92 mM sucrose and about 160 to about 170 mM mannitol.

In a preferred embodiment, in the AXL-ADC of the liquid formulation,
  the antibody moiety comprises the VH and VL CDRs, optionally the VH (SEQ ID NO: 1) and VL (SEQ ID NO:2) sequences, of human anti-ADC antibody 107, and
  the linker is mc-vc-PAB and the cytotoxic agent is MMAE.

In another preferred embodiment, in the AXL-ADC of the liquid formulation,
  the antibody moiety comprises the VH and VL CDRs, optionally the VH (SEQ ID NO:1) and VL (SEQ ID NO:2) sequences, of human anti-ADC antibody 107, and
  the linker is SSP and the cytotoxic agent is DM1.

Additionally, the antibody moiety of the AXL-ADC may preferably be a full-length antibody, such as a full-length monoclonal IgG1,κ antibody.

3) Aqueous Formulation:

The invention also provides for an aqueous formulation (also referred to as "aqueous solution" herein) suitable for preparing a lyophilized formulation of an AXL-ADC according to any one of the preceding aspects or embodiments. The aqueous formulation of an AXL-ADC may also in itself be suitable for pharmaceutical purposes and for therapeutic applications of the AXL-ADCs.

Such an aqueous formulation may, for example, comprise
  (a) from about 7 mg/mL to about 20 mg/ml AXL-ADC, optionally comprising the VH and VL CDRs or the VH and VL sequences, of anti-AXL antibody 107,
  (b) about 10 mM to 50 mM histidine;
  (c) about 30 mM to about 150 mM sucrose;
  (d) about 150 mM to about 180 mM mannitol; or
  (e) a combination of a) and any two, three or all of (b) to (d).

The invention also provides for an aqueous formulation suitable for preparing a lyophilized formulation of an AXL-ADC, comprising
  (a) from about 7 mg/mL to about 20 mg/mL AXL-ADC, optionally comprising the VH and VL CDRs or the VH and VL sequences, of anti-AXL antibody 107,
  (b) about 10 mM to 50 mM histidine;
  (c) about 15 mM to about 120 mM sucrose;
  (d) about 150 mM to about 180 mM mannitol; or
  (e) a combination of (a) and any two, three or all of (b) to (d).

The invention also provides for an aqueous formulation suitable for preparing a lyophilized formulation of an AXL-ADC, comprising
  (a) from about 7 mg/mL to about 20 mg/mL AXL-ADC, optionally comprising the VH and VL CDRs or the VH and VL sequences, of anti-AXL antibody 107,
  (b) about 10 mM to 50 mM histidine;
  (c) about 80 mM to about 100 mM sucrose;
  (d) about 150 mM to about 180 mM mannitol; or
  (e) a combination of a) and any two, three or all of (b) to (d).

The invention also provides for an aqueous formulation suitable for preparing a lyophilized formulation of an AXL-ADC wherein the aqueous formulation does not contain a surfactant, said solution comprising:
  (a) from about 7 mg/mL to about 20 mg/mL AXL-ADC, optionally comprising the VH and VL CDRs or the VH and VL sequences, of anti-AXL antibody 107,
  (b) about 10 mM to 50 mM histidine;
  (c) about 30 mM to about 150 mM sucrose;
  (d) about 150 mM to about 180 mM mannitol; or
  (e) a combination of (a) and any two, three or all of (b) to (d).

The invention also provides for an aqueous formulation suitable for preparing a lyophilized formulation of an AXL-ADC wherein the aqueous formulation does not contain a surfactant, said solution comprising:
  (a) from about 7 mg/mL to about 20 mg/mL AXL-ADC, optionally comprising the VH and VL CDRs or the VH and VL sequences, of anti-AXL antibody 107,
  (b) about 10 mM to 50 mM histidine;
  (c) about 80 mM to about 100 mM sucrose;
  (d) about 150 mM to about 180 mM mannitol; or
  (e) a combination of (a) and any two, three or all of (b) to (d).

The invention also provides for an aqueous formulation suitable for preparing a lyophilized formulation of an AXL-ADC, consisting of:
  (a) from about 7 mg/mL to about 20 mg/mL AXL-ADC, optionally comprising the VH and VL CDRs or the VH and VL sequences, of anti-AXL antibody 107,
  (b) about 10 mM to 50 mM histidine;
  (c) about 80 mM to about 100 mM sucrose;
  (d) about 150 mM to about 180 mM mannitol; or
  (e) a combination of (a) and any two, three or all of (b) to (d).

Preferably, the histidine buffer provides for a pH in the range from about 5 to about 7, preferably from about 5.5 to about 6.5, such as about pH6, in the aqueous formulation.

In a preferred embodiment, in the AXL-ADC of any aqueous formulation,
  the antibody moiety comprises the VH and VL CDRs, optionally the VH (SEQ ID NO:1) and VL (SEQ ID NO:2) sequences, of human anti-ADC antibody 107, and
  the linker is mc-vc-PAB and the cytotoxic agent is MMAE.

In another preferred embodiment, in the AXL-ADC of any aqueous formulation,
  the antibody moiety comprises the VH and VL CDRs, optionally the VH (SEQ ID NO: 1) and VL (SEQ ID NO: 2) sequences, of human anti-ADC antibody 107, and
  the linker is SSP and the cytotoxic agent is DM1.

Additionally, the antibody moiety of the AXL-ADC may preferably be a full-length antibody, such as a full-length monoclonal IgG1,κ antibody.

Anti-AXL Antibody:

In one aspect, the invention relates to an aqueous formulation of an anti-AXL antibody, comprising one or more pharmaceutically acceptable excipients, wherein the aqueous formulation is free of any surfactant. In one embodiment, the one or more pharmaceutically acceptable excipients comprise a buffer and at least one stabilizer, wherein the pH of the aqueous formulation is between about 5 and about 7, preferably between about 5.5 and about 6.5, such as between about 5.8 to about 6.2, such as about 6.

Non-limiting examples of suitable buffers include histidine, citrate, MES, phosphate, carbonic acid, succinate, glycolate, and a combination of any thereof. One preferred buffer is histidine. The aqueous formulation may, for example, comprise a buffer at a concentration of about 10 to about 50 mM, such as from about 20 mM to about 40 mM buffer, such as from about 28 mM to about 34 mM, such as from about 29 mM to about 31 mM, such as about 30 mM buffer.

Suitable stabilizers include mannitol, sucrose and trehalose, and combinations thereof. In one embodiment, the stabilizer is mannitol. The aqueous formulation may, for example, comprise a stabilizer at a concentration of about 20 mM to about 400 mM, such as from about 20 mM to about 200 mM or from about 30 mM to about 300 mM, such as from about 30 mM to about 100 mM, such as from about 40 mM to about 80 mM, such as about 50 mM to about 60 mM, such as about 55 mM. In one embodiment, the aqueous formulation comprises a stabilizer at a concentration of about 5% (w/v) or less, such as about 4% (w/v) or less, such as about 3% (w/v) or less, such as about 2% (w/v) or less, such as about 1% (w/v) or less, such as about 1% (w/v), such as between 0.4% to about 7% (w/v), such as between 0.5% to about 5% (w/v), such as between 0.5% and 1.5% (w/v), such as about 1% (w/v). In one embodiment, the stabilizer is mannitol.

Optionally, the aqueous formulation further comprises a non-reducing sugar selected from sucrose, trehalose and a combination thereof.

In one embodiment, the aqueous formulation of an anti-AXL antibody is free of any one or more of arginine, glycine, glutamic acid, sorbitol, trehalose, sucrose and sodium chloride.

In one embodiment, the antibody concentration is from about 5 mg/mL to about 40 mg/mL, such as from about 8 mg/mL to about 35 mg/mL, such as from about 10 mg/mL to about 30 mg/mL, such as from about 15 mg/mL to about 25 mg/mL, such as about 20 mg/mL.

In one embodiment, the aqueous formulation has a pH of about 5 to about 7 and comprises
(a) from about 5 mg/mL to about 40 mg/mL of an anti-AXL antibody and
(b) from about 10 mM to about 50 mM histidine;
(c) from about 50 mM to about 300 mM mannitol.

In one embodiment, the aqueous formulation has a pH in the range of about 5.5 to about 6.5 and comprises
(a) from about 15 mg/mL to about 25 mg/mL anti-AXL antibody, such as about 20 mg/ml of the anti-AXL antibody;
(b) from about 20 mM to about 40 mM histidine, such as about 30 mM histidine;
(c) from about 50 mM to about 60 mM mannitol, such as about 55 mM,
wherein the aqueous formulation is free of any added surfactant, amino acid excipient and/or sodium chloride.

In one embodiment, the anti-AXL antibody binds to the same epitope on human AXL as a reference antibody comprising an antigen-binding region comprising the VH and VL region sequences of SEQ ID NOS: 1 and 2, respectively. In one embodiment, the anti-AXL antibody comprises the VH and VL CDRs of anti-AXL antibody 107.

In one embodiment, the invention relates to a frozen aqueous formulation of an anti-AXL antibody, obtained or obtainable by freezing the aqueous formulation of any preceding aspect or embodiment.

In one preferred embodiment, the anti-AXL antibody comprises at least one antigen-binding region which comprises a VH region comprising the CDR1, CDR2, and CDR3 sequences of SEQ ID Nos.: 36, 37, and 38, respectively; and a VL region comprising the CDR1, CDR2, and CDR3 sequences of SEQ ID Nos.: 39, GAS, and 40, respectively, [107].

Antibodies

The anti-AXL antibodies described in this section are suitable both for the aqueous formulations of the invention and for use in the AXL-ADCs of the lyophilized formulations of the invention, as described in the aspects and embodiments herein.

Although generally applicable to any anti-AXL antibody, anti-AXL antibodies that share one or more physicochemical and/or antigen-binding binding properties with any one or more of the anti-AXL antibodies for which VH and VL sequences are provided herein are particularly suitable (see Table 1). The VH, VL and CDR sequences of preferred anti-AXL antibodies are shown in Table 1. The antibody designated 107, optionally in an IgG1,κ format (also called "HuMax AXL" or "IgG1-HuMax-AXL") is particularly preferred.

In one embodiment, the anti-AXL antibody comprises at least one binding region comprising a VH region and a VL region selected from the group consisting of:

(a) a VH region comprising the CDR1, CDR2, and CDR3 sequences of SEQ ID Nos.: 36, 37, and 38, respectively; and a VL region comprising the CDR1, CDR2, and CDR3 sequences of SEQ ID Nos.: 39, GAS, and 40, respectively, [107];

(b) a VH region comprising the CDR1, CDR2, and CDR3 sequences of SEQ ID Nos.: 46, 47, and 48, respectively; and a VL region comprising the CDR1, CDR2, and CDR3 sequences of SEQ ID Nos.: 49, AAS, and 50, respectively, [148];

(c) a VH region comprising the CDR1, CDR2, and CDR3 sequences of SEQ ID Nos.: 114, 115, and 116, respectively, and a VL region comprising the CDR1, CDR2, and CDR3 sequences of SEQ ID Nos.: 117, DAS, and 118, respectively [733];

(d) a VH region comprising the CDR1, CDR2, and CDR3 sequences of SEQ ID Nos.: 51, 52, and 53, respectively; and a VL region comprising the CDR1, CDR2, and CDR3 sequences of SEQ ID Nos.: 55, GAS, and 56, respectively [154];

(e) a VH region comprising the CDR1, CDR2, and CDR3 sequences of SEQ ID Nos.: 51, 52, and 54, respectively; and a VL region comprising the CDR1, CDR2, and CDR3 sequences of SEQ ID Nos.: 55, GAS, and 56, respectively [154-M103L];

(f) a VH region comprising the CDR1, CDR2, and CDR3 sequences of SEQ ID Nos.: 57, 58, and 59, respectively; and a VL region comprising the CDR1, CDR2, and CDR3 sequences of SEQ ID Nos.: 60, GAS, and 61, respectively, [171];

(g) a VH region comprising the CDR1, CDR2, and CDR3 sequences of SEQ ID Nos.: 62, 63, and 64, respectively; and a VL region comprising the CDR1, CDR2, and CDR3 sequences of SEQ ID Nos.: 65, GAS, and 66, respectively, [172];

(h) a VH region comprising the CDR1, CDR2, and CDR3 sequences of SEQ ID Nos.: 67, 68, and 69, respectively; and a VL region comprising the CDR1, CDR2, and CDR3 sequences of SEQ ID Nos.: 70, GAS, and 71, respectively, [181];

(i) a VH region comprising the CDR1, CDR2, and CDR3 sequences of SEQ ID Nos.: 72, 73, and 75, respectively; and a VL region comprising the CDR1, CDR2, and CDR3 sequences of SEQ ID Nos.: 76, ATS, and 77, respectively, [183];

(j) a VH region comprising the CDR1, CDR2, and CDR3 sequences of SEQ ID Nos.: 72, 74, and 75, respectively; and a VL region comprising the CDR1, CDR2, and CDR3 sequences of SEQ ID Nos.: 76, ATS, and 77, respectively, [183-N52Q];

(k) a VH region comprising the CDR1, CDR2, and CDR3 sequences of SEQ ID Nos.: 78, 79, and 80, respectively; and a VL region comprising the CDR1, CDR2, and CDR3 sequences of SEQ ID Nos.: 81, AAS, and 82, respectively, [187];

(l) a VH region comprising the CDR1, CDR2, and CDR3 sequences of SEQ ID Nos.: 83, 84, and 85, respectively; and a VL region comprising the CDR1, CDR2, and CDR3 sequences of SEQ ID Nos.: 86, GAS, and 87, respectively, [608-01];

(m) a VH region comprising the CDR1, CDR2, and CDR3 sequences of SEQ ID Nos.: 88, 89, and 90, respectively; and a VL region comprising the CDR1, CDR2, and CDR3 sequences of SEQ ID Nos.: 91, GAS, and 92, respectively, [610-01];

(n) a VH region comprising the CDR1, CDR2, and CDR3 sequences of SEQ ID Nos.: 93, 94, and 95, respectively; and a VL region comprising the CDR1, CDR2, and CDR3 sequences of SEQ ID Nos.: 96, GAS, and 97, respectively, [613];

(o) a VH region comprising the CDR1, CDR2, and CDR3 sequences of SEQ ID Nos.: 98, 99, and 100, respectively; and a VL region comprising the CDR1, CDR2, and CDR3 sequences of SEQ ID Nos.: 101, DAS, and 102, respectively, [613-08];

(p) a VH region comprising the CDR1, CDR2, and CDR3 sequences of SEQ ID Nos.: 103, 104, and 105, respectively; and a VL region comprising the CDR1, CDR2, and CDR3 sequences of SEQ ID Nos.: 106, GAS, and 107, respectively, [620-06];

(q) a VH region comprising the CDR1, CDR2, and CDR3 sequences of SEQ ID Nos.: 108, 109, and 110, respectively; and a VL region comprising the CDR1, CDR2, and CDR3 sequences of SEQ ID Nos.: 112, AAS, and 113, respectively, [726];

(r) a VH region comprising the CDR1, CDR2, and CDR3 sequences of SEQ ID Nos.: 108, 109, and 111, respectively; and a VL region comprising the CDR1, CDR2, and CDR3 sequences of SEQ ID Nos.: 112, AAS, and 113, respectively, [726-M101L];

(s) a VH region comprising the CDR1, CDR2, and CDR3 sequences of SEQ ID Nos.: 41, 42, and 43, respectively; and a VL region comprising the CDR1, CDR2, and CDR3 sequences of SEQ ID Nos.: 44, AAS, and 45, respectively, [140];

(t) a VH region comprising the CDR1, CDR2, and CDR3 sequences of SEQ ID Nos.: 93, 94, and 95, respectively, and a VL region comprising the CDR1, CDR2, and CDR3 sequences of SEQ ID Nos.: 128, XAS, wherein X is D or G, and 129, respectively, [613/613-08];

(u) a VH region comprising the CDR1, CDR2, and CDR3 sequences of SEQ ID Nos.: 46, 119, and 120, respectively; and a VL region comprising CDR1, CDR2, and CDR3 sequences of SEQ ID Nos.: 49, AAS, and 50, respectively, [148/140];

(v) a VH region comprising the CDR1, CDR2, and CDR3 sequences of SEQ ID Nos.: 123, 124, and 125, respectively; and a VL region comprising CDR1, CDR2, and CDR3 sequences of SEQ ID Nos.: 60, GAS, and 61, respectively [171/172/181]; and (w) a VH region comprising the CDR1, CDR2, and CDR3 sequences of SEQ ID Nos.: 121, 109, and 122, respectively; and a VL region comprising the CDR1, CDR2, and CDR3 sequences of SEQ ID Nos.: 112, AAS, and 113, respectively [726/187]; and (x) a VH region comprising the CDR1, CDR2, and CDR3 sequences of SEQ ID Nos.: 93, 126, and 127, respectively; and a VL region comprising the CDR1, CDR2, and CDR3 sequences of SEQ ID Nos.: 96, GAS, and 97, respectively [613/608-01/610-01/620-06].

In one embodiment, the anti-AXL antibody comprises at least one binding region comprising a VH region and a VL region selected from the group consisting of VH and VL sequences at least 90%, such as at least 95%, such as at least 97%, such as at least 99% identical to:

(a) a VH region comprising SEQ ID No: 1 and a VL region comprising SEQ ID No: 2 [107];

(b) a VH region comprising SEQ ID No: 5 and a VL region comprising SEQ ID No:6 [148];

(c) a VH region comprising SEQ ID No:34 and a VL region comprising SEQ ID No:35

(d) a VH region comprising SEQ ID No: 7 and a VL region comprising SEQ ID No:9 [154];

(e) a VH region comprising SEQ ID No:10 and a VL region comprising SEQ ID No: 11 [171];

(f) a VH region comprising SEQ ID No:16 and a VL region comprising SEQ ID No: 18 [183];

(g) a VH region comprising SEQ ID No:25 and a VL region comprising SEQ ID No:26 [613];

(h) a VH region comprising SEQ ID No:31 and a VL region comprising SEQ ID No:33 [726];

(i) a VH region comprising SEQ ID No:3 and a VL region comprising SEQ ID No: 4 [140];

(j) a VH region comprising SEQ ID No:8 and a VL region comprising SEQ ID No:9 [154-M103L];

(k) a VH region comprising SEQ ID No:12 and a VL region comprising SEQ ID No: 13 [172];

(l) a VH region comprising SEQ ID No:14 and a VL region comprising SEQ ID No: 15 [181];

(m) a VH region comprising SEQ ID No:17 and a VL region comprising SEQ ID No: 18 [183-N52Q];

(n) a VH region comprising SEQ ID No:19 and a VL region comprising SEQ ID No:20 [187];

(o) a VH region comprising SEQ ID No:21 and a VL region comprising SEQ ID No:22 [608-01];

(p) a VH region comprising SEQ ID No:23 and a VL region comprising SEQ ID No:24 [610-01];

(q) a VH region comprising SEQ ID No:27 and a VL region comprising SEQ ID No:28 [613-08];

(r) a VH region comprising SEQ ID No:29 and a VL region comprising SEQ ID No:30 [620-06]; and(s) a VH region comprising SEQ ID No:32 and a VL region comprising SEQ ID No:33 [726-M101L].

In one embodiment, the anti-AXL antibody comprises at least one binding region comprising a VH region and a VL region selected from the group consisting of:

(a) a VH region comprising SEQ ID No: 1 and a VL region comprising SEQ ID No: 2 [107];

(b) a VH region comprising SEQ ID No: 5 and a VL region comprising SEQ ID No: 6 [148];

(c) a VH region comprising SEQ ID No:34 and a VL region comprising SEQ ID No:35

(d) a VH region comprising SEQ ID No:7 and a VL region comprising SEQ ID No:9 [154];

(e) a VH region comprising SEQ ID No:10 and a VL region comprising SEQ ID No: 11 [171];

(f) a VH region comprising SEQ ID No:16 and a VL region comprising SEQ ID No: 18 [183];

(g) a VH region comprising SEQ ID No:25 and a VL region comprising SEQ ID No:26 [613];

(h) a VH region comprising SEQ ID No:31 and a VL region comprising SEQ ID No:33 [726];
(i) a VH region comprising SEQ ID No:3 and a VL region comprising SEQ ID No: 4 [140];
(j) a VH region comprising SEQ ID No: 8 and a VL region comprising SEQ ID No:9 [154-M103L];
(k) a VH region comprising SEQ ID No:12 and a VL region comprising SEQ ID No:13 [172];
(l) a VH region comprising SEQ ID No:14 and a VL region comprising SEQ ID No:15 [181];
(m) a VH region comprising SEQ ID No:17 and a VL region comprising SEQ ID No: 18 [183-N52Q];
(n) a VH region comprising SEQ ID No:19 and a VL region comprising SEQ ID No:20 [187];
(o) a VH region comprising SEQ ID No:21 and a VL region comprising SEQ ID No:22 [608-01];
(p) a VH region comprising SEQ ID No:23 and a VL region comprising SEQ ID No:24 [610-01];
(q) a VH region comprising SEQ ID No:27 and a VL region comprising SEQ ID No:28 [613-08];
(r) a VH region comprising SEQ ID No:29 and a VL region comprising SEQ ID No:30 [620-06]; and (s) a VH region comprising SEQ ID No:32 and a VL region comprising SEQ ID No:33 [726-M101L].

In one embodiment, the anti-AXL antibody binds to the same epitope on AXL as any one or more of the antibodies according to the aforementioned embodiment, as defined by their VH and VL sequences, e.g., a VH region comprising SEQ ID No: 1 and a VL region comprising SEQ ID No: 2 [107].

Methods of determining an epitope to which an antibody binds are well-known in the art. One such method was used in Example 15, wherein the AXL epitope and/or domain specificity was mapped by preparing a panel of human-mouse chimeric AXL mutants where the human Ig1-like, Ig2-like, FN1 or FN2 domain has been replaced by its murine analog and determining which mutant an anti-AXL antibody bound to. So, in separate and specific embodiments, the antibody binds to the Ig1-like domain of AXL, the Ig2-like domain of AXL, the FN1 domain of AXL, or the FN2 domain of AXL.

A more high-resolution epitope mapping method was also used in this Example. Specifically, this method analyzed binding of the anti-AXL antibody to a library of AXL sequence variants generated by recombination of AXL sequences derived from species with variable levels of homology with the human AXL sequence (SEQ ID NO: 130) in the extracellular domain.

A more high-resolution epitope-mapping method, identifying AXL extracellular domain amino acids involved in antibody binding, was also used in this Example. Specifically, this method analyzed binding of the anti-AXL antibody to a library of AXL sequence variants generated by recombination of AXL sequences derived from species with variable levels of homology with the human AXL sequence (SEQ ID NO: 130) in the extracellular domain. This method was based on the principle that these human AXL-specific antibodies recognize human AXL, but not the AXL from any of the other species used in the example.

So, in one embodiment, the antibody binds to an epitope within the Ig1 domain of AXL, and the antibody binding is dependent on one or more or all of the amino acids corresponding to positions L121 to Q129 or one or more or all of T112 to Q124 of human AXL, wherein the numbering of amino acid residues refers to their respective positions in human AXL (SEQ ID NO: 130). In one embodiment, the antibody binds to an epitope within the Ig1 domain of AXL, and antibody binding is dependent on the amino acids corresponding to positions L121 to Q129 or T112 to Q124 of human AXL. In a preferred embodiment antibody binding is dependent on one or more or all amino acids in position L121, G122, H123, Q124, T125, F126, V127, S128 and Q129, corresponding to the amino acids involved in the binding of the antibody herein designated 107. In one embodiment, antibody binding is dependent on one or more or all amino acid in position T112, G113, Q114, Y115, Q116, C117, L118, V119, F120, L121, G122, H123 and Q124.

In another embodiment, the antibody binds to an epitope within the Ig2 domain of AXL, and antibody binding is dependent on one or more or all of the amino acids corresponding to position D170 or the combination of D179 or one or more or all of the amino acids in positions T182 to R190 of human AXL. In one embodiment antibody binding is dependent on the amino acids in position T182, A183, P183, G184, H185, G186, P187, Q189 and R190.

In another embodiment, the antibody binds to an the FN1 domain of human AXL, and antibody binding is dependent on one or more or all of the amino acids corresponding to positions Q272 to A287 and G297 to P301 of human AXL. In one embodiment, antibody binding is dependent on the amino acids corresponding to positions Q272 to A287 and G297 to P301 of human AXL.

In another embodiment, the antibody binds to the FN2 domain of human AXL and antibody binding is dependent on one or more or all of the amino acids corresponding to positions A359, R386, and Q436 to K439 of human AXL.

In yet another embodiment, the antibody binds to an epitope within the Ig1 domain of AXL, and the epitope comprises or requires one or more or all of the amino acids corresponding to positions L121 to Q129 or one or more or all of T112 to Q124 of human AXL, wherein the numbering of amino acid residues refers to their respective positions in human AXL (SEQ ID NO: 130). In one embodiment, the antibody binds to an epitope within the Ig1 domain of AXL, and the epitope comprises or requires the amino acids corresponding to positions L121 to Q129 or T112 to Q124 of human AXL. In a preferred embodiment the epitope comprises one or more or all amino acid in position L121, G122, H123, Q124, T125, F126, V127, S128 and Q129, corresponding to the amino acids involved in the binding of the antibody herein designated 107. In one embodiment, the epitope comprises one or more or all amino acid in position T112, G113, Q114, Y115, Q116, C117, L118, V119, F120, L121, G122, H123 and Q124.

In another embodiment, the antibody binds to an epitope within the Ig2 domain of AXL, and the epitope comprises or requires one or more or all of the amino acids corresponding to position D170 or the combination of D179 or one or more or all of the amino acids in positions T182 to R190 of human AXL. In one embodiment the epitope comprises or requires the amino acids in position T182, A183, P183, G184, H185, G186, P187, Q189 and R190.

In another embodiment, the antibody binds to an epitope within the FN1 domain of human AXL, which epitope comprises or requires one or more or all of the amino acids corresponding to positions Q272 to A287 and G297 to P301 of human AXL. In one embodiment, the epitope comprises or requires the amino acids corresponding to positions Q272 to A287 and G297 to P301 of human AXL.

In another embodiment, the antibody binds to an epitope within the FN2 domain of human AXL, which epitope comprises or requires one or more or all of the amino acids corresponding to positions A359, R386, and Q436 to K439 of human AXL.

In one embodiment, the antibody binds to an epitope within the FN1-like domain of human AXL.

Antibody-Drug Conjugates (ADCs)

The lyophilized formulations according to any aspect or embodiment of the present invention may comprise an AXL-ADC comprising an anti-AXL antibody according to any embodiment in the previous section, conjugated to a therapeutic moiety, such as a cytotoxic agent, a chemotherapeutic drug, a cytokine, an immunosuppressant, antibiotic, or a radioisotope.

In one embodiment, when conjugated to the drug in question, the anti-AXL antibody can have a pI in the range of about 5 to about 12, such as about 7 to about 10, such as about 8.5 to about 9.5, such as about 8.5 to about 9.0.

In some instances it may be desired to use anti-AXL antibodies which undergo internalization for AXL-ADCs. The term "internalized" or "internalization" as used herein, refers to a biological process in which molecules such as the antibody according to the present invention, are engulfed by the cell membrane and drawn into the interior of the cell. It may also be referred to as "endocytosis".

ADCs are often designed such that the cytotoxic payload is inactive when conjugated to the antibody. Once internalized, the ADC may be delivered to lysosomes in most cases, where effective drug release takes advantage of the catabolic environment found with these organelles. The cytotoxic payload may then be released intracellularly upon internalization of the ADC after binding to the plasma-membrane of cells, or alternatively in response to proteolytic activity in the tumor microenvironment. So, one option is to conjugate the anti-AXL antibody to the therapeutic moiety via a linker which is designed to be cleaved intracellularly.

Specialized linkers have been designed to be cleaved only in a specific microenvironment found in or on the target tumor cell or in the tumor microenvironment. Examples include linkers that are cleaved by acidic conditions, reducing conditions, or specific proteases.

The stability of the antibody-linker-drug in circulation is important because this allows antibody-mediated delivery of the drug to specific target cells. In addition, the long circulating half-life of the ADC provides exposure for several days to weeks post injection. Drugs that are conjugated through non-cleavable linkers and protease-cleavable linkers are generally more stable in circulation than disulfide and hydrazone linkers, although the stability of the latter two linkers can be tuned by altering the neighboring chemical structure.

In one embodiment, the therapeutic moiety is a cytotoxic agent.

A cytotoxin or cytotoxic agent includes any agent that is detrimental to (e.g., kills) cells. Suitable cytotoxic agents for forming ADCs for use in the present invention include taxol, tubulysins, cytochalasin B, gramicidin D, ethidium bromide, emetine, mitomycin, etoposide, tenoposide, vincristine, vinblastine, colchicin, doxorubicin, daunorubicin, dihydroxy anthracin dione, maytansine or an analog or derivative thereof, mitoxantrone, mithramycin, actinomycin D, 1-dehydrotestosterone, glucocorticoids, procaine, tetracaine, lidocaine, propranolol, and puromycin; calicheamicin or analogs or derivatives thereof; antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thiopea, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin; as well as duocarmycin A, duocarmycin SA, CC-1065 (a.k.a. rachelmycin), or analogs or derivatives of CC-1065), dolastatin, auristatin, pyrrolo[2,1-c][1,4] benzodiazepins (PDBs), indolinobenzodiazepine (IGNs) or analogues thereof, antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), anti-mitotic agents (e.g., tubulin-targeting agents), such as diphtheria toxin and related molecules (such as diphtheria A chain and active fragments thereof and hybrid molecules); ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, and enomycin toxins. Other suitable conjugated molecules include antimicrobial/lytic peptides such as CLIP, Magainin 2, mellitin, Cecropin, and P18; ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Therapeutic agents that may be administered in combination with anti-AXL antibodies or antibody-drug conjugates of the present invention as described elsewhere herein, such as, e.g., anti-cancer cytokines or chemokines, are also candidates for therapeutic moieties useful for conjugation to an antibody disclosed in the present invention.

In one embodiment, the cytotoxic agent is linked to said antibody, or fragment thereof, with a cleavable linker, such as N-succinimydyl 4-(2-pyridyldithio)-pentanoate (SSP), maleimidocaproyl-valine-citrulline-p-aminobenzyloxycarbonyl (mc-vc-PAB) or AV-1 K-lock valine-citrulline.

The term "cleavable linker" as used herein, refers to a subset of linkers that are catalyzed by specific proteases in the targeted cell or in the tumor microenvironment, resulting in release of the cytotoxic agent. Examples of cleavable linkers are linkers based on chemical motifs including disulfides, hydrazones or peptides. Another subset of cleavable linker, adds an extra linker motif between the cytotoxic agent and the primary linker, i.e. the site that attaches the linker-drug combination to the antibody. In some embodiments, the extra linker motif is cleavable by a cleavable agent that is present in the intracellular environment (e. g. within a lysosome or endosome or caveola). The linker can be, e. g. a peptidyl linker that is cleaved by an intracellular peptidase or protease enzyme, including but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside the target cells (see e. g. Dubowchik and Walker, 1999, Pharm. Therapeutics 83:67-123). In a specific embodiment, the peptidyl linker cleavable by an intracellular protease is a Val-Cit (valine-citrulline) linker or a Phe-Lys (phenylalanine-lysine) linker (see e.g.

U.S. Pat. No. 6,214,345, which describes the synthesis of doxorubicin with the Val-Cit linker). An advantage of using intracellular proteolytic release of the therapeutic agent is that the agent is typically attenuated when conjugated and the serum stabilities of the conjugates are typically high.

In another embodiment, the cytotoxic agent is linked to said antibody, or fragment thereof, with a non-cleavable linker, such as succinimidyl-4 (N-maleimidomethyl)cyclohexane-1-carboxylate (MCC) or maleimidocaproyl (MC).

The term "non-cleavable linker" as used herein, refers to a subset of linkers which, in contrast to cleavable linkers, do not comprise motifs that are specifically and predictably recognized by intracellular or extracellular proteases. Thus, ADCs based on non-cleavable linkers are not released or cleaved form the antibody until the complete antibody-linker-drug complex is degraded in the lysosomal compartment. Examples of a non-cleavable linker are thioethers. In yet another embodiment, the linker unit is not cleavable and the drug is released by antibody degradation (see US 2005/0238649). Typically, such a linker is not substantially sensitive to the extracellular environment. As used herein, "not substantially sensitive to the extracellular environment" in the context of a linker means that no more than 20%, typically no more than about 15%, more typically no more than about 10%, and even more typically no more than about 5%, no more than about 3%, or no more than about 1% of the linkers, in a sample of antibody drug conjugate compound, are cleaved when the antibody drug conjugate compound is present in an extracellular environment (e.g. plasma). Whether a linker is not substantially sensitive to the extracellular environment can be determined for example by incubating with plasma the antibody drug conjugate compound for a predetermined time period (e.g. 2, 4, 8, 16 or 24 hours) and then quantitating the amount of free drug present in the plasma.

In one embodiment, cytotoxic agent is selected from the group: DNA-targeting agents, e.g. DNA alkylators and cross-linkers, such as calicheamicin, duocarmycin, rachelmycin (CC-1065), pyrrolo[2,1-c][1,4] benzodiazepines (PBDs), and indolinobenzodiazepine (IGN); microtubule-targeting agents, auristatin, such as monomethylauristatin E (MMAE) and monomethylauristatin F (MMAF), dolastatin, maytansine, N (2')-deacetyl-N(2')-(3-mercapto-1-oxopropyl)-maytansine (DM1), and tubulysin; and nucleoside analogs; or an analogs, derivatives, or prodrugs thereof.

In one embodiment, the immunoconjugate comprise a combination of;
  i) the cytotoxic agent and said cleavable linker having bystander kill capacity;
  ii) the cytotoxic agent and said cleavable linker not having bystander kill capacity;
  iii) the cytotoxic agent and said non-cleavable linker having bystander kill capacity; or
  iv) the cytotoxic agent and said non-cleavable linker not having bystander kill capacity.

The term "bystander killing effect", "bystander kill", "bystander kill capacity" or "bystander cytotoxicity" as used herein, refers to the effect where the cytotoxic agent that is conjugated to the antibody by either a cleavable or non-cleavable linker has the capacity to diffuse across cell membranes after the release from the antibody and thereby cause killing of neighboring cells. When the cytotoxic agent is conjugated by a cleavable or non-cleavable linker, it may be either the cytotoxic agent only or the cytotoxic agent with a part of the linker that has the bystander kill capacity. The capacity to diffuse across cell membranes is related to the hydrophobicity of the the cytotoxic agent or the combination of the cytotoxic agent and the linker. Such cytotoxic agents may advantageously be membrane-permeable toxins, such as MMAE that has been released from the antibody by proteases. Especially in tumors with heterogeneous target expression and in solid tumors where antibody penetration may be limited, a bystander killing effect may be desirable.

The term "no bystander kill capacity", "no bystander killing effect", "no-bystander kill" or "no bystander cytotoxicity" as used herein, refers to the effect where the cytotoxic agent that is conjugated to the antibody by either a cleavable or non-cleavable linker does not have the capacity to diffuse across cell membranes after release from the antibody. Thus, such cytotoxic agents or combinations of the cytotoxic agent with the linker, will not be able to kill neighboring cells upon release from the antibody. It is believed without being bound by theory, that such combinations of a cytotoxic agent and either a cleavable or non-cleavable linker will only kill cells expressing the target that the antibody binds.

A stable link between the antibody and cytotoxic agent is an important factor of an ADC. Both cleavable and non-cleavable types of linkers have been proven to be safe in preclinical and clinical trials.

In one embodiment, the cytotoxic agent is chosen from the group of microtubule targeting agents, such as auristatins and maytansinoids.

The term "microtubule-targeting agent" as used herein, refers to an agent or drug which inhibits mitosis (cell division). Microtubules are structures that are essential for proper separation of DNA during cell division, and microtubule function critically depends on 'dynamic instability', i.e. the process in which microtubule structures are continuously elongated and shortened. Microtubule-targeting agents disrupt or stabilize microtubules, which prevents formation of the mitotic spindle, resulting in mitotic arrest and apoptosis. The microtubule-targeting agents can be derived from e.g. natural substances such as plant alkaloids, and prevent cells from undergoing mitosis by disrupting or stabilizing microtubule polymerization, thus preventing formation of the mitotic spindle and subsequent cell division, resulting in inhibition of cancerous growth. Examples of microtubule-targeting agents are paclitaxel, docetaxel, vinblastine, vincristine, vinorelbine, auristatins, maytansanoids, tubulysins, and dolastatin.

In one embodiment, the cytotoxic agent is auristatins or auristatin peptide analogs and derivates [45][46]. Auristatins have been shown to interfere with microtubule dynamics, GTP hydrolysis and nuclear and cellular division and have anti-cancer and anti-fungal activity. The auristatin drug moiety may be attached to the antibody via a linker, through the N (amino) terminus or the C (terminus) of the peptidic drug moiety.

Exemplary auristatin embodiments include the N-terminus-linked monomethyl auristatin drug moieties DE and DF [48].

In a particular embodiment, the cytotoxic agent is monomethyl auristatin E (MMAE);

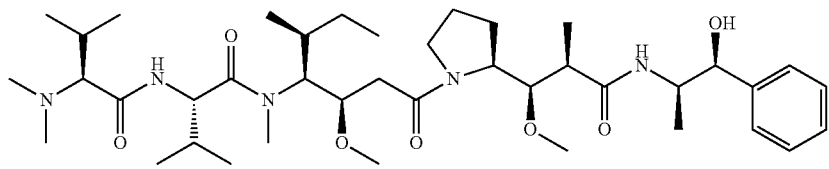 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C)C(C)C]

wherein the antibody is linked to MMAE at the nitrogen (N) on the left-hand side of the chemical structure above by the appropriate linker.

In one embodiment, the cytotoxic agent monomethyl auristatin E (MMAE) is linked to the antibody via a valine-citrulline (VC) linker.

In another embodiment, the cytotoxic agent monomethyl auristatin E (MMAE) is linked to the antibody via a valine-citrulline (VC) linker and the maleimidocaproyl (MC) linker, wherein the combination of the cytotoxic agent and the linkers has the chemical structure;

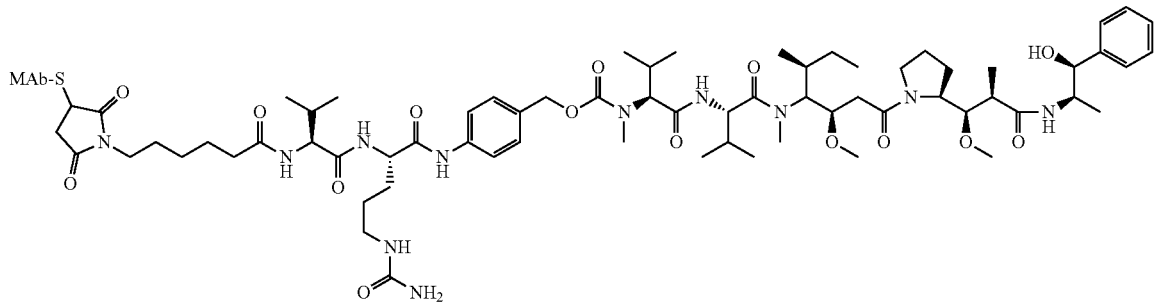

wherein MAb is the antibody.

In one embodiment, the cytotoxic agent is monomethyl auristatin F (MMAF);

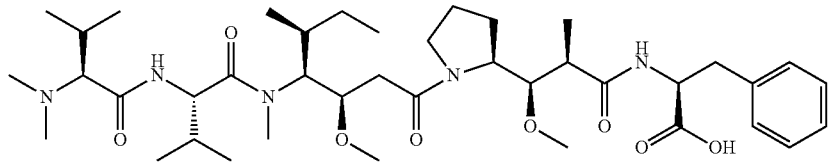 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C)C(C)C]

wherein the antibody is linked to MMAF at the nitrogen (N) on the left-hand side of the chemical structure above by the appropriate linker.

In one embodiment, the cytotoxic agent monomethyl auristatin F (MMAF) is linked to the antibody via a maleimidocaproyl (mc)-linker, wherein the combination of the cytotoxic agent and linker has the chemical structure;

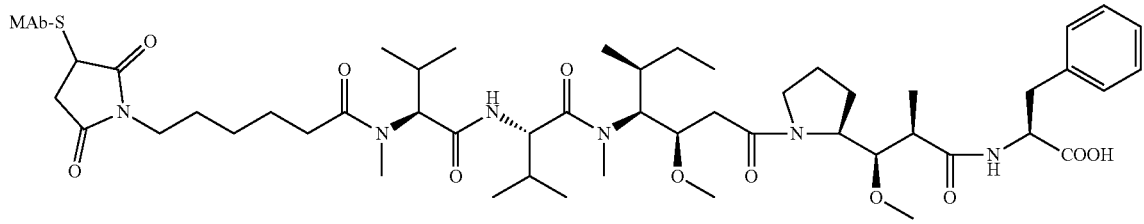

wherein MAb is the antibody.

In another particular embodiment, the cytotoxic agent is a DNA-targeting agent.

The term "DNA-acting agent" as used herein, refers to a specific class of cytotoxic agents which are able to alkylate and/or cross-link DNA. An example of such a DNA-acting agent is IGN agents comprising indolino-benzodiazepinedimers and pyrrolo[2,1-c][1,4] benzodiazepines (PBDs) which are highly potent by virtue of their ability to alkylate and cross-link DNA. Another example is IGN agents comprising indolino-benzodiazepinemonomers which are highly potent by virtue of the ability to alkylate only DNA. Duocarmycins are another class of DNA-acting agents. Duocarmycins are small-molecule, synthetic DNA minor groove binding alkylating agents. These compounds are suitable to target solid tumors as well as hematological tumors.

In one embodiment, the immunoconjugate comprises two to four cytotoxic molecules per antibody. Depending on the chemical properties of the toxin and the linker-toxin combination, two to four cytotoxic molecules per antibody may be superior to more heavily loaded conjugates that are cleared more rapidly from the circulation than less loaded conjugates. The cytotoxic agent loading is represented by p and is the average number of cytotoxic agent moieties per antibody in a molecule (also designated as the drug to antibody ratio, DAR). The cytotoxic agent loading may range from 1 to 20 drug moieties per antibody and may occur on amino acids with useful functional groups such as, but not limited to, amino or sulfhydryl groups, as in lysine or cysteine.

In one embodiment, the number of cytotoxic agents per antibody is from 1 to 8, such as 2 to 7, such as 2 to 6, such as 2 to 5, such as 2 to 4, and such as 2 to 3.

In another embodiment, the immunoconjugate comprises four to eight cytotoxic molecules per antibody. In another embodiment, the immunoconjugate comprises six to ten cytotoxic molecules per antibody. In yet another embodiment, the immunoconjugate comprises 10 to 30, such as 15 to 25, such as 20, cytotoxic molecules per antibody.

Depending on the way of conjugation, the number of cytotoxic molecules per antibody may be limited by the number of attachment sites on the antibody, for example where the attachment is a cysteine thiol or a lysine. Generally, antibodies do not contain many free and reactive cysteine thiol groups which may be linked to a drug moiety as most cysteine thiol residues in antibodies exist as disulfide bridges. Therefore, in those embodiments, where the cytotoxic agent is conjugated via a cysteine thiol, the antibody may be reduced with reducing agent such as dithiothreitol (DTT) or tricarbonylethylphosphine (TCEP), under partial or fully reducing conditions, to generate reactive cysteine thiol groups. In certain embodiments, the drug loading for an ADC of the invention ranges from 1 to about 8, as a maximum of 8 free cysteine thiol groups becomes available after (partial) reduction of the antibody (there are 8 cysteines involved in inter-chain disulfide bonding).

In one embodiment, the drug linker moiety is vcMMAE. The vcMMAE drug linker moiety and conjugation methods are disclosed in [49], [50], [51], and (which are incorporated herein by reference). vcMMAE is formed by conjugation of the linker mc-vc-PAB and the cytotoxic moiety MMAE, and the vcMMAE drug linker moiety is bound to the anti-AXL antibodies at the cysteine residues using a method similar to those disclosed therein.

In one embodiment, the drug linker moiety is mcMMAF. The mcMMAF drug linker moiety and conjugation methods are disclosed in [54], [55], and (which are incorporated herein by reference), and the mcMAF drug linker moiety is bound to the anti-AXL antibodies at the cysteine residues using a method similar to those disclosed therein.

Other linker technologies may be used in the anti-AXL antibody drug conjugates of the invention, such as linkers comprising a hydroxyl group.

In one embodiment, the linker is attached to free cysteine residues of the anti-AXL antibody obtained by (partial) reduction of the anti-AXL antibody.

The VH, VL and CDR sequences of specific anti-AXL antibodies suitable for AXL-ADCs of the lyophilized formulations of the invention are shown in Table 1. In a particular embodiment, the linker is mc-vc-PAB and the cytotoxic agent is MMAE; or the linker SSP and the cytotoxic agent is DM1. In another particular embodiment, the linker is MMC and the cytotoxic agent is DM1; or the linker is MC and the cytotoxic agent is MMAF. The antibody designated 107, optionally in an IgG1, K format (also called "IgG1-HuMax-AXL") is particularly preferred.

In one embodiment, the ADC comprises the linker mc-vc-PAB, the cytotoxic agent MMAE and an anti-AXL antibody according to any aspect or embodiment of the preceding section, such as antibody 107.

Formulations

Therapeutic formulations for the anti-AXL antibodies and ADCs in accordance with the present invention are prepared for storage by formulating an antibody or ADC having the desired degree of purity with optional pharmaceutically acceptable carriers, excipients or stabilizers (Remington's Pharmaceutical Sciences 16th edition, Osol, A. Ed. (1980)), in the form of aqueous or lyophilized formulations. Acceptable carriers, excipients, or stabilizers are nontoxic to recipients at the dosages and concentrations employed.

Generally, the lyophilized and reconstituted formulations of AXL-ADCs comprise an AXL-ADC, a buffering agent, a stabilizing agent (typically a non-reducing sugar), and a bulking agent. Preferred stabilizing agents are sucrose, trehalose and combinations thereof. Preferred bulking agents are mannitol, glycine and combinations thereof.

Generally, the aqueous formulations of anti-AXL antibodies comprise an anti-AXL antibody, a buffering agent, and a stabilizing agent. Preferred stabilizing agents are mannitol, sucrose and trehalose.

The term "buffer" as used herein denotes a pharmaceutically acceptable buffer. Generally, the buffer has a pka and buffering capacity suitable for the pH range of about 5 to about 7, preferably of about 5.5 to 6.5, such as about pH 6 or about pH 6.0. For lyophilized formulations, the buffer components should not crystallize at sub-ambient temperatures at the concentration used. Buffers having a higher collapse temperature are preferred, since it will enable a faster and more robust lyophilization cycle. Suitable pharmaceutically acceptable buffers include, but are not limited to, histidine-buffers, citrate-buffers, succinate-buffers, carbonic acid-buffers, MES buffers, phosphate buffers, TRIS® (tris (hydroxymethyl) aminomethane) buffers and mixtures thereof. Preferred buffers are based on L-histidine, citrate, phosphate, carbonic acid, and/or succinate e, such as histidine and/or citrate, and include also mixtures, e.g., of L-histidine with L-histidine hydrochloride or with TRIS® (tris (hydroxymethyl) aminomethane). Potentially, pH adjustment with an acid or a base known in the art may be needed. The above-mentioned L-histidine, citrate, phosphate, carbonic acid, and/or succinate buffers are generally used in an amount of about 1 mM to about 120 mM, such as from about 5 mM to about 100 mM, preferably of about 10 mM to about 50 mM, more preferably of about 20 mM to about 40 mM, and still more preferably of about 30 mM. Independently from the buffer used, the pH can be adjusted at a value in the range of about 5 to about 7 and preferably about 5.5 to about 6.5 and most preferably about 6 or about 6.0 by adjustment with an acid or base known in the art or by using adequate mixtures of buffer components or both. Optionally, the pH can be adjusted to within the desired range or to the desired value when also other ingredients, e.g., bulking agents stabilizing agents, or both, are present in the buffer. Preferably, the buffer comprises a histidine and/or citrate buffer at a concentration of about 10 mM to about 50 mM, such as a histidine buffer at a concentration of about 30 mM.

The formulation of the invention can further comprise one or more pharmaceutically acceptable stabilizers as defined hereinabove and ingredients also known in the art as "lyoprotectants" such as sugars, sugar alcohols, amino sugars, amino acids and dextrans as known in the art. Typically, pharmaceutically acceptable stabilizer can be used in an amount of about 1 mM to about 500 mM. Suitable sugars comprise but are not limited to monosaccharides and disaccharides. Non-limiting examples of sugars and sugar alcohols for use according to the invention include trehalose, sucrose, mannitol, sorbitol, mannose, maltose, galactose, fructose, sorbose, raffinose, glucosamine, N-methylglucosamine (also referred to as "meglumine"), galactosamine and neuraminic acid and combinations thereof. Preferred are non-reducing sugars and sugar alcohols, such as sucrose or trehalose, at concentrations of about 15 mM to about 200 mM, such as about 30 mm to 150 mM or about 15 to about 120 mM, such as about 20 mM to about 100 mM, such as about 30 mM to about 90 mM or about 80 mM to about 100 mM, such as about 70 mM to about 90 mM, such as about 84 mM to 92 mM. Most preferred is sucrose.

In one embodiment, the formulation comprises one or more non-reducing sugars, such as sucrose, trehalose or a combination thereof, at a total concentration of about 5% (w/v) or less, such as from about 0.5% (w/v) to about 4% (w/v), such as from about 1% (w/v) to about 3% (v/w), such as about 2.5% to about 3.5% (w/v), such as about 3% (w/v).

In one embodiment the formulation comprises 84 mM to 92 mM sucrose, such as 85 mM, 86 mM, 87 mM, 88 mM, 89 mM, 90 mM, 91 mM or 92 mM sucrose. Most preferred the formulation comprises 88 mM sucrose.

Particularly, sugar alcohols such as mannitol may also be used as bulking agent to produce a homogeneous and stable lyophilization cake, which can be reconstituted within an acceptable time, more specifically within 0-600 seconds. In general, a "bulking agent" is used when the total amount of API is too small to provide adequate structure to the cake. Bulking agents should provide an inert matrix which gives a pharmaceutically elegant cake. The bulking agent also modifies the thermal characteristics of a formulation. The concentration of the active drug is often so low that the freeze-drying characteristics of the system are due solely to the bulking agent. Common bulking agents are including mannitol, glycine as crystalline bulking agents; sucrose, trehalose, gelatin, dextran as amorphous bulking agents. Preferred bulking agents are mannitol and glycine, and combinations thereof.

In one embodiment, the formulation comprises one or more bulking agents, such as mannitol, glycine or a combination thereof, at a total concentration of about 10% or less, such as about 7% or less, such as about 5% (w/v) or less, such as from about 1% (w/v) to about 5% (w/v), such as about 2% (w/v) to about 4% (w/v), such as from about 2.5 (w/v) to about 3.5% (w/v), such as about 3%.

In one embodiment, particularly for AXL-ADCs, the formulation comprises a bulking agent such as mannitol at a concentration of about 50 mM to about 300 mM, such as from about 100 mM to about 225 mM, such as from about 150 mM to about 180 mM, such as about 165 mM.

In one embodiment, particularly for AXL-ADCs, the formulation comprises from about 100 mM to about 225 mM mannitol, such as 160 mM, or 162 mM, or 165 mM, or 170 mM, or 180 mM, or 200 mM mannitol. Most preferred it comprises about 165 mM mannitol, or 165 mM mannitol.

In one embodiment, particularly for anti-AXL antibodies, the formulation comprises from about 20 mM to about 400 mM, such as from about 30 mM to about 300 mM, such as from about 40 mM to about 80 mM, such as about 50 mM to about 60 mM, such as about 55 mM mannitol.

Certain lyophilized formulations according to the invention are designed so that it is possible to exclude surfactants. However, as a person skilled in the art can appreciate, while not necessary for preserving stability of the anti-AXL antibody or ADCs, for some purposes it may nonetheless be desirable to include a surfactant. Suitable pharmaceutically acceptable surfactants comprise but are not limited to polyethylen-sorbitan-fatty acid esters, polyethylene-polypropylene glycols, polyoxyethylene-stearates and sodium dodecyl sulphates. Polyethylen-sorbitan-fatty acid esters include polyethylen (20)-sorbitan-esters (synonym to polysorbate 20, sold under the trademark™ Tween 20™ and polyoxyethylene (20) sorbitanmonooleate (synonym to polysorbate 80 sold under the trademark Tween 80 ™). Polyethylenepolypropylene glycols are those sold under the names Pluronic (R) F68 or Poloxamer 188 ™. Polyoxyethylene-stearates are sold under the trademark Myrj™. Polyoxyethylene monolauryl ether are those sold under the trademark Brij™. When desirable, polyethylen-sorbitan-polyethylen (20)-sorbitan-esters (Tween 20 ™) and polyoxyethylene (20) sorbitanmonooleate (Tween 80 ™) can be used, e.g., in an amount of about 0.01% to about 0.06%, such as about 0.02% to about 0.04%.

Certain lyophilized formulations according to the invention are designed so that it is possible to exclude inorganic salts such as sodium chloride (NaCl), often used as isotonicity agent, from the pre-lyophilization liquid and lyophilized formulation. Other examples of salts include salts of any combinations of the cations sodium potassium, calcium or magnesium with anions chloride, phosphate, citrate, succinate, sulphate or mixtures thereof. However, as a person of skill in the art can appreciate, for some purposes it may nonetheless be desirable to include an inorganic salts, e.g., for reconstitution of the lyophilized formulation, i.e., as a diluent as described below.

The formulation of the invention can further comprise one or more of the following ingredients: antioxidants, ascorbic acid, glutathione, preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); cyclodextrin, e.g. hydroxypropyl--cyclodextrin, sulfobutylethyl--cyclodextrin, [beta]-cyclodextrin, polyethyleneglycol, e.g. PEG 3000, 3350, 4000, or 6000; low molecular weight (less than about 10 residues) polypeptides; proteins, such as serum albumin, gelatin, or immunoglobulins; chelating agents such as EDTA; salt-forming counterions such as sodium;

and metal complexes (e.g. Zn-protein complexes).

Process

Freeze drying generally contains three main steps: freezing, primary drying, and secondary drying. The first stage is for the product to be frozen at a temperature lower than eutectic or glass transition temperature of the product. Rate of freezing affects size of water crystals and subsequent rate of drying. The second stage is primary drying, which removes the solvent (ice) water. It is important that product temperature remains below the collapse temperature and all ice/water is sublimed. The third stage is secondary drying which removes "bound" water or water from solute, during which the shelf temperature often is raised higher than 40° C. to accelerate desorption process. Lyophilization methods suitable for antibody- and other protein or protein conjugate formulations are well-known by a person the skilled in the art and are described in, e.g. "Lyophilization of Biopharmaceuticals" by Henry R. Costantino and Michael J. Pikal; "Freeze Drying/Lyophilization of Pharmaceuticals and Biological Products" by Louis Rey and Joan C. May. A non-limiting example of a lyophilization process is described in Example 10.

Use

In another aspect the invention provides an AXL-ADC formulation as defined in any of aspects or embodiments herein for use in the treatment of cancer. Exemplary cancers include, but are not limited to, colorectal cancer, such as colorectal carcinoma and colorectal adenocarcinoma, bladder cancer, bone cancer such as chondrosarcoma, breast cancer such as triple-negative breast cancer, cancers of the central nervous system such as glioblastoma, astrocytoma, neuroblastoma, cervical cancer, connective tissue cancer, endometrium cancer, fibroblast cancer, gastric cancer such as gastric carcinoma, head and neck cancer, kidney cancer, liver cancer such as hepatocellular carcinoma, lung cancer such as NSCLC and lung squamous cell carcinoma, muscle cancer, neural tissue cancer, ovarian cancer, pancreatic cancer such as pancreatic ductal carcinoma and pancreatic adenocarcinoma, skin cancer such as malignant melanoma and soft tissue sarcoma.

Prior to administration to a subject, a lyophilized formulation of the invention comprising a therapeutically effective amount of ADC is dissolved, i.e., reconstituted, into a pharmaceutically acceptable diluent. Exemplary, non-limiting diluents include sterile pharmaceutical grade water (water for injection, WFI) or saline, bacteriostatic water for injection (BWFI), a pH buffered solution (e.g. phosphate-buffered saline), Ringer's solution and dextrose solution. For example, a lyophilized formulation of the invention can be reconstituted in water, pH buffered solution (e.g. phosphate-buffered saline), Ringer's solution and dextrose solution. For example, a lyophilized formulation of the invention can be reconstituted in sterile water for injection (WFI) to a concentration of about 5 to about 30 mg/ml AXL-ADC, such as about 7 to about 20 mg/mL ADC, such as about 8 to 15 mg/ml ADC, such as about 9 to about 11 mg/mL ADC, such as about 10 mg/mL ADC. The concentrate may optionally be further diluted for, e.g., infusion into a pH buffered solution (e.g. phosphate-buffered saline, Ringer's solution and/or dextrose solution) to a concentration of about 0.05 mg/ml to 30 mg/mL ADC, such as, e.g., 0.12 mg/ml to 2.40 mg/mL ADC.

Typically, the reconstituted formulation of the present invention is suitable for parenteral administration. The phrases "parenteral administration" and "administered parentally" as used herein means modes of administration other than enteral and topical administration, usually by injection or infusion, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. In one embodiment the pharmaceutical composition is administered by intravenous or subcutaneous injection or infusion, e.g., by reconstituting the lyophilized formulation in sterile water or saline and held in IV bags or syringes before administration to a subject.

The invention also provides for a kit comprising the lyophilized formulation of an AXL-ADC according to the invention, typically in a hermetically sealed container such as a vial, an ampoule or sachette, indicating the quantity of the active agent. Where the pharmaceutical is administered by injection, an ampoule of sterile water for injection or saline can be, for example, provided, optionally as part of the kit, so that the ingredients can be mixed prior to administration. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

TABLE 1

Amino acid sequences of antibody VHs, VLs and CDRs, as well as of AXL. The CDR sequences are indicated in bold, underlined text in the variable region sequences.

| SEQ ID NO: | Name | Amino acid sequence | Comments |
|---|---|---|---|
| SEQ ID NO: 1 | 107 VH | EVQLLESGGGLVQPGGSLRLSCAASGFTFSSYAMNWV RQAPGKGLEWVSTTSGSGASTYYADSVKGRFTISRDNS KNTLYLQMNSLRAEDTAVYYCAKIWIAFDIWGQGTMV TVSS | HCo12-BalbC Ig1 domain binding Ab |
| SEQ ID NO: 2 | 107 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGSSPYTFGQGTKLEIK | |
| SEQ ID NO: 3 | 140 VH | EVQLLESGGGLVQPGGSLRLSCAASGFTFSSYAMTWVR QAPGKGLEWVSAISISGASTFYADSVKGRFTISRDNSKN TLSLQMNSLRAEDTAVYFCRGYSGYVYDAFDIWGQGT MVTVSS | |

TABLE 1-continued

Amino acid sequences of antibody VHs, VLs and CDRs, as well as of AXL. The CDR sequences are indicated in bold, underlined text in the variable region sequences.

| SEQ ID NO: | Name | Amino acid sequence | Comments |
|---|---|---|---|
| SEQ ID NO: 4 | 140 VL | DIQMTQSPSSLSASVGDRVTITCRASQGISNWLAWYQQKPEKAPKSLIYAASSLQSGVPSRFSGSGSGTDFTLTISSLQPEDFATYYCQQYNSYPLTFGGGTKVEIK | |
| SEQ ID NO: 5 | 148 VH | EVQLLESGGGLVQPGGSLRLSCAASGFTFSSYAMTWVRQAPGKGLEWVSAISISGGSTFYADSVKGRFTISRDNSKNTLYLQMNSLRAEDTAVYYCRGYSGYVYDAFDFWGQGTMVTVSS | HCo12-BalbC Ig2 domain binding Ab |
| SEQ ID NO: 6 | 148 VL | DIQMTQSPSSLSASVGDRVTITCRASQGISNWLAWYQQKPEKAPKSLIYAASSLQSGVPSRFSGSGSGTDFTLTISSLQPEDFATYYCQQYNSYPLTFGGGTKVEIK | |
| SEQ ID NO: 7 | 154 VH | EVQLLDSGGGLVQPGGSLRLSCAASGFTFSSYAMSWVRQAPGKGLEWVSAISIGGGNAYYADSVKGRFTISRDNSKNTLYLQMNSLRAADTAVYYCAKPGFIMVRGPLDYWGQGALVTVSS | HCo12-BalbC FN1 domain binding Ab |
| SEQ ID NO: 8 | 154-M103L VH | EVQLLDSGGGLVQPGGSLRLSCAASGFTFSSYAMSWVRQAPGKGLEWVSAISIGGGNAYYADSVKGRFTISRDNSKNTLYLQMNSLRAADTAVYYCAKPGFILVRGPLDYWGQGALVTVSS | |
| SEQ ID NO: 9 | 154 VL | EIVLTQSPGTLSLSPGERATLSCRASQSVSNSYLAWYQQKPGQAPRLLIYGASSRATGIPDRFSGSGSGTDFTLTISRLEPEDFAVYYCQQYGSSPYTFGQGTKLEIK | |
| SEQ ID NO: 10 | 171 VH | EVQLLESGGGLVQPGGSLRLSCAASGFTFSSYAMSWVRQAPGKGLEWVSDISVSGGSTYYADSVKGRFTISRDNSKNTLYLQMNSLRAEDTAVYYCAKEGYIWFGESLSYAFDIWGQGTMVTVSS | HCo17-BalbC Ig2 domain binding Ab |
| SEQ ID NO: 11 | 171 VL | EIVLTQSPGTLSLSPGERATLSCRASQSVSSSYLAWYQQKPGQAPRLLIYGASSRATGIPDRFSGSGSGTDFTLTISRLEPEDFAVYYCQQYGRSFTFGPGTKVDIK | |
| SEQ ID NO: 12 | 172 VH | EVQLLESGGGLVQPGGSLRLSCAASGFTFSNYAMSWVRQAPGKGLEWVSDISVSGGSTYYADSVKGRFTISRDNSKNTLYLQMNSLRAEDTAVYYCAKEGYIWFGESLSYAFDIWGQGTMVTVSS | |
| SEQ ID NO: 13 | 172 VL | EIVLTQSPGTLSLSPGERATLSCRASQSVSSSYLAWYQQKPGQAPRLLIYGASSRATGIPDRFSGSGSGTDFTLTISRLEPEDFAVYYCQQYGRSFTFGPGTKVDIK | |
| SEQ ID NO: 14 | 181 VH | EVQLLESGGGLVQPGGSLRLSCAASGFTFSSYAMSWVRQAPGKGLEWVSDISVSGGSTYYADSVKGRFTISRDNSKNTLYLHMNSLRAEDTAVYYCAKEGYIWFGESLSYAFDIWGQGTMVTVSS | |
| SEQ ID NO: 15 | 181 VH | EIVLTQSPGTLSLSPGERATLSCRASQSVSSSYLAWYQQKPGQAPRLLIYGASSRATGIPDRFSGSGSGTDFTLTISRLEPEDFAVYYCQQYGRSFTFGPGTKVDIK | |
| SEQ ID NO: 16 | 183 VH | QVQLQQWGAGLLKPSETLSLTCAVYGGSFSGYYWSWIRQPPGKGLEWIGEINQSGSTNYNPSLKSRVTISVDTSKNQFSLKLSSVTAADTSVYYCASGNWDHFFDYWGQGTLVTVSS | HCo17-BalbC FN1 domain binding Ab |
| SEQ ID NO: 17 | 183-N52Q VH | QVQLQQWGAGLLKPSETLSLTCAVYGGSFSGYYWSWIRQPPGKGLEWIGEIQQSGSTNYNPSLKSRVTISVDTSKNQFSLKLSSVTAADTSVYYCASGNWDHFFDYWGQGTLVTVSS | |
| SEQ ID NO: 18 | 183 VL | DIQMTQSPSSVSASVGDRVTITCRASQGISSWLAWYQHKPGKAPKLLIYATSSLQSGVTSRFSGSGSGTDFTLTISSLQPEDFATYYCQQAKSFPWTFGQGTKVEIK | |
| SEQ ID NO: 19 | 187 VH | QVPLQQWGAGLLKPSETLSLTCAVYGGSFSGYHWSWIRQPPGKGLEWIGEISHSGRTNYNPSLKSRVTISIDTSKNQFSLKLSSVTAADTAVYYCASFITMIRGTIITHFDYWGQGTLVTVSS | |

TABLE 1-continued

Amino acid sequences of antibody VHs, VLs and CDRs, as well as of AXL. The CDR sequences are indicated in bold, underlined text in the variable region sequences.

| SEQ ID NO: | Name | Amino acid sequence | Comments |
|---|---|---|---|
| SEQ ID NO: 20 | 187 VL | DIQMTQSPSSLSASVGDRVTITCRASQGISSWLAWYQQ KPEKAPKSLIYAASSLQSGVPSRFSGSGSGTDFTLTISSLQ PEDFATYYCQQYHSYPYTFGQGTKLEIK | |
| SEQ ID NO: 21 | 608-01 VH | QVQLVQSGAEVKKPGSSVKVSCKASGGTFSSYAISWVR QAPGQGLEWMGRIIPIFGIANYVQKFQGRVTITADKST STAYMELSSLRAEDTAVYYCARRGDYYGSGSPDVFDIW GQGTMVTVSS | |
| SEQ ID NO: 22 | 608-01 VL | EIVLTQSPGTLSLSPGRATLSCRASQSVSSSYLAWYQQ KPGQAPRLLIYGASSRATGIPDRFSGSGSGTDFTLTISRLE PEDFAVYYCQQYGSSYTFGQGTKLEIK | |
| SEQ ID NO: 23 | 610-01 VH | QVQLVQSGAEVKKPGSSVKVSCKASGGTFSSYAISWVR QAPGQGLEWMGRIIPIFGIANYVQKFQGRVTITADKST STAYMELSSLRAEDTAVYYCARRGNYYGSGSPDVFDIW GQGTMVTVSS | |
| SEQ ID NO: 24 | 610-01 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGSSYTFGQGTKLEIK | |
| SEQ ID NO: 25 | 613 VH | QVQLVQSGAEVKKPGSSVKVSCKASGGTFSSYAINWM RQAPGQGLEWMGRIIPIFGIVNYAQKFQGRVTLTADKS TSTAYMELSSLRSEDTAVYYCARRGNYYGSGSPDVFDI WGQGTMVTVSS | HCo20 Ig1 domain binding Ab |
| SEQ ID NO: 26 | 613 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGSSYTFGQGTKLEIK | |
| SEQ ID NO: 27 | 613-08 VH | QVQLVQSGAEVKKPGSSVKVSCKASGGTFSSYAINWM RQAPGQGLEWMGRIIPIFGIVNYAQKFQGRVTLTADKS TSTAYMELSSLRSEDTAVYYCARRGNYYGSGSPDVFDI WGQGTMVTVSS | |
| SEQ ID NO: 28 | 613-08 VL | EIVLTQSPATLSLSPGERATLSCRASQSVSSYLAWYQQK PGQAPRLLIYDASNRATGIPARFSGSGSGTDFTLTISSLEP EDFAVYYCQQRSNWLTFGGGTKVEIK | |
| SEQ ID NO: 29 | 620-06 VH | QVQLVQSGAEVKKPGSSVKVSCKASGGTFSSYAISWVR QAPGQGLEWMGRIIPIFGIANYAQKFQGRVTITADKST STAYMELSSLRSEDTAVYYCARRGNYYGSGSPDVFDIW GQGTMVTVSS | |
| SEQ ID NO: 30 | 620-06 VL | EIVLTQSPGTLSLSPGERATLSCRASQSVSSSYLAWYQQ KPGQAPRLLIYGASSRATGIPDRFSGSGSGTDFTLTISRLE PEDFAVYYCQQYGSSYTFGQGTKLEIK | |
| SEQ ID NO: 31 | 726 VH | QVQLQQWGAGLLKPSETLSLTCAIDGGSFSGYYWSWIR QPPGKGLEWIGEISHSGRTNYNPSLKSRVTISIDTSKNQF SLKLSSVAAADTAVYYCARFITMIRGAIITHFDYWGQGA LVTVSS | HCo17-BalbC FN2 domain binding Ab |
| SEQ ID NO: 32 | 726-M 101L VH | QVQLQQWGAGLLKPSETLSLTCAIDGGSFSGYYWSWIR QPPGKGLEWIGEISHSGRTNYNPSLKSRVTISIDTSKNQF SLKLSSVAAADTAVYYCARFITLIRGAIITHFDYWGQGAL VTVSS | |
| SEQ ID NO: 33 | 726 VL | DIQMTQSPSSLSASVGDRVTITCRASQGISSWLAWYQQ KPEKAPKSLIYAASSLQSGVPSRFSGSGSGTDFTLTISSLQ PEDFATYYCQQYHSYPYTFGQGTKLEIK | |
| SEQ ID NO: 34 | 733 VH | QVQLVESGGGVVQPGRSLRLSCAASGFSFSTYAMHWV RQAPGKGLEWVAISYDGDNKYSADSVKGRFTISRDNS KNTLYLQMNSLRAEDTAVYYCARGKLGIDAFDIWGQ GTMVTVSS | HCo17-BalbC FN1 domain binding Ab |
| SEQ ID NO: 35 | 733 VL | AIQLTQSPSSLSASVGDRVTITCRASQGISSALAWYQQK PGKAPKLLIYDASSLESGVPSRFSGSGSGTDFTLTISGLQP EDFATYYCQQFNSYPFTFGPGTKVDIK | |
| SEQ ID NO: 36 | 107 VH CDR1 | GFTFSSYA | |
| SEQ ID NO: 37 | 107 VH CDR2 | TSGSGAST | |

TABLE 1-continued

Amino acid sequences of antibody VHs, VLs and CDRs, as well as of AXL. The CDR sequences are indicated in bold, underlined text in the variable region sequences.

| SEQ ID NO: | Name | Amino acid sequence | Comments |
| --- | --- | --- | --- |
| SEQ ID NO: 38 | 107 VH CDR3 | AKIWIAFDI | |
| SEQ ID NO: 39 | 107 VL CDR1 | QSVSSSY | |
| | 107 VL CDR2 | GAS | |
| SEQ ID NO: 40 | 107 VL CDR3 | QQYGSSPYT | |
| SEQ ID NO: 41 | 140 VH CDR1 | GFTFSSYA | |
| SEQ ID NO: 42 | 140 VH CDR2 | ISISGAST | |
| SEQ ID NO: 43 | 140 VH CDR3 | RGYSGYVYDAFDI | |
| SEQ ID NO: 44 | 140 VL CDR1 | QGISNW | |
| | 140 VL CDR2 | AAS | |
| SEQ ID NO: 45 | 140 VL CDR3 | QQYNSYPLT | |
| SEQ ID NO: 46 | 148 VH CDR1 | GFTFSSYA | |
| SEQ ID NO: 47 | 148 VH CDR2 | ISISGGST | |
| SEQ ID NO: 48 | 148 VH CDR3 | RGYSGYVYDAFDF | |
| SEQ ID NO: 49 | 148 VL CDR1 | QGISNW | |
| | 148 VL CDR2 | AAS | |
| SEQ ID NO: 50 | 148 VL CDR3 | QQYNSYPLT | |
| SEQ ID NO: 51 | 154 VH CDR1 | GFTFSSYA | |
| SEQ ID NO: 52 | 154 VH CDR2 | ISIGGGNA | |
| SEQ ID NO: 53 | 154 VH CDR3 | AKPGFIMVRGPLDY | |
| SEQ ID NO: 54 | 154-M103L VH CDR3 | AKPGFILVRGPLDY | |
| SEQ ID NO: 55 | 154 VL CDR1 | QSVSNSY | |
| | 154 VL CDR2 | GAS | |
| SEQ ID NO: 56 | 154 VL CDR3 | QQYGSSPYT | |
| SEQ ID NO: 57 | 171 VH CDR1 | GFTFSSYA | |
| SEQ ID NO: 58 | 171 VH CDR2 | ISVSGGST | |
| SEQ ID NO: 59 | 171 VH CDR3 | AKEGYIWFGESLSYAFDI | |
| SEQ ID NO: 60 | 171 VL CDR1 | QSVSSSY | |
| | 171 VL CDR2 | GAS | |
| SEQ ID NO: 61 | 171 VL CDR3 | QQYGRSFT | |
| SEQ ID NO: 62 | 172 VH CDR1 | GFTFSNYA | |
| SEQ ID NO: 63 | 172 VH CDR2 | ISVSGGST | |
| SEQ ID NO: 64 | 172 VH CDR3 | AKEGYIWFGESLSYAFDI | |
| SEQ ID NO: 65 | 172 VL CDR1 | QSVSSSY | |
| | 172 VL CDR2 | GAS | |
| SEQ ID NO: 66 | 172 VL CDR3 | QQYGRSFT | |
| SEQ ID NO: 67 | 181 VH CDR1 | GFTFSSYA | |
| SEQ ID NO: 68 | 181 VH CDR2 | ISVSGGST | |

TABLE 1-continued

Amino acid sequences of antibody VHs, VLs and CDRs, as well as of AXL. The CDR sequences are indicated in bold, underlined text in the variable region sequences.

| SEQ ID NO: | Name | Amino acid sequence | Comments |
|---|---|---|---|
| SEQ ID NO: 69 | 181 VH CDR3 | AKEGYIWFGESLSYAFDI | |
| SEQ ID NO: 70 | 181 VL CDR1 | QSVSSSY | |
| | 181 VL CDR2 | GAS | |
| SEQ ID NO: 71 | 181 VL CDR3 | QQYGRSFT | |
| SEQ ID NO: 72 | 183 VH CDR1 | GGSFSGYY | |
| SEQ ID NO: 73 | 183 VH CDR2 | INQSGST | |
| SEQ ID NO: 74 | 183-N52Q VH CDR2 | IQQSGST | |
| SEQ ID NO: 75 | 183 VH CDR3 | ASGNWDHFFDY | |
| SEQ ID NO: 76 | 183 VL CDR1 | QGISSW | |
| | 183 VL CDR2 | ATS | |
| SEQ ID NO: 77 | 183 VL CDR3 | QQAKSFPWT | |
| SEQ ID NO: 78 | 187 VH CDR1 | GGSFSGYH | |
| SEQ ID NO: 79 | 187 VH CDR2 | ISHSGRT | |
| SEQ ID NO: 80 | 187 VH CDR3 | ASFITMIRGTIITHFDY | |
| SEQ ID NO: 81 | 187 VL CDR1 | QGISSW | |
| | 187 VL CDR2 | AAS | |
| SEQ ID NO: 82 | 187 VL CDR3 | QQYHSYPYT | |
| SEQ ID NO: 83 | 608-01 VH CDR1 | GGTFSSYA | |
| SEQ ID NO: 84 | 608-01 VH CDR2 | IIPIFGIA | |
| SEQ ID NO: 85 | 608-01 VH CDR3 | ARRGDYYGSGSPDVFDI | |
| SEQ ID NO: 86 | 608-01 VL CDR1 | QSVSSSY | |
| | 608-01 VL CDR2 | GAS | |
| SEQ ID NO: 87 | 608-01 VL CDR3 | QQYGSSYT | |
| SEQ ID NO: 88 | 610-01 VH CDR1 | GGTFSSYA | |
| SEQ ID NO: 89 | 610-01 VH CDR2 | IIPIFGIA | |
| SEQ ID NO: 90 | 610-01 VH CDR3 | ARRGNYYGSGSPDVFDI | |
| SEQ ID NO: 91 | 610-01 VL CDR1 | QSVSSSY | |
| | 610-01 VL CDR2 | GAS | |
| SEQ ID NO: 92 | 610-01 VL CDR3 | QQYGSSYT | |
| SEQ ID NO: 93 | 613 VH CDR1 | GGTFSSYA | |
| SEQ ID NO: 94 | 613 VH CDR2 | IIPIFGIV | |
| SEQ ID NO: 95 | 613 VH CDR3 | ARRGNYYGSGSPDVFDI | |
| SEQ ID NO: 96 | 613 VL CDR1 | QSVSSSY | |
| | 613 VL CDR2 | GAS | |
| SEQ ID NO: 97 | 613 VL CDR3 | QQYGSSYT | |
| SEQ ID NO: 98 | 613-08 VH CDR1 | GGTFSSYA | |
| SEQ ID NO: 99 | 613-08 VH CDR2 | IIPIFGIV | |

TABLE 1-continued

Amino acid sequences of antibody VHs, VLs and CDRs, as well as of AXL. The CDR sequences are indicated in bold, underlined text in the variable region sequences.

| SEQ ID NO: | Name | Amino acid sequence | Comments |
|---|---|---|---|
| SEQ ID NO: 100 | 613-08 VH CDR3 | ARRGNYYGSGSPDVFDI | |
| SEQ ID NO: 101 | 613-08 VL CDR1 | QSVSSY | |
| | 613-08 VL CDR2 | DAS | |
| SEQ ID NO: 102 | 613-08 VL CDR3 | QQRSNWLT | |
| SEQ ID NO: 103 | 620-06 VH CDR1 | GGTFSSYA | |
| SEQ ID NO: 104 | 620-06 VH CDR2 | IIPIFGIA | |
| SEQ ID NO: 105 | 620-06 VH CDR3 | ARRGNYYGSGSPDVFDI | |
| SEQ ID NO: 106 | 620-06 VL CDR1 | QSVSSSY | |
| | 620-06 VL CDR2 | GAS | |
| SEQ ID NO: 107 | 620-06 VL CDR3 | QQYGSSYT | |
| SEQ ID NO: 108 | 726 VH CDR1 | GGSFSGYY | |
| SEQ ID NO: 109 | 726 VH CDR2 | ISHSGRT | |
| SEQ ID NO: 110 | 726 VH CDR3 | ARFITMIRGAIITHFDY | |
| SEQ ID NO: 111 | 726-M101L VH CDR3 | ARFITLIRGAIITHFDY | |
| SEQ ID NO: 112 | 726 VL CDR1 | QGISSW | |
| | 726 VL CDR2 | AAS | |
| SEQ ID NO: 113 | 726 VL CDR3 | QQYHSYPYT | |
| SEQ ID NO: 114 | 733 VH CDR1 | GFSFSTYA | |
| SEQ ID NO: 115 | 733 VH CDR2 | ISYDGDNK | |
| SEQ ID NO: 116 | 733 VH CDR3 | ARGRKLGIDAFDI | |
| SEQ ID NO: 117 | 733 VL CDR1 | QGISSA | |
| | 733 VL CDR2 | DAS | |
| SEQ ID NO: 118 | 733 VL CDR3 | QQFNSYPFT | |
| SEQ ID NO: 119 | Ig2 domain VH CDR2 | ISISGXST-wherein X is A or G | |
| SEQ ID NO: 120 | Ig2 domain VH CDR3 | RGYSGYVYDAFDX-wherein X is I or F | |
| SEQ ID NO: 121 | FN2 domain VH CDR1 | GGSFSGYX-wherein X is H or Y | |
| SEQ ID NO: 122 | FN2 domain VH CDR3 | AX1FITMIRGX2IITHFDY-wherein X1 is S or R; and X2 is T or A | |
| SEQ ID NO: 123 | FN1 domain VH CDR1 | GFTFSXYA-wherein X is S or N | |
| SEQ ID NO: 124 | FN1 domain VH CDR2 | ISVSGGST | |
| SEQ ID NO: 125 | FN1 domain VH CDR3 | AKEGYIWFGESLSYAFDI | |
| SEQ ID NO: 126 | Ig1 domain VH CDR2 | IIPIFGIX-wherein X is A or V | |
| SEQ ID NO: 127 | Ig1 domain VH CDR3 | ARRGXYYGSGSPDVFDI-wherein Xis D or N | |

TABLE 1-continued

Amino acid sequences of antibody VHs, VLs and CDRs, as well as of AXL. The CDR sequences are indicated in bold, underlined text in the variable region sequences.

| SEQ ID NO: | Name | Amino acid sequence | Comments |
| --- | --- | --- | --- |
| SEQ ID NO: 128 | Ig1 domain VL CDR1 | QSVXSSY-wherein X is S or del | |
| | Ig1 domain VL CDR2 | XAS-wherein X is D or G | |
| SEQ ID NO: 129 | Ig1 domain VL CDR3 | QQX1X2X3X4X5T-wherein X1 is R or Y; X2 is S or G; X3 is N or S; X4 is W or S; and X5 is L or Y | |
| SEQ ID NO: 130 | Human AXL protein (Swissprot P30530) | MAWRCPRMGRVPLAWCLALCGWACMAPRGTQAEES PFVGNPGNITGARGLTGTLRCQLQVQGEPPEVHWLRD GQILELADSTQTQVPLGEDEQDDWIVVSQLRITSLQLSD TGQYQCLVFLGHQTFVSQPGYVGLEGLPYFLEEPEDRTV AANTPFNLSCQAQGPPEPVDLLWLQDAVPLATAPGHG PQRSLHVPGLNKTSSFSCEAHNAKGVTTSRTATITVLPQ QPRNLHLVSRQPTELEVAWTPGLSGIYPLTHCTLQAVLS DDGMGIQAGEPDPPEEPLTSQASVPPHQLRLGSLHPHT PYHIRVACTSSQGPSSWTHWLPVETPEGVPLGPPENISA TRNGSQAFVHWQEPRAPLQGTLLGYRLAYQGQDTPEV LMDIGLRQEVTLELQGDGSVSNLTVCVAAYTAAGDGP WSLPVPLEAWRPGQAQPVHQLVKEPSTPAFSWPWWY VLLGAVVAAACVLILALFLVHRRKKETRYGEVFEPTVERG ELVVRYRVRKSYSRRTTEATLNSLGISEELKEKLRDVMVD RHKVALGKTLGEGEFGAVMEGQLNQDDSILKVAVKTM KIAICTRSELEDFLSEAVCMKEFDHPNVMRLIGVCFQGS ERESFPAPVVILPFMKHGDLHSFLLYSRLGDQPVYLPTQ MLVKFMADIASGMEYLSTKRFIHRDLAARNCMLNENM SVCVADFGLSKKIYNGDYYRQGRIAKMPVKWIAIESLAD RVYTSKSDVWSFGVTMWEIATRGQTPYPGVENSEIYDY LRQGNRLKQPADCLDGLYALMSRCWELNPQDRPSFTE LREDLENTLKALPPAQEPDEILYVNMDEGGGYPEPPGA AGGADPPTQPDPKDSCSCLTAAEVHPAGRYVLCPSTTP SPAQPADRGSPAAPGQEDGA | |
| SEQ ID NO: 131 | *Mus musculus* AXL | MAWRCPRMGRVPLAWCLALCGWACMYPYDVPDYAA HKDTQTEAGSPFVGNPGNITGARGLTGTLRCELQVQGE PPEVVWLRDGQILELADNTQTQVPLGEDWQDEWKVV SQLRISALQLSDAGEYQCMVHLEGRTFVSQPGFVGLEG LPYFLEEPEDKAVPANTPFNLSCQAQGPPEPVTLLWLQ DAVPLAPVTGHSSQHSLQTPGLNKTSSFSCEAHNAKGV TTSRTATITVLPQRPHHLHVVSRQPTELEVAWTPGLSGI YPLTHCNLQAVLSDDGVGIWLGKSDPPEDPLTQVSVP PHQLRLEKLLPHTPYHIRISCSSSQGPSPWTHWLPVETTE GVPLGPPENVSAMRNGSQVLVRWQEPRVPLQGTLLGY RLAYRGQDTPEVLMDIGLTREVTLELRGDRPVANLTVSV TAYTSAGDGPWSLPVPLEPWRPGQGQPLHHLVSEPPP RAFSWPWWYVLLGAVVAAACVLILALFLVHRRKKETRY GEVFEPTVERGELVVRYRVRKSYSRRTTEATLNSLGISEEL KEKLRDVMVDRHKVALGKTLGEGEFGAVMEGQLNQD DSILKVAVKTMKIAICTRSELEDFLSEAVCMKEFDHPNV MRLIGVCFQGSERESFPAPVVILPFMKHGDLHSFLLYSRL GDQPVYLPTQMLVKFMADIASGMEYLSTKRFIHRDLAA RNCMLNENMSVCVADFGLSKKIYNGDYYRQGRIAKMP VKWIAIESLADRVYTSKSDVWSFGVTMWEIATRGQTPY PGVENSEIYDYLRQGNRLKQPADCLDGLYALMSRCWEL NPQDRPSFTELREDLENTLKALPPAQEPDEILYVNMDEG GGYPEPPGAAGGADPPTQPDPKDSCSCLTAAEVHPAG RYVLCPSTTPSPAQPADRGSPAAPGQEDGA | |
| SEQ ID NO: 132 | *Homo sapiens*-AXL *Mus musculus* Ig1 domain | MAWRCPRMGRVPLAWCLALCGWACMAPRGTQAEES PFVGNPGNITGARGLTGTLRCQLQVQGEPPEVHWLRD GQILELADSTQTQVPLGEDEQDDWIVVSQLRITSLQLSD TGQYQCLVFLGHQTFVSQPGYVGLEGLPYFLEEPEDKAV PANTPFNLSCQAQGPPEPVTLLWLQDAVPLAPVTGHSS QHSLQTPGLNKTSSFSCEAHNAKGVTTSRTATITVLPQQ PRNLHLVSRQPTELEVAWTPGLSGIYPLTHCTLQAVLSD DGMGIQAGEPDPPEEPLTSQASVPPHQLRLGSLHPHTP YHIRVACTSSQGPSSWTHWLPVETPEGVPLGPPENISAT RNGSQAFVHWQEPRAPLQGTLLGYRLAYQGQDTPEVL MDIGLRQEVTLELQGDGSVSNLTVCVAAYTAAGDGPW SLPVPLEAWRPGQAQPVHQLVKEPSTPAFSWPWWYV LLGAVVAAACVLILALFLVHRRKKETRYGEVFEPTVERGE LVVRYRVRKSYSRRTTEATLNSLGISEELKEKLRDVMVDR HKVALGKTLGEGEFGAVMEGQLNQDDS | |

TABLE 1-continued

Amino acid sequences of antibody VHs, VLs and CDRs, as well as of AXL. The CDR sequences are indicated in bold, underlined text in the variable region sequences.

| SEQ ID NO: | Name | Amino acid sequence | Comments |
|---|---|---|---|
| | | ILKVAVKTMKIAICTRSELEDFLSEAVCMKEFDHPNVMR LIGVCFQGSERESFPAPVVILPFMKHGDLHSFLLYSRLGD QPVYLPTQMLVKFMADIASGMEYLSTKRFIHRDLAARN CMLNENMSVCVADFGLSKKIYNGDYYRQGRIAKMPVK WIAIESLADRVYTSKSDVWSFGVTMWEIATRGQTPYPG VENSEIYDYLRQGNRLKQPADCLDGLYALMSRCWELNP QDRPSFTELREDLENTLKALPPAQEPDEILYVNMDEGG GYPEPPGAAGGADPPTQPDPKDSCSCLTAAEVHPAGRY VLCPSTTPSPAQPADRGSPAAPGQEDGA | |
| SEQ ID NO: 133 | Homo sapiens AXL-Mus musculus Ig2 domain | MAWRCPRMGRVPLAWCLALCGWACMAPRGTQAEES PFVGNPGNITGARGLTGTLRCQLQVQGEPPEVHWLRD GQILELADSTQTQVPLGEDEQDDWIVVSQLRITSLQLSD TGQYQCLVFLGHQTFVSQPGYVGLEGLPYFLEEPEDKAV PANTPFNLSCQAQGPPEPVTLLWLQDAVPLAPVTGHSS QHSLQTPGLNKTSSFSCEAHNAKGVTTSRTATITVLPQQ PRNLHLVSRQPTELEVAWTPGLSGIYPLTHCTLQAVLSD DGMGIQAGEPDPPEEPLTSQASVPPHQLRLGSLHPHTP YHIRVACTSSQGPSSWTHWLPVETPEGVPLGPPENISAT RNGSQAFVHWQEPRAPLQGTLLGYRLAYQGQDTPEVL MDIGLRQEVTLELQGDGSVSNLTVCVAAYTAAGDGPW SLPVPLEAWRPGQAQPVHQLVKEPSTPAFSWPWWYV LLGAVVAAACVLILALFLVHRRKKETRYGEVFEPTVERGE LVVRYRVRKSYSRRTTEATLNSLGISEELKEKLRDVMVDR HKVALGKTLGEGEFGAVMEGQLNQDDS ILKVAVKTMKIAICTRSELEDFLSEAVCMKEFDHPNVMR LIGVCFQGSERESFPAPVVILPFMKHGDLHSFLLYSRLGD QPVYLPTQMLVKFMADIASGMEYLSTKRFIHRDLAARN CMLNENMSVCVADFGLSKKIYNGDYYRQGRIAKMPVK WIAIESLADRVYTSKSDVWSFGVTMWEIATRGQTPYPG VENSEIYDYLRQGNRLKQPADCLDGLYALMSRCWELNP QDRPSFTELREDLENTLKALPPAQEPDEILYVNMDEGG GYPEPPGAAGGADPPTQPDPKDSCSCLTAAEVHPAGRY VLCPSTTPSPAQPADRGSPAAPGQEDGA | |
| SEQ ID NO: 134 | Homo sapiens AXL-Mus musculus FN1 domain | MAWRCPRMGRVPLAWCLALCGWACMAPRGTQAEES PFVGNPGNITGARGLTGTLRCQLQVQGEPPEVHWLRD GQILELADSTQTQVPLGEDEQDDWIVVSQLRITSLQLSD TGQYQCLVFLGHQTFVSQPGYVGLEGLPYFLEEPEDRTV AANTPFNLSCQAQGPPEPVDLLWLQDAVPLATAPGHG PQRSLHVPGLNKTSSFSCEAHNAKGVTTSRTATITVLPQ RPHHLHVVSRQPTELEVAWTPGLSGIYPLTHCNLQAVLS DDGVGIWLGKSDPPEDPLTLQVSVPPHQLRLEKLLPHTP YHIRISCSSSQGPSPWTHWLPVETTEGVPLGPPENISAT RNGSQAFVHWQEPRAPLQGTLLGYRLAYQGQDTPEVL MDIGLRQEVTLELQGDGSVSNLTVCVAAYTAAGDGPW SLPVPLEAWRPGQAQPVHQLVKEPSTPAFSWPWWYV LLGAVVAAACVLILALFLVHRRKKETRYGEVFEPTVERGE LVVRYRVRKSYSRRTTEATLNSLGISEELKEKLRDVMVDR HKVALGKTLGEGEFGAVMEGQLNQDDS ILKVAVKTMKIAICTRSELEDFLSEAVCMKEFDHPNVMR LIGVCFQGSERESFPAPVVILPFMKHGDLHSFLLYSRLGD QPVYLPTQMLVKFMADIASGMEYLSTKRFIHRDLAARN CMLNENMSVCVADFGLSKKIYNGDYYRQGRIAKMPVK WIAIESLADRVYTSKSDVWSFGVTMWEIATRGQTPYPG VENSEIYDYLRQGNRLKQPADCLDGLYALMSRCWELNP QDRPSFTELREDLENTLKALPPAQEPDEILYVNMDEGG GYPEPPGAAGGADPPTQPDPKDSCSCLTAAEVHPAGRY VLCPSTTPSPAQPADRGSPAAPGQEDGA | |
| SEQ ID NO: 135 | Homo sapiens AXL-Mus musculus FN2 domain | MAWRCPRMGRVPLAWCLALCGWACMAPRGTQAEES PFVGNPGNITGARGLTGTLRCQLQVQGEPPEVHWLRD GQILELADSTQTQVPLGEDEQDDWIVVSQLRITSLQLSD TGQYQCLVFLGHQTFVSQPGYVGLEGLPYFLEEPEDRTV AANTPFNLSCQAQGPPEPVDLLWLQDAVPLATAPGHG PQRSLHVPGLNKTSSFSCEAHNAKGVTTSRTATITVLPQ QPRNLHLVSRQPTELEVAWTPGLSGIYPLTHCTLQAVLS DDGMGIQAGEPDPPEEPLTSQASVPPHQLRLGSLHPHT PYHIRVACTSSQGPSSWTHWLPVETPEGVPLGPPENVS AMRNGSQVLVRWQEPRVPLQGTLLGYRLAYRGQDTPE VLMDIGLTREVTLELRGDRPVANLTVSVTAYTSAGDGP WSLPVPLEPWRPGQGQPLHHLVSEPPPRAFSWPWWY VLLGAVVAAACVLILALFLVHRRKKETRYGEVFEPTVERG ELVVRYRVRKSYSRRTTEATLNSLGISEELKEKLRDVMVD RHKVALGKTLGEGEFGAVMEGQLNQDDSILKVAVKTM | |

TABLE 1-continued

Amino acid sequences of antibody VHs, VLs and CDRs, as well as of AXL. The CDR sequences are indicated in bold, underlined text in the variable region sequences.

| SEQ ID NO: | Name | Amino acid sequence | Comments |
|---|---|---|---|
| | | KIAICTRSELEDFLSEAVCMKEFDHPNVMRLIGVCFQGS ERESFPAPVVILPFMKHGDLHSFLLYSRLGDQPVYLPTQ MLVKFMADIASGMEYLSTKRFIHRDLAARNCMLNENM SVCVADFGLSKKIYNGDYYRQGRIAKMPVKWIAIESLAD RVYTSKSDVWSFGVTMWEIATRGQTPYPGVENSEIYDY LRQGNRLKQPADCLDGLYALMSRCWELNPQDRPSFTE LREDLENTLKALPPAQEPDEILYVNMDEGGGYPEPPGA AGGADPPTQPDPKDSCSCLTAAEVHPAGRYVLCPSTTP SPAQPADRGSPAAPGQEDGA | |
| SEQ ID NO: 136 | 511 VH | EVQLLESGGGLVQPGGSLRLSCAASGFTFSSYAMNWV RQAPGKGLEWVSGISGSGGHTYHADSVKGRFTISRDNS KNTLYLQMNSLRAEDTAVYYCAKDRYDILTGYYNLLDY WGQGTLVTVSS | Ig2 domain binding Ab |
| SEQ ID NO: 137 | 511 VH CDR1 | GFTFSSYA | |
| SEQ ID NO: 138 | 511 VH CDR2 | ISGSGGHT | |
| SEQ ID NO: 139 | 511 VH CDR3 | AKDRYDILTGYYNLLDY | |
| SEQ ID NO: 140 | 511 VL | DIQMTQSPSSLSASVGDRVTITCRASQGISSWLAWYQQ KPEEAPKSLIYAASSLQSGVPSRFSGSGSGTDFTLTISSLQ PEDFATYYCQQYNSYPLTFGGGAKVEIK | |
| SEQ ID NO: 141 | 511 VL CDR1 | QGISSW | |
| | 511 VL CDR2 | AAS | |
| SEQ ID NO: 142 | 511 VL CDR3 | QQYNSYPLT | |
| SEQ ID NO: 143 | 061 VH | QVQLVQSGAEVKKPGASVKVSCKASGYAFTGYGISWVR QAPGQGLEWIGWISAYNGNTNYVQNLQDRVTMTTDT STSTAYMELRSLRSDDTAVYYCARDHISMLRGIIIRNYW GQGTLVTVSS | Ig1 domain binding Ab |
| SEQ ID NO: 144 | 061 VL | EIVLTQSPATLSLSPGERATLSCRASQSVSSYLAWYQQKP GQAPRLLIYDASNRATGIPARFSGSGSGTDFTLTISSLEPE DFAVYYCQQRSSWPRLTFGGGTKVEIK | |
| SEQ ID NO: 145 | 137 VH | QVQLVQSGAEVKKPGSSVKVSCKASGGTFSRYAISWVR QAPGQGLEWMGRIIPIVGIANYAQKFQGRVTLTADKST STAYMELSSLRSEDTAVYYCAREAGYSSSWYAEYFQHW GQGTLVTVSS | |
| SEQ ID NO: 146 | 137 VL | EIVLTQSPGTLSLSPGERATLSCRASQSVSSNYLAWYQQ KPGQAPRLLIYGASSRATGFPDRFSGSGSGTDFTLTISRL EPEDFAVYYCQQYGSSPYTFGQGTKLEIK | |
| SEQ ID NO: 147 | Cynomolgus monkey AXL (GenBank number HB387229.1) | AWRCPRMGRVPLAWCLALCGWVCMAPRGTQAEESP FVGNPGNITGARGLTGTLRCQLQVQGEPPEVHWLRDG QILELADSTQTQVPLGEDEQDDWIVVSQLRIASLQLSDA GQYQCLVFLGHQNFVSQPGYVGLEGLPYFLEEPEDRTV AANTPFNLSCQAQGPPEPVDLLWLQDAVPLATAPGHG PQRNLHVPGLNKTSSFSCEAHNAKGVTTSRTATITVLPQ QPRNLHLVSRQPTELEVAWTPGLSGIYPLTHCTLQAVLS DDGMGIQAGEPDPPEEPLTLQASVPPHQLRLGSLHPHT PYHIRVACTSSQGPSSWTHWLPVETPEGVPLGPPENISA TRNGSQAFVHWQEPRAPLQGTLLGYRLAYQGQDTPEV LMDIGLRQEVTLELQGDGSVSNLTVCVAAYTAAGDGP WSLPVPLEAWRPGQAQPVHQLVKETSAPAFSWPWW YILLGAVVAAACVLILALFLVHRRKKETRYGEVFEPTVER GELVVRYRVRKSYSRRTTEATLNSLGISEELKEKLRDVMV DRHKVALGKTLGEGEFGAVMEGQLNQDDSILKVAVKT MKIAICTRSELEDFLSEAVCMKEFDHPNVMRLIGVCFQG SERESFPAPVVILPFMKHGDLHSFLLYSRLGDQPVYLPTQ MLVKFMADIASGMEYLSTKRFIHRDLAARNCMLNENM SVCVADFGLSKKIYNGDYYRQGRIAKMPVKWIAIESLAD RVYTSKSDVWSFGVTMWEIATRGQTPYPGVENSEIYDY LRQGNRLKQPADCLDGLYALMSRCWELNPQDRPSFTE LREDLENTLKALPPAQEPDEILYVNMDEGGGYPEPPGA AGGADPPTQLDPKDSCSCLTSAEVHPAGRYVLCPSTAPS PAQPADRGSPAAPGQEDGA | |

EXAMPLES

Example 1: Testing of pH, Buffers, Ionic Strength and Excipients Using Chemical Denaturation [HuMax-AXL]

Chemical denaturation by urea was used to screen different formulation components to assess their effect on the thermodynamic stability of anti-AXL human antibody 107, a.k.a. IgG1-AXL-107 or HuMax-AXL. This example shows the effect of pH, buffer type (Histidine, Citrate, and 2-(N-morpholino) ethanesulfonic acid (MES), buffer concentration and various excipients (sugars, amino acids, polyols and surfactant) on the thermodynamic stability of HuMax-AXL.

In this example, the thermodynamic value $C_{1/2}$, the concentration of denaturant where the fraction of folded to unfolded protein is equal, is used as the parameter to compare the stabilizing effect of different formulation components. The higher the $C_{1/2}$ value the higher the thermodynamic stability.

Multiple buffers used to screen for pH, showed that the $C_{1/2}$ values increased significantly with increasing pH, but leveled off around pH 6.5 as shown in Table 2. Screening of three different buffers with $pK_a$ values close to pH 6.5 (Histidine, Citrate and 2-(N-morpholino) ethanesulfonic acid (MES)) showed no marked difference in the $C_{1/2}$ values as shown in Table 3. Further analysis of Histidine in the range from 10 to 50 mM, as shown in Table 4, showed that the thermodynamic stability was not dependent on the Histidine concentration. Increasing the ionic strength from 0 to 500 mM NaCl also did not affect the thermodynamic stability of HuMax-AXL as shown in Table 5.

TABLE 2

$C_{1/2}$ values as an effect of different buffers used to screen for pH in chemical denaturation of HuMax-AXL

| Sample | Formulation | C½ |
|---|---|---|
| 0.75 mg/mL HuMax-AXL | 10 mM Histidine pH 5.0 | 4.91 |
| | 10 mM Histidine pH 5.5 | 6.16 |
| | 10 mM Histidine pH 6.0 | 6.09 |
| | 10 mM Histidine pH 6.5 | 6.34 |
| | 10 mM HEPES pH 7.0 | 6.39 |
| | 10 mM HEPES pH 7.5 | 6.40 |
| | 10 mM Glycine pH 8.0 | 6.41 |

TABLE 3

$C_{1/2}$ values as an effect of a Histidine, Citrate and MES buffer (pKa in 6.5 range) in chemical denaturation of HuMax-AXL.

| Sample | Formulation | C½ |
|---|---|---|
| 0.75 mg/mL HuMax-AXL | 10 mM Histidine pH 6.5 | 6.39 |
| | 10 mM Citrate pH 6.5 | 6.35 |
| | 10 mM MES pH 6.5 | 6.45 |

TABLE 4

$C_{1/2}$ values as an effect of Histidine in different concentrations from 10 to 50 mM in chemical denaturation of HuMax-AXL.

| Sample | Formulation | C½ |
|---|---|---|
| 0.75 mg/mL HuMax-AXL | 10 mM Histidine pH 6.5 | 6.30 |
| | 20 mM Histidine pH 6.5 | 6.34 |
| | 30 mM Histidine pH 6.5 | 6.19 |
| | 40 mM Histidine pH 6.5 | 6.25 |
| | 50 mM Histidine pH 6.5 | 6.29 |

TABLE 5

$C_{1/2}$ values as an effect of increasing ionic strength from 2-500 mM NaCl in chemical denaturation of HuMax-AXL

| Sample | Formulation | Ionic Strength (mM NaCl) | C½ |
|---|---|---|---|
| 0.75 mg/mL HuMax-AXL | 30 mM Histidine pH 6.5 | 0 | 6.47 |
| | | 25 | 6.43 |
| | | 50 | 6.30 |
| | | 100 | 6.37 |
| | | 150 | 6.39 |
| | | 250 | 6.42 |
| | | 500 | 6.52 |

Screening for different excipients (sugars, amino acids, polyols and surfactant) using a formulation of 30 mM Histidine pH 6.5, showed that the three sugars tested (sucrose, Trehalose, and Mannitol) all had a stabilizing effect, with the higher sugar concentration providing greater thermodynamic stability, and with Mannitol showing higher $C_{1/2}$ value than Trehalose and Sucrose, Table 6.

TABLE 6

$C_{1/2}$ values as an effect of using Sucrose, Trehalose, and Mannitol at different concentrations as stabilizers in chemical denaturation of HuMax-AXL

| Sample | Formulation | Sugar | Sugar Concentration (%) | C½ |
|---|---|---|---|---|
| 0.75 mg/mL HuMax-AXL | 30 mM Histidine pH 6.5 | Sucrose | 1 | 6.45 |
| | | | 5 | 6.62 |
| | | Trehalose | 1 | 6.36 |
| | | | 5 | 6.74 |
| | | Mannitol | 1 | 7.00 |
| | | | 5 | 7.32 |

Screening for different amino acids (Arginine, Glycine, and Glutamic acid) indicated that these did not confer additional stability to the formulation. Data was somewhat dissimilar as higher $C_{1/2}$ values were obtained for formulations with Glycine and Glutamic acid at higher concentrations, whereas the $C_{1/2}$ values decreased for higher concentrations of Arginine. As the pH for the Glycine and Glutamic Acid formulations were unstable, the higher $C_{1/2}$ values obtained for these formulations, was probably more a result of the thermodynamic stability conferred by the higher pH of the formulations. Table 7, shows the respective $C_{1/2}$ values.

TABLE 7

$C_{1/2}$ values as an effect of using Arginine, Glutamic Acid, and Glycine at different concentrations as stabilizers in chemical denaturation of HuMax-AXL.

| Sample | Formulation | Sugar | Amino Acid Concentration (mM) | $C_{1/2}$ |
|---|---|---|---|---|
| 0.75 mg/mL HuMax-AXL | 30 mM Histidine pH 6.5 (unstable pH) | Arginine | 25 | 6.21 |
| | | | 100 | 6.12 |
| | | | 150 | 5.85 |
| | | Glycine | 25 | 6.46 |
| | | | 100 | 6.62 |
| | | Glutamic Acid | 25 | 6.70 |
| | | | 100 | 6.92 |

The polyols Sorbitol and Glycerol both showed to have a stabilizing effect on the thermodynamic stability of HuMax-AXL, with the higher concentration providing greater thermodynamic stability, and with Sorbitol showing higher $C_{1/2}$ value than Glycerol, Table 8.

TABLE 8

$C_{1/2}$ values as an effect of using the polyols Sorbitol and Glycerol at different concentrations as stabilizers in chemical denaturation of HuMax-AXL.

| Sample | Formulation | Sugar | Polyol Concentration | $C_{1/2}$ |
|---|---|---|---|---|
| 0.75 mg/mL HuMax-AXL | 30 mM Histidine pH 6.5 | Sorbitol | 100 mM | 6.59 |
| | | | 200 mM | 6.71 |
| | | Glycerol | 1% | 6.46 |
| | | | 5% | 6.64 |

The data for screening of surfactant (PS-20 and PS-80) were inconclusive because at a lower concentration of surfactant (0.03% w/v), the formulation containing PS-20 had a higher $C_{1/2}$ value than the formulation containing PS-80, and at higher concentration of surfactant (0.06% w/v), the formulation containing PS-80 had a higher $C_{1/2}$ value than the formulation containing PS-20, Table 9. The data thus do not indicate enhanced protein stability for either surfactant.

TABLE 9

$C_{1/2}$ values as an effect of using the surfactants Polysorbate 80 and Polysorbate 20 at different concentrations as stabilizers in chemical denaturation of HuMax-AXL.

| Sample | Formulation | Sugar | Surfactant Concentration (%) | $C_{1/2}$ |
|---|---|---|---|---|
| 0.75 mg/mL HuMax-AXL | 30 mM Histidine pH 6.5 | Polysorbate-80 | 0.03 | 6.45 |
| | | | 0.06 | 6.73 |
| | | Polysorbate-20 | 0.03 | 6.63 |
| | | | 0.06 | 6.36 |

Example 2: Freeze/Thaw Stability of HuMax-AXL Using Surfactant, Cryoprotectant and NaCl Evaluation of formulations containing either surfactant or cryoprotectant was investigated as protective agents during freeze-thaw stress of Humax-AXL. In addition, the effect of NaCl on the solubility of HuMax-AXL during freezing was investigated.

Three concentrations of Polysorbate 80 (0.0%, 0.03% and 0.06%) and three concentrations of Sucrose (0, 5, or 10% sucrose) in 30 mM Histidine (pH 6.5) were used to investigate their protective effect on the degradation of HuMax-AXL upon three cycles of freeze-thaw. The formulations were subsequently evaluated by Appearance, concentration, turbidity (A550), reducing and non-reducing CE-SDS, and SEC. All formulations were clear and free of visible particles and as shown in Table 10 and Table 11, no changes in protein concentration, turbidity, or purity was observed between unstressed and stressed samples, indicating that neither Polysorbate 80 nor Sucrose enhances the stability of HuMax-AXL upon freeze-thaw.

TABLE 10 effect of Polysorbate 80 at different concentrations on the stability of HuMax-AXL during freeze-thaw measured by Concentration (A280 nm), turbidity (A550 nm), CE-SDS (reduced and non-reduced), SEC.

| Sample | Conc. mg/mL | A550 | Purity % (CE-SDS, Red) | Purity % (CE-SDS, Non-red) | Purity % (SEC) |
|---|---|---|---|---|---|
| 0 F/T, 0% PS80 | 22.1 | 0.02547 | 96.7 | 91.6 | 98.0 |
| 0 F/T, 0.03% PS80 | 22.7 | 0.04425 | 96.7 | 91.5 | 98.3 |
| 0 F/T, 0.06% PS80 | 21.1 | 0.04576 | 96.7 | 92.7 | 98.2 |
| 3 F/T, 0% PS80 | 21.9 | 0.04951 | 96.6 | 93.0 | 98.4 |
| 3 F/T, 0.03% PS80 | 22.4 | 0.03540 | 96.6 | 92.9 | 98.6 |
| 3 F/T, 0.06% PS80 | 21.4 | 0.01299 | 96.6 | 93.1 | 98.6 |

TABLE 11 effect of Sucrose at different concentration on the stability of HuMax-AXL during freeze-thaw measured by Concentration (A280 nm), turbidity (A550 nm), CE-SD (reduced and non-reduced), SEC.

| Sample | Conc. mg/mL | A550 | Purity % (CE-SDS, Red) | Purity % (CE-SDS, Non-red) | Purity % (SEC) |
|---|---|---|---|---|---|
| 0 F/T, 0% sucrose | 20.6 | −0.04932 | 97.6 | 95.1 | 98.3 |
| 0 F/T, 5% sucrose | 22.5 | −0.00205 | 97.7 | 94.9 | 99.1 |
| 0 F/T, 10% sucrose | 21.2 | 0.02576 | 97.4 | 95.2 | 98.4 |
| 3 F/T, 0% sucrose | 20.4 | 0.03282 | 97.4 | 94.9 | 99.1 |
| 3 F/T, 5% sucrose | 22.7 | 0.06612 | 96.7 | 94.5 | 98.2 |
| 3 F/T, 10% sucrose | 21.2 | 0.04265 | 97.5 | 94.7 | 98.7 |

Also, it was shown that NaCl (0 mM, 25 mM, 50 mM and 100 mM of NaCl) did not enhance the solubility when tested at a 40 mg/mL concentration of HuMax-AXL. Samples were stored at −5° C. on a pre-cooled lyophilizer shelf and evaluated by visual appearance for phase separation after 24 hrs. No phase separation was observed in any of the samples. Accordingly, no effect of NaCl on the solubility and phase separation of HuMax-AXL during freezing could be seen.

Example 3: Design of Experiment (DoE) [HuMax-AXL]

This example describes a DoE study using a design space for pH, mannitol, and sorbitol concentrations for HuMax-AXL formulations. Histidine buffer concentration was used as a fourth parameter, see table below. Table 12 shows the experimental design space and table 13 shows the outline of the DoE study

TABLE 12

Excipient Experimental Design Space in the DoE for HuMax-AXL.

| Mannitol | Sorbitol (mM) | | |
|---|---|---|---|
| | 0 | 100 | 200 |
| 0% | x | x* | X |
| 1% | x* | x* | X |
| 5% | X | x | x |

*Center points

The samples were evaluated initially and after storage at 4 weeks at 40° C. A subset of the formulations were subjected to additional 5 freeze-thaw cycles and additional 2 weeks of storage at 40° C. (6 week time point). Samples were tested using product specific analysis, i.e. size-exclusion chromatography (SEC), capillary isoelectric focusing (cIEF) and capillary electrophoresis-sodium dodecyl sulfate (CE-SDS) (red and non-red). Selected results are shown and discussed below.

TABLE 13

HuMax-AXL DoE study

| Formulation Designation | HuMax-AXL Conc. | Buffer | pH | Sorbitol (mM) | Mannitol (%) |
|---|---|---|---|---|---|
| F1 | 20 mg/mL | 30 mM Histidine | 6.5 | 200 | 0 |
| F2 | | | | 100 | 0 |
| F3 | | | | 100 | 1 |
| F4 | | | | 0 | 1 |
| F5 | | | | 0 | 5 |
| F6 | | | | 100 | 5 |
| F7 | | | | 200 | 1 |
| F8 | | | 7.0 | 200 | 0 |
| F9 | | | | 100 | 0 |
| F10 | | | | 100 | 1 |
| F11 | | | | 0 | 1 |
| F12 | | | | 0 | 5 |
| F13 | | | | 100 | 5 |
| F14 | | | | 200 | 1 |
| F15 | | | 6.0 | 200 | 0 |
| F16 | | | | 100 | 0 |
| F17 | | | | 100 | 1 |
| F18 | | | | 0 | 1 |
| F19 | | | | 0 | 5 |
| F20 | | | | 100 | 5 |
| F21 | | | | 200 | 1 |
| F22 | | 20 mM Histidine | 6.5 | 200 | 0 |
| F23 | | | | 100 | 0 |
| F24 | | | | 100 | 1 |
| F25 | | | | 0 | 1 |
| F26 | | | | 0 | 5 |
| F27 | | | | 100 | 5 |
| F28 | | | | 200 | 1 |
| F29 | | 40 mM Histidine | | 200 | 0 |
| F30 | | | | 100 | 0 |
| F31 | | | | 100 | 1 |
| F32 | | | | 0 | 1 |
| F33 | | | | 0 | 5 |
| F34 | | | | 100 | 5 |
| F35 | | | | 200 | 1 |

Figure 1:
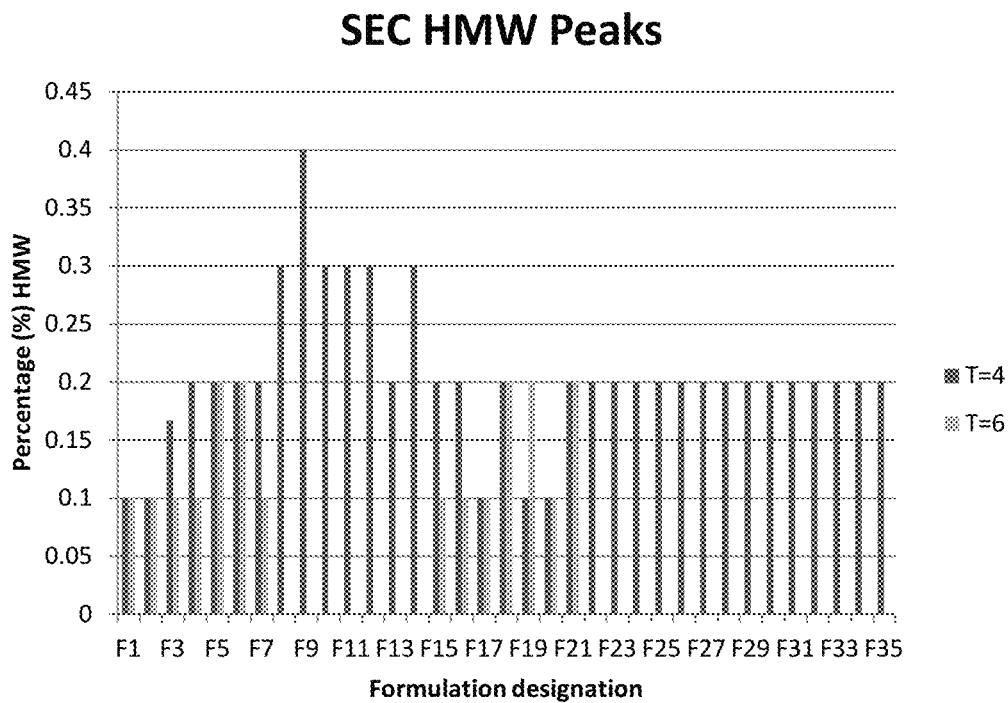
FIG. 1 shows the SEC (HMW species) result for HuMax-AXL DoE study.
Figure 2:
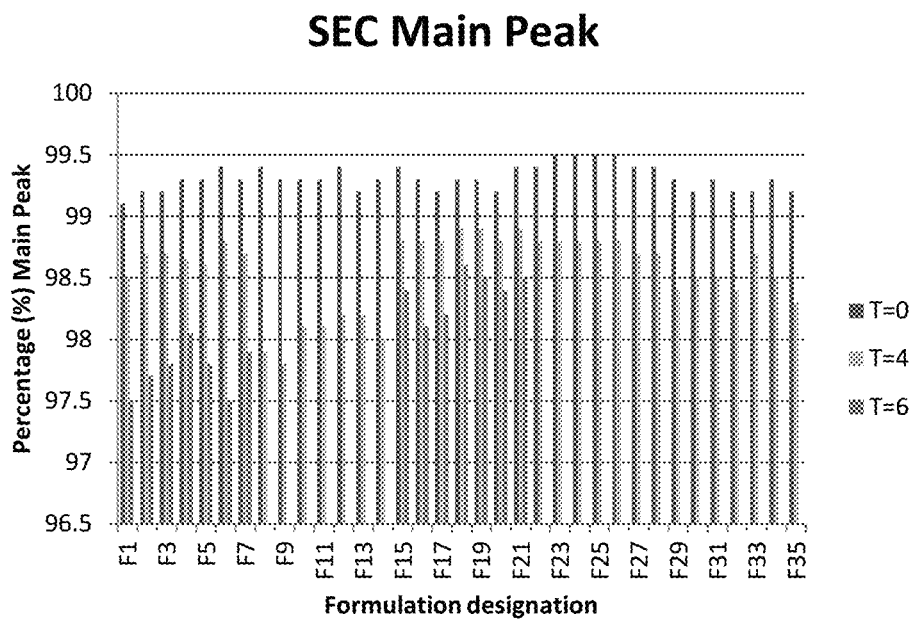
FIG. 2 shows the SEC (Main Peak) result for HuMax-AXL DoE study.
Figure 3:
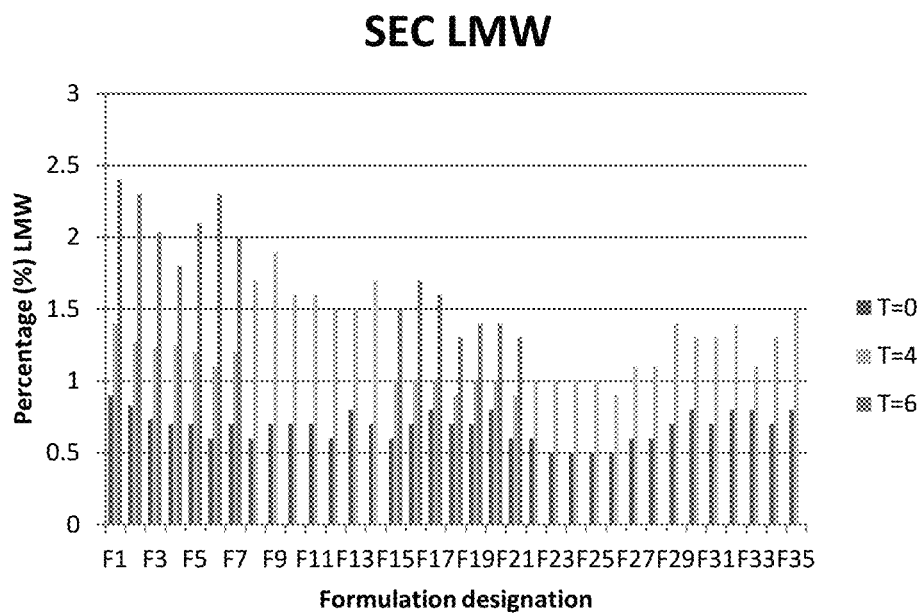
FIG. 3 shows the SEC (LMW species) result for HuMax-AXL DoE study.

The HuMax-AXL samples incubated at 40° C. for 4 weeks and 6 weeks were evaluated by SEC to determine the effect of various formulations on the extent of aggregation (high molecular weight species (HMW)) and degradation (low molecular weight species (LMW)). At the initial time point, no HMW) species were detected by SEC in any of the sample preparations and only low amounts of LMW species were detected. At the 4 week and 6 week time point, an increase in both the percentage of HMW and LHW species were detected. The formulations a pH 7.0 appeared to result in larger percentages of HMW species than the other formulations at the 4 week time point, FIG. 1, and was not included in the 6 week time point, together with the samples F22-F35. The samples containing 30 mM Histidine (pH 6.0), showed the highest percentage of main peak and lowest percentage of LMW species, as shown in FIGS. 2 and 3, respectively.

Figure 4:
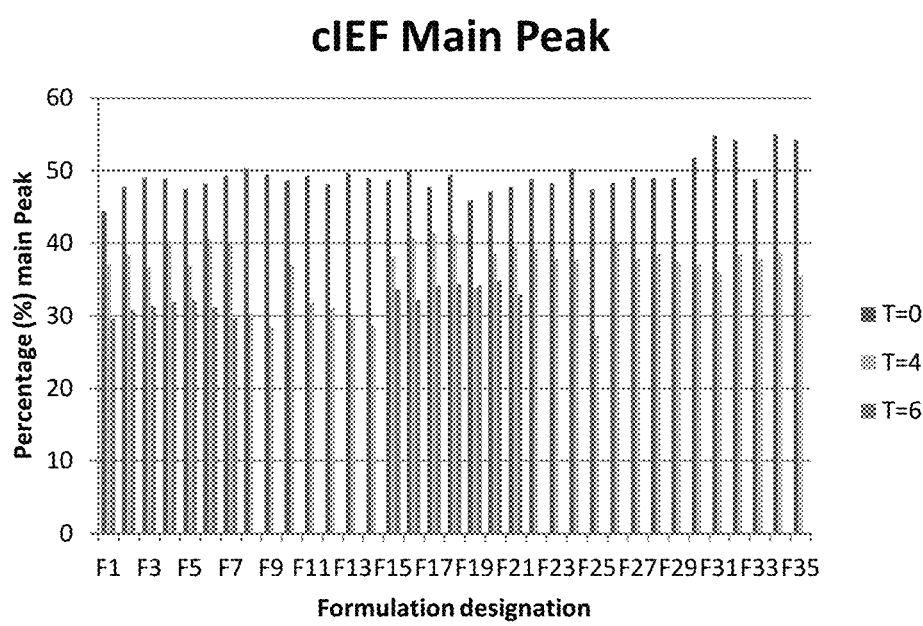
FIG. 4 shows the cIEF (Main Peak) result for HuMax-AXL DoE study.

The HuMax-AXL samples incubated at 40° C. for 4 weeks and 6 weeks were evaluated by cIEF to determine the effect of various formulations on the charge profile, i.e. presence of acidic and basic isoforms. The initial time point did not suggest any significant trends in percent main and acidic isoforms on the basis of differences in Histidine concentration, pH, Mannitol concentration, or Sorbitol concentration. Over the time course of the stability study, there was a significant decrease in main isoform, which trended inversely to the change in percent acidic peak, and hence can be attributed primarily to deamidation of the main peak isoform. The formulations at pH 7.0 appeared to result in larger percentages of acidic and basic isoforms than the other formulations at the 4 week time point, as well as lower percentage of the main peak isoform, with the remaining formulations being very similar. As shown in FIG. 4, the 6-week time point showed the highest percentage of main peak isoforms in the formulations with 30 mM Histidine, pH 6.0, the difference being statistically significant.

The HuMax-AXL samples incubated at 40° C. for 4 weeks and 6 weeks were evaluated by CE-SDS (red and non-red) to determine the effect of various formulations on the purity of HuMax-AXL. At the initial time point, the variation in the purity was within method variability, with no significant difference in purity for the formulations tested. At the 4 week time point an increase in impurities were observed for all formulations both in the reduced and non-reduced SDS, with that of the pH 7.0 formulations having the highest percentage of impurities. Only pH 6.0 and pH 6.5 was tested at the 6 week time point, with no appearance of new impurities (bands) from the 4 week time point. All the pH 6.0 formulations showed a lower percentage of impurities, although this could be within the expected method variability.

Example 4: Effect of Polysorbate-Freeze/Thaw and Agitation [HuMax-AXL-ADC]

Figure 5:
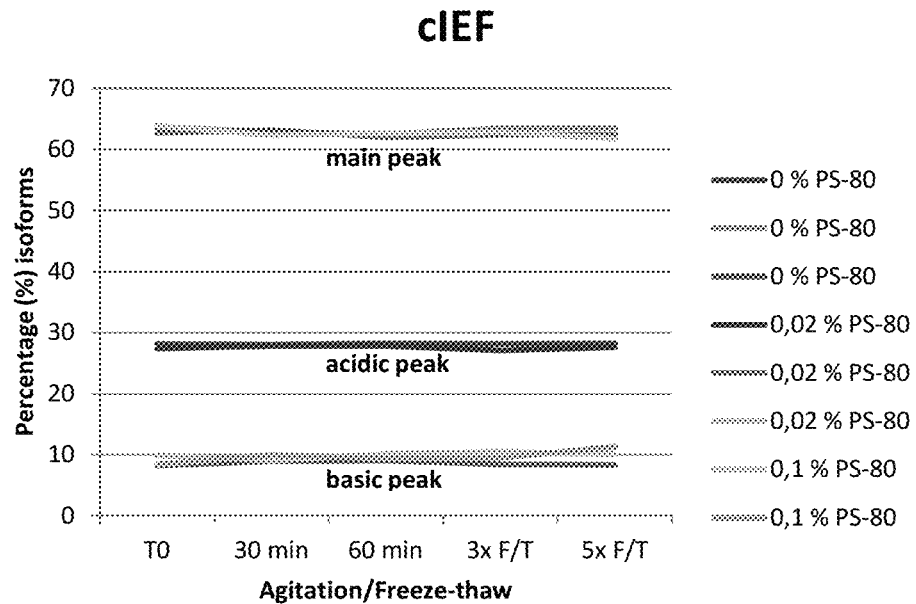
FIG. 5 shows the cIEF data (% main, acidic, and basic isoforms) for HuMax-AXL-ADC samples containing Polysorbate and exposed to agitation and freeze-thaw cycles.

A study was designed to test the effect of Polysorbate 80 (PS-80) on interfacial stress of an antibody-drug conjugate of HuMax-AXL; IgG1-AXL-107-vcMMAE, herein referred to as "HuMax-AXL-ADC", in solution by means of freeze-thaw and agitation. 10 mg/ml HuMax-AXL-ADC in 30 mM Histidine, 200 mM Sorbitol (pH 6.0) was formulated with three Polysorbate concentrations, i.e. 0, 0.02 and 0.1%. The samples with and without PS-80 were either exposed to agitation for 30 and 60 minutes or exposed to 3 and 5 freeze/thaw cycles after which the samples were evaluated by A280 (concentration), SEC (aggregation), and by cIEF (change in isoforms). As can be seen in Table 14, FIG. 5, and Table 15, no decrease was observed in concentration, percent main peak measured by cIEF, or percent main peak measured by SEC after exposure to agitation or freeze-thaw, respectively. The data suggest that HuMax-AXL-ADC formulations do not require Polysorbate 80 for protection of interfacial denaturation and the formulation may thus be free of surfactant.

TABLE 14

Concentration data (A280nm) for HuMax-AXL-ADC samples containing Polysorbate and exposed to agitation and freeze-thaw cycles.
Concentration mg/mL (A280)

| Polysorbate | Agitation | | | Freeze-thaw | |
|---|---|---|---|---|---|
| conc. (%) | T0 | 30 min | 60 min | 3x | 5x |
| 0 | 9.39 | 9.37 | 9.39 | 9.26 | 9.43 |
|  | 9.36 | 9.39 | 9.39 | 9.44 | 9.44 |
| 0.02 | 9.42 | 9.31 | 9.44 | 9.27 | 9.39 |
|  | 9.39 | 9.39 | 9.48 | 9.35 | 9.48 |
| 0.10 | 9.27 | 9.30 | 9.16 | 8.88 | 9.47 |
|  | 9.32 | 9.34 | 9.36 | 8.64 | 9.61 |

TABLE 15

SEC data (% Main Peak) for HuMax-AXL-ADC samples containing Polysorbate and exposed to agitation and freeze-thaw cycles.
SEC Percentage (%) Main Peak

| Polysorbate | Agitation | | | Freeze-thaw | |
|---|---|---|---|---|---|
| conc. (%) | T0 | 30 min | 60 min | 3x | 5x |
| 0 | 99.6 | 99.7 | 99.6 | 99.7 | 99.6 |
| 0.02 | 99.7 | 99.6 | 99.5 | 99.5 | 99.4 |
| 0.10 | 99.5 | 99.5 | 99.5 | 99.5 | 99.5 |

Example 5: Effect of Buffer Type, Concentration, and pH-DoE [HuMax-AXL-ADC]

This example describes a DoE (Design of Experiment) study for HuMax-AXL-ADC using a design space for pH, buffer type, and buffer concentrations using fifteen formulations, see Table 16 below. The samples were evaluated initially and after storage for 2 weeks at 25° C. and 40° C. Samples were tested using product specific analysis, i.e. A280, SEC, cIEF. Selected results are discussed below.

TABLE 16

HuMax-AXL-ADC study

| Formulation Designation | HuMax-AXL-ADC Conc. | Buffer Type | Buffer Concentration (mM) | pH |
|---|---|---|---|---|
| 1 | 10 mg/mL | Histidine | 50 | 7 |
| 2 |  | Histidine | 10 | 5 |
| 3 |  | Phosphate | 10 | 7 |
| 4 |  | Citrate | 10 | 6 |
| 5 |  | Citrate | 10 | 5 |
| 6 |  | Citrate | 50 | 5 |
| 7 |  | Phosphate | 50 | 6 |
| 8 |  | Phosphate | 10 | 6 |
| 9 |  | Phosphate | 50 | 7 |
| 10 |  | Citrate | 50 | 6 |
| 11 |  | Histidine | 10 | 7 |
| 12 |  | Histidine | 50 | 5 |
| 13 |  | Histidine | 30 | 6 |
| 14 |  | Citrate | 30 | 6 |
| 15 |  | Phosphate | 30 | 6 |

The HuMax-AXL-ADC samples incubated at 25° C. and 40° C. were evaluated by SEC to determine the effect of various formulations on the extent of aggregation (HMW species) and degradation (LMW species). A decrease in the average percent main peak was observed for samples stored at 25° C. and 40° C., the effect increasing with time and temperature, FIG. 6. These data corresponded well with an observed increase in the average percent high molecular weight species (HMW) and average percent low molecular weight species (LMW). Statistical analyses of the SEC data (ANOVA-one way analysis of variance), suggested that the average percentage of HMW species and the average percent main peak were not affected by buffer concentration or pH of the solution, whereas the stability appeared to be dependent by the buffer as a formulation prepared with Histidine exhibited less aggregation. FIG. 7 depicts the ANOVA plots of the main peak by buffer type, buffer concentration and pH.

The HuMax-AXL-ADC samples incubated at 25° C. and 40° C. were evaluated by cIEF to determine the effect of various formulations on the formation of charge isomers, i.e. acidic and basic. cIEF data suggest that the stability of HuMax-AXL-ADC is mostly affected by pH of the solution. The average percent main peak decreased and the average percent acidic peak increased, after storage at 40° C. for 2 weeks as the pH of the solution increased. Furthermore, the ANOVA analysis suggested that the means of the average main peaks were equal with respect to buffer type. However, visual observations of the graphs suggested that the average percent main peak decreased in formulations prepared with the phosphate buffer. This was found to correlate well with statistical analyses of the data for the average percent acidic peak. Thus it appears that the stability of HuMax-AXL-ADC is affected by the type of buffer with the formulations prepared using a phosphate buffer exhibiting greater increases in the acidic peak. Although cIEF data suggested that pH and buffer type impacted the stability of HuMax-AXL-ADC, the data did not indicate that the buffer concentration had any effect on the stability. FIG. 8 depicts the ANOVA plots of the main peak by buffer type, buffer concentration and pH.

Example 6: Lyophilization Cycle Study

This example describes a screening study to examine the effect of an amorphous (trehalose/sucrose) and a crystallizing (mannitol) sugar on the stability of the lyophilized formulation of HuMax-AXL-ADC at different pH. Four formulations contained 10 mg/ml HuMax-AXL-ADC, 30 mM Histidine, and 5% Mannitol and remaining four formulations were used as center points for the statistical design and contained 10 mg/ml HuMax-AXL-ADC, 30 mM Histidine, 3% Sucrose or Trehalose, with 3% Mannitol prepared at pH 5.5 and 6.5. Samples were lyophilized using a conservative cycle and samples were stored at 25° C. and 40° C. for 2 months and evaluated by A280, SEC, cIEF, and Dynamic Light Scattering DLS. Outline of the study is shown in Table 17. Selected results are discussed below.

TABLE 17

Lyophilization cycle study design

| Formulation Designation | HuMax-AXL-ADC Conc. | Buffer | Sugar Type | Concentration (%) | Mannitol (%) | pH |
|---|---|---|---|---|---|---|
| 1 | 10 mg/mL | 30 mM histidine | Trehalose | 1 | 5 | 5.0 |
| 2 |  |  | Sucrose | 5 | 5 | 5.0 |
| 3 |  |  | Sucrose | 1 | 5 | 6.0 |

TABLE 17-continued

Lyophilization cycle study design

| Formulation Designation | HuMax-AXL-ADC Conc. | Buffer | Sugar Type | Concentration (%) | Mannitol (%) | pH |
|---|---|---|---|---|---|---|
| 4 | | | Trehalose | 5 | 5 | 6.0 |
| 5 | | | Sucrose | 3 | 3 | 5.5 |
| 6 | | | Trehalose | 3 | 3 | 5.5 |
| 7 | | | Sucrose | 3 | 3 | 6.5 |
| 8 | | | Trehalose | 3 | 3 | 6.5 |

The HuMax-AXL-ADC samples incubated at 25° C. and 40° C. were evaluated by SEC to determine the effect of various formulations on the extent of aggregation (HMW species) and degradation (LMW species). The average percent main peak showed no changes in the pre- and post-lyophilization at T0. A slight increase in average percent HMW species was observed after storage at 25° C. for 2 months, with no presence of LMW species. An increase in average percent HMW species was observed after storage at 40° C. for 2 months, with presence of LMW species in some of the formulations.

Statistical analysis, FIG. 9, for the average percent main peak suggested that the data were affected by the concentration of the amorphous sugars (Sucrose and Trehalose-Prob >F=0.0031 at 25° C. and 0.0510 at 40° C.). A decrease in average percent main peak as well as an increase in average percent HMW species was observed when the concentration of the amorphous sugar was 5%. Although the data are not statistically significant, graphs of the average percent main and HMW species seem to show a possible effect of pH on the formulations. Less main peak and more HMW species are observed at pH 5. FIG. 10 shows the average percent main peak in the eight formulations, following 2 months of storage at 40° C.

The HuMax-AXL-ADC samples incubated at 25° C. and 40° C. were evaluated by cIEF to determine the effect of various formulations on the formation of charge isomers, i.e. acidic and basic. cIEF data suggested that no statistical significance was observed for any of the variables when the data was compared, FIG. 11.

In conclusion the data suggested that the sugar concentration and pH of the solution were most important for stability of the formulation. Overall the data suggested that similar results were obtained using Sucrose or Trehalose at a concentration of less than 5%, with a pH between pH 5.5 and 6.5.

Example 7: Determination of Primary Drying Conditions for the Lyophilization Process of HuMax-AXL-ADC The lyophilization cycle for a HuMax-AXL-ADC preparation (10 mg/ml HuMax-AXL-ADC, 30 mM histidine, 88 mM sucrose, 165 mM mannitol, pH 6.0) was determined based on thermal characterization of the frozen solution and of the dried solid and by identification of the failure point during primary drying. The failure point was defined as the product temperature during primary drying that lead to changes in the visual appearance of the dried solid. Thermal characterization studies were conducted using modulated differential scanning calorimetry (DSC) and freeze-dry microscopy (FDM). Freeze-dry microscopy experiments were conducted by cooling a sample of the formulation to −40° C. and then annealing at −15° C. for 30 minutes to crystallize the mannitol in the formulation. The sample was cooled back to −40° C. and a vacuum of 100 mTorr was initiated. An acceptable dried layer was established and then the product temperature was increased by increments of 2° C. until complete failure of the sample was observed. Complete failure was observed when the product temperature reached -16° C. This corresponded well with in-process lyophilization cycle data from an experiment used to identify the failure point. The lyophilization cycle developed for the formulation was designed to ensure the product temperature of all vials remains approximately 4° C. colder than the temperature identified as the point of failure. This ensures that the product temperature for vials located along the edges of the shelves remains well below the critical product temperature.

Samples of the dried solids were examined using modulated differential scanning calorimetry to determine if mannitol completely crystallized when using a 3 hour annealing step at −15° C. during the thermal treatment step of the lyophilization cycle. The data support that mannitol is completely crystalline in the dried solid by demonstrating no evidence of exothermal events during warming of the sample and thus is a suitable as a crystalline bulking agent in the HuMax-AXL-ADC formulation.

Example 8: Effect of Residual Moisture on the Stability of HuMax-AXL-ADC

This example describes the effect of residual moisture in lyophilized HuMax-AXL-ADC (prepared from an aqueous solution comprising 10 mg/mL HuMax-AXL-ADC, 30 mM histidine, 88 mM sucrose, 165 mM mannitol, pH 6.0). Samples with a defined residual moisture level of app. 2.28%, 0.84% and 0.44% were removed during secondary drying of lyophilization and subsequently stored at 40° C./75% RH for up to 2 months and evaluated by Appearance, A280, SEC, cIEF, and DLS. Selected results are discussed below.

No changes were observed in the appearance of any of the samples over the 2 month time frame of the study. However, an increase in the level of residual moisture was measured in the samples as expected, Table 18. This was also confirmed by DSC, measuring the midpoint Tg (glass transition temperature) value of the solids which decreased over time, i.e. the moisture acts as a plasticizer lowering the Tg. The Tg values ranged from approximately 78° C. for the low moisture sample to approximately 60° C. for the high moisture sample at the beginning of the study, but decreased to approximately 60° C. for the low moisture sample to approximately 45° C. for the medium and high moisture samples, FIG. 12.

TABLE 18

Residual Moisture values of HuMax-AXL-ADC lyophilized samples after 1 and 2 months of storage at 40° C./75% RH.

| Sample | Theoretical Residual moisture (%) | Actual Residual moisture (%) T0 | Actual Residual moisture (%) 1 month | Actual Residual moisture (%) 2 month |
|---|---|---|---|---|
| 20 | 0.44 | 0.29 | 0.97 | n/a |
| 21 | (low moisture) | 0.48 | 1.23 | |
| 22 | | 0.35 | 1.04 | |
| 27 | 0.44 | 0.41 | n/a | 1.30 |
| 26 | (low moisture) | 0.36 | | 1.22 |
| 23 | | 0.40 | | 1.29 |

TABLE 18-continued

Residual Moisture values of HuMax-AXL-ADC lyophilized samples after 1 and 2 months of storage at 40° C./75% RH.

| Sample | Theoretical Residual moisture (%) | Actual Residual moisture (%) T0 | Actual Residual moisture (%) 1 month | Actual Residual moisture (%) 2 month |
|---|---|---|---|---|
| 10 | 0.84 (medium moisture) | 0.83 | 1.98 | n/a |
| 13 | | 1.10 | 1.93 | |
| 14 | | 0.75 | 1.84 | |
| 18 | 0.84 (medium moisture) | 0.88 | n/a | 2.12 |
| 17 | | 0.86 | | 2.11 |
| 16 | | 0.98 | | 2.20 |
| 1 | 2.28 (high moisture) | 2.58 | 3.66 | n/a |
| 4 | | 2.22 | 3.40 | |
| 5 | | 2.26 | 3.44 | |
| 9 | 2.28 (high moisture) | 2.48 | n/a | 3.80 |
| 8 | | 2.44 | | 3.59 |
| 7 | | 2.31 | | 3.71 |

Analysis of the samples with SEC and cIEF showed that at a moisture level below 3% the characteristics of the product, as the percentage of main peak (Table 19) measured by SEC and percentage of main isoform (FIG. 13) measured by cIEF did not decrease, thus supporting the stability of the formulations.

TABLE 19

SEC data (% Main Peak) for High, Medium, and Low Moisture samples after 2 months at 40° C.

| Sample | SEC Percentage (%) Main Peak | | |
|---|---|---|---|
| | T0 | 1 month | 2 month |
| Pre-Lyo | 99.6 | n/a | |
| High Moisture | 99.6 | 99.1 | 98.9 |
| Medium Moisture | 99.4 | 99.1 | 99.0 |
| Low Moisture | 99.3 | 99.1 | 99.0 |

Example 9: Demonstration Batch

Lyophilized HuMax-AXL-ADC from a demonstration batch using the final lyophilization cycle, was evaluated on long-term stability at 5±3° C. The composition of Humax-AXL-ADC after reconstitution was 10 mg/ml, 30 mM histidine, 88 mM sucrose, 165 mM mannitol, pH 6.0. The long term stability samples were analyzed at T0, T1, T3, T6, T12, T18, and T24 months, and analyzed by product specific assays (SEC, cIEF, CE-SDS, etc.) as well as by freeze-drying based test (Residual Moisture, Reconstitution Time, and Appearance).

After at least 1 month of storage at 5±3° C. all samples remained stable, i.e. the samples showed no significant change by any of the test methods, Table 20. These data supports the formulation for HuMax-AXL-ADC being acceptable for pharmaceutical use.

TABLE 20

HuMax-AXL-ADC demonstration batch

| Assay | Time points (months) at 5 ± 3° C. | | | | |
|---|---|---|---|---|---|
| | 0 | 1 | 3 | 6 | 12 |
| Appearance | Acceptable | Acceptable | Acceptable | Acceptable | Acceptable |
| Reconstitution Time | ≤30 sec | ≤30 sec | ≤30 sec | ≤30 sec | ≤30 sec |
| Concentration (A280) | 10.04 | 10.02 | 10.50 | 9.88 | 10.40 |
| Residual Moisture | 0.87 | NA | 1.2 | 0.9 | 0.9 |
| Sub-visible Particles 10 μM | 45 | NA | 156 | 82 | 39 |
| Sub-visible Particles 25 μM | 5 | | 12 | 4 | 1 |
| pH | 5.98 | 5.98 | 5.92 | 5.87 | 5.99 |
| SEC % Main | 98.0 | 97.9 | 98.0 | 98.0 | 98.3 |
| SEC % HMW | 1.4 | 1.4 | 1.3 | 1.4 | 1.1 |
| SEC % LMW | 0.6 | 0.6 | 0.7 | 0.6 | 0.6 |
| CE-SDS, red (%) | 99.1 | 99.2 | 99.1 | 99.1 | 99.1 |
| CE-SDS, non-red | | | | | |
| LC | 23.25 | 23.24 | 23.22 | 22.72 | 22.41 |
| HC | 12.77 | 12.84 | 12.57 | 12.49 | 12.42 |
| HL | 25.24 | 25.17 | 25.33 | 25.47 | 25.82 |
| HH | 20.44 | 20.46 | 20.40 | 20.58 | 20.78 |
| HHL | 15.88 | 15.89 | 16.09 | 16.23 | 15.97 |
| Whole | 2.41 | 2.41 | 2.38 | 2.51 | 2.45 |
| cIEF | 68.59 | 68.35 | 68.6 | 68.3 | 64.9 |
| DAR-HIC | 4.0 | 3.9 | 3.8 | 3.9 | 3.9 | n.d. = not determined

Example 10: Lyophilization Cycle

The lyophilization cycle for the lyophilized formulation of HuMax-AXL-ADC of the invention may be performed as described below with the following steps specified below: freezing, annealing, primary drying and secondary drying.

In the freezing step the vials may be cooled at 0.5° C./min to 1° C./min to −40° C. or less and held isothermally for at least 120 min. At the annealing step the temperature is raised to between−20° C. and −15° C. at a rate of 0.5° C./min to 1° C./min and held isothermally for at least 180 min. Primary drying is initiated with a decrease in pressure between 50-200 mTorr, at a temperature between −15° C. to 0° C. At the secondary drying, the temperature is increased between 30° C. and 40° C. at a rate of 0.5° C./min and held isothermally for the least 8 hours. The residual moisture should not be more than 2% by weight.

Example 11: Generation of Anti-AXL Antibodies

The generation and testing of anti-AXL antibodies is described in detail in International Application Number PCT/EP2015/065900, which is hereby incorporated by reference in its entirety. Briefly:

Various full-length and chimeric constructs of human and other mammalian AXL were prepared and used for immunizing transgenic mice (Medarex, San José, CA, USA). The following codon-optimized constructs for expression of various full-length AXL variants were generated: human (*Homo sapiens*) AXL (Genbank accession no. NP_068713.2), human-cynomolgus monkey chimeric AXL in which the human extracellular domain (ECD) was replaced with the ECD of cynomolgus monkey (*Macaca fascicularis*) AXL (translation of Genbank accession HB387229.1; aa 1-447), human-mouse chimeric AXL in which the human ECD was replaced with the ECD of mouse (*Mus musculus*) AXL (Genbank accession NP_033491.2; aa 1-441), human-mouse chimeric AXL in which the human Ig-like domain I (aa 1-134, also termed "Ig1 domain" herein) was replaced with the Ig-like domain I of mouse AXL, human-mouse chimeric AXL in which the human Ig-like domain II (aa 148-194, also termed "Ig2 domain" herein) was replaced by the Ig-like domain II of mouse AXL, human-mouse chimeric ALX in which the human FNIII-like domain I (aa 227-329, also termed "FN1 domain" herein) was replaced with the FNIII-like domain I of mouse AXL, human-mouse chimeric AXL in which the human FNIII-like domain II (aa 340-444, also termed "FN2 domain" herein) was replaced by the FNIII-like domain II of mouse AXL. In addition, the following codon-optimized constructs for various AXL ECD variants were generated: the extracellular domain (ECD) of human AXL (aa 1-447) with a C-terminal His tag (AXLECDHis), the FNIII-like domain II of human AXL (aa 327-447) with a N-terminal signal peptide and a C-terminal His tag (AXL-FN2ECDHis), and the Ig1- and Ig2-like domains of human AXL (aa 1-227) with a C-terminal His tag (AXL-Ig12ECDHis).

The HuMab mouse with sufficient antigen-specific titer development was sacrificed and the spleen and lymph nodes flanking the abdominal aorta and vena cava were collected. Fusion of splenocytes and lymph node cells to a mouse myeloma cell line (SP2.0 cells) was done by electrofusion using a CytoPulse CEEF 50 Electrofusion System (Cellectis, Paris, France), essentially according to the manufacturer's instructions.

The primary wells were sub-cloned using the ClonePix system (Genetix, Hampshire, UK). The presence of anti-AXL antibodies in sera of immunized mice or HuMab (human monoclonal antibody) hybridoma or transfectoma culture supernatant was determined by homogeneous antigen specific screening assays using Fluorometric Micro volume Assay Technology (FMAT; Applied Biosystems, Foster City, CA, USA).

Total RNA was prepared from 0.2 to 5×10$^6$ hybridoma cells and 5'-RACE-Complementary DNA (DNA) was prepared from 100 ng total RNA, using the SMART RACE cDNA Amplification kit (Clontech), according to the manufacturer's instructions. VH and VL coding regions were amplified by PCR and cloned directly, in frame, in the pG1f and pKappa expression vectors, by ligation independent cloning (Aslanidis, C. and P. J. de Jong, Nucleic Acids Res 1990;18 (20): 6069-74). For each antibody, 12 VL clones and 12 VH clones were sequenced. The resulting sequences are shown in the Table 1. CDR sequences were defined according to IMGT [42].

In some of the Examples, a comparison antibody against AXL was used (IgG1-YW327.6S2) that have been previously described (EP 2 220 131; U3 Pharma [43]; WO 2011/159980; Genentech [44]. The VH and VL sequences for these AXL-specific antibodies were cloned into the pG1f and pKappa expression vectors.

In some of the examples the antibody b12, a gp120 specific antibody was used as a negative control.

Antibodies were expressed as IgG1,κ. Plasmid DNA mixtures encoding both heavy and light chains of antibodies were transiently transfected to Freestyle HEK293F cells (Invitrogen, US) using 293fectin (Invitrogen, US) essentially as described by the manufacturer.

Example 12: Expression of Anti-AXL Antibodies in CHO Cells

HuMax AXL 107 is produced in a CHO cell line, CHO K1SV GS-KO, subcloned from the parental, CHO cell line, transfected with a GS vector carrying the variable region genes derived from a human anti AXL mAb producing hybridoma cell line. Standard mammalian cell culture conditions and purification technologies are employed in the manufacture of HuMax AXL.

Example 13-Binding Characteristics of AXL Antibodies

Binding Affinity of AXL Antibodies

The affinities of the panel of 9 anti-AXL antibodies as well as 3 variants of these antibodies with single amino acid mutations in the variable domains (IgG1-AXL-154-M103L, IgG1-AXL-183-N52Q, IgG1-AXL-726-M101L), were determined.

Affinities were determined using Bio-Layer Interferometry on a ForteBio OctetRED384. Anti-human Fc Capture (AHC) biosensors (ForteBio, Portsmouth, UK; cat no. 18-5064) were loaded for 150 s with hIgG (1 µg/mL) aiming at a loading response of 1 nm. After a baseline (150 s) the association (1000 s) and dissociation (2000 s) of AXLECDHis (as described in Example 1) was determined, using a concentration range of 10 µg/mL-0.16 µg/ml (218 nM-3 nM) with 2-fold dilution steps. For calculations, the theoretical molecular mass of AXLECDHis based on the amino acid sequence was used, i.e. 46 kDa. Experiments were carried out on an OctetRED384, while shaking at 1000 rpm and at 30° C. Each antibody was tested in three independent experiments.

Data was analyzed with ForteBio Data Analysis Software v7.0.3.1, using the 1:1 model and a global full fit with 1000 s association time and 1000 s dissociation time unless stated otherwise. A dissociation time of 1000 s (instead of the 2000 s dissociation time that was acquired) was used since this resulted in better fits. For antibody IgG1-AXL-154 and IgG1-AXL-154-M103L a dissociation time of 500 s was used. For IgG1-AXL-012 and IgG1-AXL-094 dissociation times of 200 s were used. Data traces were corrected by subtraction of a reference curve (antibody without AXLEC-DHis), the Y-axis was aligned to the last 5 s of the baseline, and interstep correction as well as Savitzky-Golay filtering was applied.

The affinities ($K_D$) of the anti-AXL antibodies ranged from $0.3*10^{-9}$M to $63*10^{-9}$M (Table 21). For mutant IgG1-AXL-183-N52Q the $K_D$ was lower than for wild-type IgG1-AXL-183, due to an approximately 2.5-fold higher dissociation rate. The observed kinetics of the other two mutants were similar to the kinetics of the wild-type IgGs.

TABLE 21

Binding of antibodies to AXL

| Antibody | Binding affinity (OCTET) | | |
|---|---|---|---|
| | KD (M) | Kon (1/Ms) | Kdis (1/s) |
| IgG1-AXL-107 | $16 * 10^{-9}$ | $2.8 * 10^5$ | $4.1 * 10^{-3}$ |
| IgG1-AXL-148 | $20 * 10^{-9}$ | $2.3 * 10^5$ | $4.4 * 10^{-3}$ |
| IgG1-AXL-154 | $7.2 * 10^{-9}$ | $2.6 * 10^5$ | $1.9 * 10^{-3}$ |
| IgG1-AXL-154-M103L | $7.8 * 10^{-9}$ | $2.7 * 10^5$ | $2.0 * 10^{-3}$ |
| IgG1-AXL-171 | $17 * 10^{-9}$ | $1.1 * 10^5$ | $1.8 * 10^{-3}$ |
| IgG1-AXL-183 | $10.2 * 10^{-9}$ | $4.1 * 10^4$ | $4.2 * 10^{-4}$ |
| IgG1-AXL-183-N52Q | $24 * 10^{-9}$ | $4.2 * 10^4$ | $1.0 * 10^{-3}$ |
| IgG1-AXL-613 | $1.5 * 10^{-9}$ | $5.4 * 10^5$ | $8.0 * 10^{-4}$ |
| IgG1-AXL-726 | $0.6 * 10^{-9}$ | $2.4 * 10^5$ | $1.3 * 10^{-4}$ |
| IgG1-AXL-726-M101L | $0.3 * 10^{-9}$ | $2.1 * 10^5$ | $6.9 * 10^{-5}$ |
| IgG1-AXL-733 | $63 * 10^{-9}$ | $1.6 * 10^5$ | $9.7 * 10^{-3}$ |

Binding of AXL Antibodies to Human, Mouse and Cynomolqus AXL

HEK293T cells were transiently transfected with expression constructs for full length human AXL, human AXL with a cynomolgus monkey extracellular domain (ECD) or human AXL with a mouse ECD. Binding of HuMab-AXL antibodies to these cells was evaluated by flow cytometry. Transfected HEK293 cells were incubated with serial dilutions of AXL-antibodies (final concentration range 0.0024-10 µg/mL) for 30 minutes at 4° C. After washing three times in PBS/0.1% BSA/0.02% azide, cells were incubated with R-Phycoerythrin (PE)-conjugated goat-anti-human IgG F(ab')2 (Jackson ImmunoResearch Laboratories, Inc., West Grove, PA; cat. No. 109-116-098) diluted 1/100 in PBS/0.1% BSA/0.02% azide (final volume 100 µL). Next, cells were washed twice in PBS/0.1% BSA/0.02% azide, resuspended in 120 UL PBS/0.1% BSA/0.02% azide and analyzed on a FACS Cantoll (BD Biosciences).

Binding curves were analyzed using non-linear regression (sigmoidal dose-response with variable slope) using GraphPad Prism V5.04 software (GraphPad Software, San Diego, CA, USA).

HuMab-AXL antibodies showed dose-dependent binding to the HEK293 cells expressing human AXL-ECD. Furthermore, HuMab-AXL antibodies recognized AXL with a cynomolgus monkey ECD, with $EC_{50}$ values in the same range as for fully human AXL. In contrast, binding of HuMabs to AXL with a mouse ECD was low (IgG1-AXL-107, IgG1-AXL-154, IgG1-AXL-154-M103L, IgG1-AXL-733, IgG1-AXL-183, IgG1-AXL-183-N52Q) or not detectable (IgG1-AXL-171, IgG1-AXL-613, IgG1-AXL-726, IgG1-AXL-726-M101L, IgG1-AXL-148). As expected, the negative control antibody IgG1-b12 showed no binding to cells expressing any of the AXL variants. The Table below shows the EC50 values and standard deviations for binding of the anti-AXL antibodies to human AXL or human AXL with a cynomolgus AXL ECD (determined in at least 3 experiments). EC50 values for binding to human AXL with a mouse AXL ECD could not be determined to very low or absent binding.

TABLE 22

Binding of anti-AXL antibodies to human AXL or human AXL with a cynomolgus AXL ECD

| Antibody | Binding EC50 (µg/mL) | |
|---|---|---|
| | human AXL Average (s.d.) | cynomolgus AXL Average (s.d.) |
| IgG1-AXL-107 | 0.050 (0.004) | 0.149 (0.021) |
| IgG1-AXL-154 | 0.105 (0.003) | 0.160 (0.027) |
| IgG1-AXL-154-M103L | 0.110 (0.038) | 0.161 (0.042) |
| IgG1-AXL-171 | 0.073 (0.023) | 0.157 (0.057) |
| IgG1-AXL-613 | 0.040 (0.023) | 0.146 (0.023) |
| IgG1-AXL-726 | 0.288 (0.206) | 0.349 (0.160) |
| IgG1-AXL-726-M101L | 0.184 (0.117) | 0.250 (0.066) |
| IgG1-AXL-733 | 0.176 (0.094) | 0.254 (0.114) |
| IgG1-AXL-148 | 0.094 (0.059) | 0.152 (0.080) |
| IgG1-AXL-183 | 0.526 (0.177) | 0.309 (0.086) |
| IgG1-AXL-183-N52Q | 0.350 (0.206) | 0.324 (0.121) |

Competition Between AXL Antibodies and Gas6 for AXL Binding

It was tested whether the AXL ligand Gas6 interfered with binding of the AXL antibodies to AXL. Therefore, AXL-positive A431 cells were incubated for 15 minutes at 4° C. with 10 µg/mL recombinant human Gas6 (R&D Systems, Abingdon, UK; cat. No. 885-GS). Subsequently, serial dilutions of AXL antibodies were prepared (final concentration range 0.014-10 µg/mL), added to the cells and incubated for 30 minutes at 4° C. After washing three times in PBS/0.1% BSA/0.02% azide, cells were incubated in 100 µL with secondary antibody at 4° C. for 30 min in the dark. As a secondary antibody binding the Fc region, R-Phycoerythrin (PE)-conjugated goat-anti-human IgG F(ab')2 (Jackson ImmunoResearch Laboratories, Inc., West Grove, PA; cat. No. 109-116-098) diluted 1/100 in PBS/0.1% BSA/0.02% azide, was used. Next, cells were washed twice in PBS/0.1% BSA/0.02% azide, resuspended in 120 µL PBS/0.1% BSA/0.02% azide and analyzed on a FACS Cantoll (BD Biosciences).

Alternatively, A431 cells were pre-incubated with 10 µg/mL AXL antibodies (15 minutes, 4° C.) to assess if the AXL ligand Gas6 could still bind in presence of AXL antibodies. After antibody pre-incubation, serial dilutions of recombinant human Gas6 (R&D Systems, Abingdon, UK; cat. No. 885-GS) were added to the cells at final concentrations of 0.001-20 µg/mL and incubated for 30 minutes at 4° C. After washing three times in PBS/0.1% BSA/0.02% azide, cells were incubated with mouse anti-Gas6 IgG2a (R&D Systems; cat no. MAB885) at 4° C. for 30 min. After washing three times in PBS/0.1% BSA/0.02% azide, cells were incubated with FITC-labelled goat anti-mouse IgG (Dako, Heverlee, Belgium; cat no. F049702) at 4° C. for 30 min in the dark. Next, cells were washed twice in PBS/0.1% BSA/0.02% azide, resuspended in 120 μL PBS/0.1% BSA/0.02% azide and analyzed on a FACS Cantoll (BD Biosciences).

Binding curves were analyzed using non-linear regression (sigmoidal dose-response with variable slope) using GraphPad Prism V5.04 software (GraphPad Software, San Diego, CA, USA).

In experiments (n=3) in which A431 cells were pre-incubated with Gas6, the maximal binding values of anti-AXL antibodies was comparable to antibody binding in absence of Gas6 (maximal binding after Gas6 pre-incubation was 90-108% of binding without Gas6 pre-incubation). The EC50 values for AXL antibody binding with or without Gas6 pre-incubation were in the same range, or somewhat enhanced after Gas6 pre-incubation (Table 23).

The binding of control AXL antibody YW327.6S2 to A431 cells was greatly reduced in the presence of Gas6 compared to binding without Gas. Maximal binding of YW327.6S2 in the presence of Gas6 was 19% of binding without Gas6, and the EC50 value for binding to A431 cells was 21-fold higher when cells had been pre-incubated with Gas6.

In experiments in which A431 cells were pre-incubated with anti-AXL antibodies, Gas6 binding was evaluated (n=3). Binding of Gas6 to A431 cells was similar with or without pre-incubation with HuMab-AXL antibodies. Average EC50 concentrations of Gas6 binding when cells were pre-incubated with HuMabs (0.34-0.83 μg/mL) and maximal Gas6 binding were similar to Gas6 binding in the presence of negative control antibody b12 (EC50 concentration: 0.40 μg/mL; 95-115% of Gas6 binding in the presence of the b12 control antibody). The binding of Gas6 to A431 cells was greatly reduced in the presence of control AXL antibody YW327.6S2 compared to pre-incubation with b12 (the EC50 concentration was 14-fold higher). Maximal binding of Gas6 in the presence of control antibody YW327.6S2 was 17% of binding in the presence of negative control antibody b12.

TABLE 23

Competition between AXL antibodies and Gas6 for AXL binding

| | Antibody binding to A431 cells | | | Gas6 binding to A431 cells | |
|---|---|---|---|---|---|
| Antibody | EC50 w/o Gas6 EC50 (μg/mL) mean (s.d.) | EC50 in presence of Gas6 (μg/mL) mean (s.d.) | Maximal binding in presence of Gas6 (% of binding in absence of Gas6) mean (s.d.) | EC50 in presence of AXL antibodies (μg/mL) mean (s.d.) | Maximal binding in presence of AXL antibodies (% of binding in prescence of control antibody) mean (s.d.) |
| IgG1-AXL-107 | 0.16 (0.17) | 0.94 (1.18) | 91 (5) | 0.78 (0.54) | 96 (8) |
| IgG1-AXL-148 | 0.11 (0.13) | 0.20 (0.30) | 93 (5) | 0.73 (0.52) | 106 (7) |
| IgG1-AXL-154 | 0.42 (0.55) | 0.76 (0.78) | 99 (13) | 0.44 (0.28) | 95 (10) |
| IgG1-AXL-171 | 0.18 (0.21) | 0.32 (0.40) | 95 (5) | 0.69 (0.42) | 108 (5) |
| IgG1-AXL-183 | 0.69 (0.72) | 1.19 (1.11) | 90 (19) | 0.34 (0.13) | 115 (8) |
| IgG1-AXL-511 | 0.12 (0.11) | 0.30 (0.31) | 93 (15) | 0.74 (0.44) | 113 (6) |
| IgG1-AXL-613 | 0.09 (0.09) | 0.10 (0.10) | 108 (22) | 0.57 (0.36) | 100 (11) |
| IgG1-AXL-726 | 0.32 (0.35) | 0.55 (0.69) | 97 (10) | 0.77 (0.58) | 98 (10) |
| IgG1-AXL-733 | 0.49 (0.51) | 0.62 (0.23) | 93 (5) | 0.83 (0.54) | 96 (5) |
| YW327.6S2 | 0.09 (0.09) | 1.90 (1.04)* | 41 (24) | 5.53 (7.09)* | 17 (10) |
| b12 | n.a.[a] | n.a. | n.a. | 0.40 (0.11) | 100 |

[a]n.a., not applicable
*EC50 values less accurate due to low binding.

Example 14-Binding Characteristics of AXL Antibody-Drug Conjugates (AXL-ADCs)

HEK293T cells were transiently transfected with expression constructs for full-length human AXL (see Example 1). Binding of anti-AXL antibodies and AXL-ADCs to these cells was evaluated by flow cytometry. Transiently transfected HEK293 cells were incubated with serial dilutions of anti-AXL antibodies or AXL-ADCs (4-fold dilutions; final concentration range 0.003-10 μg/mL) for 30 minutes at 4° C. After washing three times in PBS/0.1% BSA/0.02% azide, cells were incubated in 100 μL with secondary antibody at 4° C. for 30 min in the dark. As a secondary antibody, R-Phycoerythrin (PE)-conjugated goat-anti-human IgG F(ab')2 (Jackson ImmunoResearch Laboratories, Inc., West Grove, PA; cat. No. 109-116-098) diluted 1/100 in PBS/0.1% BSA/0.02% azide, was used. Next, cells were washed twice in PBS/0.1% BSA/0.02% azide, resuspended in 120 µL PBS/0.1% BSA/0.02% azide and analyzed on a FACS Cantoll (BD Biosciences).

Binding curves were analyzed using non-linear regression (sigmoidal dose-response with variable slope) using Graph-Pad Prism V5.04 software (GraphPad Software, San Diego, CA, USA). These showed that binding of the anti-AXL antibodies to the HEK293 cells expressing human AXL-ECD was similar to the binding of the AXL-ADCs.

Example 15-Epitope Mapping Studies Anti-AXL Antibody Panel

Determining the AXL Domain Specificity Using Human-Mouse AXL Chimeric Molecules

The AXL domain specificity of the AXL antibodies was determined using a panel of human-mouse chimeric AXL mutants. Five different chimeric AXL molecules were generated, in which either the human Ig-like domain I (Ig1), the Ig-like domain II (Ig2), the human FNIII-like domain I (FN1) or the human FNIII-like domain II domain (FN2) were replaced with their murine homologs. The codon-optimized constructs for expression of the AXL human-mouse chimeras were generated and expressed in HEK293F cells.

Binding of 1 µg/mL anti-AXL antibody to the human-mouse AXL chimeras was determined by flow cytometry. IgG1-b12 was included as an isotype control IgG1.

All anti-AXL antibodies showed binding to human AXL, whereas binding was abrogated or strongly reduced when the human AXL ECD was replaced with its murine homolog. The human-mouse cross-reactive monoclonal AXL antibody YW327.6S2 was included to confirm expression of hsAXL-mmECD.

Anti-AXL antibody 107 and 613 showed strongly reduced binding to hsAXL-mmIg1, indicating recognition of an epitope in the AXL Ig1 domain. IgG1-AXL-148 and IgG1-AXL-171 showed strongly reduced binding to hsAXL-mmIg2, indicating recognition of an epitope in the AXL Ig2 domain. IgG1-AXL-154, IgG1-AXL-183 and IgG1-AXL-733 showed reduced binding to hsAXL-mmFN1, indicative of a binding epitope in the AXL FN1 domain. Finally, binding of IgG1-AXL-726 was lost in hsAXL-mmFN2, indicating recognition of an epitope within the FN2 domain.

High Resolution Epitope Mapping to Identify Amino Acids in the AXL Extracellular Domain Involved in Binding of AXL Antibodies To identify amino acids in the AXL extracellular domain involved in binding of anti-AXL antibodies, a library of AXL sequence variants was generated by recombination of AXL sequences derived from species with variable levels of homology with the human AXL sequence in the extracellular domain. Briefly, an expression plasmid encoding human AXL (Hs) was mixed with cloning plasmids encoding *Mus musculus* (Mm), *Monodelphis domestica* (Md; opossum) *Anolis carolinensis* (Ac; lizard) and *Tetraodon nigroviridis* (Tn; pufferfish) AXL homologs or vice versa. A combination of two primers specific to either the cloning or the expression vector was used to perform a PCR amplifying the AXL extracellular domain (ECD) with abbreviated elongation time, forcing melting and reannealing of nascent DNA replication strands during PCR cycling. Full length ECD was amplified using a nested PCR, again specific to recombination products containing termini originating from both vectors.

Resulting AXL ECD PCR products were cloned into an expression vector creating full length AXL, and resulting plasmids were sequenced, ranked by maximal difference to the template vectors and selected to create a minimal ensemble with maximal differentiation power. Plasmids encoding AXL homologs from Hs, Mm, Md, Ac and Tn, four human/mouse chimeric plasmids encoding Hs AXL with murine Ig1, Ig2, Fn1 or Fn2 domains, and the sixteen most differentiating plasmids from the recombination library were transfected into HEK293-F cells according to the specifications supplied by the manufacturer (Life technologies). FACS binding data using 1 µg/mL anti-AXL antibodies were deconvoluted by scoring per amino acid if mutation did (+1) or did not (−1) correlate with loss of binding, after which a baseline correction and normalization to a scale of −5 to +5 was applied, resulting in an impact score per amino acid over the full ECD.

The deconvoluted binding data is summarized in Table 24 as the amino acids involved in binding. Antibodies of which the binding site could not be mapped to high resolution due to a lack of recombination events in the proximity of the binding site, are indicated as not resolved.

TABLE 24

AXL domain specificity for all anti-AXL antibodies

| Antibody | AXL domain specificity | AXL aa's involved in binding |
|---|---|---|
| IgG1-AXL-107 | Ig1 | L121-Q129 |
| IgG1-AXL-148 | Ig2 | D170-R190 |
| IgG1-AXL-154 | Fn1 | Q272-A287, G297-P301 |
| IgG1-AXL-154-M103L | n.d.$^a$ | n.d. |
| IgG1-AXL-171 | Ig2 | P170, T182-R190 |
| IgG1-AXL-183 | Fn1 | Not resolved |
| IgG1-AXL-183-N52Q | n.d. | n.d. |
| IgG1-AXL-613 | Ig1 | T112-Q124 |
| IgG1-AXL-726 | Fn2 | A359, R386, Q436-K439 |
| IgG1-AXL-726-M101L | n.d. | n.d. |
| IgG1-AXL-733 | Fn1 | Not resolved |
| IgG1-AXL-061 | Ig1 | I97-Q124 |
| IgG1-AXL-137 | Ig1 | Q57, E92-T105 |
| YW327.6S2 | Ig1 | G39-D59 |

$^a$n.d., not determined

Example 16-Antibody VH and VL Variants that Allow Binding to AXL

Protein sequences of the VH and VL regions of the anti-AXL antibody panel (described in Example 1) were aligned and compared for AXL binding to identify critical or permissive changes of amino acid residues in the VH or VL regions. Therefore, antibodies with identical VH or VL regions were grouped and compared for binding to human AXL and differences in VL or VH sequences, respectively. Binding to human AXL transiently expressed by HEK-293F cells was assessed in the homogeneous antigen specific screening assay as described in Example 1. Numbering of amino acid positions for the alignments done in the present example was done based on the sequences put forth in Table 1, i.e. the first amino acid in the shown sequence was numbered as position '1', the second as position '2', etc.

First, antibodies with identical VL sequences were grouped. IgG1-AXL-148 and IgG1-AXL-140 were found to have an identical VL sequence, and showed 1 amino acid difference in the HC CDR3 region (F for I at amino acid position 109). Both antibodies bound to human AXL (Table 7), indicating that the amino acid at position 109 is not essential for antibody binding, assuming that a mutation identified in the CDR2 region (G for A at the amino acid position 56) does not compensate for loss of binding.

IgG1-AXL-726 and IgG1-AXL-187 were found to have an identical VL sequence and both antibodies bound to human AXL (Table 25). Two amino acid residue changes in the HC CDR3 region (R for S at position 97 and A for T at position 105) were allowed without losing binding, assuming that mutations identified in the CDR1 (Y for H at position 32) and/or in the framework regions (P3Q, V24I, Y25D, T86A and T117A) do not compensate for loss of binding.

IgG1-AXL-171, IgG1-AXL-172 and IgG1-AXL-181 were found to have an identical VL sequence and all antibodies bound to human AXL (Table 7). The CDR3 regions of these three antibodies were identical, but an amino acid residue change in the HC CDR1 (S for N at position 31) or the framework region (H for Q at position 82) was allowed without losing binding.

IgG1-AXL-613, IgG1-AXL-608-01, IgG1-AXL-610-01 and IgG1-AXL-620-06 were found to have an identical VL sequence, and showed one amino acid difference in the HC CDR3 region (N for D at amino acid position 101). All antibodies bound to human AXL (Table 25), indicating that the amino acid at position 101 is not essential, assuming that mutations identified in the HC CDR2 (V for A at position 58) and/or in the framework regions (N35S, M37V, A61V, L70I, S88A) do not compensate for loss of binding.

Next, antibodies with identical VH sequences were grouped.

IgG1-AXL-613 and IgG1-AXL-613-08 were found to have an identical VH sequence, and showed five amino acid differences in the CDR3 region of the LC (RSNWL for YGSSY at positions 92 to 96). Both antibodies bound to human AXL (Table 25), indicating that the variation of amino acid at positions 92 to 96 are allowed and do not affect antibody binding, assuming that mutations identified in the CDR1 (deletion of the S at position 30), CDR2 (G51D), and/or in the framework regions (G9A, S54N, R78S, Q100G, L104V) do not compensate for loss of binding.

TABLE 25

| Antibody | EC50 (µg/mL) | Maximal binding (Arbitrary units) |
|---|---|---|
| IgG1-AXL-140 | 0.0026 | 2889 |
| IgG1-AXL-148 | 0.0036 | 3499 |
| IgG1-AXL-171 | 0.003 | 2575 |
| IgG1-AXL-172 | 0.0055 | 5378 |
| IgG1-AXL-181 | 0.008 | 3598 |
| IgG1-AXL-187 | 0.0065 | 2563 |
| IgG1-AXL-608-01 | 0.0035 | 3318 |
| IgG1-AXL-610-01 | 0.0023 | 2947 |
| IgG1-AXL-613 | 0.0072 | 5211 |
| IgG1-AXL-613-08 | 0.0242 | 2209 |
| IgG1-AXL-620-06 | 0.0034 | 4352 |
| IgG1-AXL-726 | 0.0471 | 3154 |

Example 17-In Vitro Cytotoxicity Induced by MMAE-Conjugated AXL Antibodies

Conjugation of MMAE to Anti-AXL Antibodies

Anti-AXL antibodies were purified by Protein A chromatography according to standard procedures and conjugated to vcMMAE. The drug-linker vcMMAE was alkylated to the cysteines of the reduced antibodies according to procedures described in the literature (see [150], [151], and [152]). The reaction was quenched by the addition of an excess of N-acetylcysteine. Any residual unconjugated drug was removed by purification and the final anti-AXL antibody drug conjugates were formulated in PBS. The anti-AXL antibody drug conjugates were subsequently analyzed for concentration (by absorbance at 280 nm), the drug to antibody ratio (DAR) by reverse phase chromatography (RP-HPLC) and hydrophobic interaction chromatography (HIC), the amount of unconjugated drug (by reverse phase chromatography), the percentage aggregation (by size-exclusion chromatography, SEC-HPLC) and the endotoxin levels (by LAL). The results are shown below.

TABLE 26

Overview of different characteristics of the antibody-drug conjugates.

| Assay | ADC | | | | | | | | | |
|---|---|---|---|---|---|---|---|---|---|---|
| | IgG1-AXL-107 | IgG1-AXL-148 | IgG1-AXL-154-M103L | IgG1-AXL-171 | IgG1-AXL-183-N52Q | IgG1-AXL-511 | IgG1-AXL-613 | IgG1-AXL-726-M101L | IgG1-AXL-733 | IgG1-b12 |
| Concentration (mg/mL) | 7.18 | 9.63 | 6.57 | 3.69 | 6.71 | 5.77 | 6.17 | 7.37 | 7.71 | 1.58 |
| DAR by HIC | 3.97 | 3.96 | 3.71 | 3.65 | 3.92 | 3.87 | 4.23 | 4.12 | 4.08 | 4.00 |
| % unconjugated antibody | 4.68 | 5.58 | 6.13 | 7.11 | 8.68 | 8.35 | 5.13 | 4.99 | 3.74 | 1.89 |
| % aggregate by SEC-HPLC | 6.3 | 2.28 | 2.9 | 3.3 | 5.2 | 5.1 | 6.4 | 4.0 | 3.5 | 2.5 |
| Endotoxin (EU/mg) | 2.3 | 1.2 | 2.6 | 3.1 | 5.9 | 4.5 | 2.0 | 3.6 | 7.6 | 11.5 |

Cell Culture

LCLC-103H cells (human large cell lung cancer) and A431 cells (DMSZ, Braunschweig, Germany) were cultured in RPMI 1640 with L-Glutamine (Cambrex; cat.no. BE12-115F) supplemented with 10% (vol/vol) heat inactivated Cosmic Calf Serum (Perbio; cat.no. SH30087.03), 2 mM L-glutamine (Cambrex; cat.no. US17-905C), 50 IU/mL penicillin, and 50 µg/mL streptomycin (Cambrex; cat.no. DE17-603E). MDA-MB231 cells were cultured in DMEM with high glucose and HEPES (Lonza #BE12-709F), Donor Bovine Serum with Iron (Life Technologies #10371-029), 2 mM L-glutamine (Lonza #BE17-605E), 1 mM Sodium Pyruvate (Lonza #BE13-115E), and MEM Non-Essential Amino Acids Solution (Life Technologies #11140). The cell lines were maintained at 37° C. in a 5% (vol/vol) $CO_2$ humidified incubator. LCLC-103H, A431 and MDA-MB231 cells were cultured to near confluency, after which cells were trypsinized, resuspended in culture medium and passed through a cell strainer (BD Falcon, cat.no. 352340) to obtain a single cell suspension. $1 \times 10^3$ cells were seeded in each well of a 96-well culture plate, and cells were incubated for 30 min at room temperature and subsequently for 5 hrs at 37° C., 5% $CO_2$ to allow adherence to the plate.

Cytotoxicity Assay

Serial dilutions (final concentrations ranging from 0.00015 to 10 g/mL) of MMAE-conjugated AXL-antibodies were prepared in culture medium and added to the plates. Incubation of cells with 1 µM staurosporin (#S6942-200, Sigma) was used as reference for 100% tumor cell kill. Untreated cells were used as reference for 100% cell growth. Plates were incubated for 5 days at 37° C., 5% $CO_2$. Next, CellTiter-Glo Reagent (Promega; cat.no. G7571) was added to the wells (20 µL per well) and plates were incubated for 1.5 hours at 37° C., 5% $CO_2$. Subsequently, 180 µL per well was transferred to white 96-well Optiplate™ plates (PerkinElmer, Waltham, MA; cat.no. 6005299), which were incubated for 30 min at room temperature. Finally, luminescence was measured on an EnVision multiplate reader (Envision, Perkin Elmer).

MMAE-conjugated AXL-antibodies induced 50% cell kill in LCLC-103H cells at concentrations between 0.004 and 0.219 µg/mL as shown in the Table 27a below.

Similarly, AXL-ADCs efficiently induced cytotoxicity in A431 and MDA-MB231 cells (Table 27b below).

TABLE 27a

Cytotoxicity of MMAE-conjugated-AXL-antibodies in LCLC-103H cells (EC50 values)

| ADC | EC50 (µg/mL) |
| --- | --- |
| IgG1-AXL-613-vcMMAE | 0.004 |
| IgG1-AXL-148-vcMMAE | 0.012 |
| IgG1-AXL-171-vcMMAE | 0.018 |
| IgG1-AXL-726-M101L-vcMMAE | 0.018 |
| IgG1-AXL-107-vcMMAE | 0.022 |
| IgG1-AXL-511-vcMMAE | 0.032 |
| IgG1-AXL-154-M103L-vcMMAE | 0.044 |
| IgG1-AXL-183-N52Q-vcMMAE | 0.113 |
| IgG1-AXL-733-vcMMAE | 0.219 |

TABLE 27B

Cytotoxicity of MMAE-conjugated AXL antibodies in A431 and MDA-MB-231 cells (EC50 values)

| | EC50 (µg/mL) | | | |
| --- | --- | --- | --- | --- |
| | A431 (n = 3) | | MDA-MB231 (n = 2) | |
| ADC | Mean | s.d. | Mean | s.d. |
| IgG1-AXL-107-vcMMAE | 0.154 | 0.066 | 0.037 | 0.005 |
| IgG1-AXL-148-vcMMAE | 0.070 | 0.013 | 0.012 | 0.004 |
| IgG1-AXL-154-M103L-vcMMAE | 0.719 | 0.091 | 0.396 | 0.195 |
| IgG1-AXL-171-vcMMAE | 0.206 | 0.074 | 0.035 | 0.006 |
| IgG1-AXL-183-N52Q-vcMMAE | 1.157 | 0.160 | 0.139 | 0.028 |
| IgG1-AXL-511-vcMMAE | 0.093 | 0.020 | 0.052 | 0.003 |
| IgG1-AXL-613-vcMMAE | 0.109 | 0.078 | 0.005 | 0.001 |
| IgG1-AXL-726-M101L-vcMMAE | 0.270 | 0.157 | 0.022 | 0.002 |
| IgG1-AXL-733-vcMMAE | 1.253 | 0.228 | 0.881 | 0.182 |

Example 17-Therapeutic Treatment of LCLC-103H Tumor Xenografts in SCID Mice with MMAE-Conjugated Anti-AXL Antibodies The in vivo efficacy of MMAE-conjugated anti-AXL antibodies was determined in established subcutaneous (SC) LCLC-103H xenograft tumors in SCID mice. $5 \times 10^6$ LCLC-103H (large cell lung carcinoma) tumor cells (obtained from Leibniz-Institut DSMZ-Deutsche Sammlung von Mikroorganismen und Zellkulturen GmbH (DSMZ)) in 200 µL PBS were injected subcutaneously in the right flank of female SCID mice. Starting 14-21 days after tumor cell inoculation, when the average tumor size was >100-200 mm³ and distinct tumor growth was observed, a single injection with 1 mg/kg (20 µg/mouse) IgG1-AXL-vcMMAE antibodies (as described in Supplementary Example 1) or control (unconjugated IgG1-b12) was given intraperitoneally (100 µL/mouse). Tumor volume was determined at least two times per week. Tumor volumes (mm³) were calculated from caliper (PLEXX) measurements as: $0.52 \times (length) \times (width)^2$.

The panel of anti-AXL-vcMMAE antibodies showed a broad range of anti-tumor activity in established SC LCLC-103H tumors. Clones IgG1-AXL-733-vcMMAE, IgG1-AXL-107-vcMMAE and IgG1-AXL-148-vcMMAE induced tumor regression, clones AXL-171-vcMMAE, IgG1-AXL-511-vcMMAE and IgG1-AXL-613-vcMMAE induced tumor growth inhibition, and clones IgG1-AXL-154-M103L-vcMMAE, IgG1-AXL-183-N52Q-vcMMAE, and IgG1-AXL-726-M101L-vcMMAE showed no or only minor tumor growth inhibition.

Statistical analysis on the last day that all groups were intact (day 30) using One Way ANOVA (Dunnett's multiple comparisons test versus control IgG1-b12) indicated a highly significant difference ($p<0.0001$) in tumor volume between IgG1-b12 versus IgG1-AXL-733-vcMMAE, IgG1-AXL-107-vcMMAE and IgG1-AXL-148-vcMMAE. Treatment with these clones led in some mice within these groups to complete tumor reduction. Treatment with clones IgG1-AXL-171-vcMMAE, IgG1-AXL-511-vcMMAE and IgG1-AXL-613-vcMMAE also showed significant tumor growth inhibition compared to IgG1-b12, but the differences were less pronounced ($p<0.05$ to $p<0.001$). The tumor growth of mice treated with clones IgG1-AXL-154-M103L-vcMMAE, IgG1-AXL-183-N52Q-vcMMAE, and IgG1-AXL- 726-M101L-vcMMAE was not significant affected compared to the IgG1-b12 control.

Anti-tumor activity of anti-AXL-vcMMAE antibodies was observed in various other in vivo tumor models. In two cell line-derived xenograft models (A431; epidermoid adenocarcinoma, and MDA-MB-231; breast cancer) anti-AXL-vcMMAE antibodies induced tumor growth inhibition, and tumor regression was induced by anti-AXL-vcMMAE antibodies in two patient-derived xenograft models from patients with pancreas cancer and cervical cancer.

Example 18-Anti-Tumor Efficacy of AXL-ADCs in a Pancreas Cancer Patient-Derived Xenograft (PDX) Model with Heterogeneous Target Expression The anti-tumor activity of IgG1-AXL-107-vcMMAE, IgG1-AXL-148-vcMMAE, and IgG1-AXL-733-vcMMAE was determined in the PAXF1657 pancreas cancer PDX model (experiments performed by Oncotest, Freiburg, Germany). Human pancreas tumor tissue was subcutaneously implanted in the left flank of 5-7 weeks old female NMRI nu/nu mice. Randomization of animals was performed as follows: animals bearing a tumor with a volume between 50-250 mm$^3$, preferably 80-200 mm$^3$, were distributed in 7 experimental groups (8 animals per group), considering a comparable median and mean of group tumor volume.

At day of randomization (day 0), the 3 ADCs were dosed intravenously (i.v.) at either 4 mg/kg or 2 mg/kg, and the control group received a single dose of IgG1-b12 (4 mg/kg). Tumor volumes (mm$^3$) were monitored twice weekly and were calculated from caliper (PLEXX) measurements as: 0.52×(length)×(width)$^2$.

Treatment of mice with 2 mg/kg IgG1-AXL-107-vcMMAE, IgG1-AXL-148-vcMMAE and IgG1-AXL-733-vcMMAE significantly reduced the growth of PAXF1657 tumors compared to the control group. At a dose of 4 mg/kg IgG1-AXL-107-vcMMAE, IgG1-AXL-148-vcMMAE and IgG1-AXL-733-vcMMAE induced tumor regression of PAXF1657 tumors. On day 14 after treatment, the average tumor size in mice that had been treated with 2 mg/kg or 4 mg/kg IgG1-AXL-107-MMAE, IgG1-AXL-148-MMAE or IgG1-AXL-733-MMAE was significantly smaller than in mice that had been treated with an isotype control IgG (IgG1-b12) (p<0.001; Tukey's multiple comparison test).

Treatment of mice with unconjugated IgG1-AXL-148 did not result in anti-tumor activity in the PAXF1657 model. Conjugated IgG1-AXL-148-vcMMAE, however, induced dose-dependent antitumor activity in this model, illustrating that the therapeutic capacity of AXL-ADCs is dependent on the cytotoxic activity of MMAE.

Moreover, treatment of mice with the untargeted ADC IgG1-b12-vcMMAE did not show anti-tumor activity in the PAXF1657 model, illustrating that the therapeutic capacity of AXL-ADCs also depends on specific target binding.

Example 19-AXL Antibodies Binding to the Ig1 Domain

The AXL domain specificity of AXL antibodies IgG1-AXL-061, IgG1-AXL-107, IgG1-AXL-137, and IgG1-AXL-613 was determined using a panel of human-mouse chimeric AXL mutants. The human-mouse cross-reactive monoclonal AXL antibody YW327.6S2 was included to confirm expression of hsAXL-mmECD. IgG1-b12 was included as isotype control antibody. Five different chimeric AXL molecules were generated and expressed in HEK293F. In brief, the human Ig-like domain I (Ig1), the Ig-like domain II (Ig2), the human FNIII-like domain I (FN1) or the human FNIII-like domain II domain (FN2) were replaced with their murine homologs. Binding of 1 μg/mL anti-AXL antibody to the human-mouse AXL chimeras was determined by flow cytometry . . . .

All anti-AXL antibodies showed binding to human AXL, whereas binding was abrogated when the human AXL ECD was replaced with its murine homolog. As expected, the human-mouse cross-reactive monoclonal AXL antibody YW327.6S2 showed binding to hsAXL-mmECD, confirming proper expression of hsAXL-mmECD.

AXL antibodies IgG1-AXL-061, IgG1-AXL-107, IgG1-AXL-137, and IgG1-AXL-613 showed strongly reduced binding to hsAXL-mmIg1, illustrating recognition of an epitope in the AXL Ig1 domain. In line with this, binding of IgG1-AXL-061, IgG1-AXL-107, IgG1-AXL-137, and IgG1-AXL-613 to hsAXL-mmIg2, hsAXL-mmFN1 or hsAXL-mmFN2 was not affected. The human-mouse cross-reactive monoclonal AXL antibody YW327.6S2 showed binding to all chimeric AXL variants, confirming proper expression of these proteins.

Example 20-AXL Antibodies IgG1-AXL-107 and IgG1-AXL-613 Bind to the Ig1 Domain but do not Compete with Gas6 Binding It was tested whether the binding of the AXL antibodies IgG1-AXL-061, IgG1-AXL-107, IgG1-AXL-137, or IgG1-AXL-613 interfered with binding of AXL ligand Gas6 to AXL. Therefore, binding of Gas6 to A431 cells that had been pre-incubated with 10 μg/mL AXL antibodies was tested. Pre-incubation with AXL antibody YW327.6S2, that was described to compete with Gas6 for AXL binding, IgG1-b12 (isotype control) or medium (negative control) were included as controls.

Binding curves were analyzed using non-linear regression (sigmoidal dose-response with variable slope) using Graph-Pad Prism V5.04 software (GraphPad Software, San Diego, CA, USA).

Table 28 shows that binding of Gas6 to A431 cells that had been pre-incubated with IgG1-AXL-107 and IgG1-AXL-613 antibodies was similar to the IgG1-b12 and medium controls. This illustrates that binding of IgG1-AXL-107 and IgG1-AXL-613 to AXL does not interfere with Gas6 binding, as shown in Example 13. The binding of Gas6 to A431 cells was largely reduced in the presence of IgG1-AXL-061, IgG1-AXL-137 and control AXL antibody YW327.62 compared to the IgG1-b12 and medium controls.

In experiments in which A431 cells were pre-incubated with Gas6, the maximal binding values of IgG1-AXL-107 and IgG1-AXL-613 were comparable to antibody binding in absence of Gas6 (maximal binding after Gas6 pre-incubation was 91-108% of binding without Gas6 pre-incubation) (Table 28). The $EC_{50}$ values for IgG1-AXL-107 and IgG1-AXL-613 binding with or without Gas6 pre-incubation were in the same range, or somewhat higher after Gas6 pre-incubation (Table 28), illustrating that IgG1-AXL-107 and IgG1-AXL-613 do not compete with Gas6 binding. Similar to control antibody YW327.6S2, the binding of IgG1-AXL-061 and IgG1-AXL-137 to A431 cells was greatly reduced in the presence of Gas6 compared to binding without Gas6 (maximal binding after Gas6 pre-incubation was 40-43% of binding without Gas6 pre-incubation; Table 28). The $EC_{50}$ values for IgG1-AXL-061 and IgG1-AXL-137 could not properly be determined after Gas6 pre-incubation (Table 28). This shows that IgG1-AXL-061 and IgG1-AXL-137 compete with Gas6 for binding to AXL.

These data demonstrate that antibodies binding to the AXL Ig1 domain have differential effect on Gas6 binding.

determined in the A431 (epidermoid carcinoma) tumor model, that produces high levels of Gas6, and the LCLC-103H (large cell lung carcinoma) tumor model, that produces low levels of Gas6.

TABLE 28

| | Antibody binding to A431 cells | | | Gas6 binding to A431 cells | |
|---|---|---|---|---|---|
| Antibody | EC50 w/o Gas6 EC50 (µg/mL) mean (s.d.) | EC50 in presence of Gas6 (µg/mL) mean (s.d.) | Maximal binding in presence of Gas6 (% of binding in absence of Gas6) mean (s.d.) | EC50 in presence of AXL antibodies (µg/mL) mean (s.d.) | Maximal binding in presence of AXL antibodies (% of binding in prescence of control antibody) mean (s.d.) |
| IgG1-AXL-061 | 0.15 (n.a.) | n.a. | 43 (28) | n.a. | 22 (8) |
| IgG1-AXL-107 | 0.16 (0.17) | 0.94 (1.18) | 91 (5) | 0.78 (0.54) | 96 (8) |
| IgG1-AXL-137 | 0.11 (0.10) | n.a. | 40 (18) | n.a | 36 (4) |
| IgG1-AXL-613 | 0.09 (0.09) | 0.10 (0.10) | 108 (22) | 0.57 (0.36) | 100 (11) |
| YW327.6S2 | 0.09 (0.09) | 1.90 (1.04)* | 41 (24) | 5.53 (7.09)* | 17 (10) |
| b12 | n.a.[a] | n.a. | n.a. | 0.40 (0.11) | 100 |

[a] n.a., not applicable
*EC50 values less accurate due to low binding.

Example 21-In Vivo Anti-Tumor Efficacy of AXL-ADCs in Xenograft Models with and without Autocrine (Endogenous) Gas6 Production Gas6 Production of A431 and LCLC-103H Tumor Cells It was tested whether A431 cells and LCLC-103H cells produce Gas6. Therefore, cells were grown in complete culture medium for 3 days. Gas6 levels in supernatant were determined using the Quantikine Human Gas6 ELISA (R&D Systems, Minneapolis, MN) according to manufacturer's instructions. This assay uses the quantitative sandwich ELISA technique. A monoclonal Ab specific for human Gas6 has been pre-coated onto a microplate. Standards and samples are pipetted into the wells and any human Gas6 present is bound by the immobilized Ab. After washing away any unbound substances, an enzyme-linked polyclonal Ab specific for human Gas6 is added to the wells. Following a wash to remove any unbound Ab-enzym reagent, a substrate is added to the wells and color develops in proportion to the amount of human Gas6 bound in the initial step. The color development is stopped and the intensity of the color is measured.

Cell culture medium conditioned by A431 cells was found to contain 2576 ng/ml Gas6, while the concentration of Gas6 in medium conditioned by LCLC-103H cells was more than 20-fold less (Table 29).

TABLE 29

| Gas6 production in tumor cell conditioned medium. | |
|---|---|
| Cell line | Gas6 in supernatant (ng/mL) |
| LCLC-103H | 126 |
| A431 | 2576 |

Anti-Tumor Activity of AXL-ADCs In Vivo

The in vivo anti-tumor activity of IgG1-AXL-061-vcMMAE (Ig1 binder), IgG1-AXL-107-vcMMAE (Ig1-binder), IgG1-AXL-137-vcMMAE (Ig1-binder), IgG1-AXL-148-vcMMAE (Ig2-binder), IgG1-AXL-183-vcMMAE (FN1-binder), and IgG1-AXL-726-vcMMAE (FN2-binder) was Tumor induction was performed by subcutaneous injection of $5 \times 10^6$ A431 or LCLC-103H tumor cells (both obtained from Leibniz-Institut-Deutsche Sammlung von Mikroorganismen und Zellkulturen GmbH (DSMZ)) in 200 µL PBS in the right flank of female SCID mice. Treatment was started 14-21 days after tumor cell inoculation, when the average tumor size was >100-200 mm$^3$ and distinct tumor growth was observed. Mice received a single injection or a total of 4 biweekly intraperitoneal injections with IgG1-AXL-vcMMAE ADCs or control antibody (unconjugated IgG1-b12), as indicated. Tumor volume was determined at least two times per week. Tumor volumes (mm$^3$) were calculated from caliper (PLEXX) measurements as: $0.52 \times$ (length)$\times$(width)$^2$.

Results:

Treatment of mice with 3 mg/kg IgG1-AXL-107-vcMMAE, IgG1-AXL-148-vcMMAE and IgG1-AXL-733-vcMMAE induced growth inhibition of A431 tumors.

Treatment of mice with 3 mg/kg IgG1-AXL-148-vcMMAE, IgG1-AXL-183-vcMMAE (FN1 binder) and IgG1-AXL-726-vcMMAE (FN2 binder) induced growth inhibition of A431 tumors. In contrast, clones IgG1-AXL-061-vcMMAE and IgG1-AXL-137-vcMMAE did not show anti-tumor activity in the A431 xenograft model.

Treatment of mice with 3 mg/kg IgG1-AXL-061-vcMMAE, IgG1-AXL-137-vcMMAE, IgG1-AXL-148-vcMMAE, IgG1-AXL-183-vcMMAE and IgG1-AXL-726-vcMMAE induced tumor regression in the LCLC-103H xenograft model. Similarly, treatment of mice with 1 mg/kg IgG1-AXL-107-vcMMAE or 1 mg/kg IgG1-AXL-613-vcMMAE induced regression of LCLC-103H tumors.

In summary, all AXL-ADCs showed anti-tumor activity in the LCLC-103H xenograft model that produces low levels of Gas6. In the A431 xenograft model, that produces high levels of Gas6, anti-tumor activity was only observed for those AXL-ADCs that did not compete with the AXL ligand Gas6.

Example 22-Anti-Tumor Efficacy of AXL-ADCs in an Esophageal Cancer Patient-Derived Xenograft (PDX) Model The anti-tumor activity of IgG1-AXL-107-vcMMAE was evaluated in the subcutaneous esophageal PDX model ES0195 in BALB/c nude mice (experiments performed by Crown Bioscience. Taicang Jiangsu Province, China). Tumor fragments from donor mice bearing patient-derived esophageal xenografts (ES0195) were used for inoculation into BALB/c nude mice. Each mouse was inoculated subcutaneously at the right flank with one tumor fragment (2-3 mm in diameter) and tumors were allowed to grow until the tumor volume was about 150 mm$^3$. Randomization of animals was performed as follows: animals bearing a tumor with a volume of about 150 mm$^3$ were distributed in 5 experimental groups (8 animals per group), considering a comparable median and mean of group tumor volume. The treatment groups were: IgG1-b12, IgG1-b12-vcMMAE, IgG1-AXL-107, IgG1-AXL-107-vcMMAE, and paclitaxel. The antibodies and ADCs were dosed intravenously (i.v.) at 4 mg/kg at day of randomization (day 0) and day 7. Paclitaxel was dosed intra-peritoneally (i.p.) at 20 mg/kg at day 0, 7, and 14. Tumor volumes (mm$^3$) were monitored twice weekly and were calculated from caliper (PLEXX) measurements as: $0.52 \times (length) \times (width)^2$.

Treatment of mice with IgG1-AXL-107-vcMMAE induced tumor regression of ES0195 tumors compared to the IgG1-b12 and IgG1-b12-MMAE control groups ($p<0.001$ at day 23, one-way ANOVA test). Treatment of mice with the untargeted ADC IgG1-b12-vcMMAE did not show anti-tumor activity in this model, illustrating that the therapeutic capacity of AXL-ADCs depends on specific target binding. Mice that were treated with paclitaxel showed tumor growth inhibition, but this was less effective compared to treatment with IgG1-AXL-107-vcMMAE ($p<0.05$ at day 23, one-way ANOVA test).

Example 23-In Vitro Cytotoxicity Induced by AXL-Specific Antibody Drug Conjugates is Dependent on Target Expression The in vitro cytotoxicity of IgG1-AXL-107-vcMMAE was tested in human tumor cell lines with different levels of AXL expression.

Cell Culture

LS174T cells (human colorectal adenocarcinoma cell line; ATCC, cat no CL-188) were cultured in Minimum Essential Medium (MEM) with Glutamax, Hepes and Phenol Red (Life Technologies, cat no 42360-024). Components are 10% Donor Bovine Serium with Iron (DBSI) (Life Technologies, cat no 10371-029) and 1% Sodium Pyruvate (100 mM; Lonza, cat no BE13-115E) and 1% Penicillin/Streptomycin (Lonza, cat no DE17-603E).

NCI-H226 cells (human lung squamous cell carcinoma; ATCC, cat no CRL-5826), NCI-H661 cells (human large cell lung cancer; ATCC, cat no HTB-183), and NCI-H1299 cells (human non-small cell lung cancer; ATCC, cat no CRL-5803) were cultured in RPMI 1640 Medium (ATCC Modification; Life Technologies, cat no A10491-01). Components are 10% Donor Bovine Serium with Iron (DBSI; Life Technologies, cat no 10371-029) and 1% Penicillin/Streptomycin (Lonza, cat no DE17-603E).

SKOV-3 cells (human ovarian adenocarcinoma; ATCC, cat no HTB-77) were cultured in McCoy's 5A Medium with L-glutamine and HEPES (Lonza, cat no BE12-168F). Components are 10% Donor Bovine Serium with Iron (DBSI; Life Technologies, cat no 10371-029) and 1% Penicillin/Streptomycin (Lonza, cat no DE17-603E).

Calu-1 cells (human lung epidermoid carcinoma; ATCC, cat no HTB-54) were cultured in McCoy's 5A Medium with Catopeptone, without HEPES (Life Technologies, cat no 26600-023). Components are 10% Donor Bovine Serium with Iron (DBSI; Life Technologies, cat no 10371-029) and 1% L-glutamine (200 nM) in 0.85% NaCl solution (Lonza, cat no BE17-605F) and 1% Penicillin/Streptomycin (Lonza, cat no DE17-603E). Calu-1 cells are resistant to EGFR targeted therapy.

LCLC-103H cells (human large cell lung cancer), A431 cells (human epidermoid adenocarcinoma) and MDA-MB-231 cells (human breast cancer) were cultured as described in Example 16.

Quantification of AXL Expression on the Plasma Membrane of Human Tumor Cell Lines AXL expression on the plasma membrane of human tumor cell lines was assessed by indirect immunofluorescence using QIFIKIT (DAKO, Cat nr K0078) with mouse monoclonal antibody Z49M (Santa Cruz biotechnology, Cat nr sc-73719). Adherent cells were trypsinized and passed through a cell strainer to obtain single cell suspensions. Cells were pelleted by centrifugation for 5 minutes at 1,200 rpm, washed with PBS and resuspended at a concentration of $1 \times 10^6$ cells/mL. The next steps were performed on ice. 100 µL of the single cell suspensions (100,000 cells per well) were seeded in polystyrene 96-well round-bottom plates (Greiner Bio-One, Cat nr 650101). Cells were pelleted by centrifugation for 3 minutes at 300×g and resuspended in 50 µL antibody sample or mouse IgG1 isotype control sample (BD/Pharmingen, Cat nr 555746) at a concentration of 10 µg/mL. After an incubation of 30 minutes at 4° C., cells were pelleted and resuspended in 150 µL FACS buffer. Set-up and calibration beads were added to the plate according to the manufacturer's instructions. Cells and beads in parallel were washed two more times with 150 UL FACS buffer and resuspended in 50 UL FITC-conjugated goat-anti-mouse IgG (1/50; DAKO, Cat nr K0078). Secondary antibody was incubated for 30 minutes at 4° C. in the dark. Cells and beads were washed twice with 150 µL FACS buffer and resuspended in 100 µL FACS buffer. Immunofluorescence was measured on a FACS Canto II (BD Biosciences) by recording 10,000 events within the gate of viable cells. The mean fluorescence intensity of the calibration beads was used to calculate the calibration curve using GraphPad Prism software (GraphPad Software, San Diego, CA, USA). For each cell line, the antibody binding capacity (ABC), an estimate for the number of AXL molecules expressed on the plasma membrane, was calculated using the mean fluorescence intensity of the AXL antibody-stained cells, based on the equation of the calibration curve (interpolation of unknowns from the standard curve, using GraphPad Software).

Cytotoxicity Assay

For LCLC-103H, A431, MDA-MB-231, NCI-H226, NCI-H661, NCI-H1299, LS174T and SKOV-3 cells, the in vitro cytotoxicity assay was performed as described in Example 8. For Calu-1, the cytotoxicity assay was performed as described in Example 16, with the adaptation that the cell cultures were incubated for 11 instead of 5 days. Dose-response curves were generated using Graphpad Prism software, using non-linear regression analysis. The percentage of viable cells at an IgG1-AXL-107-vcMMAE concentration of 1 µg/mL was interpolated from the dose-response curves.

IgG1-AXL-107-vcMMAE induced the most potent cytotoxicity in cell lines with high AXL expression, whereas cytotoxicity was low or absent in cell lines with low AXL expression. This illustrates that IgG1-AXL-107-vcMMAE is effective in induction of cytotoxicity in cells resistant to EGFR targeted therapy, such as Calu-1.

LIST OF REFERENCES

[1] Paccez et al, Int. J. Cancer: 134, 1024-1033 (2013)
[2] Leconet et al, Oncogene, 1-10 (2013)

[3] Linger et al, Expert Opin. Ther. Targets, 14 (10): 1073-1090 (2010)
[4] Li et al, Oncogene, 28, 3442-3455 (2009)
[5] Ye et al, Oncogene, 1-11 (2010)
[6] Alley et al, Current Opinion in Chem. Bio., 4, 529-537 (2010)
[7] Iida et al, Anticancer Research, 34:1821-1828 (2014)
[8] WO 2012/175691; INSERM
[9] WO 2012/175692; INSERM
[10] WO 2013/064685; PF Medicament
[11] WO 2013/090776; INSERM
[12] WO 2009/063965; Chugai Pharmaceuticals
[13] WO 2010/131733
[14] WO9704801
[15] WO9856418
[16] WO02011753
[17] WO02096457
[18] WO03009817
[19] WO03039485
[20] U.S. Pat. No. 8,372,396
[21] WO2004004639
[22] WO2004016286
[23] WO2004055164
[24] WO 2004071439
[25] WO2006014965
[26] WO2006044908
[27] WO2007019232
[28] WO2015075201; Genmab
[29] Wakankar A, et al., MAbs. 2011 March-April; 3 (2): 161-72.
[30] Vásquez-Rey and Lang, 2011, Biotech, Bioeng. 108 (7) p. 1494-1508.
[31] Singh et al., AAPS PharmSciTech, Vol. 13, No. 2, 2012.
[32] Bruce A. Kerwin, Journal Of Pharmaceutical Sciences, Vol. 97, No. 8, August 2008, 2924-2935.
[33] Stephan J P, et al., Bioanalysis. 2011 March; 3 (6): 677-700
[34] Stephen C Alley, Kevin E Anderson, Curr Opin Chem Biol, June 2013, 17 (3), 406-411
[35] WO 2007/059782; Genmab A/S
[36] Ward et al., Nature 341, 544 546 (1989)
[37] Holt et al; Trends Biotechnol. 2003 November; 21 (11): 484-90
[38] Revets et al; Expert Opin Biol Ther. 2005 January; 5 (1): 111-24
[39] Bird et al., Science 242, 423 426 (1988)
[40] Huston et al., PNAS USA 85, 5879 5883 (1988)
[41] Lefranc MP. et al., Nucleic Acids Research, 27, 209-212, 1999
[42] Brochet X. Nucl. Acids Res. 36, W503-508 (2008) [36
[43] EP 2 220 131; U3 Pharma
[44] WO 2011/159980; Genentech
[45] U.S. Pat. No. 5,635,483
[46] U.S. Pat. No. 5,780,588
[47] Senter et al., Proc Am Ass Cancer Res 2004; 45, abstract 623, presented Mar. 28, 2004
[48] US 2005/0238649
[49] WO 2004/010957 (Seattle Genetics, Inc.)
[50] U.S. Pat. No. 7,659,241 (Seattle Genetics, Inc.)
[51] U.S. Pat. No. 7,851,437 (Seattle Genetics, Inc.)
[52] U.S. Pat. No. 829,531 (Seattle Genetics, Inc.)
[53] U.S. Ser. No. 11/833,028 (Seattle Genetics, Inc.)
[54] U.S. Pat. No. 7,498,298 (Seattle Genetics, Inc.)
[55] U.S. Ser. No. 11/833,954 (Seattle Genetics, Inc.)
[56] WO 2005/081711 (Seattle Genetics, Inc.)

The invention claimed is:

1. A lyophilized formulation of an anti-AXL antibody-drug conjugate (AXL-ADC), the lyophilized formulation obtainable or obtained by lyophilizing an aqueous formulation comprising the AXL-ADC and one or more excipients, wherein the aqueous formulation is free of any surfactant, wherein the drug moiety of the AXL-ADC is a cytotoxic agent, and wherein the antibody moiety of the AXL-ADC comprises at least one binding region comprising a VH region and a VL region selected from the group consisting of:

(a) a VH region comprising the CDR1, CDR2, and CDR3 sequences of SEQ ID Nos: 36, 37, and 38, respectively; and a VL region comprising the CDR1, CDR2, and CDR3 sequences of SEQ ID No: 39, the sequence GAS, and SEQ ID No: 40, respectively;

(b) a VH region comprising the CDR1, CDR2, and CDR3 sequences of SEQ ID Nos.: 46, 47, and 48, respectively; and a VL region comprising the CDR1, CDR2, and CDR3 sequences of SEQ ID No: 49, the sequence AAS, and SEQ ID No: 50, respectively;

(c) a VH region comprising the CDR1, CDR2, and CDR3 sequences of SEQ ID Nos.: 114, 115, and 116, respectively, and a VL region comprising the CDR1, CDR2, and CDR3 sequences of SEQ ID No: 117, the sequence DAS, and SEQ ID No: 118, respectively;

(d) a VH region comprising the CDR1, CDR2, and CDR3 sequences of SEQ ID Nos.: 51, 52, and 53, respectively; and a VL region comprising the CDR1, CDR2, and CDR3 sequences of SEQ ID No: 55, the sequence GAS, and SEQ ID No: 56, respectively;

(e) a VH region comprising the CDR1, CDR2, and CDR3 sequences of SEQ ID Nos.: 51, 52, and 54, respectively; and a VL region comprising the CDR1, CDR2, and CDR3 sequences of SEQ ID No: 55, the sequence GAS, and SEQ ID No: 56, respectively;

(f) a VH region comprising the CDR1, CDR2, and CDR3 sequences of SEQ ID Nos.: 57, 58, and 59, respectively; and a VL region comprising the CDR1, CDR2, and CDR3 sequences of SEQ ID No: 60, the sequence GAS, and SEQ ID No: 61, respectively;

(g) a VH region comprising the CDR1, CDR2, and CDR3 sequences of SEQ ID Nos.: 62, 63, and 64, respectively; and a VL region comprising the CDR1, CDR2, and CDR3 sequences of SEQ ID No: 65, the sequence GAS, and SEQ ID No: 66, respectively;

(h) a VH region comprising the CDR1, CDR2, and CDR3 sequences of SEQ ID Nos.: 67, 68, and 69, respectively; and a VL region comprising the CDR1, CDR2, and CDR3 sequences of SEQ ID No: 70, the sequence GAS, and SEQ ID No: 71, respectively;

(i) a VH region comprising the CDR1, CDR2, and CDR3 sequences of SEQ ID Nos.: 72, 73, and 75, respectively; and a VL region comprising the CDR1, CDR2, and CDR3 sequences of SEQ ID No: 76, the sequence ATS, and SEQ ID No: 77, respectively;

(j) a VH region comprising the CDR1, CDR2, and CDR3 sequences of SEQ ID Nos.: 72, 74, and 75, respectively; and a VL region comprising the CDR1, CDR2, and CDR3 sequences of SEQ ID No: 76, the sequence ATS, and SEQ ID No: 77, respectively;

(k) a VH region comprising the CDR1, CDR2, and CDR3 sequences of SEQ ID Nos.: 78, 79, and 80, respectively; and a VL region comprising the CDR1, CDR2, and CDR3 sequences of SEQ ID No: 81, the sequence AAS, and SEQ ID No: 82, respectively;

(l) a VH region comprising the CDR1, CDR2, and CDR3 sequences of SEQ ID Nos.: 83, 84, and 85, respectively; and a VL region comprising the CDR1, CDR2, and CDR3 sequences of SEQ ID No: 86, the sequence GAS, and SEQ ID No: 87, respectively;

(m) a VH region comprising the CDR1, CDR2, and CDR3 sequences of SEQ ID Nos.: 88, 89, and 90, respectively; and a VL region comprising the CDR1, CDR2, and CDR3 sequences of SEQ ID No: 91, the sequence GAS, and SEQ ID No: 92, respectively;

(n) a VH region comprising the CDR1, CDR2, and CDR3 sequences of SEQ ID Nos.: 93, 94, and 95, respectively; and a VL region comprising the CDR1, CDR2, and CDR3 sequences of SEQ ID No: 96, the sequence GAS, and SEQ ID No: 97, respectively;

(o) a VH region comprising the CDR1, CDR2, and CDR3 sequences of SEQ ID Nos.: 98, 99, and 100, respectively; and a VL region comprising the CDR1, CDR2, and CDR3 sequences of SEQ ID No: 101, the sequence DAS, and SEQ ID No: 102, respectively;

(p) a VH region comprising the CDR1, CDR2, and CDR3 sequences of SEQ ID Nos.: 103, 104, and 105, respectively; and a VL region comprising the CDR1, CDR2, and CDR3 sequences of SEQ ID No: 106, the sequence GAS, and SEQ ID No: 107, respectively;

(q) a VH region comprising the CDR1, CDR2, and CDR3 sequences of SEQ ID Nos.: 108, 109, and 110, respectively; and a VL region comprising the CDR1, CDR2, and CDR3 sequences of SEQ ID No: 112, the sequence AAS, and SEQ ID No: 113, respectively;

(r) a VH region comprising the CDR1, CDR2, and CDR3 sequences of SEQ ID Nos.: 108, 109, and 111, respectively; and a VL region comprising the CDR1, CDR2, and CDR3 sequences of SEQ ID No: 112, the sequence AAS, and SEQ ID No: 113, respectively; and (s) a VH region comprising the CDR1, CDR2, and CDR3 sequences of SEQ ID Nos.: 41, 42, and 43, respectively; and a VL region comprising the CDR1, CDR2, and CDR3 sequences of SEQ ID No: 44, the sequence AAS, and SEQ ID No: 45, respectively.

2. The lyophilized formulation of claim 1, wherein the aqueous formulation comprises:
   (a) a buffer providing for a pH of between about 5 and about 7 in the aqueous formulation;
   (b) at least one bulking agent; and
   (c) at least one non-reducing sugar which forms an amorphous phase with the AXL-ADC in solid state.

3. The lyophilized formulation of claim 1,
   wherein the aqueous formulation comprises a buffer selected from the group consisting of histidine, citrate, 2-(N-morpholino) ethanesulfonic acid (MES), succinate, glycolate, carbonic acid and phosphate, and a combination of any thereof;
   wherein the pH of the aqueous formulation is in a range from about 5 to about 7; and
   wherein the aqueous formulation comprises a buffer at a concentration of about 5 mM to about 100 mM.

4. The lyophilized formulation of claim 1, comprising a bulking agent selected from the group consisting of mannitol, glycine, and a combination thereof.

5. The lyophilized formulation of claim 1, wherein the aqueous formulation comprises a bulking agent at a concentration of about 1% (w/v) to about 5% (w/v), or at a concentration of about 50 mM to about 300 mM.

6. The lyophilized formulation of claim 1, comprising a non-reducing sugar selected from the group consisting of sucrose, trehalose, and a combination thereof.

7. The lyophilized formulation of claim 1, wherein the aqueous formulation comprises a non-reducing sugar at a concentration of about 0.5% (w/v) to about 7% (w/v), or a concentration of about 15 mM to about 200 mM.

8. The lyophilized formulation of claim 1, wherein the AXL-ADC concentration in the aqueous formulation is from about 5 mg/mL to about 30 mg/mL.

9. The lyophilized formulation of claim 1, wherein the pH of the aqueous formulation is in a range from about 5.5 to about 6.5.

10. A lyophilized formulation obtainable or obtained by lyophilizing an aqueous formulation having a pH of about 5 to about 7 and comprising
    (a) about 5 mg/mL to about 30 mg/mL of an anti-AXL antibody-drug conjugate (AXL-ADC);
    (b) about 10 mM to about 50 mM histidine;
    (c) about 15 mM to about 120 mM sucrose or trehalose; and
    (d) about 150 mM to about 180 mM mannitol or glycine,
    wherein the drug moiety of the AXL-ADC is a cytotoxic agent, and the antibody moiety of the AXL-ADC comprises at least one binding region comprising a VH region and a VL region selected from the group consisting of:
    (a) a VH region comprising the CDR1, CDR2, and CDR3 sequences of SEQ ID Nos: 36, 37, and 38, respectively; and a VL region comprising the CDR1, CDR2, and CDR3 sequences of SEQ ID No: 39, the sequence GAS, and SEQ ID No: 40, respectively;
    (b) a VH region comprising the CDR1, CDR2, and CDR3 sequences of SEQ ID Nos.: 46, 47, and 48, respectively; and a VL region comprising the CDR1, CDR2, and CDR3 sequences of SEQ ID No: 49, the sequence AAS, and SEQ ID No: 50, respectively;
    (c) a VH region comprising the CDR1, CDR2, and CDR3 sequences of SEQ ID Nos.: 114, 115, and 116, respectively, and a VL region comprising the CDR1, CDR2, and CDR3 sequences of SEQ ID No: 117, the sequence DAS, and SEQ ID No: 118, respectively;
    (d) a VH region comprising the CDR1, CDR2, and CDR3 sequences of SEQ ID Nos.: 51, 52, and 53, respectively; and a VL region comprising the CDR1, CDR2, and CDR3 sequences of SEQ ID No: 55, the sequence GAS, and SEQ ID No: 56, respectively;
    (e) a VH region comprising the CDR1, CDR2, and CDR3 sequences of SEQ ID Nos.: 51, 52, and 54, respectively; and a VL region comprising the CDR1, CDR2, and CDR3 sequences of SEQ ID No: 55, the sequence GAS, and SEQ ID No: 56, respectively;
    (f) a VH region comprising the CDR1, CDR2, and CDR3 sequences of SEQ ID Nos.: 57, 58, and 59, respectively; and a VL region comprising the CDR1, CDR2, and CDR3 sequences of SEQ ID No: 60, the sequence GAS, and SEQ ID No: 61, respectively;
    (g) a VH region comprising the CDR1, CDR2, and CDR3 sequences of SEQ ID Nos.: 62, 63, and 64, respectively; and a VL region comprising the CDR1, CDR2, and CDR3 sequences of SEQ ID No: 65, the sequence GAS, and SEQ ID No: 66, respectively;
    (h) a VH region comprising the CDR1, CDR2, and CDR3 sequences of SEQ ID Nos.: 67, 68, and 69, respectively; and a VL region comprising the CDR1, CDR2, and CDR3 sequences of SEQ ID No: 70, the sequence GAS, and SEQ ID No: 71, respectively;
    (i) a VH region comprising the CDR1, CDR2, and CDR3 sequences of SEQ ID Nos.: 72, 73, and 75, respectively; and a VL region comprising the CDR1, CDR2, and CDR3 sequences of SEQ ID No: 76, the sequence ATS, and SEQ ID No: 77, respectively;
    (j) a VH region comprising the CDR1, CDR2, and CDR3 sequences of SEQ ID Nos.: 72, 74, and 75, respectively; and a VL region comprising the CDR1, CDR2, and CDR3 sequences of SEQ ID No: 76, the sequence ATS, and SEQ ID No: 77, respectively;
    (k) a VH region comprising the CDR1, CDR2, and CDR3 sequences of SEQ ID Nos.: 78, 79, and 80, respectively; and a VL region comprising the CDR1, CDR2, and CDR3 sequences of SEQ ID No: 81, the sequence AAS, and SEQ ID No: 82, respectively;
    (l) a VH region comprising the CDR1, CDR2, and CDR3 sequences of SEQ ID Nos.: 83, 84, and 85, respectively; and a VL region comprising the CDR1, CDR2, and CDR3 sequences of SEQ ID No: 86, the sequence GAS, and SEQ ID No: 87, respectively;
    (m) a VH region comprising the CDR1, CDR2, and CDR3 sequences of SEQ ID Nos.: 88, 89, and 90, respectively; and a VL region comprising the CDR1, CDR2, and CDR3 sequences of SEQ ID No: 91, the sequence GAS, and SEQ ID No: 92, respectively;
    (n) a VH region comprising the CDR1, CDR2, and CDR3 sequences of SEQ ID Nos.: 93, 94, and 95, respectively; and a VL region comprising the CDR1, CDR2, and CDR3 sequences of SEQ ID No: 96, the sequence GAS, and SEQ ID No: 97, respectively;
    (o) a VH region comprising the CDR1, CDR2, and CDR3 sequences of SEQ ID Nos.: 98, 99, and 100, respectively; and a VL region comprising the CDR1, CDR2, and CDR3 sequences of SEQ ID No: 101, the sequence DAS, and SEQ ID No: 102, respectively;
    (p) a VH region comprising the CDR1, CDR2, and CDR3 sequences of SEQ ID Nos.: 103, 104, and 105, respectively; and a VL region comprising the CDR1, CDR2, and CDR3 sequences of SEQ ID No: 106, the sequence GAS, and SEQ ID No: 107, respectively;
    (q) a VH region comprising the CDR1, CDR2, and CDR3 sequences of SEQ ID Nos.: 108, 109, and 110, respectively; and a VL region comprising the CDR1, CDR2, and CDR3 sequences of SEQ ID No: 112, the sequence AAS, and SEQ ID No: 113, respectively;
(r) a VH region comprising the CDR1, CDR2, and CDR3 sequences of SEQ ID Nos.: 108, 109, and 111, respectively; and a VL region comprising the CDR1, CDR2, and CDR3 sequences of SEQ ID No: 112, the sequence AAS, and SEQ ID No: 113, respectively; and
(s) a VH region comprising the CDR1, CDR2, and CDR3 sequences of SEQ ID Nos.: 41, 42, and 43, respectively; and a VL region comprising the CDR1, CDR2, and CDR3 sequences of SEQ ID No: 44, the sequence AAS, and SEQ ID No: 45, respectively.

11. A pharmaceutical formulation having a pH of about 5 to about 7 and comprising, in aqueous solution:
(a) about 5 mg/mL to about 30 mg/mL of an anti-AXL antibody-drug conjugate (AXL-ADC);
(b) about 10 mM to about 50 mM histidine;
(c) about 15 mM to about 120 mM sucrose or trehalose; and
(d) about 50 mM to about 300 mM mannitol or glycine,
wherein the drug moiety of the AXL-ADC is a cytotoxic agent, and the antibody moiety of the AXL-ADC comprises at least one binding region comprising a VH region and a VL region selected from the group consisting of:
(a) a VH region comprising the CDR1, CDR2, and CDR3 sequences of SEQ ID Nos: 36, 37, and 38, respectively; and a VL region comprising the CDR1, CDR2, and CDR3 sequences of SEQ ID No: 39, the sequence GAS, and SEQ ID No: 40, respectively;
(b) a VH region comprising the CDR1, CDR2, and CDR3 sequences of SEQ ID Nos.: 46, 47, and 48, respectively; and a VL region comprising the CDR1, CDR2, and CDR3 sequences of SEQ ID No: 49, the sequence AAS, and SEQ ID No: 50, respectively;
(c) a VH region comprising the CDR1, CDR2, and CDR3 sequences of SEQ ID Nos.: 114, 115, and 116, respectively, and a VL region comprising the CDR1, CDR2, and CDR3 sequences of SEQ ID No: 117, the sequence DAS, and SEQ ID No: 118, respectively;
(d) a VH region comprising the CDR1, CDR2, and CDR3 sequences of SEQ ID Nos.: 51, 52, and 53, respectively; and a VL region comprising the CDR1, CDR2, and CDR3 sequences of SEQ ID No: 55, the sequence GAS, and SEQ ID No: 56, respectively;
(e) a VH region comprising the CDR1, CDR2, and CDR3 sequences of SEQ ID Nos.: 51, 52, and 54, respectively; and a VL region comprising the CDR1, CDR2, and CDR3 sequences of SEQ ID No: 55, the sequence GAS, and SEQ ID No: 56, respectively;
(f) a VH region comprising the CDR1, CDR2, and CDR3 sequences of SEQ ID Nos.: 57, 58, and 59, respectively; and a VL region comprising the CDR1, CDR2, and CDR3 sequences of SEQ ID No: 60, the sequence GAS, and SEQ ID No: 61, respectively;
(g) a VH region comprising the CDR1, CDR2, and CDR3 sequences of SEQ ID Nos.: 62, 63, and 64, respectively; and a VL region comprising the CDR1, CDR2, and CDR3 sequences of SEQ ID No: 65, the sequence GAS, and SEQ ID No: 66, respectively;
(h) a VH region comprising the CDR1, CDR2, and CDR3 sequences of SEQ ID Nos.: 67, 68, and 69, respectively; and a VL region comprising the CDR1, CDR2, and CDR3 sequences of SEQ ID No: 70, the sequence GAS, and SEQ ID No: 71, respectively;
(i) a VH region comprising the CDR1, CDR2, and CDR3 sequences of SEQ ID Nos.: 72, 73, and 75, respectively; and a VL region comprising the CDR1, CDR2, and CDR3 sequences of SEQ ID No: 76, the sequence ATS, and SEQ ID No: 77, respectively;
(j) a VH region comprising the CDR1, CDR2, and CDR3 sequences of SEQ ID Nos.: 72, 74, and 75, respectively; and a VL region comprising the CDR1, CDR2, and CDR3 sequences of SEQ ID No: 76, the sequence ATS, and SEQ ID No: 77, respectively;
(k) a VH region comprising the CDR1, CDR2, and CDR3 sequences of SEQ ID Nos.: 78, 79, and 80, respectively; and a VL region comprising the CDR1, CDR2, and CDR3 sequences of SEQ ID No: 81, the sequence AAS, and SEQ ID No: 82, respectively;
(l) a VH region comprising the CDR1, CDR2, and CDR3 sequences of SEQ ID Nos.: 83, 84, and 85, respectively; and a VL region comprising the CDR1, CDR2, and CDR3 sequences of SEQ ID No: 86, the sequence GAS, and SEQ ID No: 87, respectively;
(m) a VH region comprising the CDR1, CDR2, and CDR3 sequences of SEQ ID Nos.: 88, 89, and 90, respectively; and a VL region comprising the CDR1, CDR2, and CDR3 sequences of SEQ ID No: 91, the sequence GAS, and SEQ ID No: 92, respectively;
(n) a VH region comprising the CDR1, CDR2, and CDR3 sequences of SEQ ID Nos.: 93, 94, and 95, respectively; and a VL region comprising the CDR1, CDR2, and CDR3 sequences of SEQ ID No: 96, the sequence GAS, and SEQ ID No: 97, respectively;
(o) a VH region comprising the CDR1, CDR2, and CDR3 sequences of SEQ ID Nos.: 98, 99, and 100, respectively; and a VL region comprising the CDR1, CDR2, and CDR3 sequences of SEQ ID No: 101, the sequence DAS, and SEQ ID No: 102, respectively;
(p) a VH region comprising the CDR1, CDR2, and CDR3 sequences of SEQ ID Nos.: 103, 104, and 105, respectively; and a VL region comprising the CDR1, CDR2, and CDR3 sequences of SEQ ID No: 106, the sequence GAS, and SEQ ID No: 107, respectively;
(q) a VH region comprising the CDR1, CDR2, and CDR3 sequences of SEQ ID Nos.: 108, 109, and 110, respectively; and a VL region comprising the CDR1, CDR2, and CDR3 sequences of SEQ ID No: 112, the sequence AAS, and SEQ ID No: 113, respectively;
(r) a VH region comprising the CDR1, CDR2, and CDR3 sequences of SEQ ID Nos.: 108, 109, and 111, respectively; and a VL region comprising the CDR1, CDR2, and CDR3 sequences of SEQ ID No: 112, the sequence AAS, and SEQ ID No: 113, respectively; and
(s) a VH region comprising the CDR1, CDR2, and CDR3 sequences of SEQ ID Nos.: 41, 42, and 43, respectively; and a VL region comprising the CDR1, CDR2, and CDR3 sequences of SEQ ID No: 44, the sequence AAS, and SEQ ID No: 45, respectively.

12. The pharmaceutical formulation of claim 11, having a pH in the range of about 5.5 to about 6.5 and comprising:
(a) about 9 mg/mL to about 11 mg/mL AXL-ADC;
(b) about 20 mM to about 40 mM histidine;
(c) about 80 mM to about 100 mM sucrose; and
(d) about 150 mM to about 180 mM mannitol;
wherein the formulation is free of any surfactant.

13. An aqueous formulation of an anti-AXL antibody, comprising one or more pharmaceutically acceptable excipients, wherein the aqueous formulation is free of any surfactant, and wherein the anti-AXL antibody comprises a VH region and a VL region selected from the group consisting of:
(a) a VH region comprising the CDR1, CDR2, and CDR3 sequences of SEQ ID Nos: 36, 37, and 38, respectively; and a VL region comprising the CDR1, CDR2, and CDR3 sequences of SEQ ID No: 39, the sequence GAS, and SEQ ID No: 40, respectively;
(b) a VH region comprising the CDR1, CDR2, and CDR3 sequences of SEQ ID Nos.: 46, 47, and 48, respectively; and a VL region comprising the CDR1, CDR2, and CDR3 sequences of SEQ ID No: 49, the sequence AAS, and SEQ ID No: 50, respectively;
(c) a VH region comprising the CDR1, CDR2, and CDR3 sequences of SEQ ID Nos.: 114, 115, and 116, respectively, and a VL region comprising the CDR1, CDR2, and CDR3 sequences of SEQ ID No: 117, the sequence DAS, and SEQ ID No: 118, respectively;
(d) a VH region comprising the CDR1, CDR2, and CDR3 sequences of SEQ ID Nos.: 51, 52, and 53, respectively; and a VL region comprising the CDR1, CDR2, and CDR3 sequences of SEQ ID No: 55, the sequence GAS, and SEQ ID No: 56, respectively;
(e) a VH region comprising the CDR1, CDR2, and CDR3 sequences of SEQ ID Nos.: 51, 52, and 54, respectively; and a VL region comprising the CDR1, CDR2, and CDR3 sequences of SEQ ID No: 55, the sequence GAS, and SEQ ID No: 56, respectively;
(f) a VH region comprising the CDR1, CDR2, and CDR3 sequences of SEQ ID Nos.: 57, 58, and 59, respectively; and a VL region comprising the CDR1, CDR2, and CDR3 sequences of SEQ ID No: 60, the sequence GAS, and SEQ ID No: 61, respectively;
(g) a VH region comprising the CDR1, CDR2, and CDR3 sequences of SEQ ID Nos.: 62, 63, and 64, respectively; and a VL region comprising the CDR1, CDR2, and CDR3 sequences of SEQ ID No: 65, the sequence GAS, and SEQ ID No: 66, respectively;
(h) a VH region comprising the CDR1, CDR2, and CDR3 sequences of SEQ ID Nos.: 67, 68, and 69, respectively; and a VL region comprising the CDR1, CDR2, and CDR3 sequences of SEQ ID No: 70, the sequence GAS, and SEQ ID No: 71, respectively;
(i) a VH region comprising the CDR1, CDR2, and CDR3 sequences of SEQ ID Nos.: 72, 73, and 75, respectively; and a VL region comprising the CDR1, CDR2, and CDR3 sequences of SEQ ID No: 76, the sequence ATS, and SEQ ID No: 77, respectively;
(j) a VH region comprising the CDR1, CDR2, and CDR3 sequences of SEQ ID Nos.: 72, 74, and 75, respectively; and a VL region comprising the CDR1, CDR2, and CDR3 sequences of SEQ ID No: 76, the sequence ATS, and SEQ ID No: 77, respectively;
(k) a VH region comprising the CDR1, CDR2, and CDR3 sequences of SEQ ID Nos.: 78, 79, and 80, respectively; and a VL region comprising the CDR1, CDR2, and CDR3 sequences of SEQ ID No: 81, the sequence AAS, and SEQ ID No: 82, respectively;
(l) a VH region comprising the CDR1, CDR2, and CDR3 sequences of SEQ ID Nos.: 83, 84, and 85, respectively; and a VL region comprising the CDR1, CDR2, and CDR3 sequences of SEQ ID No: 86, the sequence GAS, and SEQ ID No: 87, respectively;
(m) a VH region comprising the CDR1, CDR2, and CDR3 sequences of SEQ ID Nos.: 88, 89, and 90, respectively; and a VL region comprising the CDR1, CDR2, and CDR3 sequences of SEQ ID No: 91, the sequence GAS, and SEQ ID No: 92, respectively;
(n) a VH region comprising the CDR1, CDR2, and CDR3 sequences of SEQ ID Nos.: 93, 94, and 95, respectively; and a VL region comprising the CDR1, CDR2, and CDR3 sequences of SEQ ID No: 96, the sequence GAS, and SEQ ID No: 97, respectively;
(o) a VH region comprising the CDR1, CDR2, and CDR3 sequences of SEQ ID Nos.: 98, 99, and 100, respectively; and a VL region comprising the CDR1, CDR2, and CDR3 sequences of SEQ ID No: 101, the sequence DAS, and SEQ ID No: 102, respectively;
(p) a VH region comprising the CDR1, CDR2, and CDR3 sequences of SEQ ID Nos.: 103, 104, and 105, respectively; and a VL region comprising the CDR1, CDR2, and CDR3 sequences of SEQ ID No: 106, the sequence GAS, and SEQ ID No: 107, respectively;
(q) a VH region comprising the CDR1, CDR2, and CDR3 sequences of SEQ ID Nos.: 108, 109, and 110, respectively; and a VL region comprising the CDR1, CDR2, and CDR3 sequences of SEQ ID No: 112, the sequence AAS, and SEQ ID No: 113, respectively;
(r) a VH region comprising the CDR1, CDR2, and CDR3 sequences of SEQ ID Nos.: 108, 109, and 111, respectively; and a VL region comprising the CDR1, CDR2, and CDR3 sequences of SEQ ID No: 112, the sequence AAS, and SEQ ID No: 113, respectively; and
(s) a VH region comprising the CDR1, CDR2, and CDR3 sequences of SEQ ID Nos.: 41, 42, and 43, respectively; and a VL region comprising the CDR1, CDR2, and CDR3 sequences of SEQ ID No: 44, the sequence AAS, and SEQ ID No: 45, respectively.

14. The aqueous formulation of claim 13, wherein the formulation comprises a buffer and at least one stabilizer, wherein the pH of the aqueous formulation is between about 5 and about 7.

15. The aqueous formulation of claim 13, comprising a buffer selected from the group consisting of histidine, citrate, MES, phosphate, carbonic acid, succinate, glycolate, and a combination of any thereof, wherein
the buffer is at a concentration of about 10 mM to about 50 mM, and
the pH of the aqueous formulation is in a range of about 5.5 to about 6.5.

16. The aqueous formulation of claim 13, comprising a stabilizer selected from the group consisting of mannitol, sucrose and trehalose, wherein the stabilizer is present at a concentration of about 20 mM to about 400 mM, or a concentration of about 0.4% (w/v) to about 7% (w/v).

17. The aqueous formulation of claim 13, which is free of any one or more of arginine, glycine, glutamic acid, sorbitol, trehalose, sucrose and sodium chloride.

18. The aqueous formulation of claim 13, wherein the antibody concentration is from about 5 mg/mL to about 40 mg/mL.

19. The aqueous formulation of claim 14, wherein the formulation comprises
(a) about 5 mg/mL to about 40 mg/mL of an anti-AXL antibody;
(b) about 10 mM to about 50 mM histidine; and
(c) about 50 mM to about 300 mM mannitol.

20. A frozen aqueous formulation of an anti-AXL antibody,
obtained or obtainable by freezing the aqueous formulation of claim 13.

21. A lyophilized formulation of an anti-AXL antibody-drug conjugate (AXL-ADC), the lyophilized formulation obtainable or obtained by lyophilizing an aqueous formulation comprising the AXL-ADC and one or more excipients, wherein the aqueous formulation is free of any surfactant, wherein the AXL-ADC binds to an epitope on AXL which is recognized by any of the antibodies defined in claim 13.

22. The lyophilized formulation of claim 1, wherein the AXL-ADC binds to an epitope within the Ig1-like domain of AXL, the epitope comprising one or more amino acids corresponding to positions L121 to Q129 or T112 to Q124 of human AXL; an epitope within the Ig2-like domain of AXL, the epitope comprising the amino acids corresponding to position D170 or the combination of D179 and one or more amino acids corresponding to positions T182 to R190 of human AXL; or an epitope within the FN1-like domain of human AXL, the epitope comprising one or more amino acids corresponding to positions Q272 to A287 and G297 to P301 of human AXL.

23. The lyophilized formulation of claim 1, wherein the antibody moiety of the AXL-ADC comprises a heavy chain of an isotype selected from the group consisting of IgG1, IgG2, IgG3, and IgG4.

24. The lyophilized formulation of claim 1, wherein the antibody moiety of the AXL-ADC is a full-length monoclonal antibody.

25. A lyophilized formulation obtainable or obtained by lyophilizing an aqueous formulation comprising
about 9 mg/mL to about 11 mg/mL of an anti-AXL antibody-drug conjugate (AXL-ADC), and pharmaceutically acceptable excipients comprising:
about 30 mM histidine buffer providing for a pH from about 5 to about 7;
about 88 mM sucrose; and
about 165 mM mannitol;
wherein the antibody moiety of the AXL-ADC comprises at least one binding region comprising a VH region and a VL region selected from the group consisting of:
(a) a VH region comprising the CDR1, CDR2, and CDR3 sequences of SEQ ID Nos: 36, 37, and 38, respectively; and a VL region comprising the CDR1, CDR2, and CDR3 sequences of SEQ ID No: 39, the sequence GAS, and SEQ ID No: 40, respectively;
(b) a VH region comprising the CDR1, CDR2, and CDR3 sequences of SEQ ID Nos: 46, 47, and 48, respectively; and a VL region comprising the CDR1, CDR2, and CDR3 sequences of SEQ ID No: 49, the sequence AAS, and SEQ ID No: 50, respectively;
(c) a VH region comprising the CDR1, CDR2, and CDR3 sequences of SEQ ID Nos: 114, 115, and 116, respectively, and a VL region comprising the CDR1, CDR2, and CDR3 sequences of SEQ ID No: 117, the sequence DAS, and SEQ ID No: 118, respectively;
(d) a VH region comprising the CDR1, CDR2, and CDR3 sequences of SEQ ID Nos: 51, 52, and 53, respectively; and a VL region comprising the CDR1, CDR2, and CDR3 sequences of SEQ ID No: 55, the sequence GAS, and SEQ ID No: 56, respectively;
(e) a VH region comprising the CDR1, CDR2, and CDR3 sequences of SEQ ID Nos: 51, 52, and 54, respectively; and a VL region comprising the CDR1, CDR2, and CDR3 sequences of SEQ ID Nos.: 55, the sequence GAS, and SEQ ID No: 56, respectively;
(f) a VH region comprising the CDR1, CDR2, and CDR3 sequences of SEQ ID Nos: 57, 58, and 59, respectively; and a VL region comprising the CDR1, CDR2, and CDR3 sequences of SEQ ID No: 60, the sequence GAS, and SEQ ID No: 61, respectively;
(g) a VH region comprising the CDR1, CDR2, and CDR3 sequences of SEQ ID Nos: 62, 63, and 64, respectively; and a VL region comprising the CDR1, CDR2, and CDR3 sequences of SEQ ID No: 65, the sequence GAS, and SEQ ID No: 66, respectively;
(h) a VH region comprising the CDR1, CDR2, and CDR3 sequences of SEQ ID Nos: 67, 68, and 69, respectively; and a VL region comprising the CDR1, CDR2, and CDR3 sequences of SEQ ID No: 70, the sequence GAS, and SEQ ID No: 71, respectively;
(i) a VH region comprising the CDR1, CDR2, and CDR3 sequences of SEQ ID Nos: 72, 73, and 75, respectively; and a VL region comprising the CDR1, CDR2, and CDR3 sequences of SEQ ID No: 76, the sequence ATS, and SEQ ID No: 77, respectively;
(j) a VH region comprising the CDR1, CDR2, and CDR3 sequences of SEQ ID Nos: 72, 74, and 75, respectively; and a VL region comprising the CDR1, CDR2, and CDR3 sequences of SEQ ID No: 76, the sequence ATS, and SEQ ID No: 77, respectively;
(k) a VH region comprising the CDR1, CDR2, and CDR3 sequences of SEQ ID Nos: 78, 79, and 80, respectively; and a VL region comprising the CDR1, CDR2, and CDR3 sequences of SEQ ID No: 81, the sequence AAS, and SEQ ID No: 82, respectively;
(l) a VH region comprising the CDR1, CDR2, and CDR3 sequences of SEQ ID Nos: 83, 84, and 85, respectively; and a VL region comprising the CDR1, CDR2, and CDR3 sequences of SEQ ID No: 86, the sequence GAS, and SEQ ID No: 87, respectively;
(m) a VH region comprising the CDR1, CDR2, and CDR3 sequences of SEQ ID Nos: 88, 89, and 90, respectively; and a VL region comprising the CDR1, CDR2, and CDR3 sequences of SEQ ID No: 91, the sequence GAS, and SEQ ID No: 92, respectively;
(n) a VH region comprising the CDR1, CDR2, and CDR3 sequences of SEQ ID Nos: 93, 94, and 95, respectively; and a VL region comprising the CDR1, CDR2, and CDR3 sequences of SEQ ID No: 96, the sequence GAS, and SEQ ID No: 97, respectively;
(o) a VH region comprising the CDR1, CDR2, and CDR3 sequences of SEQ ID Nos: 98, 99, and 100, respectively; and a VL region comprising the CDR1, CDR2, and CDR3 sequences of SEQ ID No: 101, the sequence DAS, and SEQ ID No: 102, respectively;
(p) a VH region comprising the CDR1, CDR2, and CDR3 sequences of SEQ ID Nos: 103, 104, and 105, respectively; and a VL region comprising the CDR1, CDR2, and CDR3 sequences of SEQ ID No: 106, the sequence GAS, and SEQ ID No: 107, respectively;
(q) a VH region comprising the CDR1, CDR2, and CDR3 sequences of SEQ ID Nos: 108, 109, and 110, respectively; and a VL region comprising the CDR1, CDR2, and CDR3 sequences of SEQ ID No: 112, the sequence AAS, and SEQ ID No: 113, respectively;
(r) a VH region comprising the CDR1, CDR2, and CDR3 sequences of SEQ ID Nos: 108, 109, and 111, respectively; and a VL region comprising the CDR1, CDR2, and CDR3 sequences of SEQ ID No: 112, the sequence AAS, and SEQ ID No: 113, respectively; and
(s) a VH region comprising the CDR1, CDR2, and CDR3 sequences of SEQ ID Nos: 41, 42, and 43, respectively; and a VL region comprising the CDR1, CDR2, and CDR3 sequences of SEQ ID No: 44, the sequence AAS, and SEQ ID No: 45, respectively;
wherein the AXL-ADC comprises a mc-vc-PAB linker and MMAE.

26. An aqueous formulation suitable for preparing a lyophilized formulation of an anti-AXL antibody-drug conjugate (AXL-ADC) and having a pH of about 5 to about 7, comprising
- (a) about 7 mg/mL to about 20 mg/mL of an AXL-ADC;
- (b) about 5 mM to about 100 mM histidine;
- (c) about 15 mM to about 120 mM sucrose; and
- (d) about 150 mM to about 180 mM mannitol, wherein the drug moiety of the AXL-ADC is a cytotoxic agent, and the antibody moiety of the AXL-ADC comprises at least one binding region comprising a VH region and a VL region selected from the group consisting of:
- (a) a VH region comprising the CDR1, CDR2, and CDR3 sequences of SEQ ID Nos: 36, 37, and 38, respectively; and a VL region comprising the CDR1, CDR2, and CDR3 sequences of SEQ ID No: 39, the sequence GAS, and SEQ ID No: 40, respectively;
- (b) a VH region comprising the CDR1, CDR2, and CDR3 sequences of SEQ ID Nos.: 46, 47, and 48, respectively; and a VL region comprising the CDR1, CDR2, and CDR3 sequences of SEQ ID No: 49, the sequence AAS, and SEQ ID No: 50, respectively;
- (c) a VH region comprising the CDR1, CDR2, and CDR3 sequences of SEQ ID Nos.: 114, 115, and 116, respectively, and a VL region comprising the CDR1, CDR2, and CDR3 sequences of SEQ ID No: 117, the sequence DAS, and SEQ ID No: 118, respectively;
- (d) a VH region comprising the CDR1, CDR2, and CDR3 sequences of SEQ ID Nos.: 51, 52, and 53, respectively; and a VL region comprising the CDR1, CDR2, and CDR3 sequences of SEQ ID No: 55, the sequence GAS, and SEQ ID No: 56, respectively;
- (e) a VH region comprising the CDR1, CDR2, and CDR3 sequences of SEQ ID Nos.: 51, 52, and 54, respectively; and a VL region comprising the CDR1, CDR2, and CDR3 sequences of SEQ ID No: 55, the sequence GAS, and SEQ ID No: 56, respectively;
- (f) a VH region comprising the CDR1, CDR2, and CDR3 sequences of SEQ ID Nos.: 57, 58, and 59, respectively; and a VL region comprising the CDR1, CDR2, and CDR3 sequences of SEQ ID No: 60, the sequence GAS, and SEQ ID No: 61, respectively;
- (g) a VH region comprising the CDR1, CDR2, and CDR3 sequences of SEQ ID Nos.: 62, 63, and 64, respectively; and a VL region comprising the CDR1, CDR2, and CDR3 sequences of SEQ ID No: 65, the sequence GAS, and SEQ ID No: 66, respectively;
- (h) a VH region comprising the CDR1, CDR2, and CDR3 sequences of SEQ ID Nos.: 67, 68, and 69, respectively; and a VL region comprising the CDR1, CDR2, and CDR3 sequences of SEQ ID No: 70, the sequence GAS, and SEQ ID No: 71, respectively;
- (i) a VH region comprising the CDR1, CDR2, and CDR3 sequences of SEQ ID Nos.: 72, 73, and 75, respectively; and a VL region comprising the CDR1, CDR2, and CDR3 sequences of SEQ ID No: 76, the sequence ATS, and SEQ ID No: 77, respectively;
- (j) a VH region comprising the CDR1, CDR2, and CDR3 sequences of SEQ ID Nos.: 72, 74, and 75, respectively; and a VL region comprising the CDR1, CDR2, and CDR3 sequences of SEQ ID No: 76, the sequence ATS, and SEQ ID No: 77, respectively;
- (k) a VH region comprising the CDR1, CDR2, and CDR3 sequences of SEQ ID Nos.: 78, 79, and 80, respectively; and a VL region comprising the CDR1, CDR2, and CDR3 sequences of SEQ ID No: 81, the sequence AAS, and SEQ ID No: 82, respectively;
- (l) a VH region comprising the CDR1, CDR2, and CDR3 sequences of SEQ ID Nos.: 83, 84, and 85, respectively; and a VL region comprising the CDR1, CDR2, and CDR3 sequences of SEQ ID No: 86, the sequence GAS, and SEQ ID No: 87, respectively;
- (m) a VH region comprising the CDR1, CDR2, and CDR3 sequences of SEQ ID Nos.: 88, 89, and 90, respectively; and a VL region comprising the CDR1, CDR2, and CDR3 sequences of SEQ ID No: 91, the sequence GAS, and SEQ ID No: 92, respectively;
- (n) a VH region comprising the CDR1, CDR2, and CDR3 sequences of SEQ ID Nos.: 93, 94, and 95, respectively; and a VL region comprising the CDR1, CDR2, and CDR3 sequences of SEQ ID No: 96, the sequence GAS, and SEQ ID No: 97, respectively;
- (o) a VH region comprising the CDR1, CDR2, and CDR3 sequences of SEQ ID Nos.: 98, 99, and 100, respectively; and a VL region comprising the CDR1, CDR2, and CDR3 sequences of SEQ ID No: 101, the sequence DAS, and SEQ ID No: 102, respectively;
- (p) a VH region comprising the CDR1, CDR2, and CDR3 sequences of SEQ ID Nos.: 103, 104, and 105, respectively; and a VL region comprising the CDR1, CDR2, and CDR3 sequences of SEQ ID No: 106, the sequence GAS, and SEQ ID No: 107, respectively;
- (q) a VH region comprising the CDR1, CDR2, and CDR3 sequences of SEQ ID Nos.: 108, 109, and 110, respectively; and a VL region comprising the CDR1, CDR2, and CDR3 sequences of SEQ ID No: 112, the sequence AAS, and SEQ ID No: 113, respectively;
- (r) a VH region comprising the CDR1, CDR2, and CDR3 sequences of SEQ ID Nos.: 108, 109, and 111, respectively; and a VL region comprising the CDR1, CDR2, and CDR3 sequences of SEQ ID No: 112, the sequence AAS, and SEQ ID No: 113, respectively; and
- (s) a VH region comprising the CDR1, CDR2, and CDR3 sequences of SEQ ID Nos.: 41, 42, and 43, respectively; and a VL region comprising the CDR1, CDR2, and CDR3 sequences of SEQ ID No: 44, the sequence AAS, and SEQ ID No: 45, respectively.

27. The aqueous formulation of claim 26, wherein the antibody moiety of the AXL-ADC comprises a VH region comprising the CDR1, CDR2, and CDR3 sequences of SEQ ID Nos: 36, 37, and 38, respectively; and a VL region comprising the CDR1, CDR2, and CDR3 sequences of SEQ ID No: 39, the sequence GAS, and SEQ ID No: 40, respectively.

28. The aqueous formulation of claim 26, wherein the AXL-ADC comprises a mc-vc-PAB linker and MMAE.

29. A pharmaceutically acceptable liquid formulation obtained by reconstituting the lyophilized formulation of claim 25 in a sterile aqueous diluent.

30. The liquid formulation of claim 29, having a pH of about 5 to about 7, and comprising about 5 mg/mL to about 30 mg/mL of the AXL-ADC; about 10 mM to about 50 mM histidine; about 15 mM to about 120 mM sucrose; and about 50 mM to about 300 mM mannitol or glycine, wherein the weight ratio of mannitol to sucrose is at least about 1.

31. The lyophilized formulation of claim 1, wherein the AXL-ADC comprises a cleavable linker selected from the group consisting of: N-succinimydyl 4-(2-pyridyldithio)-pentanoate (SSP), maleimidocaproyl-valine-citrulline-p-aminobenzyloxycarbonyl (mc-vc-PAB), and AV-1 K-lock valine-citrulline.

32. The lyophilized formulation of claim 1, wherein the cytotoxic agent is monomethylauristatin E (MMAE) or monomethylauristatin F (MMAF).

33. The lyophilized formulation of claim 1, wherein the AXL-ADC comprises a VH region and a VL region selected from the group consisting of:
(a) a VH region comprising SEQ ID No: 1 and a VL region comprising SEQ ID No: 2;
(b) a VH region comprising SEQ ID No: 5 and a VL region comprising SEQ ID No: 6;
(c) a VH region comprising SEQ ID No: 34 and a VL region comprising SEQ ID No: 35;
(d) a VH region comprising SEQ ID No: 7 and a VL region comprising SEQ ID No: 9;
(e) a VH region comprising SEQ ID No: 10 and a VL region comprising SEQ ID No: 11;
(f) a VH region comprising SEQ ID No: 16 and a VL region comprising SEQ ID No: 18;
(g) a VH region comprising SEQ ID No: 25 and a VL region comprising SEQ ID No: 26;
(h) a VH region comprising SEQ ID No: 31 and a VL region comprising SEQ ID No: 33;
(i) a VH region comprising SEQ ID No: 3 and a VL region comprising SEQ ID No: 4;
(j) a VH region comprising SEQ ID No:8 and a VL region comprising SEQ ID No:9;
(k) a VH region comprising SEQ ID No: 12 and a VL region comprising SEQ ID No:13;
(l) a VH region comprising SEQ ID No: 14 and a VL region comprising SEQ ID No: 15;
(m) a VH region comprising SEQ ID No: 17 and a VL region comprising SEQ ID No:18;
(n) a VH region comprising SEQ ID No: 19 and a VL region comprising SEQ ID No:20;
(o) a VH region comprising SEQ ID No:21 and a VL region comprising SEQ ID No:22;
(p) a VH region comprising SEQ ID No:23 and a VL region comprising SEQ ID No:24;
(q) a VH region comprising SEQ ID No:27 and a VL region comprising SEQ ID No:28;
(r) a VH region comprising SEQ ID No:29 and a VL region comprising SEQ ID No:30; and
(s) a VH region comprising SEQ ID No:32 and a VL region comprising SEQ ID No: 33.

34. The lyophilized formulation of claim 1, wherein cytotoxic agent is an auristatin.

35. The lyophilized formulation of claim 10, wherein the cytotoxic agent is an auristatin.

36. The lyophilized formulation of claim 11, wherein the cytotoxic agent is an auristatin.

37. The lyophilized formulation of claim 26, wherein the cytotoxic agent is an auristatin.

38. The lyophilized formulation of claim 1, wherein the antibody moiety of the AXL-ADC comprises at least one binding region comprising a VH region comprising the CDR1, CDR2, and CDR3 sequences of SEQ ID Nos: 36, 37, and 38, respectively, and a VL region comprising the CDR1, CDR2, and CDR3 sequences of SEQ ID No: 39, the sequence GAS, and SEQ ID No: 40, respectively.

39. The lyophilized formulation of claim 1, wherein the antibody moiety of the AXL-ADC comprises at least one binding region comprising a VH region comprising the CDR1, CDR2, and CDR3 sequences of SEQ ID Nos.: 46, 47, and 48, respectively, and a VL region comprising the CDR1, CDR2, and CDR3 sequences of SEQ ID No: 49, the sequence AAS, and SEQ ID No: 50, respectively.

40. The lyophilized formulation of claim 1, wherein the antibody moiety of the AXL-ADC comprises at least one binding region comprising a VH region comprising the CDR1, CDR2, and CDR3 sequences of SEQ ID Nos.: 114, 115, and 116, respectively, and a VL region comprising the CDR1, CDR2, and CDR3 sequences of SEQ ID No: 117, the sequence DAS, and SEQ ID No: 118, respectively.

41. The lyophilized formulation of claim 1, wherein the antibody moiety of the AXL-ADC comprises at least one binding region comprising a VH region comprising the CDR1, CDR2, and CDR3 sequences of SEQ ID Nos.: 51, 52, and 54, respectively; and a VL region comprising the CDR1, CDR2, and CDR3 sequences of SEQ ID No: 55, the sequence GAS, and SEQ ID No: 56, respectively.

42. The lyophilized formulation of claim 1, wherein the antibody moiety of the AXL-ADC comprises at least one binding region comprising a VH region comprising the CDR1, CDR2, and CDR3 sequences of SEQ ID Nos.: 57, 58, and 59, respectively; and a VL region comprising the CDR1, CDR2, and CDR3 sequences of SEQ ID No: 60, the sequence GAS, and SEQ ID No: 61, respectively.

43. The lyophilized formulation of claim 1, wherein the antibody moiety of the AXL-ADC comprises at least one binding region comprising a VH region comprising the CDR1, CDR2, and CDR3 sequences of SEQ ID Nos.: 72, 74, and 75, respectively; and a VL region comprising the CDR1, CDR2, and CDR3 sequences of SEQ ID No: 76, the sequence ATS, and SEQ ID No: 77, respectively.

44. The lyophilized formulation of claim 1, wherein the antibody moiety of the AXL-ADC comprises at least one binding region comprising a VH region comprising the CDR1, CDR2, and CDR3 sequences of SEQ ID Nos.: 93, 94, and 95, respectively; and a VL region comprising the CDR1, CDR2, and CDR3 sequences of SEQ ID No: 96, the sequence GAS, and SEQ ID No: 97, respectively.

45. The lyophilized formulation of claim 1, wherein the antibody moiety of the AXL-ADC comprises at least one binding region comprising a VH region comprising the CDR1, CDR2, and CDR3 sequences of SEQ ID Nos.: 98, 99, and 100, respectively; and a VL region comprising the CDR1, CDR2, and CDR3 sequences of SEQ ID No: 101, the sequence DAS, and SEQ ID No: 102, respectively.

46. The lyophilized formulation of claim 1, wherein the antibody moiety of the AXL-ADC comprises at least one binding region comprising a VH region comprising the CDR1, CDR2, and CDR3 sequences of SEQ ID Nos.: 108, 109, and 111, respectively; and a VL region comprising the CDR1, CDR2, and CDR3 sequences of SEQ ID No: 112, the sequence AAS, and SEQ ID No: 113, respectively.

47. The lyophilized formulation of claim 10, wherein the antibody moiety of the AXL-ADC comprises at least one binding region comprising a VH region comprising the CDR1, CDR2, and CDR3 sequences of SEQ ID Nos: 36, 37, and 38, respectively, and a VL region comprising the CDR1, CDR2, and CDR3 sequences of SEQ ID No: 39, the sequence GAS, and SEQ ID No: 40, respectively.

48. The lyophilized formulation of claim 10, wherein the antibody moiety of the AXL-ADC comprises at least one binding region comprising a VH region comprising the CDR1, CDR2, and CDR3 sequences of SEQ ID Nos.: 46, 47, and 48, respectively, and a VL region comprising the CDR1, CDR2, and CDR3 sequences of SEQ ID No: 49, the sequence AAS, and SEQ ID No: 50, respectively.

49. The lyophilized formulation of claim 10, wherein the antibody moiety of the AXL-ADC comprises at least one binding region comprising a VH region comprising the CDR1, CDR2, and CDR3 sequences of SEQ ID Nos.: 114, 115, and 116, respectively, and a VL region comprising the CDR1, CDR2, and CDR3 sequences of SEQ ID No: 117, the sequence DAS, and SEQ ID No: 118, respectively.

50. The lyophilized formulation of claim 10, wherein the antibody moiety of the AXL-ADC comprises at least one binding region comprising a VH region comprising the CDR1, CDR2, and CDR3 sequences of SEQ ID Nos.: 51, 52, and 54, respectively; and a VL region comprising the CDR1, CDR2, and CDR3 sequences of SEQ ID No: 55, the sequence GAS, and SEQ ID No: 56, respectively.

51. The lyophilized formulation of claim 10, wherein the antibody moiety of the AXL-ADC comprises at least one binding region comprising a VH region comprising the CDR1, CDR2, and CDR3 sequences of SEQ ID Nos.: 57, 58, and 59, respectively; and a VL region comprising the CDR1, CDR2, and CDR3 sequences of SEQ ID No: 60, the sequence GAS, and SEQ ID No: 61, respectively.

52. The lyophilized formulation of claim 10, wherein the antibody moiety of the AXL-ADC comprises at least one binding region comprising a VH region comprising the CDR1, CDR2, and CDR3 sequences of SEQ ID Nos.: 72, 74, and 75, respectively; and a VL region comprising the CDR1, CDR2, and CDR3 sequences of SEQ ID No: 76, the sequence ATS, and SEQ ID No: 77, respectively.

53. The lyophilized formulation of claim 10, wherein the antibody moiety of the AXL-ADC comprises at least one binding region comprising a VH region comprising the CDR1, CDR2, and CDR3 sequences of SEQ ID Nos.: 93, 94, and 95, respectively; and a VL region comprising the CDR1, CDR2, and CDR3 sequences of SEQ ID No: 96, the sequence GAS, and SEQ ID No: 97, respectively.

54. The lyophilized formulation of claim 10, wherein the antibody moiety of the AXL-ADC comprises at least one binding region comprising a VH region comprising the CDR1, CDR2, and CDR3 sequences of SEQ ID Nos.: 98, 99, and 100, respectively; and a VL region comprising the CDR1, CDR2, and CDR3 sequences of SEQ ID No: 101, the sequence DAS, and SEQ ID No: 102, respectively.

55. The lyophilized formulation of claim 10, wherein the antibody moiety of the AXL-ADC comprises at least one binding region comprising a VH region comprising the CDR1, CDR2, and CDR3 sequences of SEQ ID Nos.: 108, 109, and 111, respectively; and a VL region comprising the CDR1, CDR2, and CDR3 sequences of SEQ ID No: 112, the sequence AAS, and SEQ ID No: 113, respectively.

56. The pharmaceutical formulation of claim 11, wherein the antibody moiety of the AXL-ADC comprises at least one binding region comprising a VH region comprising the CDR1, CDR2, and CDR3 sequences of SEQ ID Nos: 36, 37, and 38, respectively, and a VL region comprising the CDR1, CDR2, and CDR3 sequences of SEQ ID No: 39, the sequence GAS, and SEQ ID No: 40, respectively.

57. The pharmaceutical formulation of claim 11, wherein the antibody moiety of the AXL-ADC comprises at least one binding region comprising a VH region comprising the CDR1, CDR2, and CDR3 sequences of SEQ ID Nos.: 46, 47, and 48, respectively, and a VL region comprising the CDR1, CDR2, and CDR3 sequences of SEQ ID No: 49, the sequence AAS, and SEQ ID No: 50, respectively.

58. The pharmaceutical formulation of claim 11, wherein the antibody moiety of the AXL-ADC comprises at least one binding region comprising a VH region comprising the CDR1, CDR2, and CDR3 sequences of SEQ ID Nos.: 114, 115, and 116, respectively, and a VL region comprising the CDR1, CDR2, and CDR3 sequences of SEQ ID No: 117, the sequence DAS, and SEQ ID No: 118, respectively.

59. The pharmaceutical formulation of claim 11, wherein the antibody moiety of the AXL-ADC comprises at least one binding region comprising a VH region comprising the CDR1, CDR2, and CDR3 sequences of SEQ ID Nos.: 51, 52, and 54, respectively; and a VL region comprising the CDR1, CDR2, and CDR3 sequences of SEQ ID No: 55, the sequence GAS, and SEQ ID No: 56, respectively.

60. The pharmaceutical formulation of claim 11, wherein the antibody moiety of the AXL-ADC comprises at least one binding region comprising a VH region comprising the CDR1, CDR2, and CDR3 sequences of SEQ ID Nos.: 57, 58, and 59, respectively; and a VL region comprising the CDR1, CDR2, and CDR3 sequences of SEQ ID No: 60, the sequence GAS, and SEQ ID No: 61, respectively.

61. The pharmaceutical formulation of claim 11, wherein the antibody moiety of the AXL-ADC comprises at least one binding region comprising a VH region comprising the CDR1, CDR2, and CDR3 sequences of SEQ ID Nos.: 72, 74, and 75, respectively; and a VL region comprising the CDR1, CDR2, and CDR3 sequences of SEQ ID No: 76, the sequence ATS, and SEQ ID No: 77, respectively.

62. The pharmaceutical formulation of claim 11, wherein the antibody moiety of the AXL-ADC comprises at least one binding region comprising a VH region comprising the CDR1, CDR2, and CDR3 sequences of SEQ ID Nos.: 93, 94, and 95, respectively; and a VL region comprising the CDR1, CDR2, and CDR3 sequences of SEQ ID No: 96, the sequence GAS, and SEQ ID No: 97, respectively.

63. The pharmaceutical formulation of claim 11, wherein the antibody moiety of the AXL-ADC comprises at least one binding region comprising a VH region comprising the CDR1, CDR2, and CDR3 sequences of SEQ ID Nos.: 98, 99, and 100, respectively; and a VL region comprising the CDR1, CDR2, and CDR3 sequences of SEQ ID No: 101, the sequence DAS, and SEQ ID No: 102, respectively.

64. The pharmaceutical formulation of claim 11, wherein the antibody moiety of the AXL-ADC comprises at least one binding region comprising a VH region comprising the CDR1, CDR2, and CDR3 sequences of SEQ ID Nos.: 108, 109, and 111, respectively; and a VL region comprising the CDR1, CDR2, and CDR3 sequences of SEQ ID No: 112, the sequence AAS, and SEQ ID No: 113, respectively.

65. The aqueous formulation of claim 13, wherein the anti-AXL antibody comprises a VH region comprising the CDR1, CDR2, and CDR3 sequences of SEQ ID Nos: 36, 37, and 38, respectively, and a VL region comprising the CDR1, CDR2, and CDR3 sequences of SEQ ID No: 39, the sequence GAS, and SEQ ID No: 40, respectively.

66. The aqueous formulation of claim 13, wherein the anti-AXL antibody comprises a VH region comprising the CDR1, CDR2, and CDR3 sequences of SEQ ID Nos.: 46, 47, and 48, respectively, and a VL region comprising the CDR1, CDR2, and CDR3 sequences of SEQ ID No: 49, the sequence AAS, and SEQ ID No: 50, respectively.

67. The aqueous formulation of claim 13, wherein the anti-AXL antibody comprises a VH region comprising the CDR1, CDR2, and CDR3 sequences of SEQ ID Nos.: 114, 115, and 116, respectively, and a VL region comprising the CDR1, CDR2, and CDR3 sequences of SEQ ID No: 117, the sequence DAS, and SEQ ID No: 118, respectively.

68. The aqueous formulation of claim 13, wherein the anti-AXL antibody comprises a VH region comprising the CDR1, CDR2, and CDR3 sequences of SEQ ID Nos.: 51, 52, and 54, respectively; and a VL region comprising the CDR1, CDR2, and CDR3 sequences of SEQ ID No: 55, the sequence GAS, and SEQ ID No: 56, respectively.

69. The aqueous formulation of claim 13, wherein the anti-AXL antibody comprises a VH region comprising the CDR1, CDR2, and CDR3 sequences of SEQ ID Nos.: 57, 58, and 59, respectively; and a VL region comprising the CDR1, CDR2, and CDR3 sequences of SEQ ID No: 60, the sequence GAS, and SEQ ID No: 61, respectively.

70. The aqueous formulation of claim 13, wherein the anti-AXL antibody comprises a VH region comprising the CDR1, CDR2, and CDR3 sequences of SEQ ID Nos.: 72, 74, and 75, respectively; and a VL region comprising the CDR1, CDR2, and CDR3 sequences of SEQ ID No: 76, the sequence ATS, and SEQ ID No: 77, respectively.

71. The aqueous formulation of claim 13, wherein the anti-AXL antibody comprises a VH region comprising the CDR1, CDR2, and CDR3 sequences of SEQ ID Nos.: 93, 94, and 95, respectively; and a VL region comprising the CDR1, CDR2, and CDR3 sequences of SEQ ID No: 96, the sequence GAS, and SEQ ID No: 97, respectively.

72. The aqueous formulation of claim 13, wherein the anti-AXL antibody comprises a VH region comprising the CDR1, CDR2, and CDR3 sequences of SEQ ID Nos.: 98, 99, and 100, respectively; and a VL region comprising the CDR1, CDR2, and CDR3 sequences of SEQ ID No: 101, the sequence DAS, and SEQ ID No: 102, respectively.

73. The aqueous formulation of claim 13, wherein the anti-AXL antibody comprises a VH region comprising the CDR1, CDR2, and CDR3 sequences of SEQ ID Nos.: 108, 109, and 111, respectively; and a VL region comprising the CDR1, CDR2, and CDR3 sequences of SEQ ID No: 112, the sequence AAS, and SEQ ID No: 113, respectively.

74. The lyophilized formulation of claim 25, wherein the antibody moiety of the AXL-ADC comprises at least one binding region comprising a VH region comprising the CDR1, CDR2, and CDR3 sequences of SEQ ID Nos: 36, 37, and 38, respectively, and a VL region comprising the CDR1, CDR2, and CDR3 sequences of SEQ ID No: 39, the sequence GAS, and SEQ ID No: 40, respectively.

75. The lyophilized formulation of claim 25, wherein the antibody moiety of the AXL-ADC comprises at least one binding region comprising a VH region comprising the CDR1, CDR2, and CDR3 sequences of SEQ ID Nos.: 46, 47, and 48, respectively, and a VL region comprising the CDR1, CDR2, and CDR3 sequences of SEQ ID No: 49, the sequence AAS, and SEQ ID No: 50, respectively.

76. The lyophilized formulation of claim 25, wherein the antibody moiety of the AXL-ADC comprises at least one binding region comprising a VH region comprising the CDR1, CDR2, and CDR3 sequences of SEQ ID Nos.: 114, 115, and 116, respectively, and a VL region comprising the CDR1, CDR2, and CDR3 sequences of SEQ ID No: 117, the sequence DAS, and SEQ ID No: 118, respectively.

77. The lyophilized formulation of claim 25, wherein the antibody moiety of the AXL-ADC comprises at least one binding region comprising a VH region comprising the CDR1, CDR2, and CDR3 sequences of SEQ ID Nos.: 51, 52, and 54, respectively; and a VL region comprising the CDR1, CDR2, and CDR3 sequences of SEQ ID No: 55, the sequence GAS, and SEQ ID No: 56, respectively.

78. The lyophilized formulation of claim 25, wherein the antibody moiety of the AXL-ADC comprises at least one binding region comprising a VH region comprising the CDR1, CDR2, and CDR3 sequences of SEQ ID Nos.: 57, 58, and 59, respectively; and a VL region comprising the CDR1, CDR2, and CDR3 sequences of SEQ ID No: 60, the sequence GAS, and SEQ ID No: 61, respectively.

79. The lyophilized formulation of claim 25, wherein the antibody moiety of the AXL-ADC comprises at least one binding region comprising a VH region comprising the CDR1, CDR2, and CDR3 sequences of SEQ ID Nos.: 72, 74, and 75, respectively; and a VL region comprising the CDR1, CDR2, and CDR3 sequences of SEQ ID No: 76, the sequence ATS, and SEQ ID No: 77, respectively.

80. The lyophilized formulation of claim 25, wherein the antibody moiety of the AXL-ADC comprises at least one binding region comprising a VH region comprising the CDR1, CDR2, and CDR3 sequences of SEQ ID Nos.: 93, 94, and 95, respectively; and a VL region comprising the CDR1, CDR2, and CDR3 sequences of SEQ ID No: 96, the sequence GAS, and SEQ ID No: 97, respectively.

81. The lyophilized formulation of claim 25, wherein the antibody moiety of the AXL-ADC comprises at least one binding region comprising a VH region comprising the CDR1, CDR2, and CDR3 sequences of SEQ ID Nos.: 98, 99, and 100, respectively; and a VL region comprising the CDR1, CDR2, and CDR3 sequences of SEQ ID No: 101, the sequence DAS, and SEQ ID No: 102, respectively.

82. The lyophilized formulation of claim 25, wherein the antibody moiety of the AXL-ADC comprises at least one binding region comprising a VH region comprising the CDR1, CDR2, and CDR3 sequences of SEQ ID Nos.: 108, 109, and 111, respectively; and a VL region comprising the CDR1, CDR2, and CDR3 sequences of SEQ ID No: 112, the sequence AAS, and SEQ ID No: 113, respectively.

83. The aqueous formulation of claim 26, wherein the antibody moiety of the AXL-ADC comprises at least one binding region comprising a VH region comprising the CDR1, CDR2, and CDR3 sequences of SEQ ID Nos: 36, 37, and 38, respectively, and a VL region comprising the CDR1, CDR2, and CDR3 sequences of SEQ ID No: 39, the sequence GAS, and SEQ ID No: 40, respectively.

84. The aqueous formulation of claim 26, wherein the antibody moiety of the AXL-ADC comprises at least one binding region comprising a VH region comprising the CDR1, CDR2, and CDR3 sequences of SEQ ID Nos.: 46, 47, and 48, respectively, and a VL region comprising the CDR1, CDR2, and CDR3 sequences of SEQ ID No: 49, the sequence AAS, and SEQ ID No: 50, respectively.

85. The aqueous formulation of claim 26, wherein the antibody moiety of the AXL-ADC comprises at least one binding region comprising a VH region comprising the CDR1, CDR2, and CDR3 sequences of SEQ ID Nos.: 114, 115, and 116, respectively, and a VL region comprising the CDR1, CDR2, and CDR3 sequences of SEQ ID No: 117, the sequence DAS, and SEQ ID No: 118, respectively.

86. The aqueous formulation of claim 26, wherein the antibody moiety of the AXL-ADC comprises at least one binding region comprising a VH region comprising the CDR1, CDR2, and CDR3 sequences of SEQ ID Nos.: 51, 52, and 54, respectively; and a VL region comprising the CDR1, CDR2, and CDR3 sequences of SEQ ID No: 55, the sequence GAS, and SEQ ID No: 56, respectively.

87. The aqueous formulation of claim 26, wherein the antibody moiety of the AXL-ADC comprises at least one binding region comprising a VH region comprising the CDR1, CDR2, and CDR3 sequences of SEQ ID Nos.: 57, 58, and 59, respectively; and a VL region comprising the CDR1, CDR2, and CDR3 sequences of SEQ ID No: 60, the sequence GAS, and SEQ ID No: 61, respectively.

88. The aqueous formulation of claim 26, wherein the antibody moiety of the AXL-ADC comprises at least one binding region comprising a VH region comprising the CDR1, CDR2, and CDR3 sequences of SEQ ID Nos.: 72, 74, and 75, respectively; and a VL region comprising the CDR1, CDR2, and CDR3 sequences of SEQ ID No: 76, the sequence ATS, and SEQ ID No: 77, respectively.

89. The aqueous formulation of claim 26, wherein the antibody moiety of the AXL-ADC comprises at least one binding region comprising a VH region comprising the CDR1, CDR2, and CDR3 sequences of SEQ ID Nos.: 93, 94, and 95, respectively; and a VL region comprising the CDR1, CDR2, and CDR3 sequences of SEQ ID No: 96, the sequence GAS, and SEQ ID No: 97, respectively.

90. The aqueous formulation of claim 26, wherein the antibody moiety of the AXL-ADC comprises at least one binding region comprising a VH region comprising the CDR1, CDR2, and CDR3 sequences of SEQ ID Nos.: 98, 99, and 100, respectively; and a VL region comprising the CDR1, CDR2, and CDR3 sequences of SEQ ID No: 101, the sequence DAS, and SEQ ID No: 102, respectively.

91. The aqueous formulation of claim 26, wherein the antibody moiety of the AXL-ADC comprises at least one binding region comprising a VH region comprising the CDR1, CDR2, and CDR3 sequences of SEQ ID Nos.: 108, 109, and 111, respectively; and a VL region comprising the CDR1, CDR2, and CDR3 sequences of SEQ ID No: 112, the sequence AAS, and SEQ ID No: 113, respectively.

* * * * *